United States Patent
Yogo et al.

(10) Patent No.: US 10,787,462 B2
(45) Date of Patent: Sep. 29, 2020

(54) HETEROCYCLIC COMPOUND

(71) Applicant: TAKEDA PHARMACEUTICAL COMPANY LIMITED, Osaka-shi, Osaka (JP)

(72) Inventors: Takatoshi Yogo, Fujisawa (JP); Masato Yoshikawa, Fujisawa (JP); Morihisa Saitoh, Fujisawa (JP); Taisuke Katoh, Fujisawa (JP); Tomohiro Seki, Fujisawa (JP); Yoshihisa Nakada, Fujisawa (JP)

(73) Assignee: TAKEDA PHARMACEUTICAL COMPANY LIMITED, Osaka-Shi, Osaka (JP)

( * ) Notice: Subject to any disclaimer, the term of this patent is extended or adjusted under 35 U.S.C. 154(b) by 227 days.

(21) Appl. No.: 15/769,201

(22) PCT Filed: Oct. 21, 2016

(86) PCT No.: PCT/JP2016/081373
§ 371 (c)(1),
(2) Date: Apr. 18, 2018

(87) PCT Pub. No.: WO2017/069279
PCT Pub. Date: Apr. 27, 2017

(65) Prior Publication Data
US 2018/0319819 A1    Nov. 8, 2018

(30) Foreign Application Priority Data

Oct. 23, 2015   (JP) .................. 2015-209280

(51) Int. Cl.
| | |
|---|---|
| C07D 519/00 | (2006.01) |
| C07D 487/04 | (2006.01) |
| C07D 471/04 | (2006.01) |
| C07D 513/04 | (2006.01) |
| A61K 31/55 | (2006.01) |
| A61K 31/553 | (2006.01) |
| A61K 31/554 | (2006.01) |
| A61P 31/12 | (2006.01) |
| A61P 13/12 | (2006.01) |
| A61P 1/16 | (2006.01) |
| A61P 25/00 | (2006.01) |

(52) U.S. Cl.
CPC ............ *C07D 519/00* (2013.01); *A61K 31/55* (2013.01); *A61K 31/553* (2013.01); *A61K 31/554* (2013.01); *A61P 1/16* (2018.01); *A61P 13/12* (2018.01); *A61P 25/00* (2018.01); *A61P 31/12* (2018.01); *C07D 471/04* (2013.01); *C07D 487/04* (2013.01); *C07D 513/04* (2013.01)

(58) Field of Classification Search
CPC .. C07D 519/00; C07D 487/04; C07D 471/04; C07D 513/04
See application file for complete search history.

(56) References Cited

FOREIGN PATENT DOCUMENTS

| | | |
|---|---|---|
| JP | 2012-514601 A | 6/2012 |
| WO | 2014/125444 A1 | 8/2014 |
| WO | 2016/027253 A1 | 2/2016 |
| WO | 2016/128936 A1 | 8/2016 |
| WO | 2017/004500 A1 | 1/2017 |
| WO | 2017/109724 A1 | 6/2017 |
| WO | 2018/073193 A1 | 4/2018 |

OTHER PUBLICATIONS

ShareCare, Can Gaucher's disease be prevented, obtained from https://www.sharecare.com/health/autosomal-recessive-genetic-disorders/can-gauchers-disease-be-prevented on Jan. 21, 2019 (Year: 2019).*
Ascherio et al. Nat. Rev. Neurol. Nov. 5, 2012; 8(11): 602-612 (Year: 2012).*
National Institute of Diabetes and Digestive and Kidney Diseases, Preventing Chronic Kidney Disease, obtained from https://www.niddk.nih.gov/health-information/kidney-disease/chronic-kidney-disease-ckd/prevention on Jan. 21, 2019 (Year: 2019).*

(Continued)

*Primary Examiner* — Matthew P Coughlin

(74) *Attorney, Agent, or Firm* — Nath, Goldberg & Meyer; Joshua B. Goldberg; Scott H. Blackman

(57) ABSTRACT

The present invention provides a heterocyclic compound having an RIP1 kinase inhibitory action, which is useful for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like.

The present invention relates to a compound represented by the following formula (I):

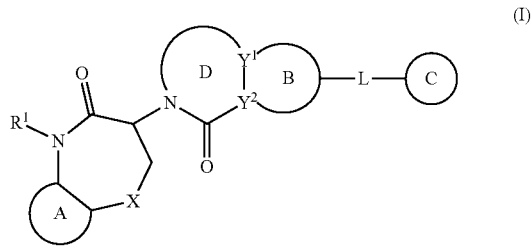

wherein each symbol is as defined in the specification, or a salt thereof.

14 Claims, 1 Drawing Sheet

(56) References Cited

OTHER PUBLICATIONS

Medline, Preventing hepatitis B or C, obtained from https://medlineplus.gov/ency/patientinstructions/000401.htm on Jan. 21, 2019 (Year: 2019).*
International Search Report dated Dec. 20, 2016 issued in corresponding International Application No. PCT/JP2016/081373.
Supplementary Search Report dated Feb. 21, 2019 issued in corresponding European Application No. 16857592.6.

* cited by examiner

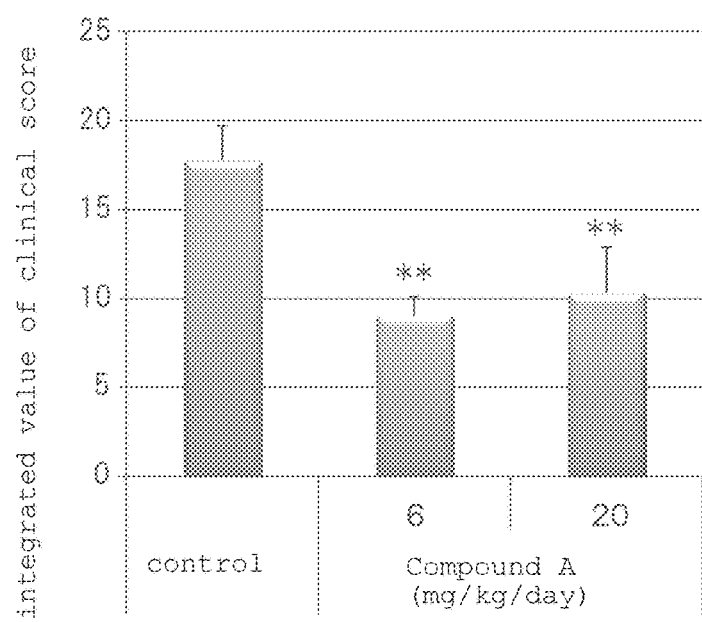
** Statistically significant difference between the both groups was confirmed at P<0.01 from a result of Dunns test, respectively.

HETEROCYCLIC COMPOUND

This is a National Phase Application filed under 35 U.S.C. 371 as a national stage of PCT/JP2016/081373, filed Oct. 21, 2016, an application claiming the benefit of Japanese Application No. 2015-209280, filed Oct. 23, 2015 and Japanese Application No. 2016-037703, filed Feb. 29, 2016, the content of each of which is hereby incorporated by reference in its entirety.

TECHNICAL FIELD

The present invention relates to a heterocyclic compound having a receptor-interacting protein-1 (in the present specification, sometimes to be referred to as "RIP1 or RIPK1") kinase inhibitory action, which is useful for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like.

BACKGROUND OF THE INVENTION

RIP1 kinase, originally referred to as RIP, is a TKL family serine/threonine protein kinase involved in innate immune signaling. RIP1 kinase is a RHIM domain containing protein, with an N-terminal kinase domain and a C-terminal death domain ((2005) Trends Biochem. Sci. 30, 151-159). The death domain of RIP1 mediates interaction with other death domain containing proteins including Fas and TNFR-1 ((1995) Cell 81 513-523), TRAIL-R1 and TRAIL-R2 ((1997) Immunity 7, 821-830) and TRADD ((1996) Immunity 4, 387-396), while the RHIM domain is crucial for binding to other RHIM domain containing proteins such as TRIF ((2004) Nat Immunol. 5, 503-507), DAI ((2009) EMBO Rep. 10, 916-922) and RIP3 ((1999) J. Biol. Chem. 274, 16871-16875); (1999) Curr. Biol. 9, 539-542) and exerts many of its effects through these interactions. RIP1 is a central regulator of cell signaling, and is involved in both pro-survival and programmed cell death pathways which will be discussed below.

The role for RIP1 in cell signaling has been assessed under various conditions [including TLR3 ((2004) Nat Immunol. 5, 503-507), TLR4 ((2005) J. Biol. Chem. 280, 36560-36566), TRAIL ((2012) J. Virol. Epub, ahead of print), FAS ((2004) J. Biol. Chem. 279, 7925-7933)], but is best understood in the context of mediating signals downstream of the death receptor TNFR1 ((2003) Cell 114, 181-190). Engagement of the TNFR by TNF leads to its oligomerization, and the recruitment of multiple proteins, including linear K63-linked polyubiquitinated RIP1 ((2006) Mol. Cell 22, 245-257), TRAF2/5 ((2010) J. Mol. Biol. 396, 528-539), TRADD ((2008) Nat. Immunol. 9, 1037-1046) and cIAPs ((2008) Proc. Natl. Acad. Sci. USA. 105, 1 1778-11783), to the cytoplasmic domain of the receptor. This complex which is dependent on RIP1 as a scaffolding protein (i.e. kinase independent), termed complex I, provides a platform for pro-survival signaling through the activation of the NFKB and MAP kinases pathways ((2010) Sci. Signal. 115, re4). Alternatively, binding of TNF to its receptor under conditions promoting the deubiquitination of RIP1 (by proteins such as A20 and CYLD or inhibition of the cIAPs) results in receptor internalization and the formation of complex II or DISC (death-inducing signaling complex) ((2011) Cell Death Dis. 2, e230). Formation of the DISC, which contains RIP1, TRADD, FADD and caspase 8, results in the activation of caspase 8 and the onset of programmed apoptotic cell death also in a RIP1 kinase independent fashion ((2012) FEBS J 278, 877-887). Apoptosis is largely a quiescent form of cell death, and is involved in processes such as development and cellular homeostasis.

Under conditions where apoptosis is inhibited (such as FADD/caspase 8 deletion, caspase inhibition or viral infection), a third RIP1 kinase-dependent function is achieved. RIP3, which is RIP1 homolog, binds to this complex, becomes phosphorylated by RIP1 and induces a caspase-independent programmed necrotic cell death through the activation of MLKL and PGAM5 ((2012) Cell 148, 213-227); ((2012) Cell 148, 228-243); ((2012) Proc. Natl. Acad. Sci. USA. 109, 5322-5327). As opposed to apoptosis, programmed necrosis (not to be confused with passive necrosis which is not programmed) results in the release of damage associated molecular patterns (DAMPs) from the cell. These DAMPs provides a "danger signal" to surrounding cells and tissues, and elicits proinflammatory responses including inflammasome activation, cytokine production and cellular recruitment ((2008 Nat. Rev. Immunol 8, 279-289).

Dysregulation of RIP1 kinase-mediated programmed cell death has been linked to various diseases, as demonstrated by use of the RIP3 knockout mouse (where RIP1-mediated programmed necrosis is completely blocked), Necrostatin-1 (a tool inhibitor of RIP1 kinase activity with poor oral bioavailability) and the like. The RIP3 knockout mouse has been shown to be protective in inflammatory bowel disease (including ulcerative colitis and Crohn's disease) ((2011) Nature 477, 330-334), psoriasis ((2011) Immunity 35, 572-582), retinal-detachment-induced photoreceptor necrosis ((2010) PNAS 107, 21695-21700), retinitis pigmentosa ((2012) Proc. Natl. Acad. Sci., 109:36, 14598-14603), non-alcohol steatohepatitis, alcohol steatohepatitis and hepatitis B and C ((2015) Clinical Science 129(8), 723-739), cerulein-induced acute pancreatits ((2009) Cell 137, 1100-1111) and sepsis/systemic inflammatory response syndrome (SIRS) ((2011) Immunity 35, 908-918). Necrostatin-1 has been shown to be effective in alleviating ischemic brain injury ((2005) Nat. Chem. Biol. 1, 112-119), retinal ischemia/reperfusion injury ((2010) J. Neurosci. Res. 88, 1569-1576), Huntington's disease ((2011) Cell Death Dis. 2 e115), inflammatory bowel disease (including ulcerative colitis and Crohn's disease) ((2011) Nature 477 (7364, 335-339), (2014) Am. J. Gastroenterol. 109, 279-287, (2015) Gut 64(4), 601-610), acute kidney injury ((2015) J. Am. Soc. Nephrol. doi: 10.1681/ASN.2014080741), chronic kidney disease ((2015) Biochem. Biophys. Res. Commun. 461(4), 575-581), acute hepatic failure and autoimmune hepatitis ((2015) Cell Death and Disease, doi:10.1038/cddis.2015.126), renal ischemia reperfusion injury ((2012) Kidney Int. 81, 751-761), cisplatin induced kidney injury ((2012) Ren. Fail. 34, 373-377) and traumatic brain injury ((2012) Neurochem. Res. 37, 1849-1858), and RIP1 kinase inhibitors have been shown to be effective in alleviating multiple sclerosis in experimental systems using other RIP1 kinase inhibitors ((2015) Cell Reports, Volume 10, Issue 11, 1836-1849). Other diseases or disorders regulated at least in part by RIP1-dependent apoptosis, necrosis or cytokine production include hematological and solid organ malignancies ((2013) Genes Dev. 27: 1640-1649), bacterial infections and viral infections ((2014) Cell Host & Microbe 15, 23-35) (including, but not limited to, tuberculosis and influenza ((2013) Cell 153, 1-14)) and Lysosomal storage diseases (particularly Gaucher disease ((2014) Nature Medicine 20, 204-208, doi: 10.1038/nm.3449)).

A potent, selective, small molecule inhibitor of RIP1 kinase activity would block RIP1-dependent cellular necrosis and thereby provide a therapeutic benefit in diseases or events associated with DAMPs, cell death and/or inflammation.

As heterocyclic compounds, Patent Document 1 discloses a compound represented by the following formula (I):

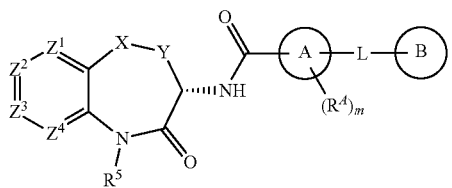

wherein each symbol is as defined in Patent Document 1, which is an RIP1 kinase inhibitor, and useful for the treatment of acute kidney injury, chronic kidney disease, autoimmune hepatitis, alcohol steatohepatitis, non-alcohol steatohepatitis, inflammatory bowel disease, multiple sclerosis and the like.

DOCUMENT LIST

Patent Document

Patent Document 1: WO 2014/125444

Non-Patent Document

Non-Patent Document 1: (2005) Trends Biochem. Sci. 30, 151-159
Non-Patent Document 2: (1995) Cell 81 513-523
Non-Patent Document 3: (1997) Immunity 7, 821-830
Non-Patent Document 4: (1996) Immunity 4, 387-396
Non-Patent Document 5: (2004) Nat Immunol. 5, 503-507
Non-Patent Document 6: (2009) EMBO Rep. 10, 916-922
Non-Patent Document 7: (1999) J. Biol. Chem. 274, 16871-16875
Non-Patent Document 8: (1999) Curr. Biol. 9, 539-542
Non-Patent Document 9: (2004) Nat Immunol. 5, 503-507
Non-Patent Document 10: (2005) J. Biol. Chem. 280, 36560-36566
Non-Patent Document 11: (2012) J. Virol. Epub, ahead of print
Non-Patent Document 12: (2004) J. Biol. Chem. 279, 7925-7933
Non-Patent Document 13: (2003) Cell 114, 181-190
Non-Patent Document 14: (2006) Mol. Cell 22, 245-257
Non-Patent Document 15: (2010) J. Mol. Biol. 396, 528-539
Non-Patent Document 16: (2008) Nat. Immunol. 9, 1037-1046
Non-Patent Document 17: (2008) Proc. Natl. Acad. Sci. USA. 105, 11778-11783
Non-Patent Document 18: (2010) Sci. Signal. 115, re4
Non-Patent Document 19: (2011) Cell Death Dis. 2, e230
Non-Patent Document 20: (2012) FEBS J 278, 877-887
Non-Patent Document 21: (2012) Cell 148, 213-227
Non-Patent Document 22: (2012) Cell 148, 228-243
Non-Patent Document 23: (2012) Proc. Natl. Acad. Sci. USA. 109, 5322-5327
Non-Patent Document 24: (2008) Nat. Rev. Immunol 8, 279-289
Non-Patent Document 25: (2011) Nature 477, 330-334
Non-Patent Document 26: (2011) Immunity 35, 572-582
Non-Patent Document 27: (2010) PNAS 107, 21695-21700
Non-Patent Document 28: (2012) Proc. Natl. Acad. Sci., 109:36, 14598-14603
Non-Patent Document 29: (2015) Clinical Science 129(8), 723-739
Non-Patent Document 30: (2009) Cell 137, 1100-1111
Non-Patent Document 31: (2011) Immunity 35, 908-918
Non-Patent Document 32: (2005) Nat. Chem. Biol. 1, 112-119
Non-Patent Document 33: (2010) J. Neurosci. Res. 88, 1569-1576
Non-Patent Document 34: (2011) Cell Death Dis. 2 e115
Non-Patent Document 35: (2011) Nature 477 (7364, 335-339) Non-Patent Document 36: (2014) Am. J. Gastroenterol. 109, 279-287
Non-Patent Document 37: (2015) Gut 64(4), 601-610
Non-Patent Document 38: (2015) J. Am. Soc. Nephrol. doi: 10.1681/ASN.2014080741
Non-Patent Document 39: (2015) Biochem. Biophys. Res. Commun. 461(4), 575-581
Non-Patent Document 40: (2015) Cell Death and Disease, doi:10.1038/cddis.2015.126
Non-Patent Document 41: (2012) Kidney Int. 81, 751-761
Non-Patent Document 42: (2012) Ren. Fail. 34, 373-377
Non-Patent Document 43: (2012) Neurochem. Res. 37, 1849-1858
Non-Patent Document 44: (2015) Cell Reports, Volume 10, Issue 11, 1836-1849
Non-Patent Document 45: (2013) Genes Dev. 27: 1640-1649
Non-Patent Document 46: (2014) Cell Host & Microbe 15, 23-35
Non-Patent Document 47: (2013) Cell 153, 1-14
Non-Patent Document 48: (2014) Nature Medicine, 20, 204-208, doi: 10.1038/nm.3449

SUMMARY OF THE INVENTION

Problems to be Solved by the Invention

The present invention aims to provide a compound having an RIP1 kinase inhibitory action, which is useful as an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like.

Means of Solving the Problems

The present inventors have conducted intensive studies in an attempt to solve the above-mentioned problems and found that a compound represented by the following formula (I) has an RIP1 kinase inhibitory action, and therefore, is useful as an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like, which resulted in the completion of the present invention.

Accordingly, the present invention provides the following.

[1] A compound represented by the following formula (I):

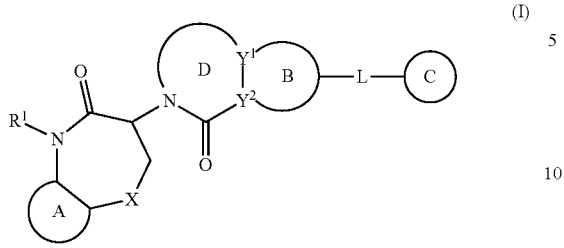

(I)

wherein
Ring A and Ring B are each independently an optionally further substituted 5- to 6-membered aromatic ring,
Ring C is an optionally further substituted ring,
Ring D is an optionally further substituted 5- to 7-membered nitrogen-containing heterocycle,
$R^1$ is a $C_{1-6}$ alkyl group or a hydrogen atom,
X is (a) an oxygen atom, (b) a sulfur atom, (c) —SO—, (d) —$SO_2$—, (e) an optionally substituted methylene group or (f) —$NR^2$—,
$R^2$ is a hydrogen atom or a substituent, or $R^2$ is optionally bonded to $R^1$ to form a bridge,
$Y^1$ and $Y^2$ are each independently a carbon atom or a nitrogen atom,
L is (a) an optionally substituted $C_{1-3}$ alkylene group, (b) an oxygen atom, (c) a sulfur atom, (d) —SO—, (e) —$SO_2$— or (f) —$NR^3$—, and
$R^3$ is a hydrogen atom or a substituent,
or a salt thereof (hereinafter sometimes to be referred to as compound (I)).

[2] The compound or salt of the above-mentioned [1], wherein Ring D is piperidine, pyrrolidine, pyrroline, piperazine, tetrahydropyridine or diazepane, each optionally further substituted.

[3] The compound or salt of the above-mentioned [1] or [2], wherein Ring B is pyrazole, triazole, imidazole, thiazole or pyridine, each optionally further substituted.

[4] The compound or salt of any of the above-mentioned [1] to [3], wherein the partial structure represented by the formula:

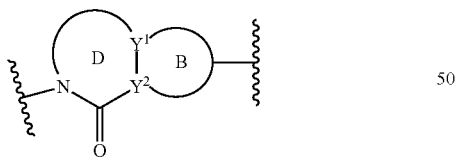

is a partial structure represented by the formula (1)-(4), (6)-(9), (11), (16), (17), (19) or (21):

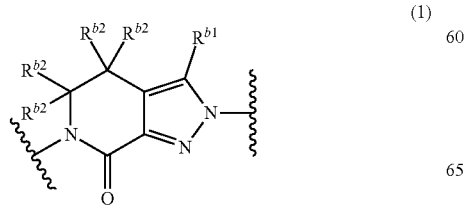

(1)

-continued

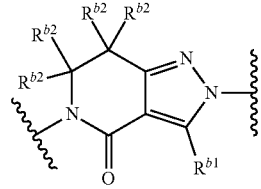

(2)

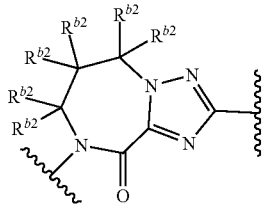

(3)

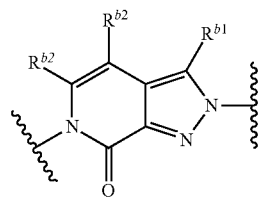

(4)

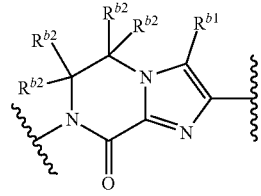

(6)

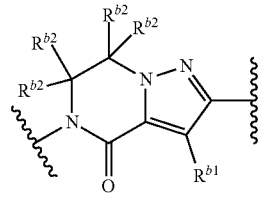

(7)

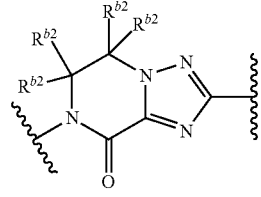

(8)

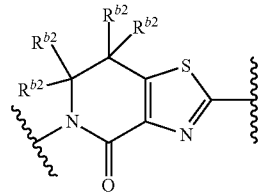

(9)

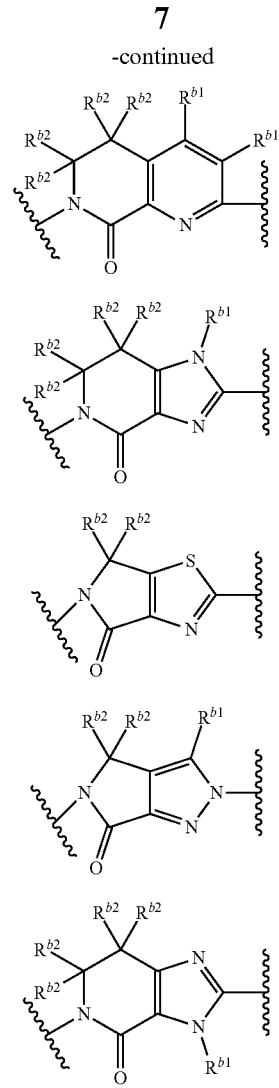

wherein $R^{b1}$ and $R^{b}2$ are each independently a substituent or a hydrogen atom.

[5] The compound or salt a of any of the above-mentioned [1] to [4], wherein

Ring A is benzene, pyridine or pyrazole, each optionally further substituted,

X is an oxygen atom, a sulfur atom, —$SO_2$—, an optionally substituted methylene group or —$NR^2$— wherein $R^2$ is a $C_{1-6}$ alkyl group or a hydrogen atom, L is an optionally substituted $C_{1-2}$ alkylene group, and Ring C is benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane, each optionally further substituted.

[6] The compound or salt of any of the above-mentioned [1] to [5], wherein

Ring A is an optionally further substituted benzene, $R^1$ is a $C_{1-6}$ alkyl group, X is an oxygen atom, Ring D is an optionally further substituted piperidine, Ring B is an optionally further substituted pyrazole, L is an optionally substituted methylene, and Ring C is an optionally further substituted benzene.

[7] (3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof.

[8] (3S)-3-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide, or a salt thereof.

[9] (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof.

[10] A medicament comprising the compound or salt of the above-mentioned [1].

[11] The medicament of the above-mentioned [10], which is an RIP1 kinase inhibitor.

[12] The medicament of the above-mentioned [10], which is an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis.

[13] A method of inhibiting RIP1 kinase in a mammal, which comprises administering an effective amount of the compound or salt of the above-mentioned [1] to the mammal.

[14] A method for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis in a mammal, which comprises administering an effective amount of the compound or salt of the above-mentioned [1] to the mammal.

[15] The compound or salt of the above-mentioned [1] for use in the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis.

[16] Use of the compound or salt of the above-mentioned [1] for the production of an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis.

Effect of the Invention

According to the present invention, a compound having an excellent RIP1 kinase inhibitory action, which is useful as an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like can be provided.

BRIEF DESCRIPTION OF THE DRAWINGS

FIG. 1 is a graph showing an average value of cumulative values of scores evaluated by quantifing clinical symptom of experimental autoimmune encephalomyelitis (EAE) on multiple sclerosis model mouse to which compound A or vehicle was administered.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{1-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) amino group (e.g., N-acetyl-N-methylamino) and a ($C_{1-6}$ alkyl) ($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-13}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The above-mentioned "optionally halogenated $C_{1-6}$ alkyl group" may be 2,2-difluoroethyl.

The "$C_{1-6}$ alkyl group" as the substituent for the above-mentioned "optionally substituted carbamoyl group" (specifically a mono- or di-$C_{1-6}$ alkyl-carbamoyl group) is optionally substituted by
(i) a hydroxy group, and
(ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from
(A) a $C_{6-14}$ aryloxy group (e.g., naphthyloxy), and
(B) a 3- to 14-membered non-aromatic heterocyclylcarbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
(1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group,
(2) a $C_{1-6}$ alkyl group (e.g., methyl), and
(3) an oxo group.

The definition of each symbol in the formula (I) is explained in detail in the following.

Ring A is an optionally further substituted 5- to 6-membered aromatic ring.

Examples of the "5- to 6-membered aromatic ring" of the "optionally further substituted 5- to 6-membered aromatic ring" represented by Ring A include benzene and a 5- to 6-membered monocyclic aromatic heterocycle.

Examples of the 5- to 6-membered monocyclic aromatic heterocycle include 5- to 6-membered monocyclic heterocycles, from among the above-mentioned "aromatic heterocycle".

The "5- to 6-membered aromatic ring" of the "optionally further substituted 5- to 6-membered aromatic ring" represented by Ring A is preferably benzene, pyridine, pyrimidine, pyrazine, pyridazine, pyrazole, furan, thiophene or pyrrole, more preferably benzene, pyridine or pyrazole, particularly preferably benzene.

The "5- to 6-membered aromatic ring" of the "optionally further substituted 5- to 6-membered aromatic ring" represented by Ring A is optionally further substituted by the "substituent". The number of the substituents is, for example, 1 to 4 (preferably 1 or 2). When the number of the substituents is 2 or more, the respective substituents may be the same or different.

Ring A is preferably an optionally further substituted benzene.

Ring A is more preferably benzene optionally further substituted by 1 to 4 (preferably 1 or 2) substituents selected from
(a) a cyano group, and
(b) a halogen atom (e.g., a bromine atom).

Ring A is further more preferably benzene optionally further substituted by one cyano group, or one cyano group and 1 to 3 halogen atoms (e.g., a bromine atom).

In this embodiment, the position of the substituent on the benzene ring is preferably the position indicated by the arrow on the partial structure represented by the formula:

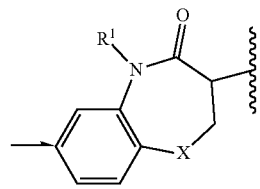

As another embodiment, Ring A is more preferably benzene optionally further substituted by 1 to 4 (preferably 1 or 2) substituents selected from
(a) a cyano group,
(b) a halogen atom (e.g., a bromine atom), and
(c) a mono- or di-$C_{1-6}$ alkyl-carbamoyl group (e.g., methylcarbamoyl).

In this embodiment, Ring A is further more preferably benzene optionally further substituted by
(1) one cyano group,
(2) one cyano group and 1 to 3 halogen atoms (e.g., a bromine atom),
(3) one mono- or di-$C_{1-6}$ alkyl-carbamoyl group (e.g., methylcarbamoyl), or
(4) one mono- or di-$C_{1-6}$ alkyl-carbamoyl group (e.g., methylcarbamoyl) and 1 to 3 halogen atoms (e.g., a bromine atom).

In this embodiment, the position of the substituent on the benzene ring is preferably the position indicated by the arrow on the partial structure represented by the formula:

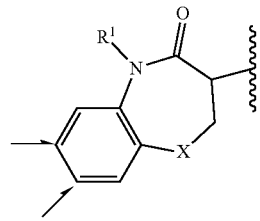

As another embodiment, Ring A is preferably benzene, pyridine or pyrazole, each optionally further substituted.

In this embodiment, Ring A is more preferably benzene, pyridine or pyrazole, each optionally further substituted by 1 to 4 (preferably 1 or 2) substituents selected from
(a) a cyano group,
(b) a halogen atom (e.g., a fluorine atom, a chlorine atom, a bromine atom),
(c) a carboxy group,
(d) a carbamoyl group,
(e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from
(i) a hydroxy group, and
(ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from (A) a $C_{6-14}$ aryloxy group (e.g., naphthyloxy), and
(B) a 3- to 14-membered non-aromatic heterocyclyl-carbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
(1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group,
(2) a $C_{1-6}$ alkyl group (e.g., methyl), and
(3) an oxo group,
(f) a $C_{1-6}$ alkyl group (e.g., methyl) optionally substituted by 1 to 3 $C_{1-6}$ alkoxy groups (e.g., methoxy),
(g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl),
(h) a 3- to 14-membered non-aromatic heterocyclic group (preferably a 3- to 8-membered monocyclic non-aromatic heterocyclic group (e.g., oxetanyl, morpholinyl)), and
(i) a 3- to 14-membered non-aromatic heterocyclylcarbamoyl group (preferably a 3- to 8-membered monocyclic non-aromatic heterocyclylcarbamoyl group (e.g., oxetanylcarbamoyl)).

In this embodiment, when Ring A is an optionally further substituted benzene, the position of the substituent on the benzene ring is preferably the position indicated by the arrow on the partial structure represented by the formula:

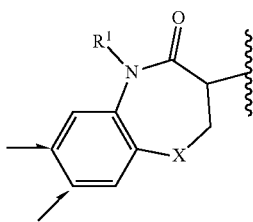

In this embodiment, Ring A is further more preferably (1) benzene optionally further substituted by 1 to 4 (preferably 1 or 2) substituents selected from
(a) a cyano group,
(b) a halogen atom (e.g., a fluorine atom, a chlorine atom, a bromine atom),
(c) a carboxy group,
(d) a carbamoyl group,
(e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from
(i) a hydroxy group, and
(ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from
(A) a $C_{6-14}$ aryloxy group (e.g., naphthyloxy), and
(B) a 3- to 14-membered non-aromatic heterocyclyl-carbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
(1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{1-16}$ aralkyl group (e.g., benzyl), a halogen atom (e.g., a chlorine atom) and an oxo group,
(2) a $C_{1-6}$ alkyl group (e.g., methyl), and
(3) an oxo group,
(f) a $C_{1-6}$ alkyl group (e.g., methyl) optionally substituted by 1 to 3 $C_{1-6}$ alkoxy groups (e.g., methoxy),
(g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl),
(h) a 3- to 14-membered non-aromatic heterocyclic group (preferably a 3- to 8-membered monocyclic non-aromatic heterocyclic group (e.g., oxetanyl, morpholinyl)), and
(i) a 3- to 14-membered non-aromatic heterocyclylcarbamoyl group (preferably a 3- to 8-membered monocyclic non-aromatic heterocyclylcarbamoyl group (e.g., oxetanylcarbamoyl)),
(2) pyridine, or
(3) pyrazole optionally substituted by 1 or 2 (preferably 1) $C_{1-6}$ alkyl groups (e.g., methyl).

In this embodiment, the position of the substituent on the benzene ring is preferably the position indicated by the arrow on the partial structure represented by the formula:

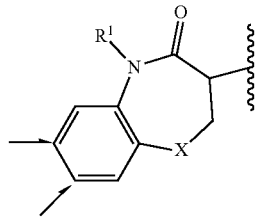

As another embodiment, Ring A is further more preferably an optionally further substituted benzene.

In this embodiment, Ring A is still more preferably benzene optionally further substituted by 1 or 2 (preferably 1) substituents selected from
(a) a cyano group, and
(b) a mono- or di-$C_{1-6}$ alkyl-carbamoyl group (e.g., methylcarbamoyl).

In this embodiment, the position of the substituent on the benzene ring is preferably the position indicated by the arrow on the partial structure represented by the formula:

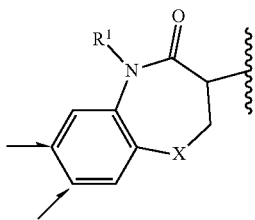

In this embodiment, Ring A is even more preferably benzene optionally further substituted by
(a) one cyano group, or
(b) one mono- or di-$C_{1-6}$ alkyl-carbamoyl group (e.g., methylcarbamoyl).

In this embodiment, the position of the substituent on the benzene ring is preferably the position indicated by the arrow on the partial structure represented by the formula:

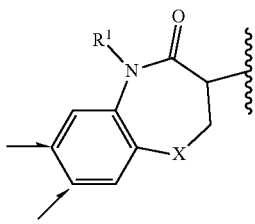

In this embodiment, Ring A is particularly preferably benzene further substituted by
(a) one cyano group, or
(b) one mono- or di-$C_{1-6}$ alkyl-carbamoyl group (e.g., methylcarbamoyl).

In this embodiment, the position of the substituent on the benzene ring is preferably the position indicated by the arrow on the partial structure represented by the formula:

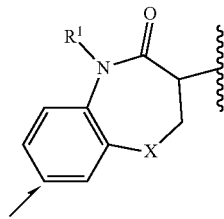

$R^1$ is a $C_{1-6}$ alkyl group (e.g., methyl) or a hydrogen atom.
$R^1$ is preferably a $C_{1-6}$ alkyl group (e.g., methyl).
X is (a) an oxygen atom, (b) a sulfur atom, (c) —SO—, (d) —SO$_2$—, (e) an optionally substituted methylene group or (f) —NR$^2$—.
$R^2$ is a hydrogen atom or a substituent, or $R^2$ is optionally bonded to $R^1$ to form a bridge.

The "methylene group" of the "optionally substituted methylene group" represented by X is optionally substituted by substituent(s) selected from the above-mentioned Substituent Group A. The number of the substituents is, for example, 1 or 2 (preferably 1). When the number of the substituents is 2 or more, the respective substituents may be the same or different.

Examples of the substituent for the "optionally substituted methylene group" represented by X include (a) a halogen atom (e.g., a fluorine atom),
(b) a $C_{1-6}$ alkyl group (e.g., methyl),
(c) a hydroxy group,
(d) an oxo group
and the like.

Examples of the bridge structure formed by $R^1$ and $R^2$ include an optionally substituted $C_{1-3}$ alkylene group.

In the present specification, Examples of the "$C_{1-3}$ alkylene group" include —CH$_2$—, —(CH$_2$)$_2$—, —(CH$_2$)$_3$—, —CH(CH$_3$)—, —C(CH$_3$)$_2$—, —CH(C$_2$H$_5$)—, —CH$_2$—CH(CH$_3$)— and —CH(CH$_3$)—CH$_2$—.

The "$C_{1-3}$ alkylene group" of the "optionally substituted $C_{1-3}$ alkylene group" formed by $R^1$ and $R^2$ is optionally substituted by substituent(s) selected from the above-mentioned Substituent Group A. The number of the substituents is, for example, 1 or 2 (preferably 1). When the number of the substituents is 2 or more, the respective substituents may be the same or different.

$R^2$ is preferably a hydrogen atom or an optionally substituted $C_{1-6}$ alkyl group (e.g., methyl, ethyl), or $R^2$ is bonded to $R^1$ form a $C_{1-3}$ alkylene group.

$R^2$ is more preferably
(1) a hydrogen atom, or
(2) a $C_{1-6}$ alkyl group (e.g., methyl, ethyl) optionally substituted by 1 to 3 $C_{3-10}$ cycloalkyl groups (e.g., cyclopropyl), or
$R^2$ is bonded to $R^1$ form a $C_{1-3}$ alkylene group.

$R^2$ is further more preferably a $C_{1-6}$ alkyl group (e.g., methyl) or a hydrogen atom.

X is preferably
(a) an oxygen atom,
(b) a sulfur atom,
(d) —SO$_2$—, or
(e) an optionally substituted methylene group.

X is more preferably
(a) an oxygen atom,
(b) a sulfur atom,
(d) —SO$_2$—, or
(e) a methylene group.

X is further more preferably an oxygen atom.

As another embodiment, X is preferably
(a) an oxygen atom,
(b) a sulfur atom,
(d) —SO$_2$—,
(e) an optionally substituted methylene group, or
(f) —NR$^2$— wherein $R^2$ is a $C_{1-6}$ alkyl group (e.g., methyl) or a hydrogen atom.

In this embodiment, X is more preferably
(a) an oxygen atom,
(b) a sulfur atom,
(d) —SO$_2$—,
(e) a methylene group, or
(f) —NR$^2$— wherein $R^2$ is a $C_{1-6}$ alkyl group (e.g., methyl).

In this embodiment, X is further more preferably an oxygen atom.

Examples of the partial structure represented by the formula:

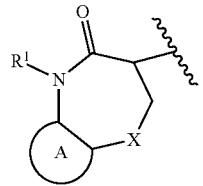

include partial structures represented by the following formulas (1)-(21):
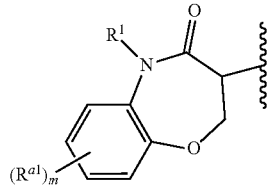 (1)
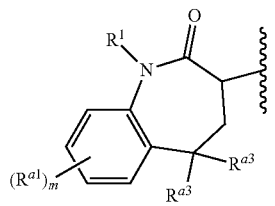 (2)
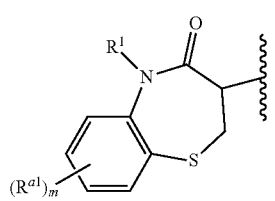 (3)
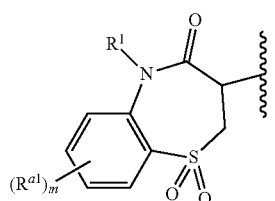 (4)
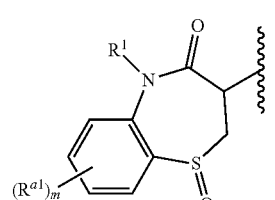 (5)
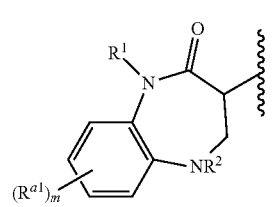 (6)
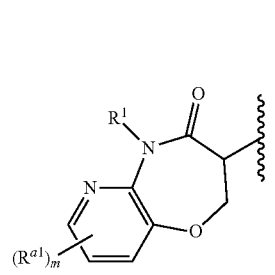 (7)
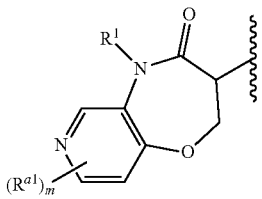 (8)
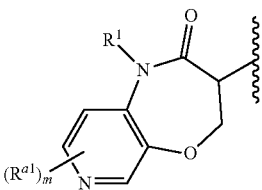 (9)
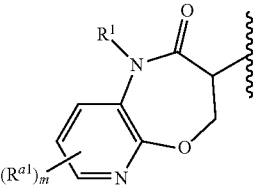 (10)
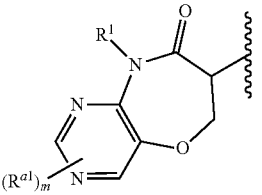 (11)
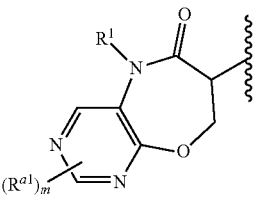 (12)
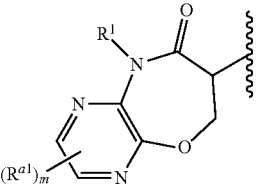 (13)
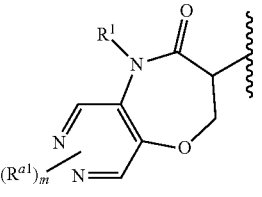 (14)

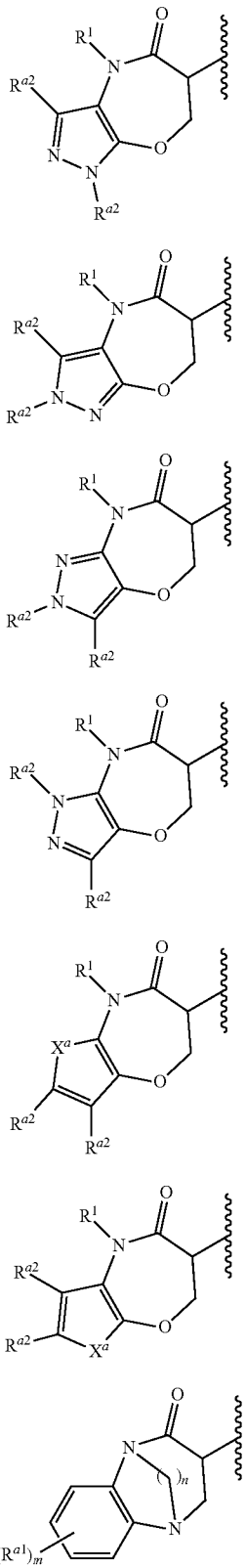

(15)

(16)

(17)

(18)

(19)

(20)

(21)

wherein $R^{a1}$ are each independently a substituent, $R^{a2}$ and $R^{a3}$ are each independently a hydrogen atom or a substituent, $X^a$ are each independently an oxygen atom, a sulfur atom or —$NR^{2a}$—, m are each independently an integer of 0 to 4, n is an integer of 1 to 3, and $R^1$ and $R^2$ are each as defined above.

The partial structure represented by the formula:

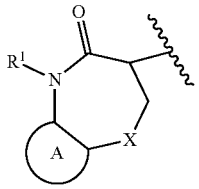

is preferably a partial structure represented by the formula (1)-(4):

(1)

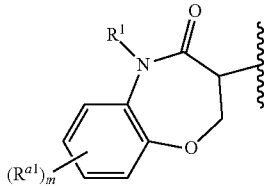

(2)

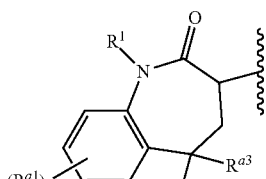

(3)

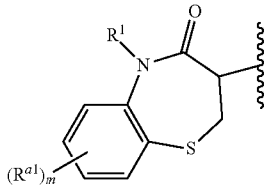

(4)

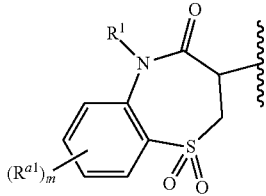

wherein each symbol is as defined above,
more preferably a partial structure represented by the formula (1):

(1)

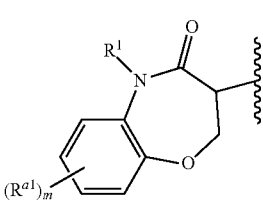

wherein each symbol is as defined above.

As another embodiment, examples of the partial structure represented by the formula:
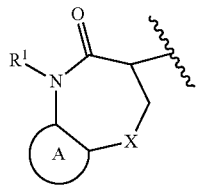
include the partial structures represented by the following formulas (1)-(29):
(1)
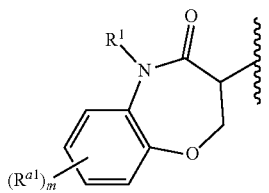
(2)
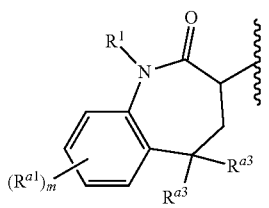
(3)
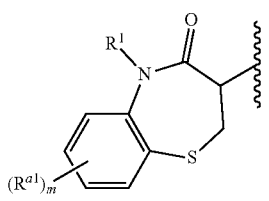
(4)
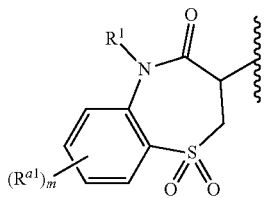
(5)
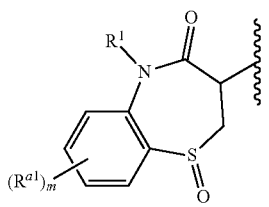
(6)
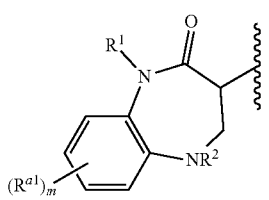
(7)
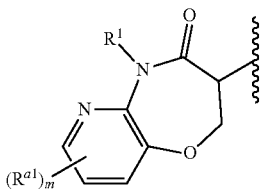
(8)
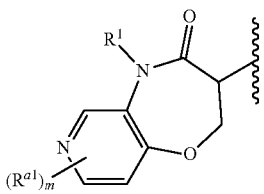
(9)
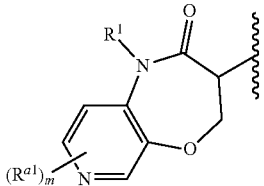
(10)
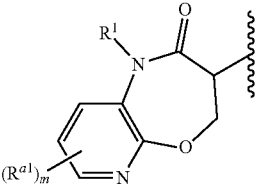
(11)
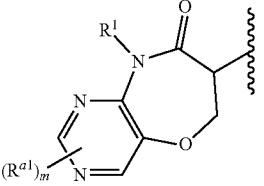
(12)
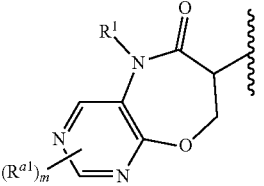
(13)
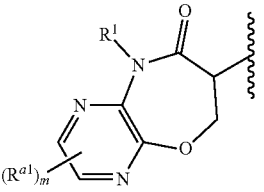
(14)
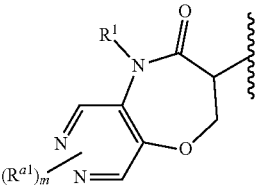

-continued
(15) 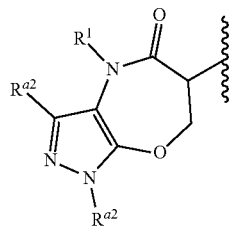
(16) 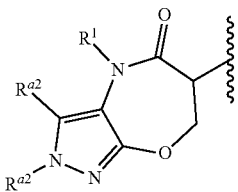
(17) 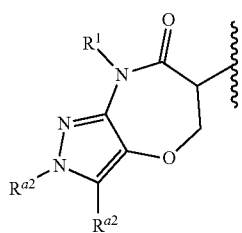
(18) 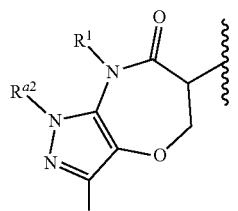
(19) 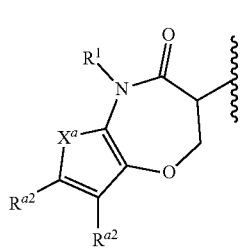
(20) 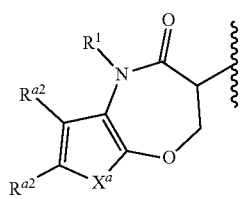
(21) 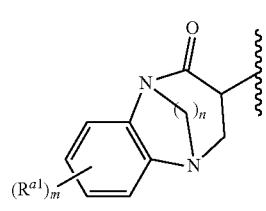
-continued
(22) 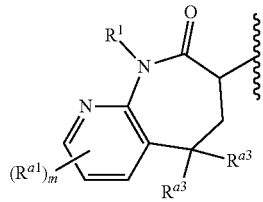
(23) 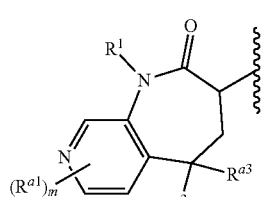
(24) 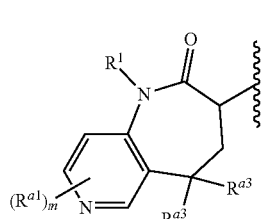
(25) 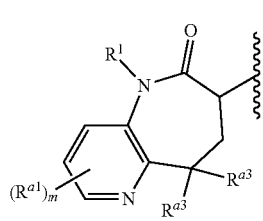
(26) 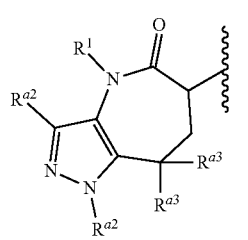
(27) 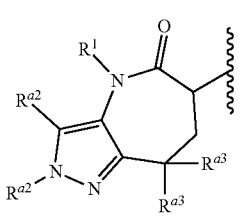
(28) 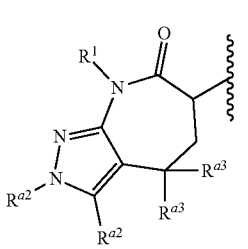

-continued

(29)
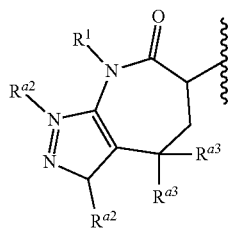

wherein $R^{a1}$ are each independently a substituent, $R^{a2}$ and $R^{a3}$ are each independently a hydrogen atom or a substituent, $X^a$ are each independently an oxygen atom, a sulfur atom or $-NR^{2a}-$, m are each independently an integer of 0 to 4, n is an integer of 1 to 3, $R^1$ and $R^2$ are as defined above.

In this embodiment, the partial structure represented by the formula:

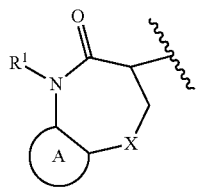

is preferably a partial structure represented by the formula (1)-(4), (6) or (22)-(28):

(1)
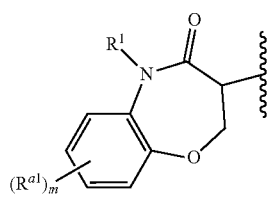

(2)
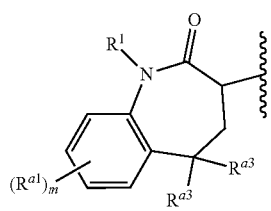

(3)
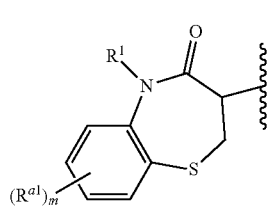

(4)
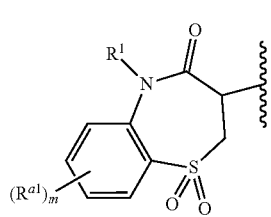

(6)
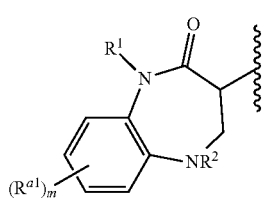

(22)
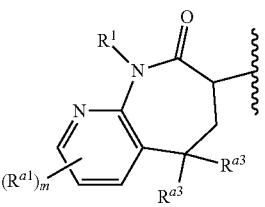

(23)
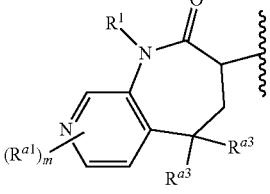

(24)
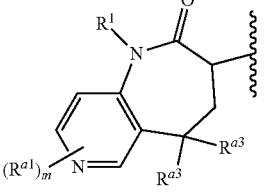

(25)
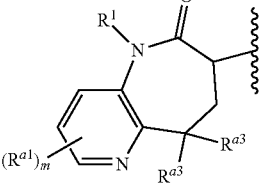

(26)
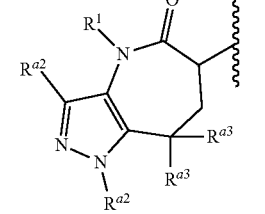

(27)

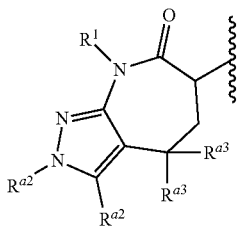

(28)

wherein each symbol is as defined above,
more preferably a partial structure represented by the formula (1)

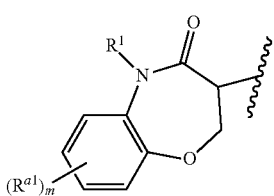

(1)

wherein each symbol is as defined above.

Preferable examples of the "substituent" represented by $R^{a1}$ include
(a) a cyano group,
(b) a halogen atom (e.g., a bromine atom), and
(c) a mono- or di-$C_{1-6}$ alkyl-carbamoyl group (e.g., methylcarbamoyl).

As another embodiment, preferable examples of the "substituent" represented by $R^{a1}$ include
(a) a cyano group,
(b) a halogen atom (e.g., a fluorine atom, a chlorine atom, a bromine atom),
(c) a carboxy group,
(d) a carbamoyl group,
(e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from
  (i) a hydroxy group, and
  (ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from
    (A) a $C_{6-14}$ aryloxy group (e.g., naphthyloxy), and
    (B) a 3- to 14-membered non-aromatic heterocyclylcarbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
      (1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group,
      (2) a $C_{1-6}$ alkyl group (e.g., methyl), and
      (3) an oxo group,
(f) a $C_{1-6}$ alkyl group (e.g., methyl) optionally substituted by 1 to 3 $C_{1-6}$ alkoxy groups (e.g., methoxy),
(g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl),
(h) a 3- to 14-membered non-aromatic heterocyclic group (preferably a 3- to 8-membered monocyclic non-aromatic heterocyclic group (e.g., oxetanyl, morpholinyl)), and
(i) a 3- to 14-membered non-aromatic heterocyclylcarbamoyl group (preferably a 3- to 8-membered monocyclic non-aromatic heterocyclylcarbamoyl group (e.g., oxetanylcarbamoyl)).

$R^{a1}$ is preferably each independently
(a) a cyano group, or
(b) a halogen atom (e.g., a bromine atom).

As another embodiment, $R^{a1}$ is preferably each independently
(a) a cyano group,
(b) a halogen atom (e.g., a bromine atom), or
(c) a mono- or di-$C_{1-6}$ alkyl-carbamoyl group (e.g., methylcarbamoyl).

As another embodiment, $R^{a1}$ is preferably each independently
(a) a cyano group,
(b) a halogen atom (e.g., a fluorine atom, a chlorine atom, a bromine atom),
(c) a carboxy group,
(d) a carbamoyl group,
(e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from
  (i) a hydroxy group, and
  (ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from
    (A) a $C_{6-14}$ aryloxy group (e.g., naphthyloxy), and
    (B) a 3- to 14-membered non-aromatic heterocyclylcarbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
      (1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group,
      (2) a $C_{1-6}$ alkyl group (e.g., methyl), and
      (3) an oxo group,
(f) a $C_{1-6}$ alkyl group (e.g., methyl) optionally substituted by 1 to 3 $C_{1-6}$ alkoxy groups (e.g., methoxy),
(g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl),
(h) a 3- to 14-membered non-aromatic heterocyclic group (preferably a 3- to 8-membered monocyclic non-aromatic heterocyclic group (e.g., oxetanyl, morpholinyl)), or
(i) a 3- to 14-membered non-aromatic heterocyclylcarbamoyl group (preferably a 3- to 8-membered monocyclic non-aromatic heterocyclylcarbamoyl group (e.g., oxetanylcarbamoyl)).

In this embodiment, $R^{a1}$ is more preferably each independently
(a) a cyano group, or
(b) a mono- or di-$C_{1-6}$ alkyl-carbamoyl group (e.g., methylcarbamoyl).

m is preferably 0, 1 or 2.
m is more preferably 0 or 1.
m is particularly preferably 1.

Examples of the "substituent" represented by $R^{a2}$ include
(a) a cyano group,
(b) a halogen atom (e.g., a bromine atom) and the like.

As another embodiment, examples of the "substituent" represented by $R^{a2}$ include a $C_{1-6}$ alkyl group (e.g., methyl) and the like.

$R^{a2}$ is preferably each independently
(1) a hydrogen atom, or
(2) a $C_{1-6}$ alkyl group (e.g., methyl).

Examples of the "substituent" represented by $R^{a3}$ include
(a) a halogen atom (e.g., a fluorine atom),
(b) a $C_{1-6}$ alkyl group (e.g., methyl),
(c) a hydroxy group,
(d) an oxo group
and the like.

$R^{a3}$ is preferably a hydrogen atom.

Ring B is an optionally further substituted 5- to 6-membered aromatic ring.

Examples of the "5- to 6-membered aromatic ring" of the "optionally further substituted 5- to 6-membered aromatic ring" represented by Ring B include benzene and a 5- to 6-membered monocyclic aromatic heterocycle.

Examples of the 5- to 6-membered monocyclic aromatic heterocycle include 5- to 6-membered monocyclic heterocycles, from among the above-mentioned "aromatic heterocycle".

The "5- to 6-membered aromatic ring" of the "optionally further substituted 5- to 6-membered aromatic ring" represented by Ring B is preferably a 5- to 6-membered monocyclic aromatic heterocycle, more preferably a 5- to 6-membered nitrogen-containing monocyclic aromatic heterocycle, further more preferably pyrazole, triazole, imidazole, thiazole, isothiazole, oxazole, isoxazole or pyridine, still more preferably pyrazole, triazole, imidazole, thiazole or pyridine, particularly preferably pyrazole.

The "5- to 6-membered aromatic ring" of the "optionally further substituted 5- to 6-membered aromatic ring" represented by Ring B is optionally further substituted by the "substituent". The number of the substituents is, for example, 1 or 2 (preferably 1). When the number of the substituents is 2 or more, the respective substituents may be the same or different.

Examples of the substituent for the "optionally further substituted 5- to 6-membered aromatic ring" represented by Ring B include
(a) a cyano group,
(b) a halogen atom (e.g., a chlorine atom, a bromine atom),
(c) a $C_{1-6}$ alkyl group (e.g., methyl, isopropyl) optionally substituted by 1 to 3 substituents selected from a hydroxy group and a $C_{1-6}$ alkoxy group (e.g., methoxy),
(d) a hydroxy group,
(e) an optionally halogenated $C_{1-6}$ alkoxy group (e.g., methoxy, difluoromethoxy, trifluoromethoxy),
(f) a $C_{3-10}$ cycloalkyl group (e.g., cyclopropyl) optionally substituted by 1 to 3 hydroxy groups,
(g) a $C_{1-6}$ alkoxy-carbonyl group (e.g., methoxycarbonyl, ethoxycarbonyl),
(h) a carbamoyl group,
(i) a mono- or di-$C_{1-6}$ alkyl-carbamoyl group (e.g., methylcarbamoyl),
(j) a thiocarbamoyl group,
(k) an amino group,
(l) a mono- or di-$C_{1-6}$ alkylamino group (e.g., methylamino),
(m) an optionally halogenated $C_{1-6}$ alkylthio group (e.g., difluoromethylthio),
(n) a $C_{1-6}$ alkylsulfonyl group (e.g., methylsulfonyl),
(o) a 5- to 14-membered aromatic heterocyclic group (preferably a 5- to 6-membered monocyclic aromatic heterocyclic group (e.g., pyrazolyl, pyridyl, imidazolyl, oxazolyl)) optionally substituted by 1 to 3 $C_{1-6}$ alkyl groups (e.g., methyl),
(p) a 3- to 14-membered non-aromatic heterocyclic group (preferably a 3- to 8-membered monocyclic non-aromatic heterocyclic group (e.g., oxetanyl, tetrahydrofuryl, azetidinyl, morpholinyl)) optionally substituted by 1 to 3 hydroxy groups and the like.

Preferable examples of the substituent for the "optionally further substituted 5- to 6-membered aromatic ring" represented by Ring B include
(a) a cyano group,
(b) a halogen atom (e.g., a chlorine atom, a bromine atom),
(c) a $C_{1-6}$ alkyl group (e.g., methyl), and
(d) a carbamoyl group,
and more preferred are
(a) a cyano group,
(b) a halogen atom (e.g., a chlorine atom, a bromine atom), and
(c) a carbamoyl group.

As another embodiment, examples of the substituent for the "optionally further substituted 5- to 6-membered aromatic ring" represented by Ring B include
(a) a cyano group,
(b) a halogen atom (e.g., a chlorine atom, a bromine atom),
(c) a $C_{1-6}$ alkyl group (e.g., methyl, isopropyl) optionally substituted by 1 to 3 substituents selected from
  (i) a hydroxy group,
  (ii) a $C_{1-6}$ alkoxy group (e.g., methoxy), and
  (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy, trifluoromethoxy),
(f) a $C_{3-10}$ cycloalkyl group (e.g., cyclopropyl) optionally substituted by 1 to 3 hydroxy groups,
(g) a $C_{1-6}$ alkoxy-carbonyl group (e.g., methoxycarbonyl, ethoxycarbonyl),
(h) a carbamoyl group,
(i) a mono- or di-$C_{1-6}$ alkyl-carbamoyl group (e.g., methylcarbamoyl),
(j) a thiocarbamoyl group,
(k) an amino group,
(l) a mono- or di-$C_{1-6}$ alkylamino group (e.g., methylamino),
(m) an optionally halogenated $C_{1-6}$ alkylthio group (e.g., difluoromethylthio),
(n) a $C_{1-6}$ alkylsulfonyl group (e.g., methylsulfonyl),
(o) a 5- to 14-membered aromatic heterocyclic group (preferably a 5- to 6-membered monocyclic aromatic heterocyclic group (e.g., pyrazolyl, pyridyl, imidazolyl, oxazolyl)) optionally substituted by 1 to 3 $C_{1-6}$ alkyl groups (e.g., methyl),
(p) a 3- to 14-membered non-aromatic heterocyclic group (preferably a 3- to 8-membered monocyclic non-aromatic heterocyclic group (e.g., oxetanyl, tetrahydrofuryl, azetidinyl, morpholinyl)) optionally substituted by 1 to 3 hydroxy groups,
(q) a carboxy group
and the like.

In this embodiment, preferable examples of the substituent for the "optionally further substituted 5- to 6-membered aromatic ring" represented by Ring B include
(a) a cyano group,
(b) a halogen atom (e.g., a chlorine atom, a bromine atom),
(c) a $C_{1-6}$ alkyl group (e.g., methyl) optionally substituted by 1 to 3 substituents selected from
   (i) a hydroxy group, and
   (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy),
(f) a $C_{3-10}$ cycloalkyl group (e.g., cyclopropyl),
(g) a $C_{1-6}$ alkoxy-carbonyl group (e.g., ethoxycarbonyl),
(h) a carbamoyl group,
(i) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), and
(j) a carboxy group, and more preferred are
(a) a cyano group, and
(b) a halogen atom (e.g., a chlorine atom, a bromine atom), and particularly preferred is
(a) a halogen atom (e.g., a chlorine atom).

Ring B is preferably an optionally further substituted 5- to 6-membered monocyclic aromatic heterocycle (e.g., pyrazole, triazole, imidazole, thiazole, pyridine).

Ring B is more preferably an optionally further substituted 5- to 6-membered nitrogen-containing monocyclic aromatic heterocycle (e.g., pyrazole, triazole, imidazole, thiazole, pyridine).

Specifically, Ring B is more preferably pyrazole, triazole, imidazole, thiazole or pyridine, each optionally further substituted.

Ring B is further more preferably a 5- to 6-membered nitrogen-containing monocyclic aromatic heterocycle (e.g., pyrazole, triazole, imidazole, thiazole, pyridine) optionally further substituted by 1 or 2 (preferably 1) substituents selected from
(a) a cyano group,
(b) a halogen atom (e.g., a bromine atom),
(c) a $C_{1-6}$ alkyl group (e.g., methyl), and
(d) a carbamoyl group.

Ring B is still more preferably pyrazole optionally further substituted by one substituent selected from
(a) a cyano group,
(b) a halogen atom (e.g., a bromine atom), and
(c) a carbamoyl group.

As another embodiment, Ring B is further more preferably a 5- to 6-membered nitrogen-containing monocyclic aromatic heterocycle (e.g., pyrazole, triazole, imidazole, thiazole, pyridine) optionally further substituted by 1 or 2 (preferably 1) substituents selected from
(a) a cyano group,
(b) a halogen atom (e.g., a chlorine atom, a bromine atom),
(c) a $C_{1-6}$ alkyl group (e.g., methyl), and
(d) a carbamoyl group.

In this embodiment, Ring B is still more preferably pyrazole optionally further substituted by one substituent selected from
(a) a cyano group,
(b) a halogen atom (e.g., a chlorine atom, a bromine atom), and
(c) a carbamoyl group.

As another embodiment, Ring B is further more preferably pyrazole, triazole, imidazole, thiazole or pyridine, each optionally further substituted by 1 or 2 (preferably 1) substituents selected from
(a) a cyano group,
(b) a halogen atom (e.g., a chlorine atom, a bromine atom),
(c) a $C_{1-6}$ alkyl group (e.g., methyl) optionally substituted by 1 to 3 substituents selected from
   (i) a hydroxy group, and
   (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy),
(f) a $C_{3-10}$ cycloalkyl group (e.g., cyclopropyl),
(g) a $C_{1-6}$ alkoxy-carbonyl group (e.g., ethoxycarbonyl),
(h) a carbamoyl group,
(i) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), and
(j) a carboxy group.

As another embodiment, Ring B is further more preferably an optionally further substituted pyrazole.

In this embodiment, Ring B is still more preferably pyrazole optionally further substituted by one substituent selected from
(a) a cyano group, and
(b) a halogen atom (e.g., a chlorine atom, a bromine atom).

In this embodiment, Ring B is particularly preferably pyrazole optionally further substituted by one substituent selected from
(a) a halogen atom (e.g., a chlorine atom).

Ring D is an optionally further substituted 5- to 7-membered nitrogen-containing heterocycle.

Examples of the "5- to 7-membered nitrogen-containing heterocycle" of the "optionally further substituted 5- to 7-membered nitrogen-containing heterocycle" represented by Ring D include 5- to 7-membered heterocycles, from among the above-mentioned "nitrogen-containing heterocycle".

The "5- to 7-membered nitrogen-containing heterocycle" of the "optionally further substituted 5- to 7-membered nitrogen-containing heterocycle" represented by Ring D is preferably piperidine, pyrrolidine, pyrroline, piperazine, tetrahydropyridine or diazepane.

The "5- to 7-membered nitrogen-containing heterocycle" of the "optionally further substituted 5- to 7-membered nitrogen-containing heterocycle" represented by Ring D is optionally further substituted by the "substituent". The number of the substituents is, for example, 1 to 3 (preferably 1). When the number of the substituents is 2 or more, the respective substituents may be the same or different.

Ring D is preferably piperidine, pyrrolidine, pyrroline, piperazine, tetrahydropyridine or diazepane, each optionally further substituted.

Ring D is more preferably piperidine, pyrrolidine, pyrroline, piperazine, tetrahydropyridine or diazepane.

As another embodiment, Ring D is more preferably an optionally further substituted piperidine.

In this embodiment, Ring D is further more preferably piperidine.

As another embodiment, Ring D is preferably a 6-membered nitrogen-containing heterocycle.

In this embodiment, Ring D is more preferably piperidine.
$Y^1$ and $Y^2$ are each independently a carbon atom or a nitrogen atom.
$Y^1$ is preferably a carbon atom.
$Y^2$ is preferably a carbon atom.
Examples of the partial structure represented by the formula:
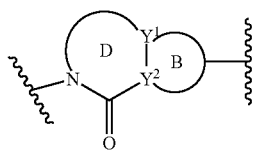
include the partial structures represented by the following formulas (1)-(20):
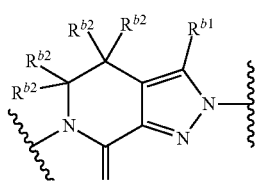
(1)
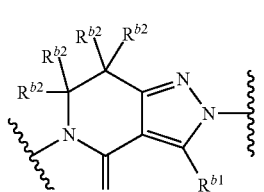
(2)
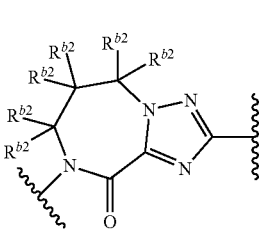
(3)
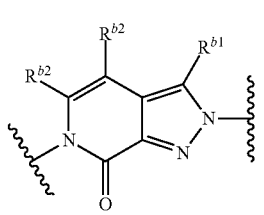
(4)
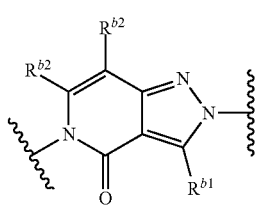
(5)
-continued
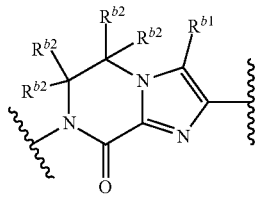
(6)
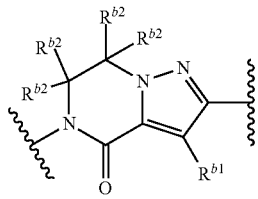
(7)
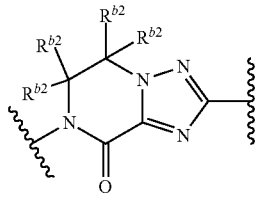
(8)
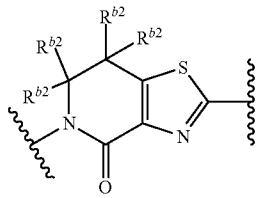
(9)
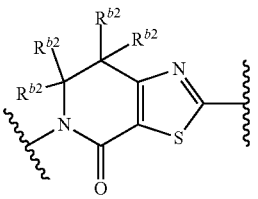
(10)
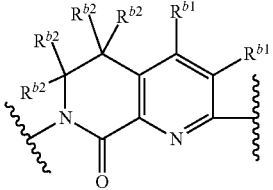
(11)
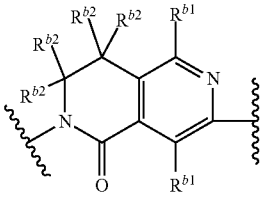
(12)

-continued
(13)
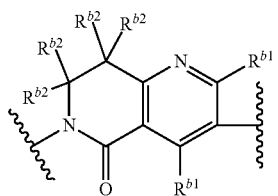
(14)
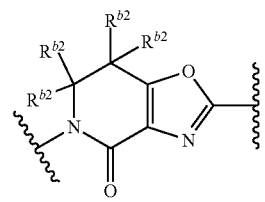
(15)
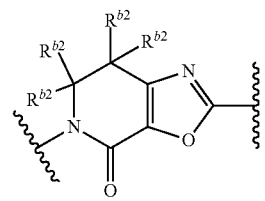
(16)
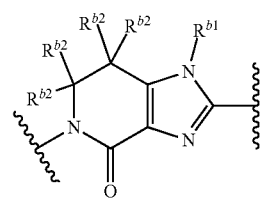
(17)
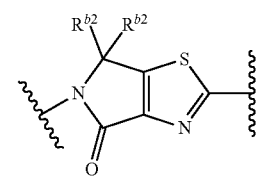
(18)
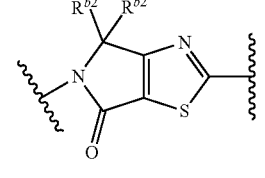
(19)
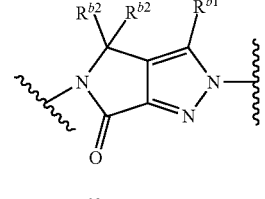
(20)
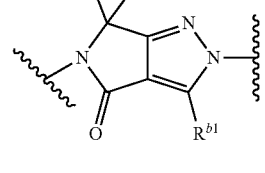
wherein $R^{b1}$ and $R^{b2}$ are each independently a hydrogen atom or a substituent.
The partial structure represented by the formula:
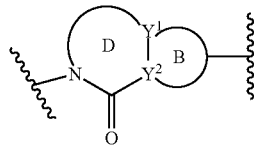
is preferably a partial structure represented by the formula (1), (3), (4), (6)-(9), (11), (17) or (19):
(1)
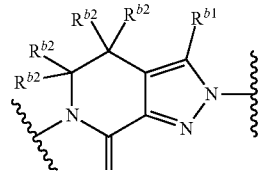
(3)
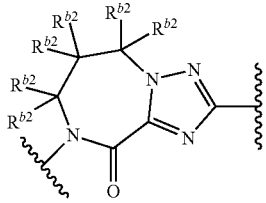
(4)
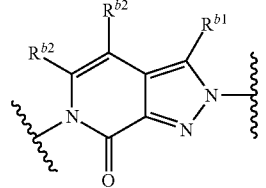
(6)
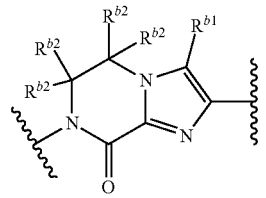
(7)
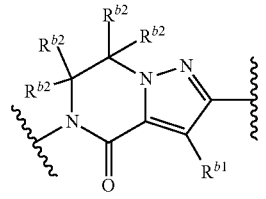
(8)
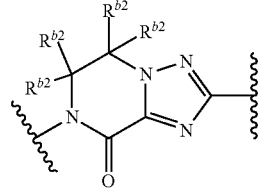

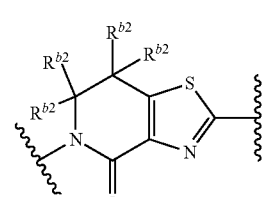 (9)
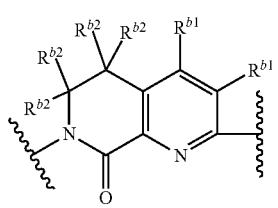 (11)
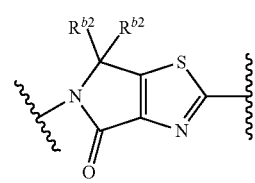 (17)
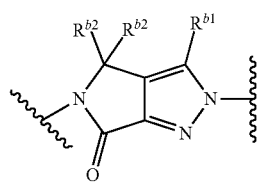 (19)
wherein each symbol is as defined above, more preferably a partial structure represented by the formula (1):
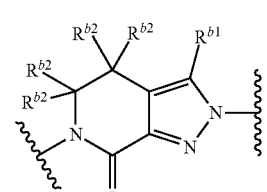 (1)
wherein each symbol is as defined above.
As another embodiment, example of the partial structure represented by the formula:
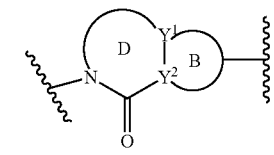
include the partial structures represented by the following formulas (1)-(21):
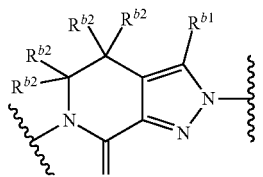 (1)
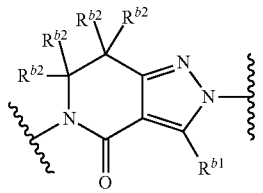 (2)
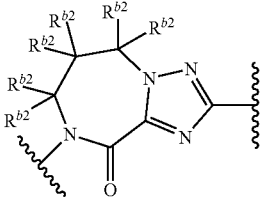 (3)
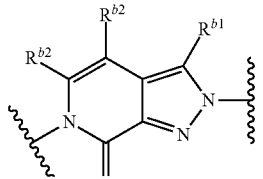 (4)
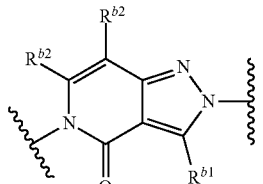 (5)
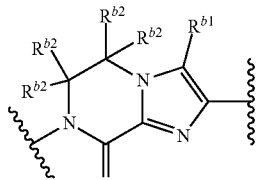 (6)
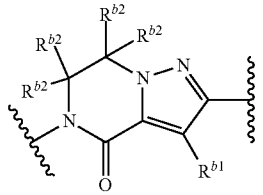 (7)

-continued
(8) 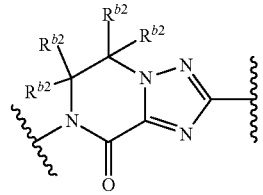
(9) 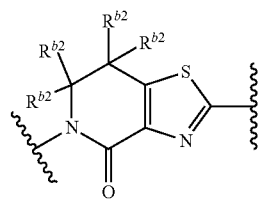
(10) 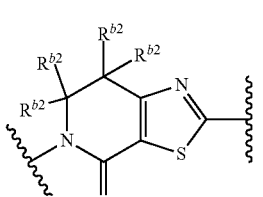
(11) 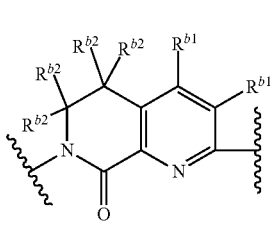
(12) 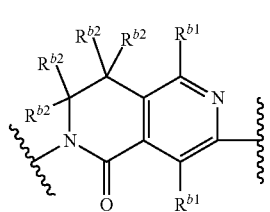
(13) 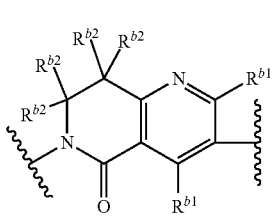
(14) 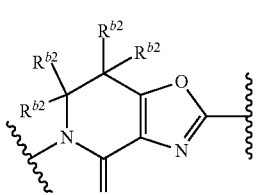
-continued
(15) 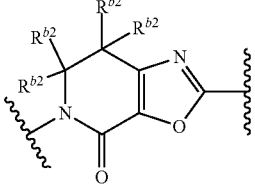
(16) 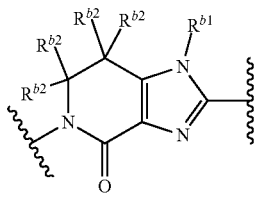
(17) 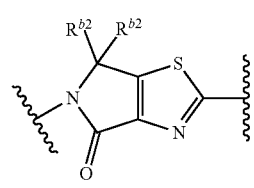
(18) 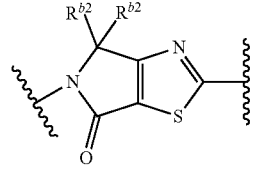
(19) 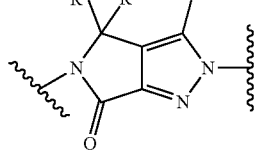
(20) 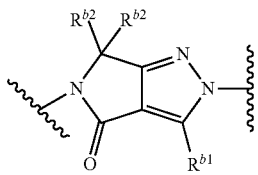
(21) 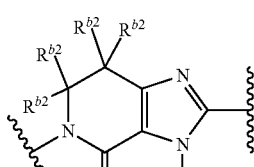
wherein $R^{b1}$ and $R^{b2}$ are each independently a hydrogen atom or a substituent.

In this embodiment, the partial structure represented by the formula:
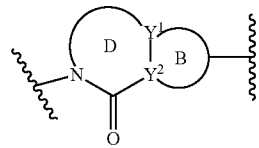
is preferably a partial structure represented by the formula (1)-(4), (6)-(9), (11), (16), (17), (19) or (21):
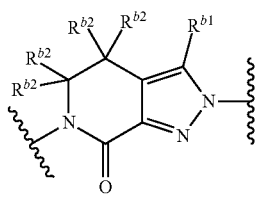
(1)
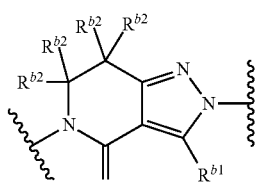
(2)
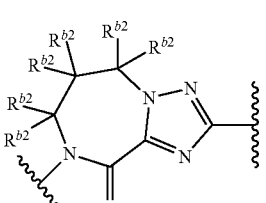
(3)
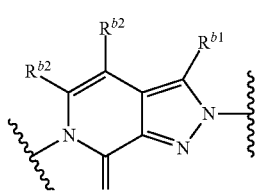
(4)
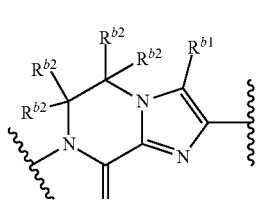
(6)
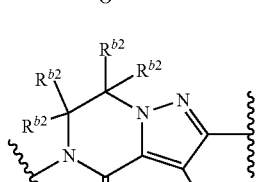
(7)
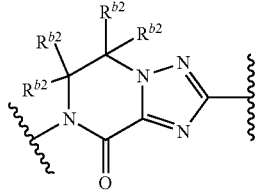
(8)
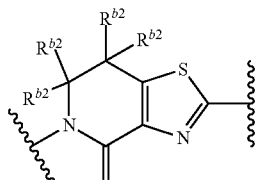
(9)
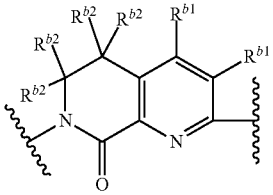
(11)
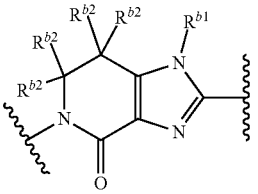
(16)
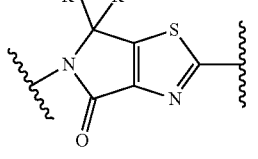
(17)
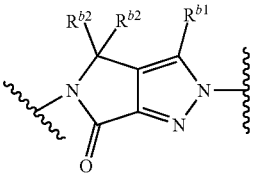
(19)
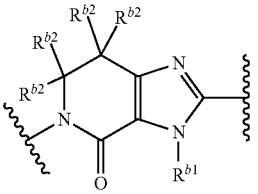
(21)
wherein each symbol is as defined above, more preferably a partial structure represented by the formula (1):
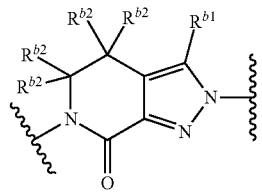
(1)
wherein each symbol is as defined above.
As another embodiment, the partial structure represented by the formula:
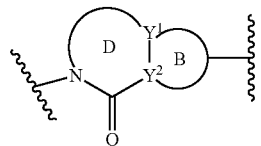
is preferably a partial structure represented by the following formula (1)-(20):
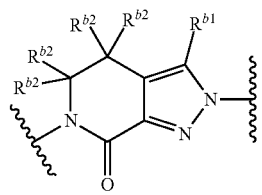
(1)
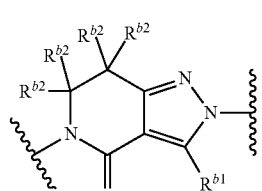
(2)
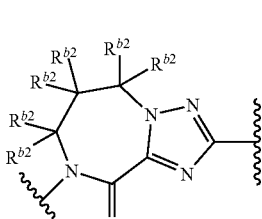
(3)
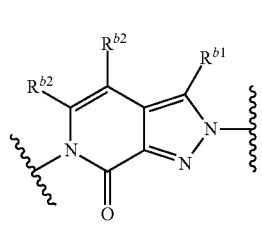
(4)
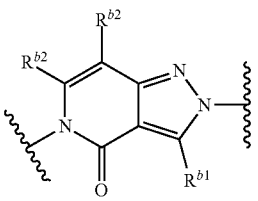
(5)
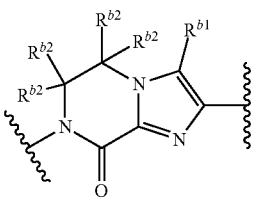
(6)
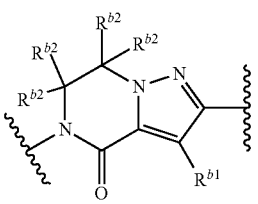
(7)
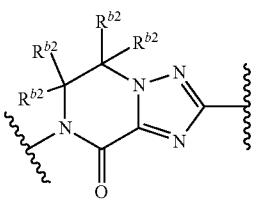
(8)
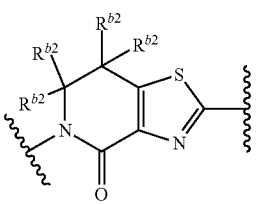
(9)
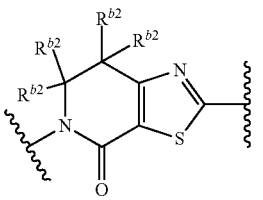
(10)
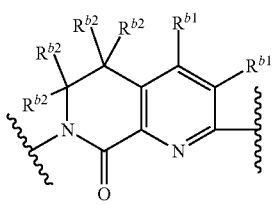
(11)

(12) 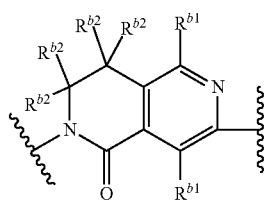
(13) 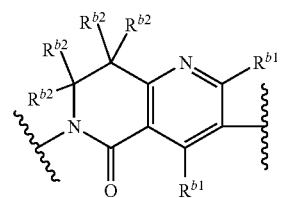
(14) 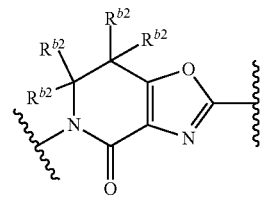
(15) 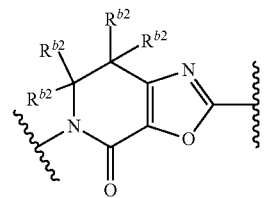
(16) 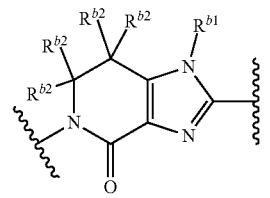
(17) 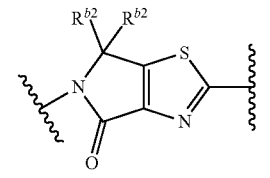
(18) 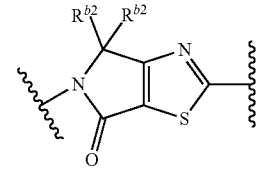
(19) 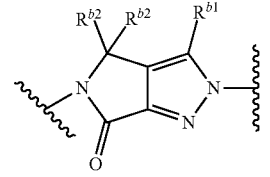
(20) 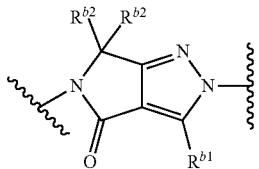
wherein $R^{b1}$ and $R^{b2}$ are each independently a hydrogen atom or a substituent.
In this embodiment, the partial structure represented by the formula:
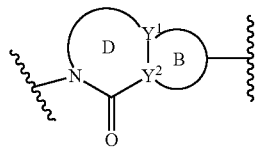
is more preferably a partial structure represented by the formula (1), (3)-(6) or (8)-(20):
(1) 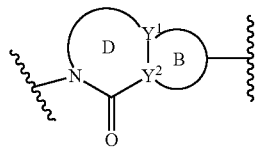
(3) 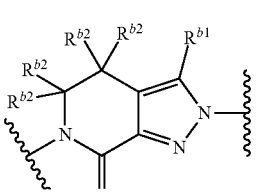
(4) 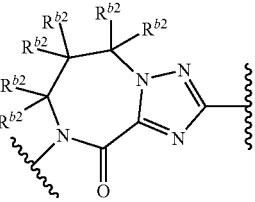
(5) 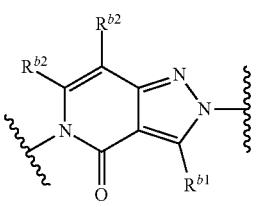

-continued (6) 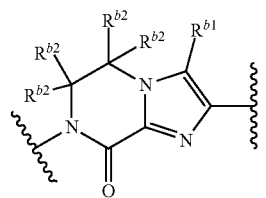

(8) 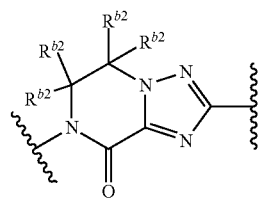

(9) 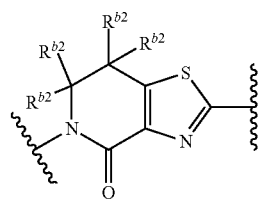

(10) 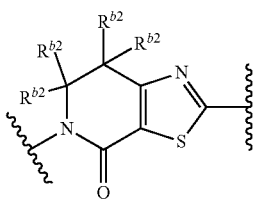

(11) 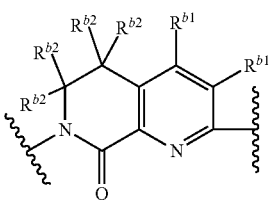

(12) 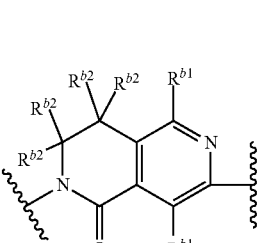

(13) 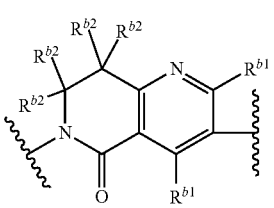

-continued

(14) 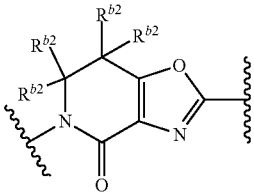

(15) 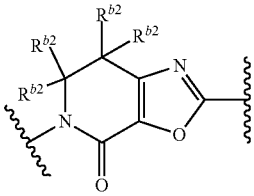

(16) 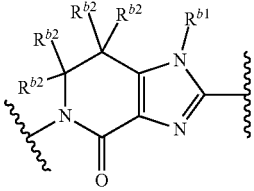

(17) 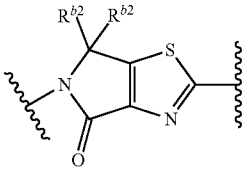

(18) 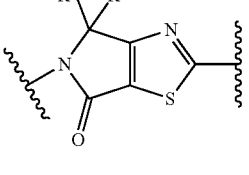

(19) 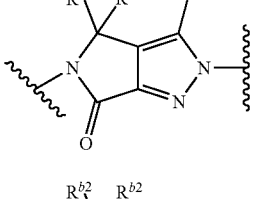

(20) 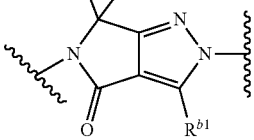

wherein $R^{b1}$ and $R^{b2}$ are each independently a hydrogen atom or a substituent.

Examples of the "substituent" represented by $R^{b1}$ include
(a) a cyano group,
(b) a halogen atom (e.g., a chlorine atom, a bromine atom),
(c) a $C_{1-6}$ alkyl group (e.g., methyl, isopropyl) optionally substituted by 1 to 3 substituents selected from a hydroxy group and a $C_{1-6}$ alkoxy group (e.g., methoxy),
(d) a hydroxy group,
(e) an optionally halogenated $C_{1-6}$ alkoxy group (e.g., methoxy, difluoromethoxy, trifluoromethoxy), (f) a $C_{3-10}$ cycloalkyl group (e.g., cyclopropyl) optionally substituted by 1 to 3 hydroxy groups,
(g) a $C_{1-6}$ alkoxy-carbonyl group (e.g., methoxycarbonyl, ethoxycarbonyl),
(h) a carbamoyl group,
(i) a mono- or di-$C_{1-6}$ alkyl-carbamoyl group (e.g., methylcarbamoyl),
(j) a thiocarbamoyl group,
(k) an amino group,
(l) a mono- or di-$C_{1-6}$ alkylamino group (e.g., methylamino),
(m) an optionally halogenated $C_{1-6}$ alkylthio group (e.g., difluoromethylthio),
(n) a $C_{1-6}$ alkylsulfonyl group (e.g., methylsulfonyl),
(o) a 5- to 14-membered aromatic heterocyclic group (preferably a 5- to 6-membered monocyclic aromatic heterocyclic group (e.g., pyrazolyl, pyridyl, imidazolyl, oxazolyl)) optionally substituted by 1 to 3 $C_{1-6}$ alkyl groups (e.g., methyl), (p) a 3- to 14-membered non-aromatic heterocyclic group (preferably a 3- to 8-membered monocyclic non-aromatic heterocyclic group (e.g., oxetanyl, tetrahydrofuryl, azetidinyl, morpholinyl)) optionally substituted by 1 to 3 hydroxy groups and the like.

Preferable examples of the "substituent" represented by $R^{b1}$ include
(a) a cyano group,
(b) a halogen atom (e.g., a chlorine atom, a bromine atom),
(c) a $C_{1-6}$ alkyl group (e.g., methyl), and
(d) a carbamoyl group,
and more preferred are
(a) a cyano group,
(b) a halogen atom (e.g., a chlorine atom, a bromine atom), and
(c) a carbamoyl group.

As another embodiment, examples of the "substituent" represented by $R^{b1}$ include
(a) a cyano group,
(b) a halogen atom (e.g., a chlorine atom, a bromine atom),
(c) a $C_{1-6}$ alkyl group (e.g., methyl, isopropyl) optionally substituted by 1 to 3 substituents selected from
    (i) a hydroxy group,
    (ii) a $C_{1-6}$ alkoxy group (e.g., methoxy), and
    (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy, trifluoromethoxy),
(f) a $C_{3-10}$ cycloalkyl group (e.g., cyclopropyl) optionally substituted by 1 to 3 hydroxy groups,
(g) a $C_{1-6}$ alkoxy-carbonyl group (e.g., methoxycarbonyl, ethoxycarbonyl),
(h) a carbamoyl group,
(i) a mono- or di-$C_{1-6}$ alkyl-carbamoyl group (e.g., methylcarbamoyl),
(j) a thiocarbamoyl group,
(k) an amino group,
(l) a mono- or di-$C_{1-6}$ alkylamino group (e.g., methylamino),
(m) an optionally halogenated $C_{1-6}$ alkylthio group (e.g., difluoromethylthio),
(n) a $C_{1-6}$ alkylsulfonyl group (e.g., methylsulfonyl),
(o) a 5- to 14-membered aromatic heterocyclic group (preferably a 5- to 6-membered monocyclic aromatic heterocyclic group (e.g., pyrazolyl, pyridyl, imidazolyl, oxazolyl)) optionally substituted by 1 to 3 $C_{1-6}$ alkyl groups (e.g., methyl),
(p) a 3- to 14-membered non-aromatic heterocyclic group (preferably a 3- to 8-membered monocyclic non-aromatic heterocyclic group (e.g., oxetanyl, tetrahydrofuryl, azetidinyl, morpholinyl)) optionally substituted by 1 to 3 hydroxy groups, (q) a carboxy group
and the like.

In this embodiment, preferable examples of the "substituent" represented by $R^{b1}$ include
(a) a cyano group,
(b) a halogen atom (e.g., a chlorine atom, a bromine atom),
(c) a $C_{1-6}$ alkyl group (e.g., methyl) optionally substituted by 1 to 3 substituents selected from
    (i) a hydroxy group, and
    (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy),
(f) a $C_{3-10}$ cycloalkyl group (e.g., cyclopropyl),
(g) a $C_{1-6}$ alkoxy-carbonyl group (e.g., ethoxycarbonyl),
(h) a carbamoyl group,
(i) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), and
(j) a carboxy group,
and more preferred are
(a) a cyano group, and
(b) a halogen atom (e.g., a chlorine atom, a bromine atom),
and particular preferred is
(a) a halogen atom (e.g., a chlorine atom).

$R^{b1}$ is preferably each independently
(a) a hydrogen atom,
(b) a cyano group,
(c) a halogen atom (e.g., a bromine atom),
(d) a $C_{1-6}$ alkyl group (e.g., methyl), or
(e) a carbamoyl group.

$R^{b1}$ is more preferably each independently
(a) a hydrogen atom,
(b) a cyano group,
(c) a halogen atom (e.g., a bromine atom), or
(d) a carbamoyl group.

As another embodiment, $R^{b1}$ is preferably each independently
(a) a hydrogen atom,
(b) a cyano group,
(c) a halogen atom (e.g., a chlorine atom, a bromine atom),
(d) a $C_{1-6}$ alkyl group (e.g., methyl), or
(e) a carbamoyl group.

In this embodiment, $R^{b1}$ is more preferably each independently
(a) a hydrogen atom,
(b) a cyano group,
(c) a halogen atom (e.g., a chlorine atom, a bromine atom), or
(d) a carbamoyl group.

As another embodiment, $R^{b1}$ is preferably each independently
(a) a hydrogen atom,
(b) a cyano group,
(c) a halogen atom (e.g., a chlorine atom, a bromine atom),
(d) a $C_{1-6}$ alkyl group (e.g., methyl) optionally substituted by 1 to 3 substituents selected from
    (i) a hydroxy group, and
    (iii) a $C_{6-14}$ aryl group (e.g., phenyl) optionally substituted by 1 to 3 $C_{1-6}$ alkoxy groups (e.g., methoxy),
(e) a hydroxy group,
(f) an optionally halogenated $C_{1-6}$ alkoxy group (e.g., methoxy, difluoromethoxy), (g) a $C_{3-10}$ cycloalkyl group (e.g., cyclopropyl),
(h) a $C_{1-6}$ alkoxy-carbonyl group (e.g., ethoxycarbonyl),
(i) a carbamoyl group,
(j) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), or
(k) a carboxy group.

In this embodiment, $R^{b1}$ is more preferably each independently
(a) a hydrogen atom,
(b) a cyano group, or
(c) a halogen atom (e.g., a chlorine atom, a bromine atom).

In this embodiment, $R^{b1}$ is particularly preferably each independently
(a) a hydrogen atom, or
(b) a halogen atom (e.g., a chlorine atom).

$R^{b2}$ is preferably a hydrogen atom.

Ring C is an optionally further substituted ring.

Examples of the "ring" of the "optionally further substituted ring" represented by Ring C include a hydrocarbon ring and a heterocycle.

The "ring" of the "optionally further substituted ring" represented by Ring C is preferably
(1) a $C_{6-14}$ aromatic hydrocarbon ring (e.g., benzene),
(2) a $C_{3-10}$ cycloalkane (preferably a $C_{3-6}$ cycloalkane (e.g., cyclopropane, cyclobutane, cyclopentane, cyclohexane)),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or
(4) a 3- to 14-membered (preferably 4- to 10-membered) non-aromatic heterocycle (preferably a 3- to 8-membered monocyclic non-aromatic heterocycle (e.g., dioxane, tetrahydropyran, tetrahydrofuran, piperidine, pyrrolidine)).

As another embodiment, the "ring" of the "optionally further substituted ring" represented by Ring C is preferably
(1) a $C_{6-14}$ aromatic hydrocarbon ring (e.g., benzene),
(2) a $C_{3-10}$ cycloalkane (preferably a $C_{3-6}$ cycloalkane (e.g., cyclopropane, cyclobutane, cyclopentane, cyclohexane)),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or
(4) a 3- to 14-membered (preferably 4- to 10-membered) non-aromatic heterocycle (preferably a 3- to 8-membered monocyclic non-aromatic heterocycle (e.g., dioxane, tetrahydropyran, tetrahydrofuran, piperidine, pyrrolidine, oxetane, 1,1-dioxidotetrahydrothiophene, 1,1-dioxidotetrahydrothiopyran)). Specifically, it is preferably benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane (e.g., cyclopropane, cyclobutane, cyclopentane, cyclohexane).

The "ring" of the "optionally further substituted ring" represented by Ring C is optionally further substituted by substituent(s) selected from the above-mentioned Substituent Group A. The number of the substituents is, for example, 1 to (preferably 1 or 2). When the number of the substituents is 2 or more, the respective substituents may be the same or different.

Ring C is preferably
(1) an optionally further substituted $C_{6-14}$ aromatic hydrocarbon ring (e.g., benzene),
(2) an optionally further substituted $C_{3-10}$ cycloalkane (preferably a $C_{3-6}$ cycloalkane (e.g., cyclopropane, cyclobutane, cyclopentane)),
(3) an optionally further substituted 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or
(4) an optionally further substituted 3- to 14-membered (preferably 4- to 10-membered) non-aromatic heterocycle (preferably a 3- to 8-membered monocyclic non-aromatic heterocycle (e.g., dioxane)).

Ring C is more preferably
(1) benzene optionally further substituted by 1 to 5 (preferably 1 or 2) substituents selected from
  (a) a cyano group,
  (b) a halogen atom (e.g., a fluorine atom, a chlorine atom), and
  (c) a $C_{1-6}$ alkyl group (e.g., methyl),
(2) a $C_{3-10}$ cycloalkane (preferably a $C_{3-6}$ cycloalkane (e.g., cyclopropane, cyclobutane, cyclopentane)) optionally further substituted by 1 to 5 (preferably 1 or 2) halogen atoms (e.g., a fluorine atom),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)) optionally further substituted by 1 to 3 (preferably 1 or 2) $C_{1-6}$ alkyl groups (e.g., methyl), or
(4) a 3- to 14-membered (preferably 4- to 10-membered) non-aromatic heterocycle (preferably a 3- to 8-membered monocyclic non-aromatic heterocycle (e.g., dioxane)).

Ring C is further more preferably benzene.

As another embodiment, Ring C is further more preferably benzene optionally further substituted by 1 to 5 (preferably 1 or 2) halogen atoms (e.g., a fluorine atom).

As another embodiment, Ring C is more preferably
(1) an optionally further substituted $C_{6-14}$ aromatic hydrocarbon ring (e.g., benzene), or
(2) an optionally further substituted $C_{3-10}$ cycloalkane (preferably a $C_{3-6}$ cycloalkane (e.g., cyclopropane, cyclobutane, cyclopentane)).

In this embodiment, Ring C is more preferably an optionally further substituted benzene.

In this embodiment, Ring C is further more preferably benzene optionally further substituted by 1 to 5 (preferably 1) substituents selected from
  (a) a cyano group, and
  (b) a halogen atom (e.g., a fluorine atom, a chlorine atom).

In this embodiment, Ring C is still more preferably benzene optionally further substituted by 1 to 5 (preferably 1 or 2) halogen atoms (e.g., a fluorine atom).

In this embodiment, the position of the substituent is preferably o-position.

As another embodiment, Ring C is preferably
(1) an optionally further substituted $C_{6-14}$ aromatic hydrocarbon ring (e.g., benzene),
(2) an optionally further substituted $C_{3-10}$ cycloalkane (preferably a $C_{3-6}$ cycloalkane (e.g., cyclopropane, cyclobutane, cyclopentane)),
(3) an optionally further substituted 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or
(4) an optionally further substituted 3- to 14-membered (preferably 4- to 10-membered) non-aromatic heterocycle (preferably a 3- to 8-membered monocyclic non-aromatic heterocycle (e.g., dioxane, oxetane, 1,1-dioxidotetrahydrothiophene, 1,1-dioxidotetrahydrothiopyran, tetrahydropyran)). Specifically, it is preferably benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane (e.g., cyclopropane, cyclobutane, cyclopentane, cyclohexane), each optionally further substituted.

In this embodiment, Ring C is more preferably
(1) benzene optionally further substituted by 1 to 5 (preferably 1 or 2) substituents selected from
  (a) a cyano group,
  (b) a halogen atom (e.g., a fluorine atom, a chlorine atom),
  (c) a $C_{1-6}$ alkyl group (e.g., methyl),
  (d) a $C_{1-6}$ alkoxy group (e.g., methoxy), and
  (e) a $C_{1-6}$ alkylsulfonyl group (e.g., methylsulfonyl),
(2) a $C_{3-10}$ cycloalkane (preferably a $C_{3-6}$ cycloalkane (e.g., cyclopropane, cyclobutane, cyclopentane)) optionally further substituted by 1 to 5 (preferably 1 or 2) substituents selected from
  (a) a halogen atom (e.g., a fluorine atom), and
  (b) a $C_{1-6}$ alkyl group (e.g., methyl),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)) optionally further substituted by 1 to 3 (preferably 1 or 2) $C_{1-6}$ alkyl groups (e.g., methyl), or
(4) a 3- to 14-membered (preferably 4- to 10-membered) non-aromatic heterocycle (preferably a 3- to 8-membered monocyclic non-aromatic heterocycle (e.g., dioxane, oxetane, 1,1-dioxidotetrahydrothiophene, 1,1-dioxidotetrahydrothiopyran, tetrahydropyran)) optionally further substituted by 1 to 3 (preferably 1 or 2) $C_{1-6}$ alkyl groups (e.g., methyl).

As another embodiment, Ring C is more preferably benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane (e.g., cyclopropane, cyclobutane, cyclopentane, cyclohexane), each optionally further substituted by 1 to 5 (preferably 1 or 2) substituents selected from
  (a) a cyano group,
  (b) a halogen atom (e.g., a fluorine atom, a chlorine atom),
  (c) a $C_{1-6}$ alkyl group (e.g., methyl),
  (d) a $C_{1-6}$ alkoxy group (e.g., methoxy), and
  (e) a $C_{1-6}$ alkylsulfonyl group (e.g., methylsulfonyl).

As another embodiment, Ring C is further more preferably an optionally further substituted benzene.

In this embodiment, Ring C is still more preferably benzene optionally further substituted by 1 to 5 (preferably 1) substituents selected from
  (a) a cyano group,
  (b) a halogen atom (e.g., a fluorine atom, a chlorine atom),
  (c) a $C_{1-6}$ alkyl group (e.g., methyl),
  (d) a $C_{1-6}$ alkoxy group (e.g., methoxy), and
  (e) a $C_{1-6}$ alkylsulfonyl group (e.g., methylsulfonyl).

In this embodiment, Ring C is particularly preferably benzene optionally further substituted by 1 to 5 (preferably 1 or 2) halogen atoms (e.g., a fluorine atom).

In this embodiment, the position of the substituent is preferably o-position.

As another embodiment, Ring C is more preferably an optionally further substituted aromatic ring [preferably a $C_{6-14}$ aromatic hydrocarbon ring (e.g., benzene) or a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine))].

In this embodiment, Ring C is still more preferably (1) benzene optionally further substituted by 1 to 5 (preferably 1 or 2) substituents selected from
  (a) a cyano group,
  (b) a halogen atom (e.g., a fluorine atom, a chlorine atom),
  (c) a $C_{1-6}$ alkyl group (e.g., methyl),
  (d) a $C_{1-6}$ alkoxy group (e.g., methoxy), and
  (e) a $C_{1-6}$ alkylsulfonyl group (e.g., methylsulfonyl), or
(2) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)) optionally further substituted by 1 to 3 (preferably 1 or 2) $C_{1-6}$ alkyl groups (e.g., methyl).

L is (a) an optionally substituted $C_{1-3}$ alkylene group, (b) an oxygen atom, (c) a sulfur atom, (d) —SO—, (e) —SO$_2$— or (f) —NR$^3$—.

$R^1$ is a hydrogen atom or a substituent.

The "$C_{1-3}$ alkylene group" of the "optionally substituted $C_{1-3}$ alkylene group" represented by L is optionally substituted by substituent(s) selected from the above-mentioned Substituent Group A. The number of the substituents is, for example, 1 or 2 (preferably 1). When the number of the substituents is 2 or more, the respective substituents may be the same or different.

Examples of the substituent for the "optionally substituted $C_{1-3}$ alkylene group" represented by L include a hydroxy group.

$R^1$ is preferably a hydrogen atom or an optionally substituted $C_{1-6}$ alkyl group (e.g., methyl, ethyl).

$R^3$ is preferably a hydrogen atom or a $C_{1-6}$ alkyl group (e.g., methyl, ethyl).

L is preferably an optionally substituted $C_{1-3}$ alkylene group (e.g., —CH$_2$—, —(CH$_2$)$_2$—, —CH(CH$_3$)—).

L is more preferably a $C_{1-3}$ alkylene group (e.g., —CH$_2$—, —(CH$_2$)$_2$—, —CH(CH$_3$)—).

As another embodiment, L is preferably an optionally substituted $C_{1-2}$ alkylene group (e.g., —CH$_2$—, —(CH$_2$)$_2$—, —CH(CH$_3$)—).

L is more preferably a $C_{1-2}$ alkylene group (e.g., —CH$_2$—, —(CH$_2$)$_2$—, —CH(CH$_3$)—).

As another embodiment, L is more preferably an optionally substituted methylene.

L is further more preferably —CH$_2$—.

Preferable examples of compound (I) include the following compounds.

[Compound A-1]

Compound (I) wherein

Ring A is an optionally further substituted benzene (the position of the substituent is preferably the position indicated by the arrow on the partial structure represented by the formula:

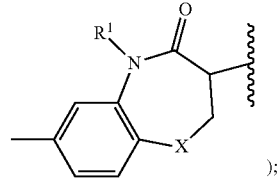

R¹ is a C$_{1-6}$ alkyl group (e.g., methyl) or a hydrogen atom;
X is
(a) an oxygen atom,
(b) a sulfur atom,
(d) —SO$_2$—, or
(e) an optionally substituted methylene group;
[specifically, the partial structure represented by the formula:

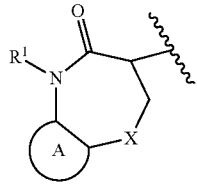

is a partial structure represented by the formula (1)-(4):

(1)
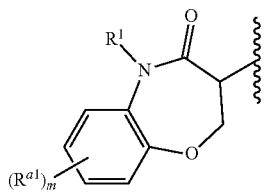

(2)
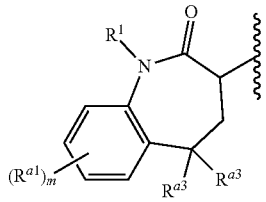

(3)
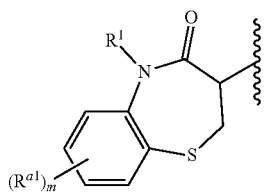

(4)
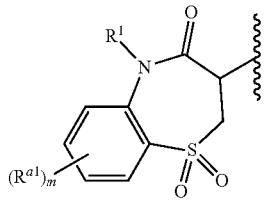

wherein
R¹ is a C$_{1-6}$ alkyl group (e.g., methyl) or a hydrogen atom;
R$^{a1}$ is each independently a substituent;
m is each independently an integer of 0 to 4; and
R$^{a3}$ is each independently a hydrogen atom or a substituent]
Ring B is an optionally further substituted 5- to 6-membered monocyclic aromatic heterocycle (preferably an optionally further substituted 5- to 6-membered nitrogen-containing monocyclic aromatic heterocycle (e.g., pyrazole, triazole, imidazole, thiazole, pyridine));
Ring D is an optionally further substituted 5- to 7-membered nitrogen-containing heterocycle;

Y¹ is a carbon atom or a nitrogen atom;
Y² is a carbon atom;
[specifically, the partial structure represented by the formula:

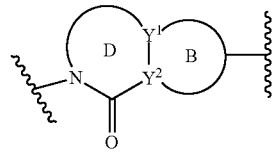

is a partial structure represented by the formula (1), (3), (4), (6)-(9), (11), (17) or (19):

(1)
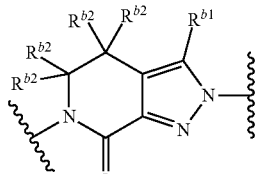

(3)
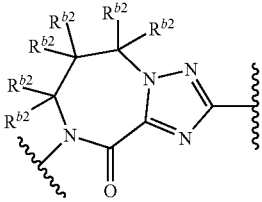

(4)
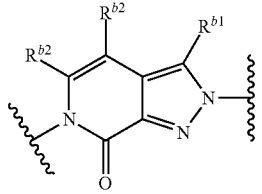

(6)
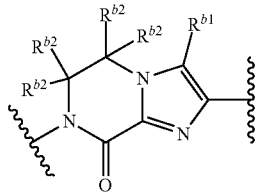

(7)
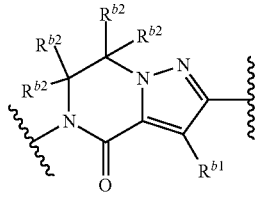

(8)
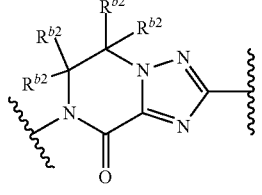

-continued (9)
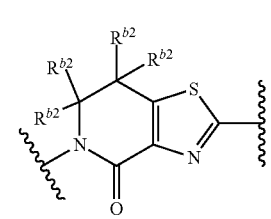

(11)
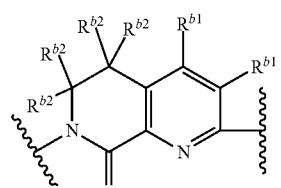

(17)
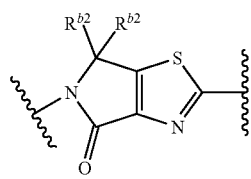

(19)
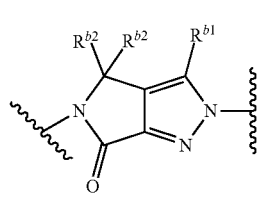

wherein $R^{b1}$ and $R^{b2}$ are each independently a hydrogen atom or a substituent]

Ring C is
(1) an optionally further substituted $C_{6-14}$ aromatic hydrocarbon ring (e.g., benzene),
(2) an optionally further substituted $C_{3-10}$ cycloalkane (preferably a $C_{3-6}$ cycloalkane (e.g., cyclopropane, cyclobutane, cyclopentane)),
(3) an optionally further substituted 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or
(4) an optionally further substituted 3- to 14-membered (preferably 4- to 10-membered) non-aromatic heterocycle (preferably a 3- to 8-membered monocyclic non-aromatic heterocycle (e.g., dioxane)); and L is an optionally substituted $C_{1-3}$ alkylene group (e.g., —CH$_2$—, —(CH$_2$)$_2$—, —CH(CH$_3$)—).

[Compound B-1]

Compound (I) wherein

Ring A is benzene optionally further substituted by 1 to 4 (preferably 1 or 2) substituents selected from
(a) a cyano group, and
(b) a halogen atom (e.g., a bromine atom)
(the position of the substituent is preferably the position indicated by the arrow on the partial structure represented by the formula:

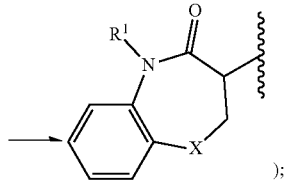

$R^1$ is a $C_{1-6}$ alkyl group (e.g., methyl) or a hydrogen atom;
X is
(a) an oxygen atom,
(b) a sulfur atom,
(d) —SO$_2$—, or
(e) a methylene group;

[specifically, the partial structure represented by the formula:

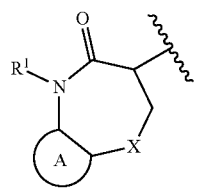

is a partial structure represented by the formula (1)-(4):

(1)
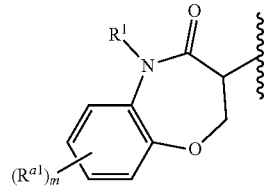

(2)
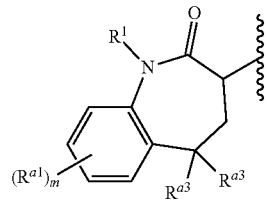

(3)
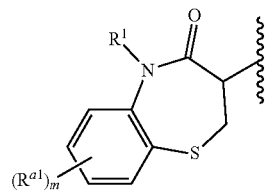

(4)
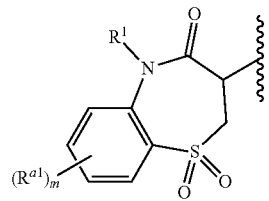

wherein
R¹ is a $C_{1-6}$ alkyl group (e.g., methyl) or a hydrogen atom;
$R^{a1}$ is each independently a substituent selected from
  (a) a cyano group, and
  (b) a halogen atom (e.g., a bromine atom);
m is each independently an integer of 0 to 4; and
$R^{a3}$ is both hydrogen atoms]
Ring B is a 5- to 6-membered nitrogen-containing monocyclic aromatic heterocycle (e.g., pyrazole, triazole, imidazole, thiazole, pyridine) optionally further substituted by 1 or 2 (preferably 1) substituents selected from
  (a) a cyano group,
  (b) a halogen atom (e.g., a bromine atom),
  (c) a $C_{1-6}$ alkyl group (e.g., methyl), and
  (d) a carbamoyl group;
Ring D is piperidine, pyrrolidine, pyrroline, piperazine, tetrahydrohydropyridine or diazepane;
$Y^1$ is a carbon atom or a nitrogen atom;
$Y^2$ is a carbon atom;
[specifically, the partial structure represented by the formula:

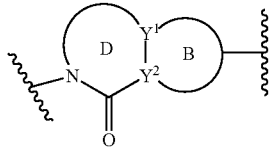

is a partial structure represented by the formula (1), (3), (4), (6)-(9), (11), (17) or (19):

(1)
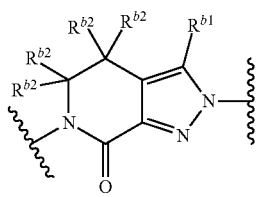

(3)
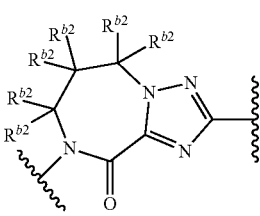

(4)
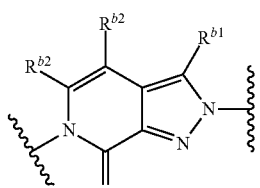

(6)
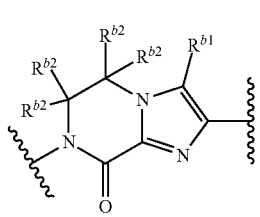

(7)
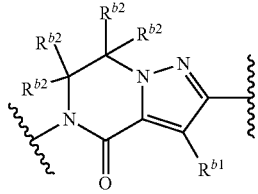

(8)
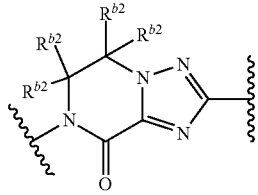

(9)
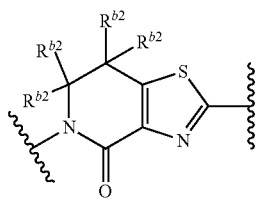

(11)
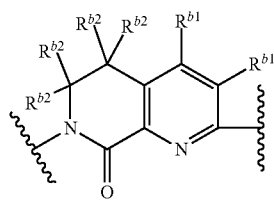

(17)
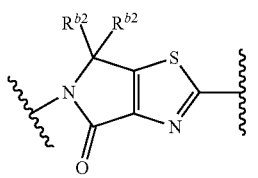

(19)
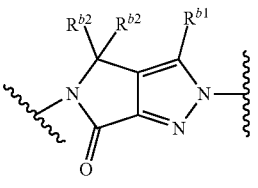

wherein
$R^{b1}$ is each independently
  (a) a hydrogen atom,
  (b) a cyano group,
  (c) a halogen atom (e.g., a bromine atom),
  (d) a $C_{1-6}$ alkyl group (e.g., methyl), or
  (e) a carbamoyl group; and
$R^{b2}$ is a hydrogen atom]
Ring C is
  (1) benzene optionally further substituted by 1 to 5 (preferably 1 or 2) substituents selected from
    (a) a cyano group,
    (b) a halogen atom (e.g., a fluorine atom, a chlorine atom), and
    (c) a $C_{1-6}$ alkyl group (e.g., methyl), (2) a $C_{3-10}$ cycloalkane (preferably a $C_{3-6}$ cycloalkane (e.g., cyclopropane, cyclobutane, cyclopentane)) optionally further substituted by 1 to 5 (preferably 1 or 2) halogen atoms (e.g., a fluorine atom),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)) optionally further substituted by 1 to 3 (preferably 1 or 2) $C_{1-6}$ alkyl groups (e.g., methyl), or
(4) a 3- to 14-membered (preferably 4- to 10-membered) non-aromatic heterocycle (preferably a 3- to 8-membered monocyclic non-aromatic heterocycle (e.g., dioxane)); and
L is a $C_{1-3}$ alkylene group (e.g., —$CH_2$—, —$(CH_2)_2$—, —$CH(CH_3)$—).

[Compound C-1]
Compound (I) wherein
Ring A is benzene optionally further substituted by one cyano group, or one cyano group and 1 to 3 halogen atoms (e.g., a bromine atom) (the position of the substituent is preferably the position indicated by the arrow on the partial structure represented by the formula:

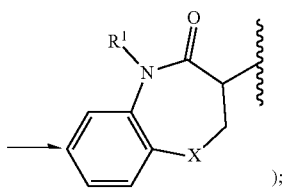
);

$R^1$ is a $C_{1-6}$ alkyl group (e.g., methyl);
X is an oxygen atom;
[specifically, the partial structure represented by the formula:

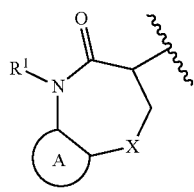

is a partial structure represented by the formula (1):

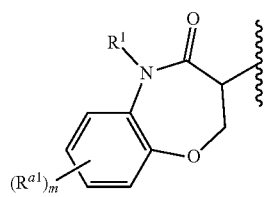
(1)

wherein
$R^1$ is a $C_{1-6}$ alkyl group (e.g., methyl);
$R^{a1}$ is each independently a substituent selected from
(a) a cyano group, and
(b) a halogen atom (e.g., a bromine atom); and
m is 0, 1 or 2]
Ring B is pyrazole optionally further substituted by one substituent selected from (a) a cyano group,
(b) a halogen atom (e.g., a bromine atom), and
(c) a carbamoyl group;
Ring D is piperidine;
$Y^1$ is a carbon atom;
$Y^2$ is a carbon atom;
[specifically, the partial structure represented by the formula:

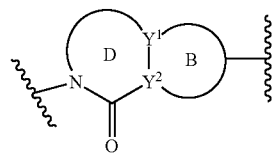

is a partial structure represented by the formula (1):

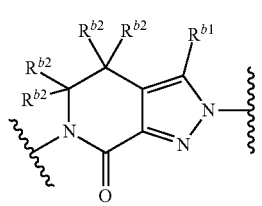
(1)

wherein
$R^{b1}$ is
(a) a hydrogen atom,
(b) a cyano group,
(c) a halogen atom (e.g., a bromine atom), or
(d) a carbamoyl group; and
$R^{b2}$ is a hydrogen atom]
Ring C is benzene; and
L is —$CH_2$—.

[Compound A-2]
Compound (I) wherein
Ring A is an optionally further substituted benzene (the position of the substituent is preferably the position indicated by the arrow on the partial structure represented by the formula:

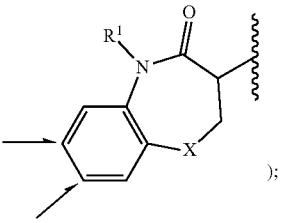
);

$R^1$ is a $C_1$-(alkyl group (e.g., methyl) or a hydrogen atom;
X is
(a) an oxygen atom,
(b) a sulfur atom,
(d) —$SO_2$—, or
(e) an optionally substituted methylene group;
[specifically, the partial structure represented by the formula:

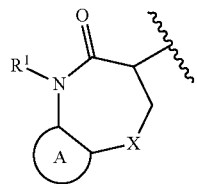

is a partial structure represented by the formula (1)-(4):

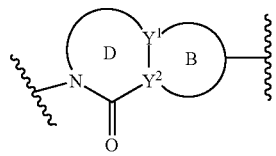

is a partial structure represented by the formula (1), (3), (4), (6)-(9), (11), (17) or (19):

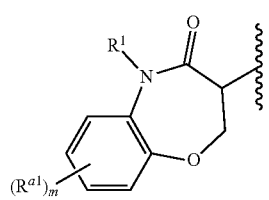
(1)

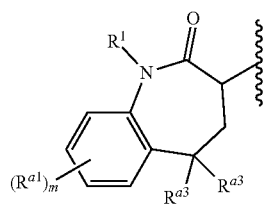
(2)

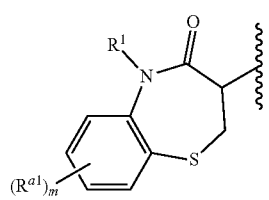
(3)

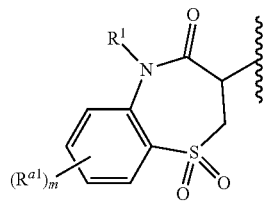
(4)

wherein $R^1$ is a $C_{1-6}$ alkyl group (e.g., methyl) or a hydrogen atom;

$R^{a1}$ is each independently a substituent;

m is each independently an integer of 0 to 4; and $R^{a3}$ is each independently a hydrogen atom or a substituent]

Ring B is an optionally further substituted 5- to 6-membered monocyclic aromatic heterocycle (preferably an optionally further substituted 5- to 6-membered nitrogen-containing monocyclic aromatic heterocycle (e.g., pyrazole, triazole, imidazole, thiazole, pyridine));

Ring D is an optionally further substituted 5- to 7-membered nitrogen-containing heterocycle;

$Y^1$ is a carbon atom or a nitrogen atom;

$Y^2$ is a carbon atom;

[specifically, the partial structure represented by the formula:

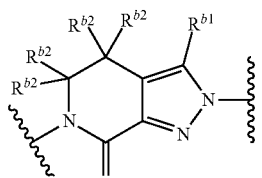
(1)

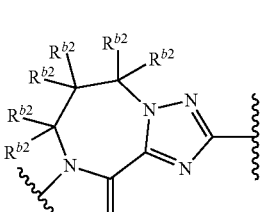
(3)

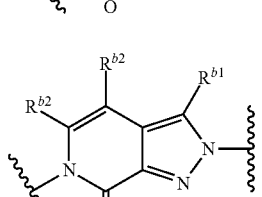
(4)

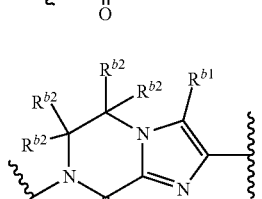
(6)

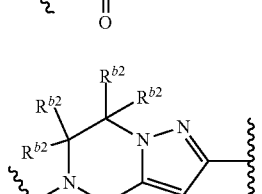
(7)

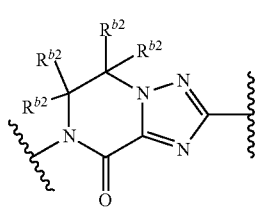
(8)

-continued

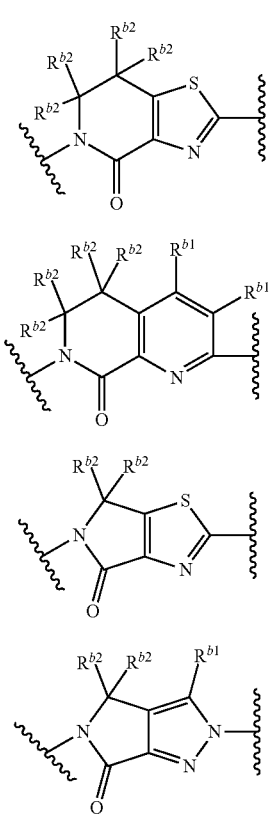

wherein $R^{b1}$ and $R^{b2}$ are each independently a hydrogen atom or a substituent]

Ring C is (1) an optionally further substituted $C_{6-14}$ aromatic hydrocarbon ring (e.g., benzene), (2) an optionally further substituted $C_{3-10}$ cycloalkane (preferably a $C_{3-6}$ cycloalkane (e.g., cyclopropane, cyclobutane, cyclopentane)), (3) an optionally further substituted 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)), or (4) an optionally further substituted 3- to 14-membered (preferably 4- to 10-membered) non-aromatic heterocycle (preferably a 3- to 8-membered monocyclic non-aromatic heterocycle (e.g., dioxane)); and L is an optionally substituted $C_{1-3}$ alkylene group (e.g., —CH$_2$—, —(CH$_2$)$_2$—, —CH(CH$_3$)—).

[Compound B-2]

Compound (I) wherein

Ring A is benzene optionally further substituted by 1 to 4 (preferably 1 or 2) substituents selected from (a) a cyano group, (b) a halogen atom (e.g., a bromine atom), and (c) a mono- or di-$C_{1-6}$ alkyl-carbamoyl group (e.g., methylcarbamoyl)

(the position of the substituent is preferably the position indicated by the arrow on the partial structure represented by the formula:

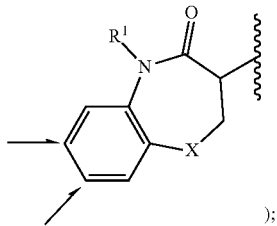

);

$R^1$ is a $C_{1-6}$ alkyl group (e.g., methyl) or a hydrogen atom;

X is (a) an oxygen atom, (b) a sulfur atom, (d) —SO$_2$—, or (e) a methylene group;

[specifically, the partial structure represented by the formula:

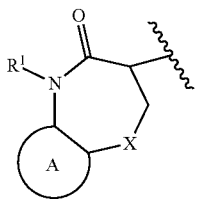

is a partial structure represented by the formula (1)-(4):

(1)

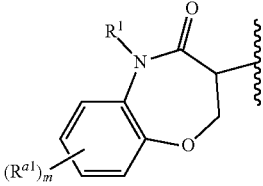

(2)

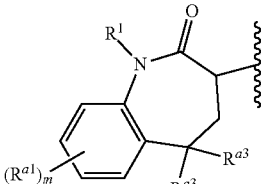

(3)

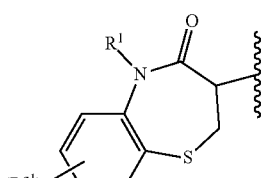

(4)

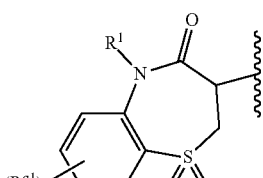

wherein
R¹ is a $C_{1-6}$ alkyl group (e.g., methyl) or a hydrogen atom;
$R^{a1}$ is each independently a substituent selected from
(a) a cyano group,
(b) a halogen atom (e.g., a bromine atom), and
(c) a mono- or di-$C_{1-6}$ alkyl-carbamoyl group (e.g., methylcarbamoyl);
m is each independently an integer of 0 to 4; and
$R^{a3}$ is both hydrogen atoms]
Ring B is a 5- to 6-membered nitrogen-containing monocyclic aromatic heterocycle (e.g., pyrazole, triazole, imidazole, thiazole, pyridine) optionally further substituted by 1 or 2 (preferably 1) substituents selected from
(a) a cyano group,
(b) a halogen atom (e.g., a chlorine atom, a bromine atom),
(c) a $C_{1-6}$ alkyl group (e.g., methyl), and
(d) a carbamoyl group;
Ring D is piperidine, pyrrolidine, pyrroline, piperazine, tetrahydrohydropyridine or diazepane;
$Y^1$ is a carbon atom or a nitrogen atom;
$Y^2$ is a carbon atom;
[specifically, the partial structure represented by the formula:

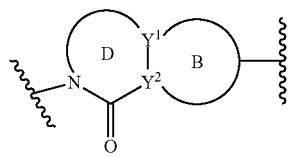

is a partial structure represented by the formula (1), (3), (4), (6)-(9), (11), (17) or (19):

(1)

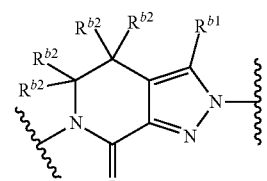

(3)

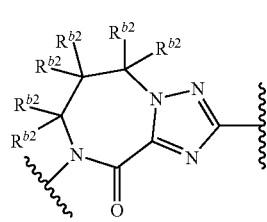

(4)

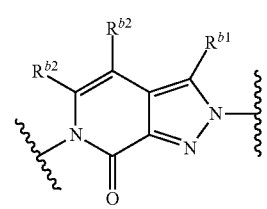

(6)

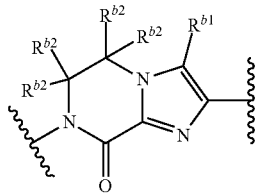

(7)

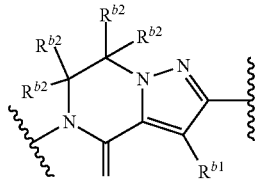

(8)

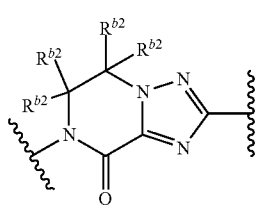

(9)

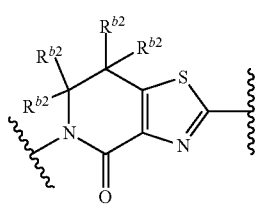

(11)

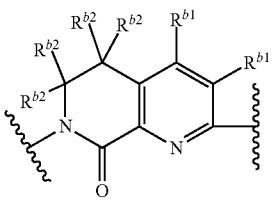

(17)

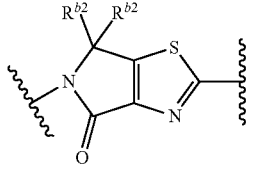

(19)

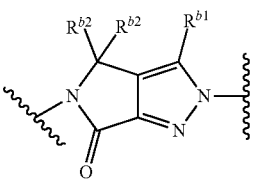

wherein
$R^{b1}$ is each independently
(a) a hydrogen atom,
(b) a cyano group,
(c) a halogen atom (e.g., a chlorine atom, a bromine atom),
(d) a $C_{1-6}$ alkyl group (e.g., methyl), or
(e) a carbamoyl group; and
$R^{b2}$ is a hydrogen atom]

Ring C is
(1) benzene optionally further substituted by 1 to 5 (preferably 1 or 2) substituents selected from
  (a) a cyano group,
  (b) a halogen atom (e.g., a fluorine atom, a chlorine atom), and
  (c) a $C_{1-6}$ alkyl group (e.g., methyl),
(2) a $C_{3-10}$ cycloalkane (preferably a $C_{3-6}$ cycloalkane (e.g., cyclopropane, cyclobutane, cyclopentane)) optionally further substituted by 1 to 5 (preferably 1 or 2) halogen atoms (e.g., a fluorine atom),
(3) a 5- to 14-membered (preferably 5- to 10-membered) aromatic heterocycle (preferably a 5- to 6-membered monocyclic aromatic heterocycle (e.g., furan, oxazole, pyrazole, pyridine, pyrimidine, pyrazine)) optionally further substituted by 1 to 3 (preferably 1 or 2) $C_{1-6}$ alkyl groups (e.g., methyl), or
(4) a 3- to 14-membered (preferably 4- to 10-membered) non-aromatic heterocycle (preferably a 3- to 8-membered monocyclic non-aromatic heterocycle (e.g., dioxane)); and L is a $C_{1-3}$ alkylene group (e.g., —$CH_2$—, —$(CH_2)_2$—, —CH($CH_3$)—)

[Compound C-2]
Compound (I) wherein
Ring A is benzene optionally further substituted by
(1) one cyano group,
(2) one cyano group and 1 to 3 halogen atoms (e.g., a bromine atom),
(3) one mono- or di-$C_{1-6}$ alkyl-carbamoyl group (e.g., methylcarbamoyl), or
(4) one mono- or di-$C_{1-6}$ alkyl-carbamoyl group (e.g., methylcarbamoyl) and 1 to 3 halogen atoms (e.g., a bromine atom)
(the position of the substituent is preferably the position indicated by the arrow on the partial structure represented by the formula:

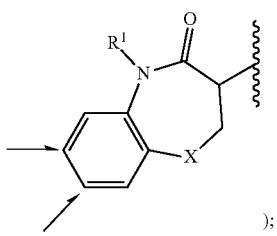

);

$R^1$ is a $C_{1-6}$ alkyl group (e.g., methyl);
X is an oxygen atom;
[specifically, the partial structure represented by the formula:

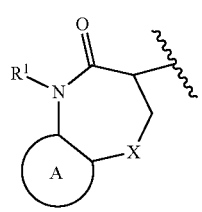

is a partial structure represented by the formula (1):

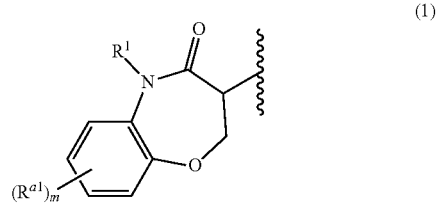

(1)

wherein
$R^1$ is a $C_{1-6}$ alkyl group (e.g., methyl);
$R^{a1}$ is each independently a substituent selected from
  (a) a cyano group,
  (b) a halogen atom (e.g., a bromine atom), and
  (c) a mono- or di-$C_{1-6}$ alkyl-carbamoyl group (e.g., methylcarbamoyl); and
m is 0, 1 or 2]
Ring B is pyrazole optionally further substituted by one substituent selected from
  (a) a cyano group,
  (b) a halogen atom (e.g., a chlorine atom, a bromine atom), and
  (c) a carbamoyl group;
Ring D is piperidine;
$Y^1$ is a carbon atom;
$Y^2$ is a carbon atom;
[specifically, the partial structure represented by the formula:

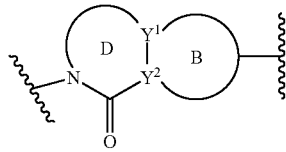

is a partial structure represented by the formula (1):

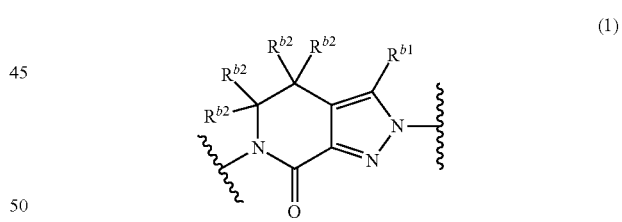

(1)

wherein
$R^{b1}$ is
  (a) a hydrogen atom,
  (b) a cyano group,
  (c) a halogen atom (e.g., a chlorine atom, a bromine atom), or
  (d) a carbamoyl group; and
$R^{b2}$ is a hydrogen atom]
Ring C is benzene optionally further substituted by 1 to 5 (preferably 1 or 2) halogen atoms (e.g., a fluorine atom); and
L is —$CH_2$—.

[Compound A-3]
Compound (I) wherein
Ring A is benzene, pyridine or pyrazole, each optionally further substituted;
$R^1$ is a $C_{1-6}$ alkyl group (e.g., methyl) or a hydrogen atom;

X is
(a) an oxygen atom,
(b) a sulfur atom,
(d) —SO$_2$—,
(e) an optionally substituted methylene group, or
(f) —NR$^2$— wherein R$^2$ is a C$_{1-6}$ alkyl group (e.g., methyl) or a hydrogen atom;
[specifically, the partial structure represented by the formula:

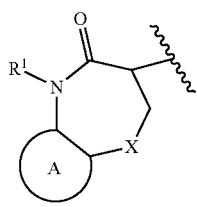

is a partial structure represented by the formula (1)-(4), (6) or (22)-(28):

(1)
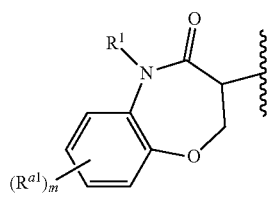

(2)
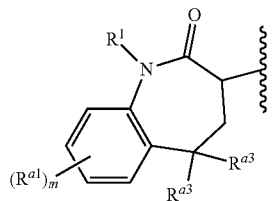

(3)
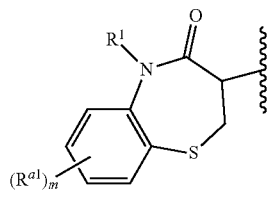

(4)
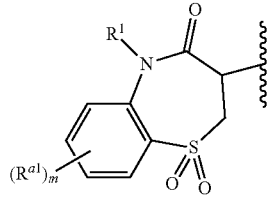

(6)
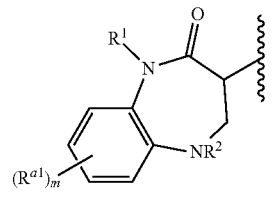

(22)
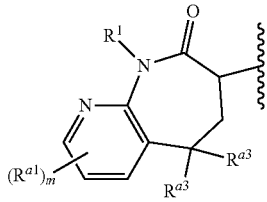

(23)
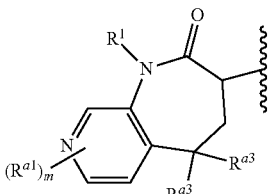

(24)
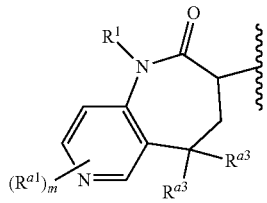

(25)
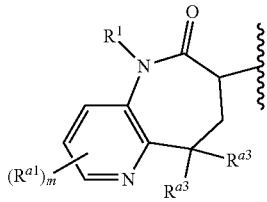

(26)
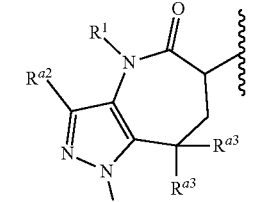

(27)
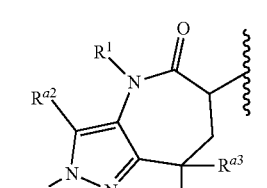

(28)
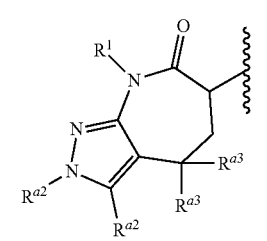

wherein
R$^1$ is a C$_{1-6}$ alkyl group (e.g., methyl) or a hydrogen atom;
R$^{a1}$ is each independently a substituent;
m is each independently an integer of 0 to 4; and $R^{a2}$ and $R^{a3}$ is each independently a hydrogen atom or a substituent]

Ring B is pyrazole, triazole, imidazole, thiazole or pyridine, each optionally further substituted;

Ring D is piperidine, pyrrolidine, pyrroline, piperazine, tetrahydropyridine or diazepane, each optionally further substituted;

$Y^1$ is a carbon atom or a nitrogen atom;

$Y^2$ is a carbon atom;

[specifically, the partial structure represented by the formula:

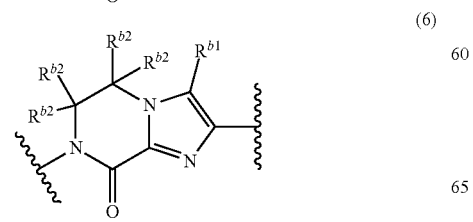

is a partial structure represented by the formula (1)-(4), (6)-(9), (11), (16), (17), (19) or (21):

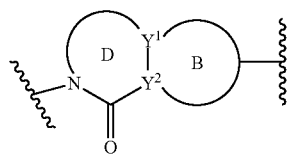
(1)

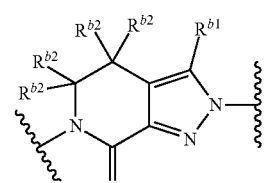
(2)

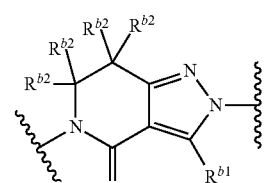
(3)

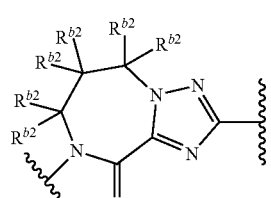
(4)

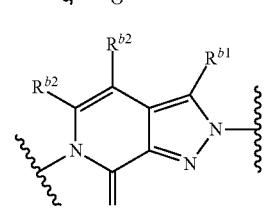
(6)

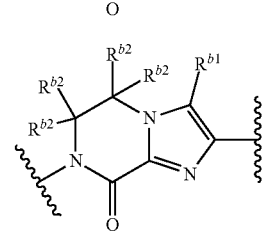

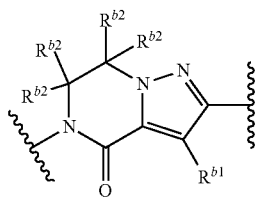
(7)

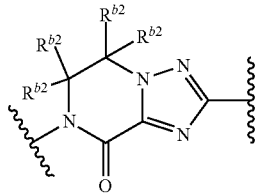
(8)

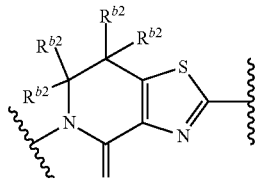
(9)

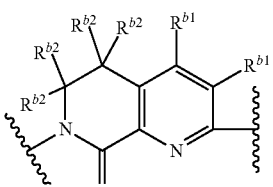
(11)

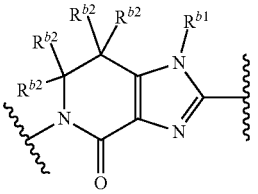
(16)

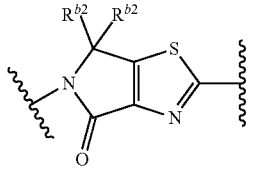
(17)

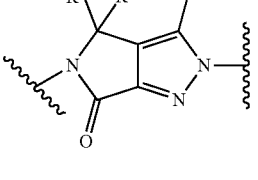
(19)

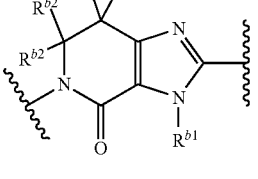
(21)

wherein $R^{b1}$ and $R^{b2}$ are each independently a hydrogen atom or a substituent]

Ring C is benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane (e.g., cyclopropane, cyclobutane, cyclopentane, cyclohexane), each optionally further substituted; and L is an optionally substituted $C_2$ alkylene group (e.g., $-CH_2-$, $-(CH_2)_2-$, $-CH(CH_3)-$).

[Compound B-3]

Compound (I) wherein

Ring A is benzene, pyridine or pyrazole, each optionally further substituted by 1 to 4 (preferably 1 or 2) substituents selected from (a) a cyano group, (b) a halogen atom (e.g., a fluorine atom, a chlorine atom, a bromine atom), (c) a carboxy group, (d) a carbamoyl group, (e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from (i) a hydroxy group, and (ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from (A) a $C_{6-14}$ aryloxy group (e.g., naphthyloxy), and (B) a 3- to 14-membered non-aromatic heterocyclylcarbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from (1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group, (2) a $C_{1-6}$ alkyl group (e.g., methyl), and (3) an oxo group, (f) a $C_{1-6}$ alkyl group (e.g., methyl) optionally substituted by 1 to 3 $C_{1-6}$ alkoxy groups (e.g., methoxy), (g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl), (h) a 3- to 14-membered non-aromatic heterocyclic group (preferably a 3- to 8-membered monocyclic non-aromatic heterocyclic group (e.g., oxetanyl, morpholinyl)), and (i) a 3- to 14-membered non-aromatic heterocyclylcarbamoyl group (preferably a 3- to 8-membered monocyclic non-aromatic heterocyclylcarbamoyl group (e.g., oxetanylcarbamoyl))

(when Ring A is an optionally further substituted benzene, the position of the substituent is preferably the position indicated by the arrow on the partial structure represented by the formula:

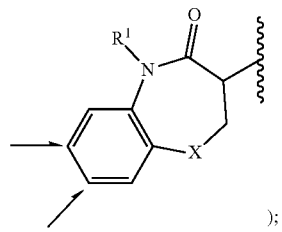

);

$R^1$ is a $C_{1-6}$ alkyl group (e.g., methyl) or a hydrogen atom;

X is (a) an oxygen atom, (b) a sulfur atom, (d) $-SO_2-$, (e) a methylene group, or (f) $-NR^2-$ wherein $R^2$ is a $C_{1-6}$ alkyl group (e.g., methyl);

[specifically, the partial structure represented by the formula:

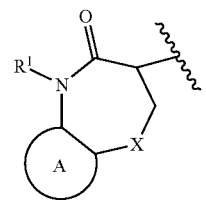

is a partial structure represented by the formula (1)-(4), (6) or (22)-(28):

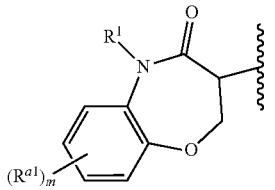

(1)

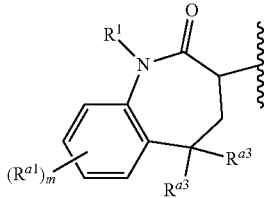

(2)

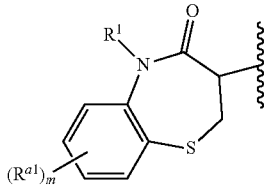

(3)

-continued (4) 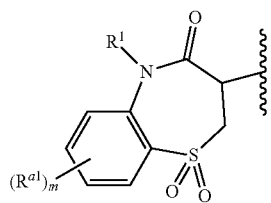

(6) 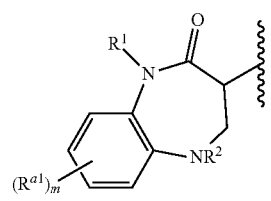

(22) 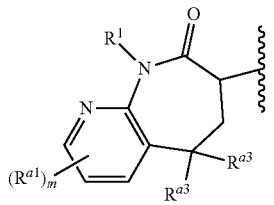

(23) 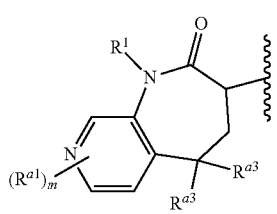

(24) 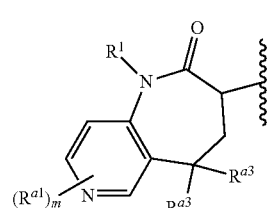

(25) 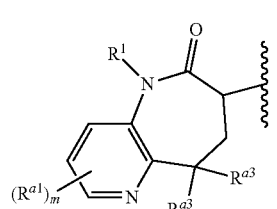

(26) 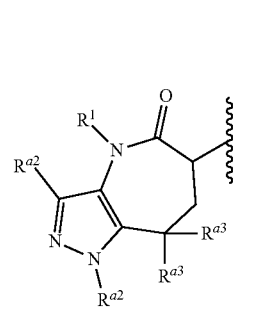

-continued

(27) 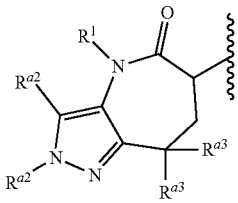

(28) 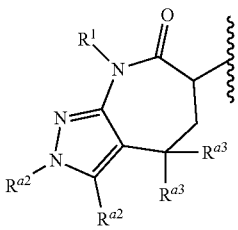

wherein
$R^1$ is a $C_{1-6}$ alkyl group (e.g., methyl) or a hydrogen atom;
$R^{a1}$ is each independently a substituent selected from
(a) a cyano group,
(b) a halogen atom (e.g., a fluorine atom, a chlorine atom, a bromine atom),
(c) a carboxy group,
(d) a carbamoyl group,
(e) a mono- or di-$C_{1-6}$ alkyl-carbamoyl group (e.g., methylcarbamoyl, ethylcarbamoyl, dimethylcarbamoyl, isobutylcarbamoyl) optionally substituted by 1 to 3 substituents selected from
(i) a hydroxy group, and
(ii) a $C_{1-6}$ alkoxy-$C_{1-6}$ alkoxy-$C_{1-6}$ alkoxy group (e.g., ethoxyethoxyethoxy) optionally substituted by 1 to 3 substituents selected from
(A) a $C_{6-14}$ aryloxy group (e.g., naphthyloxy), and
(B) a 3- to 14-membered non-aromatic heterocyclyl-carbonylamino group (a 9- to 14-membered fused polycyclic (preferably bi- or tri-cyclic) non-aromatic heterocyclylcarbonylamino group (e.g., tetrahydrobenzoxazepinylcarbonylamino)) optionally substituted by 1 to 3 substituents selected from
(1) a 3- to 14-membered non-aromatic heterocyclic group (a 9- to 14-membered fused polycyclic (preferably bi- or tri-cyclic) non-aromatic heterocyclic group (e.g., tetrahydropyrazolo[3,4-c]pyridyl)) optionally substituted by 1 to 3 substituents selected from a $C_{7-16}$ aralkyl group (e.g., benzyl), a halogen atom (e.g., a chlorine atom) and an oxo group,
(2) a $C_{1-6}$ alkyl group (e.g., methyl), and
(3) an oxo group,
(f) a $C_{1-6}$ alkyl group (e.g., methyl) optionally substituted by 1 to 3 $C_{1-6}$ alkoxy groups (e.g., methoxy),
(g) a 5- to 14-membered aromatic heterocyclic group (preferably a 5- to 6-membered monocyclic aromatic heterocyclic group (e.g., imidazolyl, pyrazolyl, oxazolyl)) optionally substituted by 1 to 3 $C_{1-6}$ alkyl groups (e.g., methyl),
(h) a 3- to 14-membered non-aromatic heterocyclic group (preferably a 3- to 8-membered monocyclic non-aromatic heterocyclic group (e.g., oxetanyl, morpholinyl)), and (i) a 3- to 14-membered non-aromatic heterocyclylcarbamoyl group (preferably a 3- to 8-membered monocyclic non-aromatic heterocyclylcarbamoyl group (e.g., oxetanylcarbamoyl));

m is each independently 0, 1 or 2;

$R^{a2}$ is each independently
(1) a hydrogen atom, or
(2) a $C_{1-6}$ alkyl group (e.g., methyl); and $R^{a3}$ is both hydrogen atoms]

Ring B is pyrazole, triazole, imidazole, thiazole or pyridine, each optionally further substituted by 1 or 2 (preferably 1) substituents selected from
(a) a cyano group,
(b) a halogen atom (e.g., a chlorine atom, a bromine atom),
(c) a $C_{1-6}$ alkyl group (e.g., methyl) optionally substituted by 1 to 3 substituents selected from
 (i) a hydroxy group, and
 (iii) a $C_{6-14}$ aryl group (e.g., phenyl) optionally substituted by 1 to 3 $C_{1-6}$ alkoxy groups (e.g., methoxy),
(d) a hydroxy group,
(e) an optionally halogenated $C_{1-6}$ alkoxy group (e.g., methoxy, difluoromethoxy),
(f) a $C_{3-10}$ cycloalkyl group (e.g., cyclopropyl),
(g) a $C_{1-6}$ alkoxy-carbonyl group (e.g., ethoxycarbonyl),
(h) a carbamoyl group,
(i) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), and
(j) a carboxy group;

Ring D is piperidine, pyrrolidine, pyrroline, piperazine, tetrahydrohydropyridine or diazepane;

$Y^1$ is a carbon atom or a nitrogen atom;

$Y^2$ is a carbon atom;

[specifically, the partial structure represented by the formula:

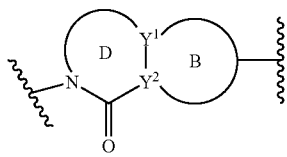

is a partial structure represented by the formula (1)-(4), (6)-(9), (11), (16), (17), (19) or (21):

(1)
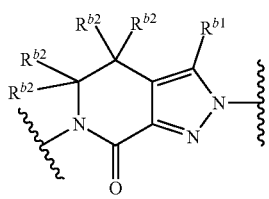

(2)
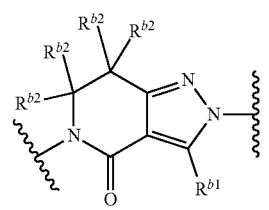

(3)
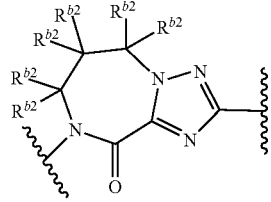

(4)
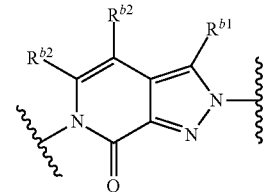

(6)
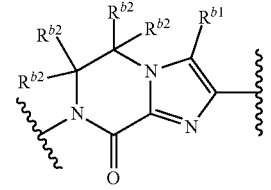

(7)
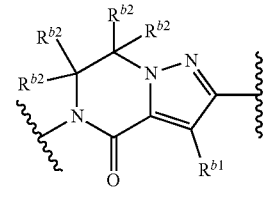

(8)
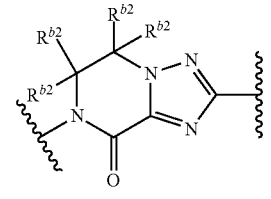

(9)
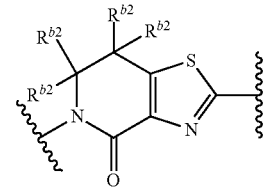

(11)
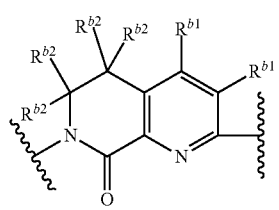

-continued

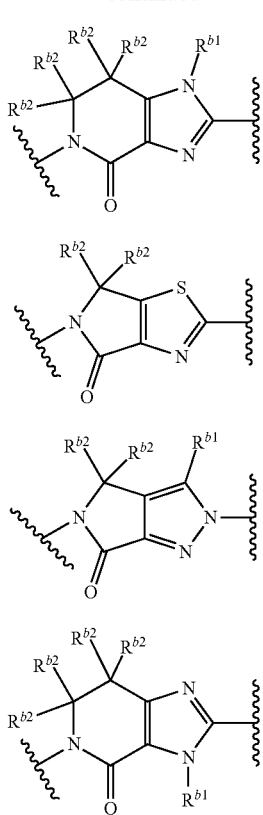

wherein
$R^{b1}$ is each independently
(a) a hydrogen atom,
(b) a cyano group,
(c) a halogen atom (e.g., a chlorine atom, a bromine atom),
(d) a $C_{1-6}$ alkyl group (e.g., methyl) optionally substituted by 1 to 3 substituents selected from
  (i) a hydroxy group, and
  (iii) a $C_{6-14}$ aryl group (e.g., phenyl) optionally substituted by 1 to 3 $C_{1-6}$ alkoxy groups (e.g., methoxy),
(e) a hydroxy group,
(f) an optionally halogenated $C_{1-6}$ alkoxy group (e.g., methoxy, difluoromethoxy),
(g) a $C_{3-10}$ cycloalkyl group (e.g., cyclopropyl),
(h) a $C_{1-6}$ alkoxy-carbonyl group (e.g., ethoxycarbonyl),
(i) a carbamoyl group,
(j) a 5- to 14-membered aromatic heterocyclic group (preferably a 5- to 6-membered monocyclic aromatic heterocyclic group (e.g., pyrazolyl)) optionally substituted by 1 to 3 $C_{1-6}$ alkyl groups (e.g., methyl), or
(k) a carboxy group; and
$R^{b2}$ is a hydrogen atom]
Ring C is benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a $C_{3-6}$ cycloalkane (e.g., cyclopropane, cyclobutane, cyclopentane, cyclohexane), each optionally further substituted by 1 to 5 (preferably 1 or 2) substituents selected from
(a) a cyano group,
(b) a halogen atom (e.g., a fluorine atom, a chlorine atom),
(c) a $C_{1-6}$ alkyl group (e.g., methyl),
(d) a $C_{1-6}$ alkoxy group (e.g., methoxy), and
(e) a $C_{1-6}$ alkylsulfonyl group (e.g., methylsulfonyl); and
L is a $C_{1-2}$ alkylene group (e.g., —CH$_2$—, —(CH$_2$)$_2$—, —CH(CH$_3$)—).

[Compound C-3]
Compound (I) wherein
Ring A is an optionally further substituted benzene;
$R^1$ is a $C_{1-6}$ alkyl group (e.g., methyl);
X is an oxygen atom;
[specifically, the partial structure represented by the formula:

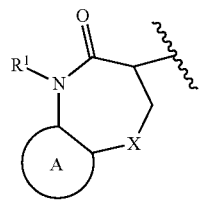

is a partial structure represented by the formula (1):

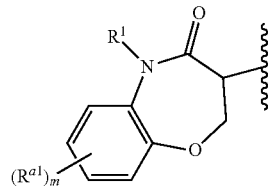

(1)

wherein
$R^1$ is a $C_{1-6}$ alkyl group (e.g., methyl);
$R^{a1}$ is each independently a substituent; and
m is each independently an integer of 0 to 4]
Ring B is an optionally further substituted pyrazole;
Ring D is an optionally further substituted piperidine;
$Y^1$ is a carbon atom;
$Y^2$ is a carbon atom;
[specifically, the partial structure represented by the formula:

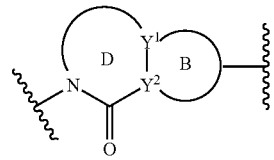

is a partial structure represented by the formula (1):

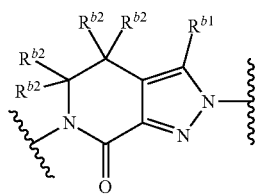

(1)

wherein $R^{b1}$ and $R^{b2}$ are each independently a hydrogen atom or a substituent]

Ring C is an optionally further substituted benzene (the position of the substituent is preferably o-position); and L is an optionally substituted methylene.

[Compound D-3]

Compound (I) wherein

Ring A is benzene optionally further substituted by 1 or 2 (preferably 1) substituents selected from
  (a) a cyano group, and
  (b) a mono- or di-$C_{1-6}$ alkyl-carbamoyl group (e.g., methylcarbamoyl)

(the position of the substituent is preferably the position indicated by the arrow on the partial structure represented by the formula:

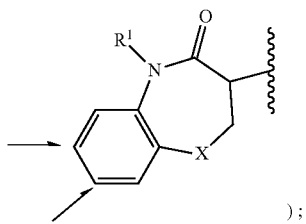

);

$R^1$ is a $C_{1-6}$ alkyl group (e.g., methyl);

X is an oxygen atom;

[specifically, the partial structure represented by the formula:

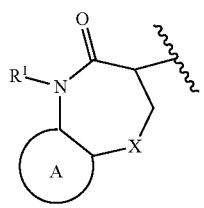

is a partial structure represented by the formula (1):

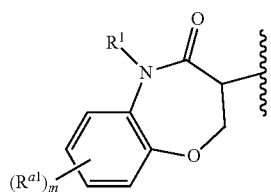

(1)

wherein $R^1$ is a $C_{1-6}$ alkyl group (e.g., methyl);

$R^{a1}$ is each independently a substituent selected from
  (a) a cyano group, and
  (b) a mono- or di-$C_{1-6}$ alkyl-carbamoyl group (e.g., methylcarbamoyl); and
m is 0 or 1]

Ring B is pyrazole optionally further substituted by one substituent selected from
  (a) a cyano group, and
  (b) a halogen atom (e.g., a chlorine atom, a bromine atom);

Ring D is piperidine;

$Y^1$ is a carbon atom;

$Y^2$ is a carbon atom;

[specifically, the partial structure represented by the formula:

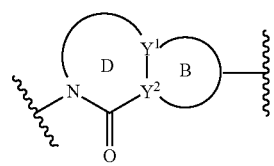

is a partial structure represented by the formula (1):

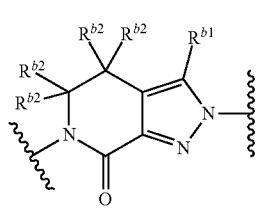

(1)

wherein $R^{b1}$ is
  (a) a hydrogen atom,
  (b) a cyano group, or
  (c) a halogen atom (e.g., a chlorine atom, a bromine atom); and $R^{b2}$ is a hydrogen atom]

Ring C is benzene optionally further substituted by 1 to 5 (preferably 1 or 2) halogen atoms (e.g., a fluorine atom) (the position of the substituent is preferably o-position); and L is —$CH_2$—.

[Compound E-3]

Compound (I) wherein

Ring A is benzene further substituted by
  (a) one cyano group, or
  (b) one mono- or di-$C_{1-6}$ alkyl-carbamoyl group (e.g., methylcarbamoyl)

(the position of the substituent is preferably the position indicated by the arrow on the partial structure represented by the formula:

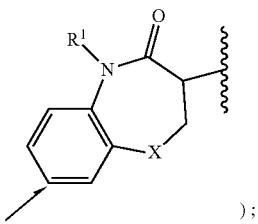

);

$R^1$ is a $C_{1-6}$ alkyl group (e.g., methyl);

X is an oxygen atom;

[specifically, the partial structure represented by the formula:

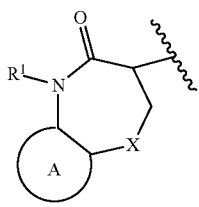

is a partial structure represented by the formula (1):

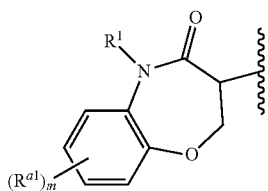

wherein
R¹ is a $C_{1-6}$ alkyl group (e.g., methyl);
$R^{a1}$ is
(a) a cyano group, or
(b) a mono- or di-$C_{1-6}$ alkyl-carbamoyl group (e.g., methylcarbamoyl); and
m is 1]
Ring B is pyrazole optionally further substituted by one substituent selected from
(a) a halogen atom (e.g., a chlorine atom);
Ring D is piperidine;
$Y^1$ is a carbon atom;
$Y^2$ is a carbon atom;
[specifically, the partial structure represented by the formula:

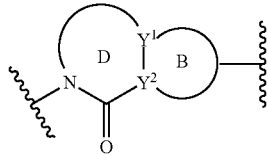

is a partial structure represented by the formula (1):

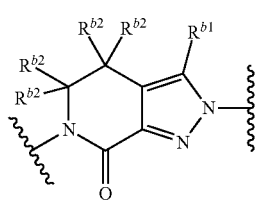

wherein
$R^{b1}$ is
(a) a hydrogen atom, or
(b) a halogen atom (e.g., a chlorine atom); and
$R^{b2}$ is a hydrogen atom]

Ring C is benzene optionally further substituted by 1 to 5 (preferably 1 or 2) halogen atoms (e.g., a fluorine atom) (the position of the substituent is preferably o-position); and L is —$CH_2$—.

[Compound F-3]
(3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof,
(3S)-3-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide, or a salt thereof, and
(3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof.

Specific examples of compound (I) include the compounds of Examples 1 to 70, 72 to 159 and 161 to 174.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, benzenesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^2$H, $^3$H, $^{11}$C, $^{14}$C, $^{18}$F, $^{35}$S, $^{125}$I, etc.) are also encompassed in compound (I). The compound labeled with or substituted by isotopes can be used as, for example, a tracer used for Positron Emission Tomography (PET) (PET tracer), and are useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature −300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, t-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as t-butylcarbonate and the like.

Examples of the protecting group for a carbonyl group of an aldehyde include acetal-type protecting groups such as dimethylacetal and the like; cyclic acetal-type protecting groups such as cyclic 1,3-dioxane and the like.

Examples of the protecting group for a carbonyl group of a ketone include ketal-type protecting groups such as dimethylketal and the like; cyclic ketal-type protecting groups such as cyclic 1,3-dioxane and the like; oxime-type protecting groups such as O-methyloxime and the like; hydrazone-type protecting groups such as N,N-dimethylhydrazone and the like.

Examples of the protecting group for a carboxyl group include ester-type protecting groups such as methyl ester and the like; amide-type protecting groups such as N,N-dimethylamide and the like.

Examples of the protecting group for a thiol include ether-type protecting groups such as benzyl thioether and the like; ester-type protecting groups such as thioacetate ester, thiocarbonate, thiocarbamate and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid and the like.

When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, t-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine) palladium(II), dichlorobis(triethylphosphine)palladium(II), tris(dibenzylideneacetone)dipalladium(0), 1,1'-bis(diphenylphosphino)ferrocene palladium(II) chloride, palladium (II) acetate and the like; nickel compounds such as tetrakis (triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis (4-methoxyphenyl)-1,3,2,4-dithiadiphosphetane-2,4-disulfide (Lawesson reagent) etc.) can also be used instead of phosphorus pentasulfide.

When Wohl-Ziegler reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two step comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of t-butyl ester, formic acid, triethylsilane and the like may be added to reductively trap t-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

Compound (I) can be produced according to the following method a method analogous thereto.

As used herein, $R^a$ and $R^d$ are independently a hydrogen atom or a substituent, $R^b$ and $R^c$ are independently a hydrocarbon group, $LG^a$, $LG^b$, $LG^c$, $LG^d$, $LG^e$ and $LG^f$ are independently a leaving group, m is an integer of 0 to 2, n is an integer of 1 to 3, and the other symbols are as defined above.

Examples of the leaving group include halogen atoms (e.g., a chlorine atom, a bromine atom, an iodine atom etc.), substituted sulfonyloxy groups (e.g., $C_{1-6}$ alkylsulfonyloxy groups such as a methanesulfonyloxy group, an ethanesulfonyloxy group etc.; $C_{6-14}$ arylsulfonyloxy groups such as a benzenesulfonyloxy group, a p-toluenesulfonyloxy group etc.; $C_{7-16}$ aralkylsulfonyloxy groups such as a benzylsulfonyloxy group etc., and the like) and the like.

Compound (I) can be produced from compound (II) according to the following method.

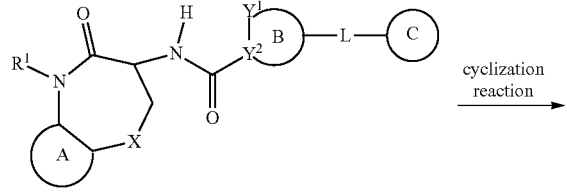

(II)

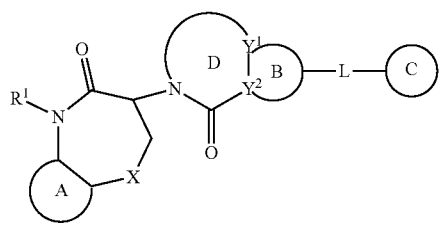

(I)

Compound (II) can be produced according to a method known per se [e.g., WO 2014/125444 A1]. Compound (I) can be produced by subjecting compound (II) to a cyclization reaction using a base and an alkyl halide. Examples of the alkyl halide include 1,2-dibromoethane, 1,3-diiodopropane and the like.

When compound (II) is compound (IIa), the compound can be produced according to the following method.

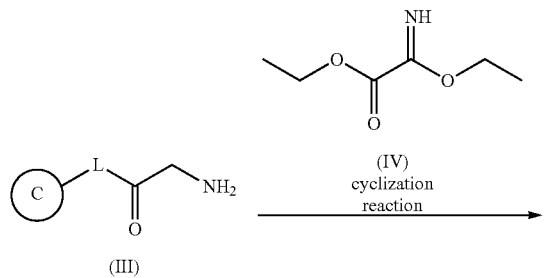

(V)

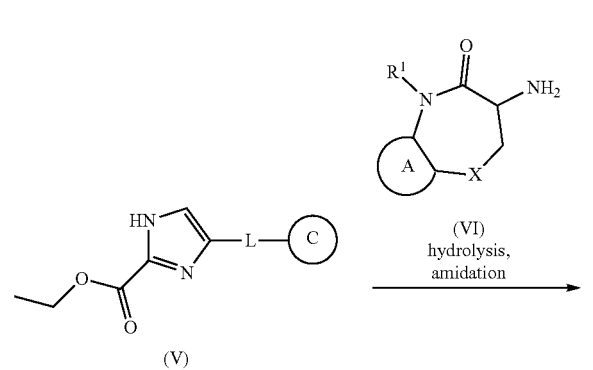

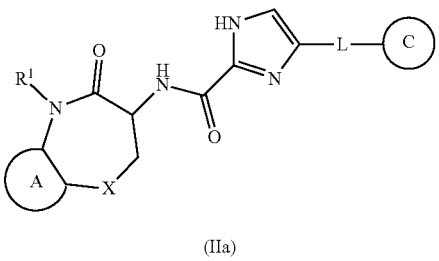

(IIa)

Compound (III) can be produced according to a method known per se (e.g., Chemical and Pharmaceutical Bulletin, 1984, 32, 2536-2543). Compound (V) can be produced by subjecting compound (III) and compound (IV) to a cyclization reaction with using a base.

When compound (I) is compound (Ia), the compound can be produced according to the following method.

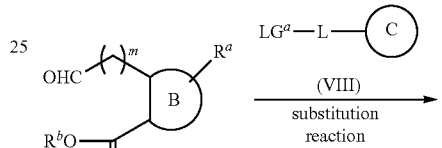

(VII)

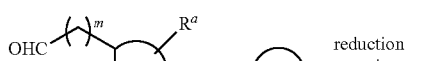

(IX)

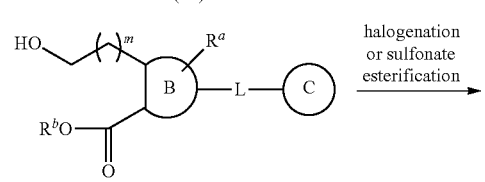

(X)

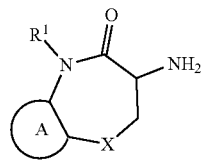

(VI)

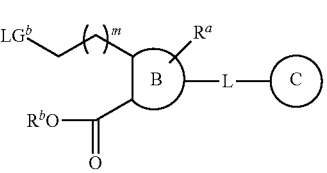

(XI)

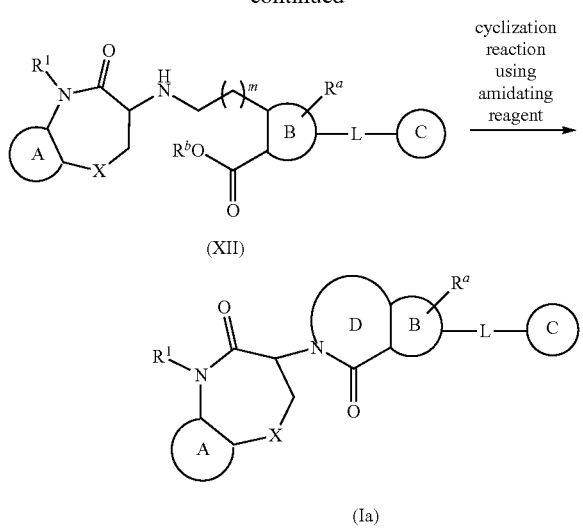

(XII)

(Ia)

Compound (VII) can be produced according to a method known per se [e.g., Synthesis, 1997, 10, 1140-1142]. Compound (IX) can be produced by subjecting compound (VII) to a substitution reaction with compound (VIII) using a base. Compound (XI) can be produced by subjecting compound (X) to a halogenation or sulfonate esterification using a base. For the halogenation, for example, a combination of triphenylphosphine and iodide, and the like can be used. Compound (Ia) can be produced by subjecting compound (XII) to a cyclization reaction using an amidating reagent. Examples of the amidating reagent include trimethylaluminium and the like.

When compound (X) is compound (Xa), the compound can be produced according to the following method.

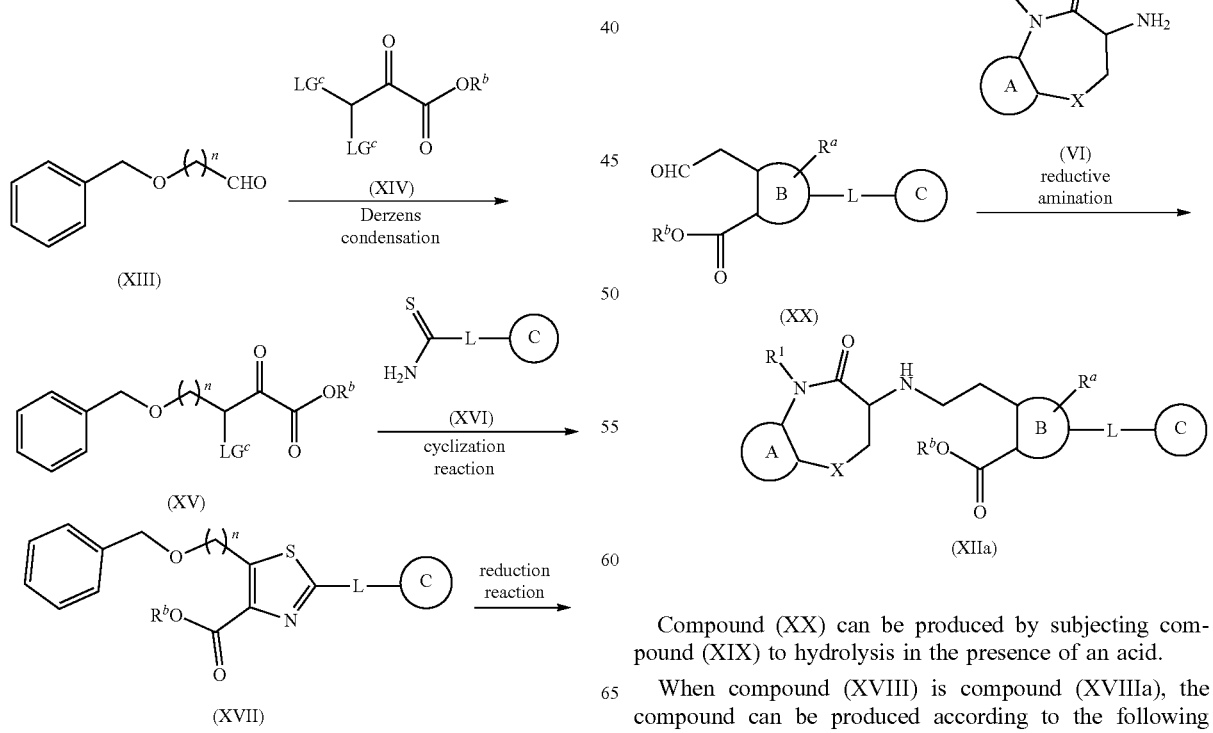

(XIII)

(XV)

(XVII)

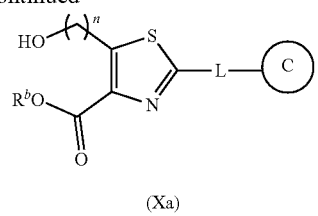

(Xa)

Compound (XV) can be produced by subjecting compound (XIII) and compound (XIV) to a Derzens condensation. Examples of the compound (XIV) include 2,2-dichloroethyl acetate and the like. Compound (XVII) can be produced by subjecting compound (XV) and compound (XVI) to a cyclization reaction. Examples of the compound (XVI) include 2-phenylethanethioamide and the like.

When compound (XII) is compound (XIIa), the compound can be produced according to the following method.

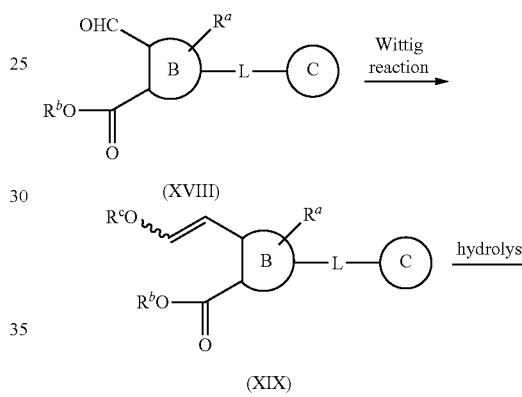

(XVIII)

(XIX)

(XX)

(XIIa)

Compound (XX) can be produced by subjecting compound (XIX) to hydrolysis in the presence of an acid.

When compound (XVIII) is compound (XVIIIa), the compound can be produced according to the following method.

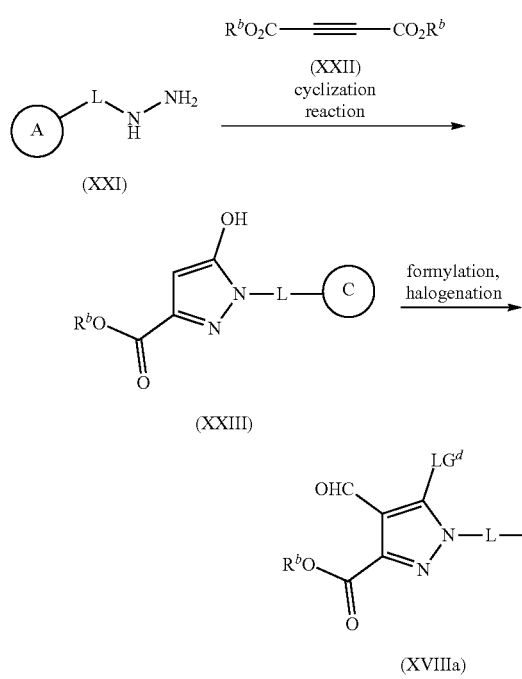

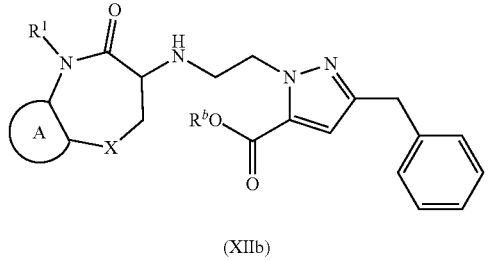

Compound (XXIII) can be produced by subjecting compound (XXI) and compound (XXII) to a cyclization reaction using a base. Compound (XVIIIa) can be produced by subjecting compound (XXIII) to a formylation, followed by a halogenation. For the formylation and halogenation, phosphoryl chloride, phosphoryl bromide and the like can be used.

When compound (XII) is compound (XIIb), the compound can be produced according to the following method.

Compound (XXIV) can be produced according to a method known per se [e.g., Journal of Medicinal Chemistry, 2003, 46, 3945-3951]. Compound (XXVI) can be produced by subjecting compound (XXIV) to a substitution reaction with compound (XXV). Examples of compound (XXV) include 1,2-dibromoethane and the like. Compound (XIIb) can be produced by subjecting compound (XXVI) to a substitution reaction with compound (VI) using a base, under microwave irradiation if necessary, and using an additive if necessary. Examples of the additive include potassium iodide and the like.

When compound (I) is compound (Ib), the compound can be produced according to the following method.

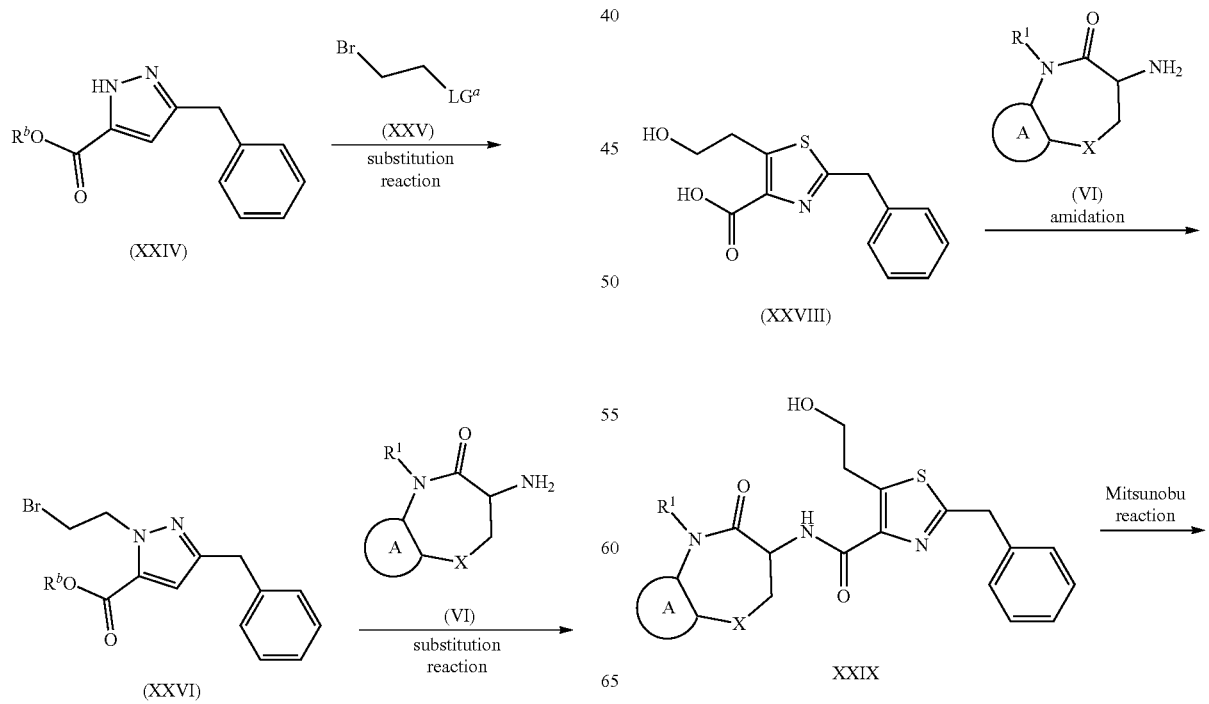

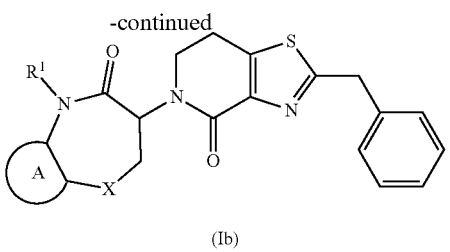

(Ib)

Compound (Ib) can be produced by subjecting compound (XXIX) obtained in the above-mentioned production method to Mitsunobu reaction using cyanomethylene tri-n-butyl phosphorane.

When compound (I) is compound (Ic), the compound can be produced from compound (XXX) obtained in the above-mentioned production method according to the following method.

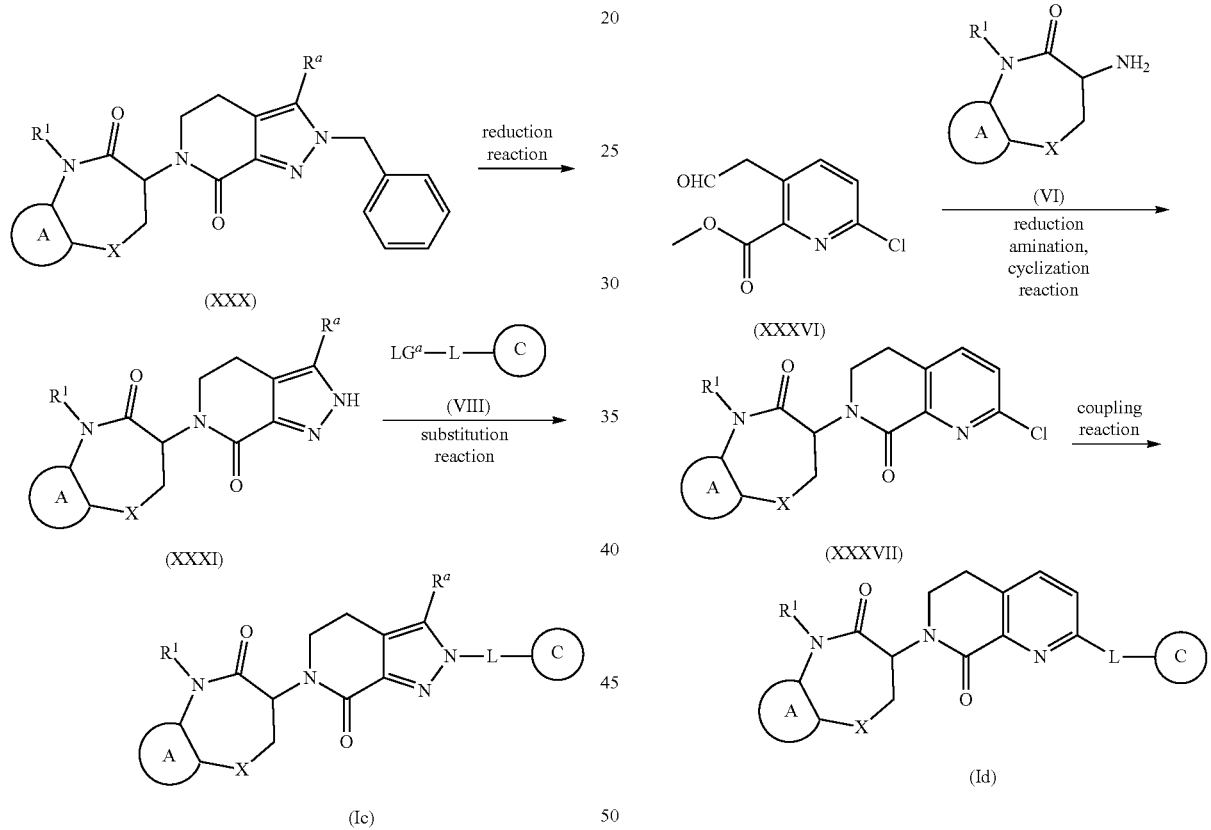

Compound (Ic) can be produced by subjecting compound (XXXI) to a substitution reaction using a base, under microwave irradiation if necessary.

When compound (I) is compound (Id), the compound can be produced according to the following method.

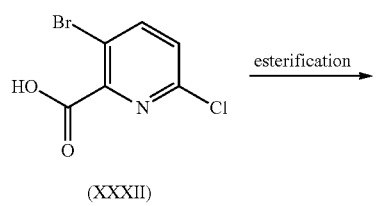

(XXXII)

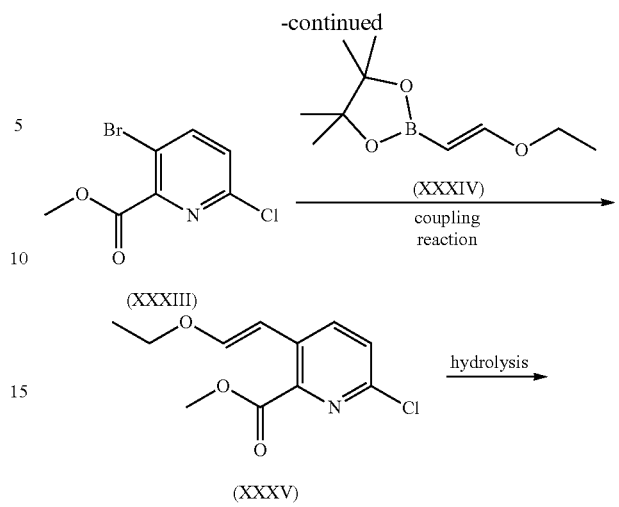

(Id)

Compound (XXXIII) can be produced by subjecting compound (XXXII) to an esterification using an acid and methanol. Compound (XXXV) can be produced by subjecting compound (XXXIII) and compound (XXXIV) to a coupling reaction using a ligand. Examples of the ligand include 2-dicyclohexylphosphino-2',6'-dimethoxybiphenyl and the like. Compound (XXXVI) can be produced by subjecting compound (XXXV) to a hydrolysis using an acid. Compound (XXXVII) can be produced by subjecting compound (XXXVI) and compound (VI) to a reduction amination, followed by a cyclization reaction using an acid. Compound (Id) can be produced by subjecting compound (XXXVII) and a zinc compound having a substituent to a coupling reaction using a ligand. Examples of the ligand include 2-dicyclohexylphosphino-2',4',6'-triisopropylbiphenyl and the like.

When compound (I) is compound (Ie), the compound can be produced from compound (XXXVIII) obtained in the above-mentioned production method according to the following method.

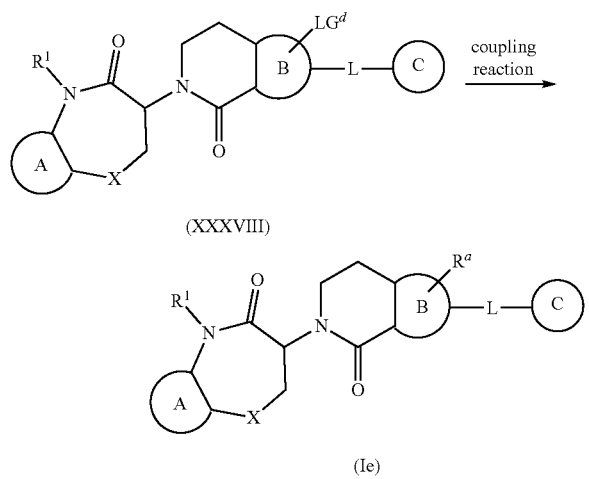

(XXXVIII)

(Ie)

Compound (Ie) can be produced by subjecting compound (XXXVIII) and a zinc compound having a substituent or a boron compound having a substituent to a coupling reaction.

When compound (I) is compound (If), the compound can be produced from compound (XXXIX) obtained in the above-mentioned production method according to the following method.

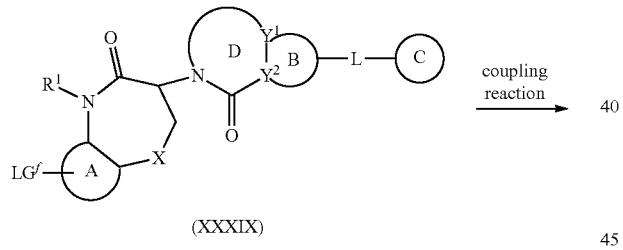

(XXXIX)

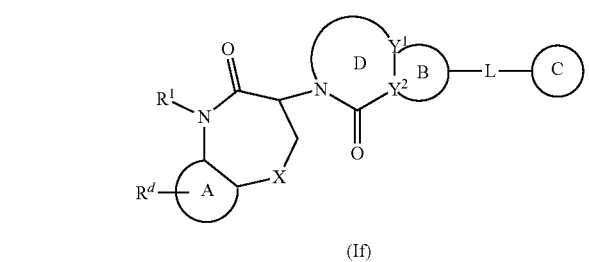

(If)

Compound (If) can be produced by subjecting compound (XXXIX) and a zinc compound having a substituent or a boron compound having a substituent to a coupling reaction.

When compound (I) is compound (Ig) or compound (Ih), the compound can be produced from above-mentioned compound (XIX) according to the following method.

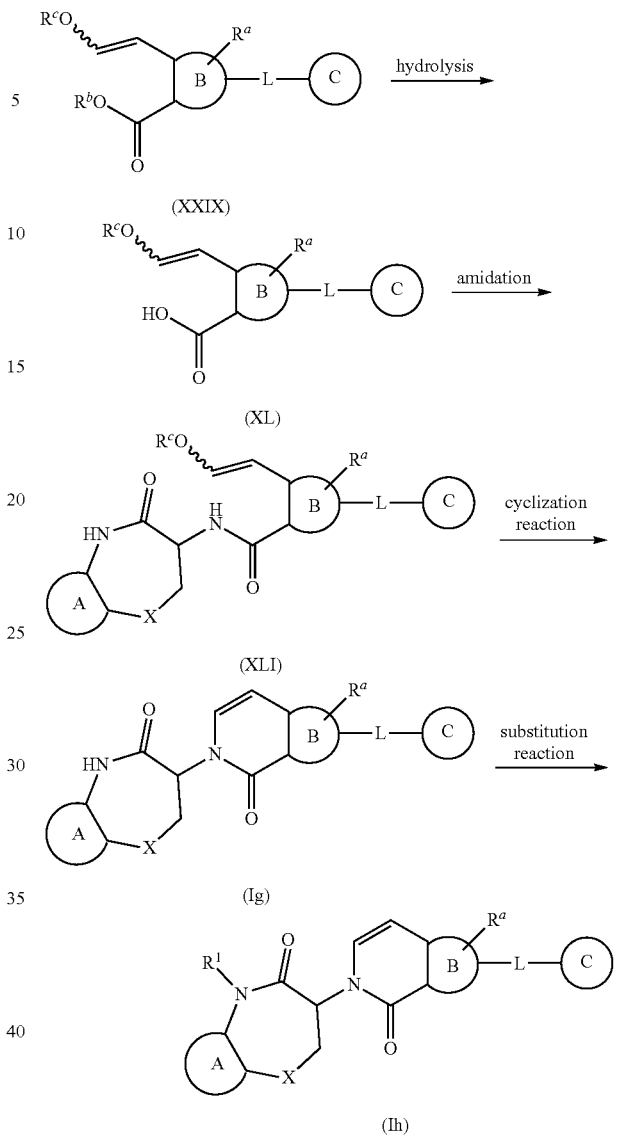

(XXIX)

(XL)

(XLI)

(Ig)

(Ih)

Compound (Ig) can be produced by subjecting compound (XLI) to a cyclization reaction using an acid. Compound (Ih) can be produced by subjecting compound (Ig) to a substitution reaction with an alkyl halide using a base.

The starting compound and/or production intermediate for compound (I) may form a salt. While the salt is not particularly limited as long as the reaction can be performed, examples thereof include those similar to the salts optionally formed by compound (I) and the like.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

Compound (I) may be a hydrate or a non-hydrate.

When desired, compound (I) can be synthesized by performing deprotection reaction, acylation reaction, alkylation reaction, hydrogenation reaction, oxidation reaction, reduction reaction, reaction of carbon chain extension, halogenation reaction, substituent exchange reaction, coupling reaction, nucleophilic addition reaction by a carbo anion, and Grignard reaction singly or two or more thereof in combination.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as phase transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and 1-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

When compound (I) contains a configurational isomer, a diastereomer, a conformer and the like, each can be isolated according to the above-mentioned separation and purification methods, if desired. In addition, when compound (I) is racemic, S-form and R-form can be isolated according to a conventional optical resolution.

When compound (I) contains a stereoisomer, each isomer and a mixture thereof are encompassed in the present invention.

The compounds of the present invention may be particularly useful for the prophylaxis or treatment of RIP1 kinase-mediated diseases or disorders. Such RIP1 kinase-mediated diseases or disorders are diseases or disorders that are mediated by activation of RIP1 kinase, and as such, are diseases or disorders where inhibition of RIP1 kinase would provide benefit. The compounds of the present invention may be particularly useful for the prophylaxis or treatment of diseases/disorders which are likely to be regulated at least in part by programmed necrosis, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondylarthritis, gout and SoJIA), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), hepatitis B, hepatitis C, acute hepatic failure), nephritis, Celiac disease, autoimmune ITP, transplant rejection, ischemia reperfusion injury of solid organs, sepsis, systemic inflammatory response syndrome (SIRS), cerebrovascular accident (CVA), myocardial infarction (MI), Huntington's disease, Alzheimer's disease, Parkinson's disease, allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS) and peridontitis.

The compounds of the present invention may be particularly useful for the prophylaxis or treatment of diseases/disorders which are likely to be regulated at least in part by programmed necrosis, apoptosis or the production of inflammatory cytokines, particularly inflammatory bowel disease (including Crohn's disease and ulcerative colitis), psoriasis, retinal detachment, retinitis pigmentosa, macular degeneration, pancreatitis, atopic dermatitis, arthritis (including rheumatoid arthritis, spondyloarthritis, gout, systemic onset juvenile idiopathic arthritis (SoJIA) and psoriatic arthritis), systemic lupus erythematosus (SLE), Sjogren's syndrome, systemic scleroderma, anti-phospholipid syndrome (APS), vasculitis, osteoarthritis, liver damage/diseases (non-alcohol steatohepatitis, alcohol steatohepatitis, autoimmune hepatitis, autoimmune hepatobiliary diseases, primary sclerosing cholangitis (PSC), acetaminophen toxicity, hepatotoxicity, hepatitis B, hepatitis C, acute hepatic failure), kidney damage/injury (nephritis, renal transplant, surgery, administration of nephrotoxic drugs e.g. cisplatin, acute kidney injury (AKI), chronic kidney disease), Celiac disease, autoimmune idiopathic thrombocytopenic purpura (autoimmune ITP), transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), peridontitis, NEMO (NFκB essential modulator gene) (also known as IKKγ or IKKG) deficiency syndrome, HOIL-1 (heme-oxidized IRP2 ubiquitin ligase-1) (also known as RBCK1) deficiency syndrome, linear ubiquitin chain assembly complex (LUBAC) deficiency syndrome, hematological and solid organ malignancies, bacterial infections and viral infections (such as tuberculosis and influenza), and lysosomal storage diseases (particularly, Gaucher Disease, and including GM2 gangliosidosis, α-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick Disease, neuronal ceroid lipofuscinoses, Pompe disease, pycnodysostosis, Sandhoff disease, Schindler disease, sialic acid storage disease, Tay-Sachs and Wolman disease).

The treatment of the above-mentioned diseases/disorders may concern, more specifically, the amelioration of organ injury or damage sustained as a result of the above-mentioned diseases. For example, the compounds of the present invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with acute hepatic failure, non-alcohol steatohepatitis, alcohol steatohepatitis, autoimmune hepatitis, hepatitis B, hepatitis C, autoimmune hepatobiliary diseases or primary sclerosing cholangitis, or for amelioration of kidney tissue injury or damage associated with acute kidney injury or chronic kidney disease. In addition, the treatment of diseases/disorders selected from those described herein may concern, more specifically, the amelioration of liver tissue injury or damage associated with overdose of acetaminophen, or for amelioration of kidney tissue injury or damage following renal transplant or the administration of nephrotoxic drugs or substances (e.g. cisplatin).

The compounds of the present invention may be particularly useful for the prophylaxis or treatment of inflammatory bowel disease (including Crohn's disease and ulcerative colitis), psoriasis, retinal detachment, retinitis pigmentosa, arthritis (including rheumatoid arthritis, spondylarthritis, gout and SoJIA), transplant rejection, ischemia reperfusion injury of solid organs, multiple sclerosis, and/or tumor necrosis factor receptor-associated periodic syndrome. More specifically, the compounds of the present invention may be particularly useful for the prophylaxis or treatment of inflammatory bowel disease (including Crohn's disease and ulcerative colitis), psoriasis, retinal detachment, retinitis pigmentosa, arthritis (including rheumatoid arthritis, spondyloarthritis, gout and systemic onset juvenile idiopathic arthritis (SoJIA)), transplant rejection, and/or ischemia reperfusion injury of solid organs.

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.), and reduces the risk of CYP induction. The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with ulcerative colitis (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like. Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

The compounds of this invention may be administered in combination with other drug for any of the indications above, including oral, intravenous or topical corticosteroids (e.g., prednisone, bundesonide etc.), anti-TNF preparations (including anti-TNF biologic drugs such as infliximab, adalimumab, certolizumab), 5-aminosalicyclic acid preparations (including mesalamine preparations and sulfasalazine preparations), hydroxycloroquine, thiopurines (including azathioprin, mercaptopurin), methotrexate, cyclophosphamide, cyclosporine, calcineurin inhibitors (including cyclosporine, pimecrolimus, tacrolimus), mycophenolic acid preparations (including mycophenolate mofetil), mTOR inhibitors (including temsirolimus, everolimus), JAK inhibitors (including tofacitinib), CCR9 inhibitors (including vercirnon), Syk inhibitors (including fostamatinib), anti-IL-6 biologics, anti-IL-1 biologics (including anakinra), canakinumab, rilonacept, anti-IL-12 and IL-23 biologics (including ustekinumab), anti-IL-17 biologics (including secukinumab), anti-CD22 biologics (including epratuzumab), anti-integrin preparations (including natalizumab and vedolizumab), anti-IFN-α biologics (including sifalimumab), anti-CD20 or CD4 biologics, antimicrobial drugs (including metronidazole and ciprofloxacin), gatiramer acetate preparations, gene recombinant interferon-β preparations, fingolimod, tecfidera, lquinimod, and other cytokine inhibitors or preparations to T-cell or B-cell receptors or interleukins.

Examples of suitable anti-inflammatory biologic agents include Actemra (registered trademark) (anti-IL6R mAb), anti-CD20 mAbs (rituximab (Rituxan (registered trademark)) and ofatumumab (Arzerra (registered trademark))), abatacept (Orencia (registered trademark)), anakinra (Kineret (registered trademark)), ustekinumab (Stelara (registered trademark)) and belimumab (Benlysta (registered trademark)). Examples of other suitable anti-inflammatory biologic agents include Canakinumab (Ilaris (registered trademark)), rilonacept (Arcalyst (registered trademark)), secukinumab, epratuzumab, sifalimumab and ustekinumab (Stelara (registered trademark)). Examples of suitable anti-TNF agents biologic agents include etanecept (Enbrel (registered trademark)), adalimumab (Humira (registered trademark)), infliximab (Remicade (registered trademark)), certolizumab (Cimzia (registered trademark)), and golimumab (Simponi (registered trademark)).

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent of the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, an appropriate amount of conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In silica gel column chromatography, CO2H means use of N-(1)-oxo-3-carboxypropyl)-3-aminopropylsilane-bonded silica gel, NH means use of aminopropylsilane-bonded silica gel, Diol means use of 3-(2,3-dihydroxypropoxy)propylsilane-bonded silica gel, and DiNH means use of N-(2-aminoethyl)-3-aminopropylsilane-bonded silica gel. In HPLC (high-performance liquid chromatography), C18 means use of octadecyl-bonded silica gel. The ratios of elution solvents are volume mixing ratios, unless otherwise specified.

In Examples, the following abbreviations are used.
mp: melting point
MS: mass spectrum
[M+H]$^+$, [M−H]$^−$: molecular ion peak
M: mol concentration
N: normality
CDCl$_3$: deuterated chloroform
DMSO-d$_6$: deuterated dimethyl sulfoxide
$^1$H NMR: proton nuclear magnetic resonance
LC/MS: liquid chromatograph mass spectrometer
ESI: Electron Spray Ionization
APCI: Atmospheric Pressure Chemical Ionization
THF: tetrahydrofuran
DME: 1,2-dimethoxyethane
DMF: N,N-dimethylformamide
DMA: N,N-dimethylacetamide
HATU: 2-(7-azabenzotriazol-1-yl)-1,1,3,3-tetramethyluronium hexafluorophosphate
HOBt: 1-hydroxybenzotriazole $^1$H NMR was measured by Fourier-transform type NMR. For the analysis, ACD/SpecManager (trade name) and the like were used. Peaks of a hydroxy group, an amino group and the like, which having very mild proton peaks are not described.

MS was measured by LC/MS. As ionization method, ESI method or APCI method was used. The data indicates actual measured value (found). Generally, molecular ion peaks are observed. For example, in the case of a compound having a tert-butoxycarbonyl group, a peak after elimination of a tert-butoxycarbonyl group or a tert-butyl group may be observed as a fragment ion. In the case of a compound having a hydroxy group, a peak after elimination of H$_2$O may be observed as a fragment ion. In the case of a salt, a molecular ion peak or fragment ion peak of free form is generally observed.

The unit of sample concentration (c) for optical rotation ([α]$_D$) is g/100 mL.

Elemental analysis value (Anal.) indicates calculated value (Calcd) and actual measured value (Found).

Example 1

(3S)-3-(2-benzyl-7-oxo-2,4,5,7-tetrahydro-6H-pyrazolo[3,4-c]pyridin-6-yl)-5-methyl-2,3-dihydro-1,5-benzoxazepin-4(5H)-one A) ethyl 1-benzyl-4-formyl-1H-pyrazole-3-carboxylate To a mixture of ethyl 4-formyl-1H-pyrazole-3-carboxylate (2.0 g), potassium carbonate (4.96 g) and DMF (20 mL) was added benzyl bromide (1.56 mL), and the mixture was stirred at room temperature for 3 hr. The reaction mixture was diluted with water, and extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (2.05 g).
MS: [M+H]$^+$ 259.3.

B) ethyl 1-benzyl-4-(2-methoxyvinyl)-1H-pyrazole-3-carboxylate

To a mixture of (methoxymethyl)triphenylphosphonium chloride (995 mg) and THF (5 mL) was added potassium tert-butoxide (326 mg), and the mixture was stirred at room temperature for 1 hr (Mixture A). A solution of ethyl 1-benzyl-4-formyl-1H-pyrazole-3-carboxylate (500 mg) in THF (5 mL) was added to Mixture A, and the mixture was stirred at room temperature for 3 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane). A solution of the obtained mixture in THF (5 mL) was added to Mixture A prepared separately, and the mixture was stirred overnight at room temperature. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (515 mg).
MS: [M+H]$^+$ 287.3.

C) ethyl 1-benzyl-4-(2-oxoethyl)-1H-pyrazole-3-carboxylate

To a solution of ethyl 1-benzyl-4-(2-methoxyvinyl)-1H-pyrazole-3-carboxylate (1.22 g) in THF (10 mL) was added 6 M hydrochloric acid (8 mL), and the mixture was stirred at room temperature for 3 hr. The reaction mixture was diluted with water, and extracted with ethyl acetate. The extract was washed with saturated brine, and dried over anhydrous sodium sulfate, and the solvent was evaporated under reduced pressure to give the title compound (1.13 g).
MS: [M+H]$^+$ 273.2.

D) (S)-ethyl 1-benzyl-4-(2-((5-methyl-4-oxo-2,3,4,5-tetrahydrobenzo[b][1,4]oxazepin-3-yl)amino)ethyl)-1H-pyrazole-3-carboxylate To a solution of ethyl 1-benzyl-4-(2-oxoethyl)-1H-pyrazole-3-carboxylate (0.69 g), (S)-3-amino-5-methyl-2,3-dihydrobenzo[b][1,4]oxazepin-4(5H)-one hydrochloride (0.753 g) and acetic acid (0.5 mL) in methanol (6 mL) was added 2-picoline borane (0.415 g), and the mixture was stirred overnight at room temperature. The solvent of the reaction mixture was evaporated under reduced pressure, to the residue was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (702 mg).
MS: [M+H]$^+$ 449.2.

E) (3S)-3-(2-benzyl-7-oxo-2,4,5,7-tetrahydro-6H-pyrazolo[3,4-c]pyridin-6-yl)-5-methyl-2,3-dihydro-1,5-benzoxazepin-4(5H)-one To a solution of (S)-ethyl 1-benzyl-4-(2-((5-methyl-4-oxo-2,3,4,5-tetrahydrobenzo[b][1,4]oxazepin-3-yl)amino)ethyl)-1H-pyrazole-3-carboxylate (1.07 g) in toluene (5 mL)

was added 1.8 M trimethylaluminium toluene solution (1.325 mL) at 0° C., and the mixture was stirred at room temperature for 1 hr, and then at 100° C. for 3 hr. To the reaction mixture was added saturated aqueous potassium sodium tartrate solution, and the mixture was stirred at room temperature for 30 min, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane, methanol/ethyl acetate) to give the title compound (0.903 g).

$^1$H NMR (300 MHz, CDCl$_3$) δ 2.70 (1H, dt, J=15.5, 4.7 Hz), 3.02-3.21 (1H, m), 3.38 (3H, s), 3.54 (1H, ddd, J=11.8, 10.7, 4.3 Hz), 4.22 (1H, dt, J=11.8, 5.2 Hz), 4.42 (1H, dd, J=10.0, 8.1 Hz), 4.63 (1H, dd, J=11.7, 9.8 Hz), 5.34 (2H, s), 5.96 (1H, dd, J=11.7, 8.3 Hz), 7.11-7.26 (7H, m), 7.29-7.39 (3H, m).

Example 2

(3S)-3-(2-benzyl-9-oxo-6,7-dihydro-5H-[1,2,4]triazolo[1,5-a][1,4]diazepin-8(9H)-yl)-5-methyl-2,3-dihydro-1,5-benzoxazepin-4(5H)-one To a solution of (S)-5-benzyl-N-(5-methyl-4-oxo-2,3,4,5-tetrahydrobenzo[b][1,4]oxazepin-3-yl)-4H-1,2,4-triazole-3-carboxamide (99 mg) and sodium hydride (60%, 23 mg) in DMF (1 mL) was added 1,3-diiodopropane (0.036 mL), and the mixture was stirred at 60° C. for 24 hr. The reaction mixture was purified by silica gel column chromatography (methanol/ethyl acetate), and then silica gel column chromatography (ethyl acetate/hexane). The residue was subjected to preparative HPLC (C18, mobile phase: water/acetonitrile (containing 0.1% TFA)), and the obtained fraction was concentrated under reduced pressure. To the residue was added saturated aqueous sodium hydrogencarbonate solution, and the mixture was extracted with ethyl acetate. The extract was dried over anhydrous sodium sulfate, and the solvent was evaporated under reduced pressure to give the title compound (2 mg).

$^1$H NMR (300 MHz, CDCl$_3$) δ 2.09-2.30 (1H, m), 2.69-2.93 (1H, m), 3.39 (3H, s), 3.41-3.58 (1H, m), 3.77 (1H, dt, J=15.2, 5.8 Hz), 4.00-4.18 (2H, m), 4.32-4.62 (4H, m), 5.77 (1H, dd, J=11.5, 8.1 Hz), 7.07-7.44 (9H, m).

Example 3

3-(2-benzyl-7-oxo-2,4,5,7-tetrahydro-6H-pyrazolo[3,4-c]pyridin-6-yl)-1,3,4,5-tetrahydro-2H-1-benzazepin-2-one A) ethyl 1-benzyl-4-(2-hydroxyethyl)-1H-pyrazole-3-carboxylate A solution of ethyl 1-benzyl-4-(2-oxoethyl)-1H-pyrazole-3-carboxylate (6.12 g) in ethanol (60 mL) was cooled to 0° C., sodium borohydride (1.28 g) was added thereto, and the mixture was stirred at room temperature for 30 min. To the reaction mixture was added water, and the solvent was evaporated under reduced pressure. The residue was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (4.39 g).

MS: [M+H]$^+$ 275.3.

B) ethyl 1-benzyl-4-(2-((2-oxo-2,3,4,5-tetrahydro-1H-benzo[b]azepin-3-yl)amino)ethyl)-1H-pyrazole-3-carboxylate A solution of ethyl 1-benzyl-4-(2-hydroxyethyl)-1H-pyrazole-3-carboxylate (264 mg) and methanesulfonyl chloride (165 mg) in THF (3 mL) was cooled to 0° C., triethylamine (0.201 mL) was added thereto, and the mixture was stirred at room temperature for 2 hr. To the reaction mixture was added water, and the mixture was extracted with ethyl acetate. The extract was washed with saturated brine, and dried over anhydrous sodium sulfate, and the solvent was evaporated under reduced pressure. The residue was dissolved in acetonitrile (3 mL), potassium iodide (32 mg) and 3-amino-4,5-dihydro-1H-benzo[b]azepin-2(3H)-one (252 mg) were added thereto, and the mixture was stirred under microwave irradiation in a sealed tube at 100° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (133 mg).

MS: [M+H]$^+$ 433.3.

C) 3-(2-benzyl-7-oxo-2,4,5,7-tetrahydro-6H-pyrazolo[3,4-c]pyridin-6-yl)-1,3,4,5-tetrahydro-2H-1-benzazepin-2-one To a solution of ethyl 1-benzyl-4-(2-((2-oxo-2,3,4,5-tetrahydro-1H-benzo[b]azepin-3-yl)amino)ethyl)-1H-pyrazole-3-carboxylate (133 mg) in toluene (3 mL) was added 1.4 M trimethylaluminium hexane solution (0.546 mL), and the mixture was stirred at 100° C. for 3 hr. To the reaction mixture was added saturated aqueous potassium sodium tartrate solution, and the mixture was stirred for 30 min, and extracted with ethyl acetate. The extract was washed with saturated brine, and dried over anhydrous sodium sulfate, and the solvent was evaporated under reduced pressure. The residue was purified by silica gel column chromatography (methanol/ethyl acetate). The obtained solid was washed with a mixed solution of ethyl acetate/heptane to give the title compound (27 mg).

$^1$H NMR (300 MHz, CDCl$_3$) δ 2.28-2.52 (2H, m), 2.63-2.84 (2H, m), 2.90-3.11 (2H, m), 3.57 (1H, ddd, J=12.0, 10.3, 4.5 Hz), 4.01-4.14 (1H, m), 5.34 (2H, s), 5.62 (1H, dd, J=11.3, 8.7 Hz), 6.99 (1H, d, J=7.9 Hz), 7.10-7.21 (2H, m), 7.22-7.41 (8H, m).

Example 4

3-(2-benzyl-6-oxo-2,6-dihydropyrrolo[3,4-c]pyrazol-5(4H)-yl)-1,3,4,5-tetrahydro-2H-1-benzazepin-2-one A) ethyl 1-benzyl-4-(hydroxymethyl)-1H-pyrazole-3-carboxylate To a solution of ethyl 1-benzyl-4-formyl-1H-pyrazole-3-carboxylate (500 mg) in ethanol (5 mL) was added sodium borohydride (110 mg) at 0° C., and the mixture was stirred at room temperature for 2 hr. To the reaction mixture was added water, and the mixture was extracted with ethyl acetate. The extract was washed with saturated brine, and dried over anhydrous sodium sulfate, and the solvent was evaporated under reduced pressure to give the title compound (478 mg).

MS, found: 283.3.

B) ethyl 1-benzyl-4-(((2-oxo-2,3,4,5-tetrahydro-1H-benzo[b]azepin-3-yl)amino)methyl)-1H-pyrazole-3-carboxylate A solution of ethyl 1-benzyl-4-(hydroxymethyl)-1H-pyrazole-3-carboxylate (478 mg) and methanesulfonyl chloride (0.284 mL) in THF (3 mL) was cooled to 0° C., triethylamine (0.512 mL) was added thereto, and the mixture was stirred at room temperature for 1 hr. To the reaction mixture were added again methanesulfonyl chloride (0.284 mL) and triethylamine (0.512 mL), and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was dissolved in acetonitrile (10 mL), potassium iodide (61 mg) and 3-amino-4,5-dihydro-1H-benzo[b]azepin-2(3H)-one (648 mg) were added thereto, and the mixture was stirred under microwave irradiation in a sealed tube at 120° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (25 mg).

MS: [M+H]$^+$ 419.3.

C) 3-(2-benzyl-6-oxo-2,6-dihydropyrrolo[3,4-c]pyrazol-5(4H)-yl)-1,3,4,5-tetrahydro-2H-1-benzazepin-2-one To a solution of ethyl 1-benzyl-4-(((2-oxo-2,3,4,5-tetrahydro-1H-benzo[b]azepin-3-yl)amino)methyl)-1H-pyrazole-3-carboxylate (25 mg) in toluene (2 mL) was added 1.4 M trimethylaluminium hexane solution (0.107 mL), and the mixture was stirred at 100° C. for 3 hr. To the reaction mixture was added saturated aqueous potassium sodium tartrate solution, and the mixture was stirred at room temperature for 30 min, and extracted with ethyl acetate. The extract was washed with saturated brine, and dried over anhydrous sodium sulfate, and the solvent was evaporated under reduced pressure. The residue was subjected to preparative HPLC (C18, mobile phase: water/acetonitrile (containing 0.1% TFA)). To the obtained fraction was added saturated aqueous sodium hydrogencarbonate solution, and the mixture was extracted with ethyl acetate. The extract was dried over anhydrous sodium sulfate, and the solvent was evaporated under reduced pressure to give the title compound (1 mg).

$^1$H NMR (300 MHz, CDCl$_3$) δ 2.29-2.45 (1H, m), 2.47-2.63 (1H, m), 2.78 (1H, dd, J=14.2, 6.6 Hz), 2.93-3.09 (1H, m), 4.32 (1H, d, J=15.5 Hz), 5.03 (1H, d, J=15.5 Hz), 5.13 (1H, dd, J=12.3, 8.1 Hz), 5.41 (2H, s), 7.03 (1H, d, J=7.9 Hz), 7.14-7.42 (10H, m).

Example 5

3-(2-benzyl-7-oxo-2,7-dihydro-6H-pyrazolo[3,4-c]pyridin-6-yl)-1,3,4,5-tetrahydro-2H-1-benzazepin-2-one A) 1-benzyl-4-(2-methoxyvinyl)-N-(2-oxo-2,3,4,5-tetrahydro-1H-benzo[b]azepin-3-yl)-1H-pyrazole-3-carboxamide To a solution of ethyl 1-benzyl-4-(2-methoxyvinyl)-1H-pyrazole-3-carboxylate (811 mg) in a mixed solvent of THF (5 mL) and ethanol (5 mL) was added 2 M aqueous sodium hydroxide solution (4.25 mL), and the mixture was stirred at room temperature for 1 hr, and then at 50° C. for 2 hr. The reaction mixture was neutralized with 1 M hydrochloric acid, and extracted with ethyl acetate. The extract was washed with saturated brine, and dried over anhydrous sodium sulfate, and the solvent was evaporated under reduced pressure. The residue was dissolved in DMF (7 mL), 3-amino-4,5-dihydro-1H-benzo[b]azepin-2(3H)-one (426 mg), HATU (1.19 g) and N,N'-diisopropylethylamine (1.26 mL) were added thereto, and the mixture was stirred at room temperature for 1 hr, and then at 50° C. for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (347 mg).

MS: [M+H]$^+$ 417.2.

B) 3-(2-benzyl-7-oxo-2,7-dihydro-6H-pyrazolo[3,4-c]pyridin-6-yl)-1,3,4,5-tetrahydro-2H-1-benzazepin-2-one A mixture of a solution of 1-benzyl-4-(2-methoxyvinyl)-N-(2-oxo-2,3,4,5-tetrahydro-1H-benzo[b]azepin-3-yl)-1H-pyrazole-3-carboxamide (347 mg) in THF (5 mL) and trifluoroacetic acid (5 mL) was stirred at 70° C. for 30 min. The reaction mixture was concentrated under reduced pressure, and the residue was purified by silica gel column chromatography (ethyl acetate/hexane). The residue was subjected to preparative HPLC (C18, mobile phase: water/acetonitrile (containing 0.1% TFA)), and the obtained fraction was concentrated under reduced pressure. The obtained solid was washed with water to give the title compound (106 mg).

$^1$H NMR (400 MHz, CDCl$_3$) δ 2.44-2.63 (2H, m), 2.83 (1H, dd, J=13.9, 4.9 Hz), 3.11 (1H, td, J=13.5, 7.7 Hz), 5.51 (2H, s), 6.08 (1H, dd, J=11.5, 8.8 Hz), 6.42 (1H, d, J=7.6 Hz), 7.05 (1H, d, J=7.8 Hz), 7.14 (1H, d, J=7.6 Hz), 7.18-7.24 (1H, m), 7.27-7.41 (8H, m), 7.50-7.59 (1H, m).

Example 6

3-(2-benzyl-7-oxo-2,7-dihydro-6H-pyrazolo[3,4-c]pyridin-6-yl)-1-methyl-1,3,4,5-tetrahydro-2H-1-benzazepin-2-one To a solution of 3-(2-benzyl-7-oxo-2,7-dihydro-6H-pyrazolo[3,4-c]pyridin-6-yl)-1,3,4,5-tetrahydro-2H-1-benzazepin-2-one (103 mg) in DMF (1 mL) was added sodium hydride (60%, 16 mg) at 0° C., and the mixture was stirred at 0° C. for 5 min. Iodomethane (0.042 mL) was added thereto, and the mixture was stirred overnight at room temperature. The reaction mixture was purified by silica gel column chromatography (ethyl acetate/hexane). The obtained mixture was dissolved in ethyl acetate, and the solution was washed with water and saturated brine, and dried over anhydrous sodium sulfate, and the solvent was evaporated under reduced pressure. The obtained solid was recrystallized from ethyl acetate/heptane to give the title compound (38 mg).
$^1$H NMR (300 MHz, CDCl$_3$) δ2.30-2.60 (2H, m), 2.67-2.84 (1H, m), 2.91-3.12 (1H, m), 3.40 (3H, s), 5.50 (2H, s), 6.01 (1H, dd, J=11.7, 8.3 Hz), 6.40 (1H, d, J=7.6 Hz), 7.16-7.42 (10H, m), 7.53 (1H, s).

Example 7

(3S)-3-(2-benzyl-8-oxo-5,6-dihydroimidazo[1,2-a]pyrazin-7(8H)-yl)-5-methyl-2,3-dihydro-1,5-benzoxazepin-4(5H)-one A) ethyl 4-benzyl-1H-imidazole-2-carboxylate To a solution of 1-amino-3-phenylpropan-2-one hydrochloride (0.93 g) and ethyl 2-ethoxy-2-iminoacetate (0.727 g) in acetic acid (10 mL) was added sodium acetate (0.74 g), and the mixture was stirred in a sealed tube at 110° C. for 6 hr. The reaction mixture was concentrated under reduced pressure, saturated aqueous sodium hydrogencarbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (105 mg).
MS: [M+H]$^+$ 231.3.

B) (S)-4-benzyl-N-(5-methyl-4-oxo-2,3,4,5-tetrahydrobenzo[b][1,4]oxazepin-3-yl)-1H-imidazole-2-carboxamide To a solution of ethyl 4-benzyl-1H-imidazole-2-carboxylate (105 mg) in ethanol (1 mL) was added 2 M aqueous sodium hydroxide solution (0.684 mL), and the mixture was stirred at 100° C. for 30 min. The reaction mixture was concentrated under reduced pressure, DMF (2 mL), HATU (225 mg), N,N'-diisopropylethylamine (0.238 mL) and (S)-3-amino-5-methyl-2,3-dihydrobenzo[b][1,4]oxazepin-4 (5H)-one hydrochloride (136 mg) were added thereto, and the mixture was stirred at room temperature for 2 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (101 mg).
MS: [M+H]$^+$ 377.2.

C) (3S)-3-(2-benzyl-8-oxo-5,6-dihydroimidazo[1,2-a]pyrazin-7(8H)-yl)-5-methyl-2,3-dihydro-1,5-benzoxazepin-4(5H)-one To a solution of (S)-4-benzyl-N-(5-methyl-4-oxo-2,3,4,5-tetrahydrobenzo[b][1,4]oxazepin-3-yl)-1H-imidazole-2-carboxamide (89 mg) and 1,2-dibromoethane (0.072 mL) in DMF (2 mL) was added cesium carbonate (308 mg), and the mixture was stirred at 100° C. for 2 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (methanol/ethyl acetate), and subjected to preparative HPLC (C18, mobile phase: water/acetonitrile (containing 0.1% TFA)). To the obtained fraction was added saturated aqueous sodium hydrogencarbonate solution, and the mixture was extracted with ethyl acetate. The extract was dried over anhydrous sodium sulfate, and the solvent was evaporated under reduced pressure to give the title compound (3 mg).
$^1$H NMR (300 MHz, CDCl$_3$) δ3.37 (3H, s), 3.74 (1H, td, J=11.6, 4.0 Hz), 3.99 (2H, s), 4.06 (1H, dt, J=12.6, 3.9 Hz), 4.28-4.66 (4H, m), 5.89 (1H, dd, J=11.7, 8.3 Hz), 6.56 (1H, s), 7.15-7.34 (9H, m).

Example 8

(3S)-3-(2-benzyl-8-oxo-5,6-dihydro[1,2,4]triazolo[1,5-a]pyrazin-7(8H)-yl)-5-methyl-2,3-dihydro-1,5-benzoxazepin-4(5H)-one To a solution of (S)-5-benzyl-N-(5-methyl-4-oxo-2,3,4,5-tetrahydrobenzo[b][1,4]oxazepin-3-yl)-4H-1,2,4-triazole-3-carboxamide (47 mg) and sodium hydride (60%, 11 mg) in DMF (1 mL) was added 1,2-dibromoethane (0.013 mL), and the mixture was stirred at 60° C. for 24 hr. The residue was purified by silica gel column chromatography (methanol/ethyl acetate), and the obtained mixture was purified again by silica gel column chromatography (ethyl acetate/hexane) to give the title compound (11 mg).
$^1$H NMR (300 MHz, CDCl$_3$) δ 3.38 (3H, s), 3.82 (1H, ddd, J=12.4, 11.0, 4.2 Hz), 4.06-4.18 (2H, m), 4.34-4.80 (5H, m), 5.82 (1H, dd, J=11.7, 8.3 Hz), 7.14-7.40 (9H, m).

Example 9

(3S)-3-(2-(2-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one A) (S)-5-methyl-3-(7-oxo-4,5-dihydro-2H-pyrazolo[3,4-c]pyridin-6 (7H)-yl)-2,3-dihydrobenzo[b][1,4]oxazepin-4(5H)-one A mixture of (3S)-3-(2-benzyl-7-oxo-2,4,5,7-tetrahydro-6H-pyrazolo[3,4-c]pyridin-6-yl)-5-methyl-2,3-dihydro-1,5-benzoxazepin-4(5H)-one (729 mg), palladium hydroxide/carbon (palladium hydroxide 20%, about 50% wet product in water) (382 mg) and 1 M hydrochloric acid (5 mL) in methanol (20 mL) was stirred under hydrogen atmosphere overnight at room temperature. The reaction mixture was filtered, and the filtrate was concentrated under reduced pressure. The obtained residue was washed with heptane/ethyl acetate to give the title compound (545 mg).
MS: [M+H]$^+$ 313.2.

B) (3S)-3-(2-(2-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one To a mixture of (S)-5-methyl-3-(7-oxo-4,5-dihydro-2H-pyrazolo[3,4-c]pyridin-6(7H)-yl)-2,3-dihydrobenzo[b][1,4]oxazepin-4(5H)-one (26 mg) and potassium carbonate (35 mg) in DMF (1 mL) was added 2-fluorobenzyl bromide (0.012 mL), and the mixture was stirred overnight at room temperature. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (18 mg).

$^1$H NMR (300 MHz, CDCl$_3$) δ2.71 (1H, dt, J=15.5, 4.7 Hz), 3.11 (1H, ddd, J=15.3, 10.4, 4.9 Hz), 3.38 (3H, s), 3.47-3.60 (1H, m), 4.22 (1H, dt, J=12.0, 5.1 Hz), 4.41 (1H, dd, J=10.0, 8.1 Hz), 4.62 (1H, dd, J=11.7, 10.2 Hz), 5.40 (2H, s), 5.94 (1H, dd, J=11.7, 8.3 Hz), 7.01-7.26 (8H, m), 7.27-7.36 (1H, m).

Example 10

(3S)-3-(2-benzyl-3-bromo-7-oxo-2,4,5,7-tetrahydro-6H-pyrazolo[3,4-c]pyridin-6-yl)-5-methyl-2,3-dihydro-1,5-benzoxazepin-4(5H)-one A) ethyl 1-benzyl-5-hydroxy-1H-pyrazole-3-carboxylate To a mixture of benzyl hydrazine dihydrochloride (25 g) and potassium carbonate (30.1 g) in ethanol (250 mL) was added diethyl but-2-ynedioate (21.8 g), and the mixture was stirred at 90° C. for 5 hr. To the reaction mixture were added 6 M hydrochloric acid (65 mL) and water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (6.4 g).
MS: [M+H]$^+$ 247.3.

B) ethyl 1-benzyl-5-bromo-4-formyl-1H-pyrazole-3-carboxylate

To a mixture of ethyl 1-benzyl-5-hydroxy-1H-pyrazole-3-carboxylate (3.60 g), phosphoryl bromide (7.80 g) and 1,2-dichloroethane (60 mL) was added DMF (2.1 mL), and the mixture was stirred at 90° C. for 3 hr. The reaction mixture was cooled to room temperature, phosphoryl bromide (19.6 g) was added again thereto, and the mixture was stirred at 90° C. for 19 hr. To the reaction mixture was added again phosphoryl bromide (9.64 g), and the mixture was stirred at 90° C. for 3 hr. The reaction mixture was poured into ice water, and the aqueous layer was extracted with ethyl acetate. The extract was dried over anhydrous sodium sulfate, and the solvent was evaporated under reduced pressure. The residue was purified by silica gel column chromatography (ethyl acetate/hexane) to give the title compound (2.34 g).
MS: [M+H]$^+$ 337.1.

C) (E)-ethyl 1-benzyl-5-bromo-4-(2-methoxyvinyl)-1H-pyrazole-3-carboxylate

To a mixture of (methoxymethyl)triphenylphosphonium chloride (346 mg) and THF (3 mL) was added potassium tert-butoxide (113 mg), and the mixture was stirred under argon atmosphere, under ice-cooling for 5 min. To the reaction mixture was added a solution of ethyl 1-benzyl-5-bromo-4-formyl-1H-pyrazole-3-carboxylate (170 mg) in THF (2 mL) under ice-cooling, and the mixture was stirred under argon atmosphere at room temperature for 3 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (55 mg).
MS: [M+H]$^+$ 365.1.

D) ethyl 1-benzyl-5-bromo-4-(2-(((3S)-5-methyl-4-oxo-2,3,4,5-tetrahydro-1,5-benzoxazepin-3-yl)amino)ethyl)-1H-pyrazole-3-carboxylate To a solution of (E)-ethyl 1-benzyl-5-bromo-4-(2-methoxyvinyl)-1H-pyrazole-3-carboxylate (55 mg) in THF (5 mL) was added 6M hydrochloric acid (1.0 mL), and the mixture was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure. To a solution of the obtained crude product, (S)-3-amino-5-methyl-2,3-dihydrobenzo[b][1,4]oxazepin-4(5H)-one hydrochloride (45 mg) and acetic acid (0.5 mL) in methanol (5 mL) was added 2-picoline borane (21 mg) at 0° C., and the mixture was stirred at room temperature for 30 min. To the reaction mixture was added water, and the mixture was extracted with ethyl acetate. The extract was washed with saturated aqueous sodium hydrogencarbonate solution and saturated brine, and dried over anhydrous sodium sulfate, and the solvent was evaporated under reduced pressure. The residue was purified by silica gel column chromatography (ethyl acetate/hexane) to give the title compound (55 mg).
MS: [M+H]$^+$ 527.1.

E) (3S)-3-(2-benzyl-3-bromo-7-oxo-2,4,5,7-tetrahydro-6H-pyrazolo[3,4-c]pyridin-6-yl)-5-methyl-2,3-dihydro-1,5-benzoxazepin-4(5H)-one To a solution of ethyl 1-benzyl-5-bromo-4-(2-(((3S)-5-methyl-4-oxo-2,3,4,5-tetrahydro-1,5-benzoxazepin-3-yl)amino)ethyl)-1H-pyrazole-3-carboxylate (55 mg) in toluene (5 mL) was added 1.4 M trimethylaluminium hexane solution (0.22 mL) under ice-cooling, and the mixture was stirred under argon atmosphere at 100° C. for 3 hr. To the reaction mixture was added saturated aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (45 mg).
$^1$H NMR (300 MHz, DMSO-d$_6$) δ 2.56-2.70 (1H, m), 2.71-2.84 (1H, m), 3.30 (3H, s), 3.63 (1H, ddd, J=12.7, 8.2, 5.1 Hz), 3.95-4.10 (1H, m), 4.34 (1H, dd, J=10.2, 7.9 Hz), 4.83 (1H, dd, J=12.1, 10.2 Hz), 5.44 (2H, s), 5.54 (1H, dd, J=11.9, 7.7 Hz), 7.12-7.20 (2H, m), 7.21-7.40 (6H, m), 7.46-7.53 (1H, m).

Example 11

(3S)-3-(2-benzyl-3-methyl-7-oxo-2,4,5,7-tetrahydro-6H-pyrazolo[3,4-c]pyridin-6-yl)-5-methyl-2,3-dihydro-1,5-benzoxazepin-4(5H)-one To a solution of (3S)-3-(2-benzyl-3-bromo-7-oxo-2,4,5,7-tetrahydro-6H-pyrazolo[3,4-c]pyridin-6-yl)-5-methyl-2,3-dihydro-1,5-benzoxazepin-4(5H)-one (25 mg), tetrakis (triphenylphosphine)palladium(0) (6 mg) and trimethylboroxin (7 mg) in THF (5 mL) was added 0.1 M potassium hydroxide aqueous solution (1.0 mL) at room temperature, and the mixture was stirred under argon atmosphere at 100° C. for 1 hr, and then overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) and then silica gel column chromatography (NH, ethyl acetate/hexane). The obtained crude product was subjected to preparative HPLC (C18, mobile phase: water/acetonitrile (containing 0.1% TFA)), and the obtained fraction was concentrated under reduced pressure. To the residue was added saturated aqueous sodium hydrogencarbonate solution, and the mixture was extracted with ethyl acetate. The extract was dried over anhydrous sodium sulfate, and the solvent was evaporated under reduced pressure. The residue was purified by silica gel column chromatography (NH, ethyl acetate/hexane) to give the title compound (2 mg).

$^1$H NMR (300 MHz, CDCl$_3$) δ 2.10 (3H, s), 2.60 (1H, dt, J=15.3, 4.8 Hz), 3.01 (1H, ddd, J=15.2, 10.4, 4.7 Hz), 3.38 (3H, s), 3.55 (1H, ddd, J=11.8, 10.5, 4.3 Hz), 4.24 (1H, dt, J=11.9, 5.2 Hz), 4.43 (1H, dd, J=9.9, 8.2 Hz), 4.64 (1H, dd, J=11.5, 10.0 Hz), 5.35 (2H, s), 5.97 (1H, dd, J=11.6, 8.2 Hz), 7.07-7.36 (9H, m).

Example 12

2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carbonitrile To a solution of (3S)-3-(2-benzyl-3-bromo-7-oxo-2,4,5,7-tetrahydro-6H-pyrazolo[3,4-c]pyridin-6-yl)-5-methyl-2,3-dihydro-1,5-benzoxazepin-4(5H)-one (15 mg) in DMF (5 mL) were added tetrakis(triphenylphosphine)palladium(0) (4 mg) and zinc dicyanide (7 mg) at room temperature, and the mixture was stirred under argon atmosphere at 100° C. for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) and then silica gel column chromatography (NH, ethyl acetate/hexane) to give the title compound (12 mg).

$^1$H NMR (300 MHz, CDCl$_3$) δ 2.86 (1H, dt, J=16.2, 4.7 Hz), 3.24 (1H, ddd, J=16.1, 10.6, 5.1 Hz), 3.38 (3H, s), 3.57 (1H, ddd, J=12.1, 10.6, 4.2 Hz), 4.29 (1H, dt, J=12.3, 5.0 Hz), 4.41 (1H, dd, J=9.8, 8.3 Hz), 4.62 (1H, dd, J=11.7, 9.8 Hz), 5.50 (2H, s), 5.88 (1H, dd, J=11.5, 8.1 Hz), 7.11-7.42 (9H, m).

Example 13

(3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile A) (S)-ethyl 1-benzyl-4-(2-((8-bromo-5-methyl-4-oxo-2,3,4,5-tetrahydrobenzo[b][1,4]oxazepin-3-yl)amino)ethyl)-1H-pyrazole-3-carboxylate To a solution of ethyl 1-benzyl-4-(2-oxoethyl)-1H-pyrazole-3-carboxylate (0.64 g), (S)-3-amino-8-bromo-5-methyl-2,3-dihydrobenzo[b][1,4]oxazepin-4(5H)-one hydrochloride (0.759 g) and acetic acid (1.5 mL) in methanol (15 mL) was added 2-picoline borane (0.327 g) at 0° C., and the mixture was stirred at room temperature for 30 min. To the reaction mixture was added saturated sodium hydrogencarbonate, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (0.83 g).

MS: [M+H]$^+$ 527.1.

B) (3S)-3-(2-benzyl-7-oxo-2,4,5,7-tetrahydro-6H-pyrazolo[3,4-c]pyridin-6-yl)-8-bromo-5-methyl-2,3-dihydro-1,5-benzoxazepin-4(5H)-one To a solution of (S)-ethyl 1-benzyl-4-(2-((8-bromo-5-methyl-4-oxo-2,3,4,5-tetrahydrobenzo[b][1,4]oxazepin-3-yl)amino)ethyl)-1H-pyrazole-3-carboxylate (0.82 g) in toluene (50 mL) was added 1.8 M trimethylaluminium toluene solution (2.59 mL) at 0° C., and the mixture was stirred at room temperature for 1 hr, and then overnight at 100° C. To the reaction mixture was added saturated aqueous ammonium chloride solution, and the mixture was diluted with ethyl acetate. The obtained mixture was filtered through Celite, and the organic layer was washed with saturated brine, and dried over anhydrous sodium sulfate, and the solvent was evaporated under reduced pressure. The residue was purified by silica gel column chromatography (ethyl acetate/hexane) to give the title compound (0.59 g).

MS: [M+H]$^+$ 481.1.

C) (3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile To a solution of (3S)-3-(2-benzyl-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (150 mg) in DMF (5 mL) were added tetrakis(triphenylphosphine)palladium(0) (36 mg) and zinc dicyanide (73 mg), and the mixture was stirred under nitrogen atmosphere at 100° C. for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (15 mg).

$^1$H NMR (300 MHz, CDCl$_3$) δ 2.72 (1H, dt, J=15.6, 4.7 Hz), 3.00-3.16 (1H, m), 3.39 (3H, s), 3.47-3.61 (1H, m), 4.12-4.24 (1H, m), 4.45 (1H, dd, J=10.0, 8.1 Hz), 4.69 (1H, dd, J=11.9, 10.0 Hz), 5.35 (2H, s), 5.94 (1H, dd, J=11.9, 8.1 Hz), 7.15 (1H, s), 7.21-7.40 (6H, m), 7.47 (1H, d, J=1.9 Hz), 7.56 (1H, dd, J=8.3, 1.9 Hz).

Example 14

(3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile A) ethyl 1-benzyl-4-(2-iodoethyl)-1H-pyrazole-3-carboxylate To a mixture of ethyl 1-benzyl-4-(2-hydroxyethyl)-1H-pyrazole-3-carboxylate (2.69 g), triphenylphosphine (3.86 g) and iodine (3.73 g) in toluene (20 mL) and THF (20 mL) was added imidazole (1.00 g), and the mixture was stirred at room temperature for 2 hr. The reaction mixture was filtered, and the filtrate was concentrated under reduced pressure. The residue was purified by silica gel column chromatography (ethyl acetate/hexane) to give the title compound (3.66 g).

MS: [M+H]$^+$ 385.1.

B) (S)-ethyl 1-benzyl-4-(2-((7-bromo-5-methyl-4-oxo-2,3,4,5-tetrahydrobenzo[b][1,4]oxazepin-3-yl)amino)ethyl)-1H-pyrazole-3-carboxylate (S)-3-Amino-7-bromo-5-methyl-2,3-dihydrobenzo[b][1,4]oxazepin-4(5H)-one hydrochloride (700 mg) was dissolved in methanol, and the solution was purified by silica gel column chromatography (NH, methanol). To a solution of the obtained compound (573 mg) and ethyl 1-benzyl-4-(2-iodoethyl)-1H-pyrazole-3-carboxylate (700 mg) in acetonitrile (10 mL) was added N,N'-diisopropylethylamine (0.317 mL), and the mixture was stirred under microwave irradiation at 100° C. for 3 hr. The reaction mixture was concentrated under reduced pressure, and the residue was purified by silica gel column chromatography (ethyl acetate/hexane) to give the title compound (622 mg).

MS: [M+H]$^+$ 527.1.

C) (3S)-3-(2-benzyl-7-oxo-2,4,5,7-tetrahydro-6H-pyrazolo[3,4-c]pyridin-6-yl)-7-bromo-5-methyl-2,3-dihydro-1,5-benzoxazepin-4(5H)-one To a solution of (S)-ethyl 1-benzyl-4-(2-((7-bromo-5-methyl-4-oxo-2,3,4,5-tetrahydrobenzo[b][1,4]oxazepin-3-yl)amino)ethyl)-1H-pyrazole-3-carboxylate (622 mg) in toluene (6 mL) was added 1.8 M trimethylaluminium toluene solution (0.655 mL) at 0° C., and the mixture was stirred at room temperature for 1 hr, and then at 100° C. for 2 hr. To the reaction mixture was added saturated aqueous potassium sodium tartrate solution, and the mixture was stirred at room temperature for 30 min, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane, methanol/ethyl acetate) to give the title compound (175 mg).

MS: [M+H]$^+$ 481.1.

D) (3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile To a solution of (3S)-3-(2-benzyl-7-oxo-2,4,5,7-tetrahydro-6H-pyrazolo[3,4-c]pyridin-6-yl)-7-bromo-5-methyl-2,3-dihydro-1,5-benzoxazepin-4(5H)-one (76 mg) in DMF (1 mL) were added tetrakis(triphenylphosphine)palladium (0) (18 mg) and zinc dicyanide (37 mg), and the mixture was stirred under argon atmosphere at 100° C. for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane), and crystallized from methanol to give the title compound (18 mg).

$^1$H NMR (300 MHz, CDCl$_3$) δ2.71 (1H, dt, J=15.6, 4.7 Hz), 3.00-3.16 (1H, m), 3.39 (3H, s), 3.48-3.59 (1H, m), 4.18 (1H, dt, J=12.0, 5.1 Hz), 4.46 (1H, dd, J=10.0, 7.7 Hz), 4.73 (1H, dd, J=11.7, 9.8 Hz), 5.35 (2H, s), 5.93 (1H, dd, J=11.9, 7.7 Hz), 7.15 (1H, s), 7.21-7.28 (3H, m), 7.31-7.39 (3H, m), 7.49-7.56 (2H, m).

Example 15

3-(2-benzyl-4-oxo-4,6-dihydro-5H-pyrrolo[3,4-d][1,3]thiazol-5-yl)-1,3,4,5-tetrahydro-2H-1-benzazepin-2-one

A) ethyl 2-benzyl-5-((benzyloxy)methyl)thiazole-4-carboxylate

To a solution of ethyl 2,2-dichloroacetate (5 g) and 2-(benzyloxy)acetaldehyde (4.11 mL) in diethyl ether (200 mL) was added sodium acetate (10.84 g) at 0° C., and the mixture was stirred at 0° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was dissolved in ethanol (150 mL), 2-phenylethanethioamide (3.85 g) was added thereto, and the mixture was stirred at 90° C. for 4 hr. The reaction mixture was concentrated under reduced pressure, and the residue was purified by silica gel column chromatography (ethyl acetate/hexane). The obtained compound was purified again by silica gel column chromatography (NH, ethyl acetate/hexane) to give the title compound (0.600 g).

MS: [M+H]$^+$ 368.2.

B) ethyl 2-benzyl-5-(hydroxymethyl)thiazole-4-carboxylate

A mixture of ethyl 2-benzyl-5-((benzyloxy)methyl)thiazole-4-carboxylate (600 mg), palladium/carbon (palladium 10%, about 50% wet product in water) (1.91 g) and acetic acid (1 mL) in methanol (10 mL) was stirred overnight under hydrogen atmosphere at 40° C. The reaction mixture was filtered, the filtrate was concentrated under reduced pressure, and the residue was purified by silica gel column chromatography (ethyl acetate/hexane) to give the title compound (35 mg).

MS: [M+H]$^+$ 278.3.

C) ethyl 2-benzyl-5-(((2-oxo-2,3,4,5-tetrahydro-1H-benzo[b]azepin-3-yl)amino)methyl)thiazole-4-carboxylate To a solution of ethyl 2-benzyl-5-(hydroxymethyl)thiazole-4-carboxylate (10 mg) and triethylamine (7.3 mg) in THF (3 mL) was added methanesulfonyl chloride (8.26 mg) at 0° C., and the mixture was stirred under nitrogen atmosphere at 0° C. for 1 hr. To the reaction mixture was added water, and the mixture was extracted with ethyl acetate. The extract was washed with saturated brine, and dried over anhydrous sodium sulfate, and the solvent was evaporated under reduced pressure. The residue was dissolved in DMF (3 mL), N-ethyl-N-isopropylpropan-2-amine (4.66 mg) and 3-amino-4,5-dihydro-1H-benzo[b]azepin-2(3H)-one (6.35 mg) were added thereto, and the mixture was stirred at 80° C. for 3 hr. To the reaction mixture was added water, and the mixture was extracted with ethyl acetate. The extract was washed with water and saturated brine, and dried over anhydrous sodium sulfate, and the solvent was evaporated D) 3-(2-benzyl-4-oxo-4,6-dihydro-5H-pyrrolo[3,4-d][1,3]thiazol-5-yl)-1,3,4,5-tetrahydro-2H-1-benzazepin-2-one To a solution of ethyl 2-benzyl-5-(((2-oxo-2,3,4,5-tetrahydro-1H-benzo[b]azepin-3-yl)amino)methyl)thiazole-4-carboxylate (8 mg) in toluene (3 mL) was added 1.4 M trimethylaluminium hexane solution (0.039 mL), and the mixture was stirred under argon atmosphere at 100° C. for 3 hr. To the reaction mixture was added aqueous ammonium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate). The residue was subjected to preparative HPLC (C18, mobile phase: water/acetonitrile (containing 0.1% TFA)), and the obtained fraction was concentrated under reduced pressure. To the residue was added saturated aqueous sodium hydrogencarbonate solution, and the mixture was extracted with ethyl acetate. The extract was dried over anhydrous sodium sulfate, and the solvent was evaporated under reduced pressure to give the title compound (1 mg).
$^1$H NMR (300 MHz, CDCl$_3$) δ 2.30-2.58 (2H, m), 2.79 (1H, dd, J=14.0, 5.9 Hz), 2.95-3.10 (1H, m), 4.39 (2H, s), 4.47 (1H, d, J=17.6 Hz), 5.13 (1H, dd, J=12.2, 8.2 Hz), 5.25 (1H, d, J=17.6 Hz), 7.04 (1H, d, J=7.9 Hz), 7.14-7.22 (1H, m), 7.24-7.39 (7H, m).

Example 16

(3S)-3-(2-benzyl-4-oxo-6,7-dihydro[1,3]thiazolo[4,5-c]pyridin-5(4H)-yl)-5-methyl-2,3-dihydro-1,5-benzoxazepin-4(5H)-one A) ethyl 5-(benzyloxy)-3-chloro-2-oxopentanoate To a mixture of 3-(benzyloxy)propanal (1.05 g), ethyl 2,2-dichloroacetate (1.00 g) and THF (6 mL) was added potassium tert-butoxide (0.718 g) at 0° C., and the mixture was stirred overnight at room temperature. The reaction mixture was cooled to 0° C., saturated aqueous sodium hydrogencarbonate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane). To the obtained compound were added THF (5 mL) and tetrabutylammonium chloride (0.178 g), and the mixture was stirred overnight at room temperature. The reaction mixture was poured into water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (1.03 g).
MS, found: 349.3.

B) ethyl 2-benzyl-5-(2-(benzyloxy)ethyl)thiazole-4-carboxylate

A solution of ethyl 5-(benzyloxy)-3-chloro-2-oxopentanoate (1.03 g) and 2-phenylethanethioamide (0.547 g) in ethanol (10 mL) was stirred overnight at 80° C. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (0.355 g).
MS: [M+H]$^+$ 382.2.

C) (S)-2-benzyl-5-(2-hydroxyethyl)-N-(5-methyl-4-oxo-2,3,4,5-tetrahydrobenzo[b][1,4]oxazepin-3-yl)thiazole-4-carboxamide A mixture of ethyl 2-benzyl-5-(2-(benzyloxy)ethyl)thiazole-4-carboxylate (0.300 g) and 6 M hydrochloric acid (2 mL) was stirred at room temperature for 3 hr, and then overnight at 90° C. The reaction mixture was concentrated under reduced pressure. To a mixture of the obtained mixture (83 mg), (S)-3-amino-5-methyl-2,3-dihydrobenzo[b][1,4]oxazepin-4(5H)-one hydrochloride (108 mg), triethylamine (47.8 mg) and DMF (5 mL) was added 4-(4,6-dimethoxy-1,3,5-triazin-2-yl)-4-methylmorpholinium chloride (131 mg), and the mixture was stirred overnight at room temperature. To the reaction mixture was added saturated aqueous sodium hydrogencarbonate solution, and the mixture was extracted with ethyl acetate. The extract was washed with water and saturated brine, and dried over anhydrous sodium sulfate, and the solvent was evaporated under reduced pressure. The residue was purified by silica gel column chromatography (NH, ethyl acetate/hexane) to give the title compound (62.7 mg). MS: [M+H]$^+$ 438.2.

D) (3S)-3-(2-benzyl-4-oxo-6,7-dihydro[1,3]thiazolo[4,5-c]pyridin-5(4H)-yl)-5-methyl-2,3-dihydro-1,5-benzoxazepin-4(5H)-one To a mixture of (S)-2-benzyl-5-(2-hydroxyethyl)-N-(5-methyl-4-oxo-2,3,4,5-tetrahydrobenzo[b][1,4]oxazepin-3-yl)thiazole-4-carboxamide (40 mg) and THF (2 mL) was added cyanomethylene tri-n-butyl phosphorane (26.5 mg) at 0° C., and the mixture was stirred under nitrogen atmosphere at room temperature for 3 hr, and then under microwave irradiation at 80° C. for 24 hr. The reaction mixture was concentrated, and the residue was purified by silica gel column chromatography (NH, THF), and subjected to preparative HPLC (C18, mobile phase: water/acetonitrile (containing 0.1% TFA)). The obtained fraction was concentrated under reduced pressure. The residue was purified by silica gel column chromatography (NH, methanol) to give the title compound (3.3 mg).
$^1$H NMR (300 MHz, CDCl$_3$) δ2.94 (1H, dt, J=16.4, 4.8 Hz), 3.37-3.39 (4H, m), 3.63 (1H, t, J=4.2 Hz), 4.31-4.34 (3H, m), 4.43 (1H, dd, J=10.0, 8.1 Hz), 4.61 (1H, dd, J=11.7, 9.8 Hz), 5.90 (1H, dd, J=11.7, 8.3 Hz), 7.14-7.38 (9H, m).

Example 17

(3S)-3-(2-benzyl-8-oxo-5,8-dihydro-1,7-naphthyridin-7(6H)-yl)-5-methyl-2,3-dihydro-1,5-benzoxazepin-4(5H)-one A) methyl 3-bromo-6-chloropyridine-2-carboxylate To a solution of 3-bromo-6-chloropyridine-2-carboxylic acid (5.00 g) in methanol (90 mL) was added 98% sulfuric acid (889 mg), and the mixture was stirred at 60° C. for 16 hr. The reaction mixture was cooled to room temperature, and the solvent was evaporated under reduced pressure. The obtained residue was dissolved in ethyl acetate, the solution was washed with saturated aqueous sodium hydrogencarbonate solution and saturated brine, and dried over anhydrous sodium sulfate, and the solvent was evaporated under reduced pressure to give the title compound (5.05 g).

$^1$H NMR (400 MHz, DMSO-d$_6$) δ 3.93 (3H, s), 7.70 (1H, d, J=8.4 Hz), 8.32 (1H, d, J=8.4 Hz).

B) methyl 6-chloro-3-((E)-2-ethoxyvinyl)pyridine-2-carboxylate

To a mixture of methyl 3-bromo-6-chloropyridine-2-carboxylate (2.00 g) in acetonitrile (30 mL) and water (20 mL) were added 2-((E)-2-ethoxyvinyl)-4,4,5,5-tetramethyl-1,3,2-dioxaborolane (1.42 g), tripotassium phosphate (3.39 g), 2-dicyclohexylphosphino-2',6'-dimethoxybiphenyl (328 mg) and palladium(II) acetate (90 mg), and the mixture was stirred under nitrogen atmosphere at 60° C. for 2 hr. The reaction mixture was cooled to room temperature, and diluted with ethyl acetate, and the insoluble substance was removed by filtration. The filtrate was washed with water and saturated brine and dried over anhydrous sodium sulfate, and the solvent was evaporated under reduced pressure. The residue was purified by silica gel column chromatography (ethyl acetate/petroleum ether) to give the title compound (560 mg).

$^1$H NMR (400 MHz, DMSO-do) δ 1.28 (3H, t, J=7.6 Hz), 3.88 (3H, s), 3.90-4.00 (2H, m), 6.27 (1H, d, J=12.8 Hz), 7.43 (1H, d, J=12.8 Hz), 7.60 (1H, d, J=8.8 Hz), 8.16 (1H, d, J=8.8 Hz).

C) (3S)-3-(2-chloro-8-oxo-5,8-dihydro-1,7-naphthyridin-7 (6H)-yl)-5-methyl-2,3-dihydro-1,5-benzoxazepin-4(5H)-one To a solution of methyl 6-chloro-3-((E)-2-ethoxyvinyl) pyridine-2-carboxylate (210 mg) in dichloromethane (2.5 mL) was added trifluoroacetic acid (3.23 g), the mixture was stirred at room temperature for 12 hr, and the solvent was evaporated under reduced pressure. To a solution of the obtained crude product in methanol (8 mL) was added (S)-3-amino-5-methyl-2,3-dihydrobenzo[b][1,4]oxazepin-4 (5H)-one hydrochloride (72 mg), and the mixture was stirred at room temperature for 3 hr. To the reaction mixture was added sodium cyanoborohydride (30 mg), and the mixture was stirred at room temperature for 12 hr. The reaction mixture was concentrated under reduced pressure, to the residue were added p-toluenesulfonic acid monohydrate (10 mg) and toluene (8 mL), and the mixture was stirred at 110° C. for 3 hr. The solvent was evaporated under reduced pressure, and to the residue was added ethyl acetate. The mixture was washed with water and saturated brine, and dried over anhydrous sodium sulfate, and the solvent was evaporated under reduced pressure. The residue was purified by silica gel column chromatography (ethyl acetate/petroleum ether) to give the title compound (100 mg).

$^1$H NMR (400 MHz, DMSO-do) δ 2.90-3.00 (1H, m), 3.05-3.15 (1H, m), 3.32 (3H, s), 3.52-3.62 (1H, m), 3.95-4.05 (1H, m), 4.32-4.45 (1H, m), 4.87 (1H, t, J=10.4 Hz), 5.51-5.61 (1H, m), 7.20-7.40 (3H, m), 7.52 (1H, d, J=7.6 Hz), 7.62 (1H, d, J=8.4 Hz), 7.89 (1H, d, J=8.0 Hz).

D) (3S)-3-(2-benzyl-8-oxo-5,8-dihydro-1,7-naphthyridin-7 (6H)-yl)-5-methyl-2,3-dihydro-1,5-benzoxazepin-4(5H)-one To a solution of (3S)-3-(2-chloro-8-oxo-5,8-dihydro-1,7-naphthyridin-7(6H)-yl)-5-methyl-2,3-dihydro-1,5-benzoxazepin-4(5H)-one (100 mg) in THF (5 mL) were added 0.5 M benzylzinc bromide THF solution (1.12 mL), 2-dicyclohexylphosphino-2',4',6'-triisopropylbiphenyl (13 mg) and palladium(II) acetate (6 mg), and the mixture was stirred under nitrogen atmosphere at 60° C. for 2 hr. The reaction mixture was cooled to room temperature, methanol (15 mL) was added thereto, and the insoluble substance was removed by filtration. The filtrate was concentrated under reduced pressure, and the residue was subjected to HPLC (C18, mobile phase: water/acetonitrile (containing 0.1% NH$_3$)), and the obtained fraction was concentrated under reduced pressure. The obtained residue was lyophilized to give the title compound (21 mg).

$^1$H NMR (400 MHz, DMSO-d$_6$) δ 2.85-2.95 (1H, m), 3.02-3.12 (1H, m), 3.32 (3H, s), 3.52-3.62 (1H, m), 3.90-4.05 (1H, m), 4.09 (2H, s), 4.38 (1H, t, J=8.0 Hz), 4.85 (1H, t, J=10.8 Hz), 5.59-5.69 (1H, m), 7.15-7.40 (9H, m), 7.51 (1H, d, J=6.4 Hz), 7.70 (1H, d, J=8.0 Hz).

Example 18

3-(2-benzyl-4-oxo-6,7-dihydropyrazolo[1,5-a] pyrazin-5(4H)-yl)-1,3,4,5-tetrahydro-2H-1-benzazepin-2-one

A) ethyl 3-benzyl-1-(2-bromoethyl)-1H-pyrazole-5-carboxylate

To a solution of ethyl 3-benzyl-1H-pyrazole-5-carboxylate (747 mg) and 1,2-dibromoethane (2.81 mL) in acetonitrile (10 mL) was added potassium carbonate (538 mg), and the mixture was heated under reflux for 3 hr. The reaction mixture was cooled to room temperature, and filtered, and the solvent was evaporated under reduced pressure. The residue was purified by silica gel column chromatography (ethyl acetate/hexane) to give the title compound (0.560 g).

MS: [M+H]$^+$ 337.1.

B) ethyl 3-benzyl-1-(2-((2-oxo-2,3,4,5-tetrahydro-1H-benzo[b]azepin-3-yl)amino)ethyl)-1H-pyrazole-5-carboxylate A mixture of ethyl 3-benzyl-1-(2-bromoethyl)-1H-pyrazole-5-carboxylate (107 mg), potassium iodide (11 mg) and 3-amino-4,5-dihydro-1H-benzo[b]azepin-2(3H)-one (559 mg) in acetonitrile (1 mL) was stirred under microwave irradiation at 100° C. for 1 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (128 mg).

MS: [M+H]$^+$ 433.3.

C) 3-(2-benzyl-4-oxo-6,7-dihydropyrazolo[1,5-a] pyrazin-5(4H)-yl)-1,3,4,5-tetrahydro-2H-1-benzazepin-2-one To a solution of ethyl 3-benzyl-1-(2-((2-oxo-2,3,4,5-tetrahydro-1H-benzo[b]azepin-3-yl)amino)ethyl)-1H-pyrazole-5-carboxylate (108 mg) in toluene (15 mL) was added 1.4 M trimethylaluminium hexane solution (0.446 mL), and the mixture was stirred at 100° C. for 3 hr. To the reaction mixture was added saturated aqueous potassium sodium tartrate solution, and the mixture was stirred at room temperature for 30 min, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (25 mg).

$^1$H NMR (300 MHz, CDCl$_3$) δ 2.22-2.54 (2H, m), 2.72-2.86 (1H, m), 2.91-3.11 (1H, m), 3.71-3.87 (1H, m), 3.98 (2H, s), 4.20-4.40 (2H, m), 4.45-4.59 (1H, m), 5.43 (1H, dd, J=11.9, 8.5 Hz), 6.54 (1H, s), 7.00 (1H, d, J=7.9 Hz), 7.13-7.32 (9H, m).

Example 43

(3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile A) ethyl 1-(2-fluorobenzyl)-4-formyl-1H-pyrazole-3-carboxylate To a mixture of ethyl 4-formyl-1H-pyrazole-3-carboxylate (5.78 g), potassium carbonate (14.26 g) and DMF (50 mL) was added 2-fluorobenzyl bromide (4.56 mL), and the mixture was stirred at room temperature for 3 hr. To the reaction mixture was added water, and the precipitated solid was collected by filtration. The obtained solid was recrystallized from ethyl acetate/hexane to give the title compound (3.47 g).

MS: [M+H]$^+$ 277.3.

B) ethyl 1-(2-fluorobenzyl)-4-(2-methoxyvinyl)-1H-pyrazole-3-carboxylate

To a mixture of (methoxymethyl)triphenylphosphonium chloride (4.74 g) and THF (60 mL) was added potassium tert-butoxide (1.55 g) at 0° C., and the mixture was stirred under argon atmosphere at 0° C. for 5 min. A solution of ethyl 1-(2-fluorobenzyl)-4-formyl-1H-pyrazole-3-carboxylate (3.47 g) in THF (40 mL) was added to the above-mentioned mixture at 0° C., and the mixture was stirred under argon atmosphere overnight at room temperature. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane), and then silica gel column chromatography (NH, ethyl acetate/hexane) to give the title compound (2.83 g).

MS: [M+H]$^+$ 305.3.

C) ethyl 1-(2-fluorobenzyl)-4-(2-oxoethyl)-1H-pyrazole-3-carboxylate

To a solution of ethyl 1-(2-fluorobenzyl)-4-(2-methoxyvinyl)-1H-pyrazole-3-carboxylate (2.83 g) in THF (9.3 mL) was added 6 M hydrochloric acid (1 mL), and the mixture was stirred at room temperature for 1 hr. The reaction mixture was neutralized with saturated aqueous sodium hydrogencarbonate solution at 0° C., and extracted with ethyl acetate. The extract was washed with saturated brine, and dried over anhydrous magnesium sulfate, and the solvent was evaporated under reduced pressure to give the title compound (2.69 g).

MS: [M+H]$^+$ 291.3.

D) (S)-ethyl 4-(2-((8-bromo-5-methyl-4-oxo-2,3,4,5-tetrahydrobenzo[b][1,4]oxazepin-3-yl)amino)ethyl)-1-(2-fluorobenzyl)-1H-pyrazole-3-carboxylate To a solution of ethyl 1-(2-fluorobenzyl)-4-(2-oxoethyl)-1H-pyrazole-3-carboxylate (570 mg), (S)-3-amino-8-bromo-5-methyl-2,3-dihydrobenzo[b][1,4]oxazepin-4(5H)-one hydrochloride (462 mg) and acetic acid (0.7 mL) in methanol (7 mL) was added 2-picoline borane (85%, 208 mg) at 0° C., and the mixture was stirred at 0° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (255 mg).

MS: [M+H]$^+$ 545.2.

E) (S)-8-bromo-3-(2-(2-fluorobenzyl)-7-oxo-4,5-dihydro-2H-pyrazolo[3,4-c]pyridin-6(7H)-yl)-5-methyl-2,3-dihydrobenzo[b][1,4]oxazepin-4(5H)-one To a mixture of (S)-ethyl 4-(2-((8-bromo-5-methyl-4-oxo-2,3,4,5-tetrahydrobenzo[b][1,4]oxazepin-3-yl)amino)ethyl)-1-(2-fluorobenzyl)-1H-pyrazole-3-carboxylate (255 mg) and toluene (5 mL) was added 1.8 M trimethylaluminium toluene solution (0.260 mL) at 0° C., and the mixture was stirred at 0° C. for 10 min, and then at 100° C. for 3 hr. To the reaction mixture was again added 1.8 M trimethylaluminium toluene solution (0.130 mL), and the mixture was stirred at 100° C. for 3 hr. To the reaction mixture was added saturated aqueous potassium sodium tartrate solution, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (132 mg).

MS: [M+H]$^+$ 499.1.

F) (3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile To a solution of (S)-8-bromo-3-(2-(2-fluorobenzyl)-7-oxo-4,5-dihydro-2H-pyrazolo[3,4-c]pyridin-6(7H)-yl)-5-methyl-2,3-dihydrobenzo[b][1,4]oxazepin-4(5H)-one (132 mg) and zinc dicyanide (46.6 mg) in DMF (3 mL) was added tetrakis(triphenylphosphine)palladium(0) (76 mg) at room temperature, and the mixture was stirred under argon atmosphere at 100° C. for 2 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane). The residue was subjected to preparative HPLC (C18, mobile phase: water/acetonitrile (containing 0.1% TFA)), saturated aqueous sodium hydrogencarbonate solution was added thereto, and the mixture was extracted with ethyl acetate. The extract was dried over anhydrous sodium sulfate, and the solvent was evaporated under reduced pressure to give the title compound (63 mg).

$^1$H NMR (300 MHz, CDCl$_3$) δ 2.73 (1H, dt, J=15.5, 4.9 Hz), 3.10 (1H, ddd, J=15.4, 10.3, 4.9 Hz), 3.39 (3H, s), 3.54 (1H, td, J=11.1, 4.5 Hz), 4.15-4.22 (1H, m), 4.44 (1H, dd, J=10.2, 7.9 Hz), 4.68 (1H, dd, J=11.9, 10.0 Hz), 5.40 (2H, s), 5.92 (1H, dd, J=11.9, 8.1 Hz), 7.03-7.14 (2H, m), 7.22 (2H, d, J=1.5 Hz), 7.29-7.39 (2H, m), 7.47 (1H, d, J=1.9 Hz), 7.56 (1H, dd, J=8.3, 1.9 Hz).

Example 44

(3S)-3-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide A) ethyl 1-benzyl-5-chloro-4-formyl-1H-pyrazole-3-carboxylate Phosphorus oxychloride (49.4 mL) was added dropwise to a mixture of ethyl 1-benzyl-5-hydroxy-1H-pyrazole-3-carboxylate (16.3 g) and DMF (20 mL) at room temperature, and the mixture was stirred at 90° C. for 10 hr. The reaction mixture was concentrated under reduced pressure, the residue was added to saturated aqueous sodium hydrogencarbonate solution at 0° C., and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (14.33 g).
MS: [M+H]$^+$ 293.2.

B) ethyl 1-benzyl-5-chloro-4-(2-methoxyvinyl)-1H-pyrazole-3-carboxylate

To a mixture of (methoxymethyl)triphenylphosphonium chloride (1142 mg) and THF (20 mL) was added potassium tert-butoxide (374 mg) at 0° C., and the mixture was stirred under argon atmosphere at 0° C. for 5 min. A solution of ethyl 1-benzyl-5-chloro-4-formyl-1H-pyrazole-3-carboxylate (650 mg) in THF (10 mL) was added to the above-mentioned mixture at 0° C., and the mixture was stirred under argon atmosphere at room temperature for 2 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (700 mg).
MS: [M+H]$^+$ 321.2.

C) ethyl 1-benzyl-5-chloro-4-(2-oxoethyl)-1H-pyrazole-3-carboxylate

A solution of ethyl 1-benzyl-5-chloro-4-(2-methoxyvinyl)-1H-pyrazole-3-carboxylate (8.64 g) in THF (90 mL) was added dropwise to 6 M hydrochloric acid (90 mL) at 0° C., and the mixture was stirred at room temperature for 3 hr. The reaction mixture was diluted with water, and extracted with ethyl acetate. The extract was washed with saturated brine, and dried over anhydrous sodium sulfate, and the solvent was evaporated under reduced pressure to give the title compound (8.32 g).
MS: [M+H]$^+$ 307.0.

D) (S)-ethyl 1-benzyl-5-chloro-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate To a solution of ethyl 1-benzyl-5-chloro-4-(2-oxoethyl)-1H-pyrazole-3-carboxylate (136 mg), (S)-3-amino-N,5-dimethyl-4-oxo-2,3,4,5-tetrahydrobenzo[b][1,4]oxazepine-8-carboxamide (85 mg) and acetic acid (0.3 mL) in methanol (3 mL) was added 2-picoline borane (85%, 47 mg) at 0° C., and the mixture was stirred at 0° C. for 10 min, and then at room temperature for 1 hr. To the reaction mixture was added saturated brine, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (88 mg).
MS: [M+H]$^+$ 540.3.

E) (3S)-3-(2-benzyl-3-chloro-7-oxo-2,4,5,7-tetrahydro-6H-pyrazolo[3,4-c]pyridin-6-yl)-N, 5-dimethyl-4-oxo-2,3,4,5-tetrahydro-1,5-benzoxazepine-8-carboxamide To a mixture of (S)-ethyl 1-benzyl-5-chloro-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate (88 mg) and toluene (4 mL) was added 1.8 M trimethylaluminium toluene solution (0.226 mL) at 0° C., and the mixture was stirred at room temperature for 10 min, and then at 90° C. for 3 hr. The reaction mixture was purified by silica gel column chromatography (NH, methanol/ethyl acetate) and then silica gel column chromatography (methanol/ethyl acetate) to give the title compound (44 mg).
$^1$H NMR (300 MHz, CDCl$_3$) δ 2.66 (1H, dt, J=15.8, 4.8 Hz), 2.91-3.12 (4H, m), 3.38 (3H, s), 3.53 (1H, td, J=11.1, 4.5 Hz), 4.17-4.28 (1H, m), 4.34 (1H, dd, J=10.0, 8.1 Hz), 4.62 (1H, dd, J=11.7, 10.2 Hz), 5.39 (2H, s), 5.86 (1H, dd, J=11.9, 8.1 Hz), 6.41 (1H, d, J=4.5 Hz), 7.19-7.37 (6H, m), 7.54-7.69 (2H, m).

Example 45

(3S)-3-(2-(2,6-difluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile A) ethyl 4-bromo-1-(2,6-difluorobenzyl)-1H-pyrazole-3-carboxylate A solution of ethyl 4-bromo-1H-pyrazole-3-carboxylate (2.07 g) in THF (10 mL) was added to a solution of sodium hydride (60%, 0.454 g) in THF (10 mL) at 0° C., and the mixture was stirred at 0° C. for 5 min. To the reaction mixture was added dropwise 2-(bromomethyl)-1,3-difluorobenzene (2.152 g) at 0° C., and the mixture was gradually warmed to room temperature, and stirred overnight at room temperature. To the reaction mixture was added saturated aqueous ammonium chloride solution, and the mixture was extracted with ethyl acetate. The extract was washed with saturated aqueous sodium hydrogencarbonate solution and saturated brine, and dried over anhydrous sodium sulfate, and the solvent was evaporated under reduced pressure. The residue was purified by silica gel column chromatography (ethyl acetate/hexane) to give the title compound (3.16 g).
MS: [M+H]$^+$ 345.1.

B) (Z)-ethyl 1-(2,6-difluorobenzyl)-4-(2-ethoxyvinyl)-1H-pyrazole-3-carboxylate A mixture of ethyl 4-bromo-1-(2,6-difluorobenzyl)-1H-pyrazole-3-carboxylate (2.80 g), (Z)-2-(2-ethoxyvinyl)-4,4,5,5-tetramethyl-1,3,2-dioxaborolane (2.89 g), [1,1'-bis(diphenylphosphino)ferrocene]dichloropalladium(II) (0.594 g), cesium carbonate (5.82 g), water (10 mL) and 1,2-dimethoxyethane (80 mL) was stirred overnight under argon atmosphere at 90° C. To the reaction mixture was added ethyl acetate, and the mixture was washed with water and saturated brine, and dried over anhydrous sodium sulfate, and the solvent was evaporated under reduced pressure. The residue was purified by silica gel column chromatography (ethyl acetate/hexane) to give the title compound (2.37 g).
MS: [M+H]$^+$ 337.2.

C) ethyl 1-(2,6-difluorobenzyl)-4-(2-oxoethyl)-1H-pyrazole-3-carboxylate

To a solution of (Z)-ethyl 1-(2,6-difluorobenzyl)-4-(2-ethoxyvinyl)-1H-pyrazole-3-carboxylate (2.37 g) in THF (30 mL) was added 6 M hydrochloric acid (15 mL), and the mixture was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure to give the title compound (2.18 g).
MS: [M+H]$^+$ 309.3.

D) (S)-ethyl 4-(2-((8-bromo-5-methyl-4-oxo-2,3,4,5-tetrahydrobenzo[b][1,4]oxazepin-3-yl)amino)ethyl)-1-(2,6-difluorobenzyl)-1H-pyrazole-3-carboxylate To a solution of ethyl 1-(2,6-difluorobenzyl)-4-(2-oxoethyl)-1H-pyrazole-3-carboxylate (1.0 g), (S)-3-amino-8-bromo-5-methyl-2,3-dihydrobenzo[b][1,4]oxazepin-4(5H)-one hydrochloride (0.998 g) and acetic acid (0.5 mL) in methanol (5 mL) was added 2-picoline borane (85%, 0.45 g) under ice-cooling, and the mixture was stirred at room temperature for 1 hr. To the reaction mixture were added saturated aqueous sodium hydrogencarbonate solution and saturated brine, and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (1.05 g).
MS: [M+H]$^+$ 563.2.

E) (S)-8-bromo-3-(2-(2,6-difluorobenzyl)-7-oxo-4,5-dihydro-2H-pyrazolo[3,4-c]pyridin-6(7H)-yl)-5-methyl-2,3-dihydrobenzo[b][1,4]oxazepin-4(5H)-one To a mixture of (S)-ethyl 4-(2-((8-bromo-5-methyl-4-oxo-2,3,4,5-tetrahydrobenzo[b][1,4]oxazepin-3-yl)amino)ethyl)-1-(2,6-difluorobenzyl)-1H-pyrazole-3-carboxylate (1.05 g) and toluene (30 mL) was added 1.8 M trimethylaluminium toluene solution (3.11 mL) under argon atmosphere at room temperature, and the mixture was stirred at 100° C. for 1 hr. To the reaction mixture was added water, and the mixture was extracted with ethyl acetate. The extract was washed with saturated aqueous potassium sodium tartrate solution and saturated brine, and dried over anhydrous sodium sulfate, and the solvent was evaporated under reduced pressure. The residue was purified by silica gel column chromatography (ethyl acetate/hexane). The obtained solid was recrystallized from ethyl acetate to give the title compound (567 mg).
MS: [M+H]$^+$ 517.1.

F) (3S)-3-(2-(2,6-difluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile To a solution of (S)-8-bromo-3-(2-(2,6-difluorobenzyl)-7-oxo-4,5-dihydro-2H-pyrazolo[3,4-c]pyridin-6(7H)-yl)-5-methyl-2,3-dihydrobenzo[b][1,4]oxazepin-4(5H)-one (200 mg) and zinc dicyanide (68 mg) in DMF (5 mL) was added tetrakis(triphenylphosphine)palladium(0) (112 mg), and the mixture was stirred under argon atmosphere at 100° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (160 mg).
$^1$H NMR (300 MHz, CDCl$_3$) δ 2.71 (1H, dt, J=15.4, 4.8 Hz), 2.99-3.16 (1H, m), 3.38 (3H, s), 3.46-3.59 (1H, m), 4.12-4.21 (1H, m), 4.42 (1H, dd, J=10.0, 8.1 Hz), 4.67 (1H, dd, J=11.9, 10.0 Hz), 5.45 (2H, s), 5.91 (1H, dd, J=11.9, 8.1 Hz), 6.88-7.00 (2H, m), 7.23 (1H, s), 7.28-7.41 (2H, m), 7.46 (1H, d, J=1.9 Hz), 7.56 (1H, dd, J=8.3, 1.9 Hz).

Example 46

(3S)-3-(3-chloro-2-(2,6-difluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide

A) ethyl 5-chloro-1-(2,6-difluorobenzyl)-4-formyl-1H-pyrazole-3-carboxylate

To a mixture of ethyl 5-chloro-4-formyl-1H-pyrazole-3-carboxylate (2.7 g), potassium carbonate (5.53 g) and DMF (30 mL) was added 2-(bromomethyl)-1,3-difluorobenzene (3.03 g), and the mixture was stirred at room temperature for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (538 mg).
MS: [M+H]$^+$ 329.2.

B) ethyl 5-chloro-1-(2,6-difluorobenzyl)-4-(2-methoxyvinyl)-1H-pyrazole-3-carboxylate To a mixture of (methoxymethyl)triphenylphosphonium chloride (992 mg) and THF (6 mL) was added potassium tert-butoxide (325 mg) under argon atmosphere at 0° C., and the mixture was stirred at 0° C. for 5 min. A solution of ethyl 5-chloro-1-(2,6-difluorobenzyl)-4-formyl-1H-pyrazole-3-carboxylate (634 mg) in THF (3 mL) was added to the above-mentioned mixture at 0° C., and the mixture was stirred at room temperature for 1 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (574 mg).

MS: [M+H]$^+$ 357.2.

C) ethyl 5-chloro-1-(2,6-difluorobenzyl)-4-(2-oxoethyl)-1H-pyrazole-3-carboxylate A solution of ethyl 5-chloro-1-(2,6-difluorobenzyl)-4-(2-methoxyvinyl)-1H-pyrazole-3-carboxylate (574 mg) in THF (6 mL) was added dropwise to 6 M hydrochloric acid (6 mL) at 0° C., and the mixture was stirred at room temperature for 3 hr. The reaction mixture was diluted with water, and extracted with ethyl acetate. The extract was washed with saturated brine, and dried over anhydrous sodium sulfate, and the solvent was evaporated under reduced pressure to give the title compound (523 mg).

MS: [M+H]$^+$ 343.2.

D) (S)-ethyl 5-chloro-1-(2,6-difluorobenzyl)-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate To a solution of ethyl 5-chloro-1-(2,6-difluorobenzyl)-4-(2-oxoethyl)-1H-pyrazole-3-carboxylate (139 mg), (S)-3-amino-N,5-dimethyl-4-oxo-2,3,4,5-tetrahydrobenzo[b][1,4]oxazepine-8-carboxamide (101 mg) and acetic acid (0.2 mL) in methanol (2 mL) was added 2-picoline borane (85%, 61 mg) at 0° C., and the mixture was stirred at room temperature for 1 hr. To the reaction mixture was added saturated aqueous sodium hydrogencarbonate solution, and the mixture was extracted with ethyl acetate. The extract was dried over anhydrous sodium sulfate, and the solvent was evaporated under reduced pressure. The residue was purified by silica gel column chromatography (NH, ethyl acetate/hexane) to give the title compound (151 mg).

MS: [M+H]$^+$ 576.2.

E) (3S)-3-(3-chloro-2-(2,6-difluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide To a mixture of (S)-ethyl 5-chloro-1-(2,6-difluorobenzyl)-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate (151 mg) and toluene (15 mL) was added 1.8 M trimethylaluminium toluene solution (0.364 mL) under argon atmosphere at room temperature, and the mixture was stirred at 100° C. for 1 hr. To the reaction mixture was added saturated aqueous potassium sodium tartrate solution, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) and then silica gel column chromatography (NH, methanol/ethyl acetate), and subjected to preparative HPLC (C18, mobile phase: water/acetonitrile (containing 0.1% TFA)), and the obtained fraction was concentrated under reduced pressure. To the residue was added saturated aqueous sodium hydrogencarbonate solution, and the mixture was extracted with ethyl acetate. The extract was dried over anhydrous sodium sulfate, and the solvent was evaporated under reduced pressure to give the title compound (49 mg).

$^1$H NMR (300 MHz, CDCl$_3$) δ2.68 (1H, dt, J=15.6, 4.9 Hz), 2.96-3.11 (4H, m), 3.38 (3H, s), 3.46-3.62 (1H, m), 4.18-4.28 (1H, m), 4.37 (1H, dd, J=10.0, 8.1 Hz), 4.63 (1H, dd, J=11.7, 9.8 Hz), 5.46 (2H, s), 5.85 (1H, dd, J=11.7, 7.9 Hz), 6.22 (1H, d, J=4.9 Hz), 6.83-6.93 (2H, m), 7.20-7.34 (2H, m), 7.53-7.68 (2H, m).

Example 47

(3S)-3-(3-chloro-2-(2-fluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide

A) ethyl 5-chloro-1-(2-fluorobenzyl)-4-formyl-1H-pyrazole-3-carboxylate

Phosphorus oxychloride (10.02 mL) was added dropwise to a mixture of ethyl 1-(2-fluorobenzyl)-5-hydroxy-1H-pyrazole-3-carboxylate (3.55 g) and DMF (4.13 mL) at room temperature, and the mixture was stirred under Ar atmosphere at 90° C. for 7 hr. The solvent was evaporated under reduced pressure, to the residue was added saturated aqueous sodium hydrogencarbonate solution at 0° C., and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (2.71 g).

MS: [M+H]$^+$ 311.2.

B) ethyl 5-chloro-1-(2-fluorobenzyl)-4-(2-methoxyvinyl)-1H-pyrazole-3-carboxylate To a mixture of (methoxymethyl)triphenylphosphonium chloride (2.681 g) and THF (60 mL) was added potassium tert-butoxide (878 mg) under argon atmosphere at 0° C., and the mixture was stirred at 0° C. for 5 min. A solution of ethyl 5-chloro-1-(2-fluorobenzyl)-4-formyl-1H-pyrazole-3-carboxylate (1620 mg) in THF (40 mL) at 0° C. was added to the above-mentioned mixture, and the mixture was stirred at room temperature for 1 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (1.60 g).

MS: [M+H]$^+$ 339.2.

C) ethyl 5-chloro-1-(2-fluorobenzyl)-4-(2-oxoethyl)-1H-pyrazole-3-carboxylate To a solution of ethyl 5-chloro-1-(2-fluorobenzyl)-4-(2-methoxyvinyl)-1H-pyrazole-3-carboxylate (1.60 g) in THF (20 mL) was added 6 M hydrochloric acid (10 mL) at room temperature, and the mixture was stirred overnight at room temperature. To the reaction mixture was added saturated aqueous sodium hydrogencarbonate solution, and the mixture was extracted with ethyl acetate. The extract was washed with saturated brine, and dried over anhydrous sodium sulfate, and the solvent was evaporated under reduced pressure to give the title compound (1.81 g).
MS: [M+H]$^+$ 325.2.

D) (S)-ethyl 5-chloro-1-(2-fluorobenzyl)-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate To a solution of ethyl 5-chloro-1-(2-fluorobenzyl)-4-(2-oxoethyl)-1H-pyrazole-3-carboxylate (130 mg), (S)-3-amino-N,5-dimethyl-4-oxo-2,3,4,5-tetrahydrobenzo[b][1,4]oxazepine-8-carboxamide (100 mg) and acetic acid (0.5 mL) in methanol (5 mL) was added 2-picoline borane (85%, 55.8 mg) at 0° C., and the mixture was stirred at room temperature for 1 hr. To the reaction mixture were added saturated aqueous sodium hydrogencarbonate solution and saturated brine, and the mixture was extracted with ethyl acetate. The extract was dried over anhydrous sodium sulfate, and the solvent was evaporated under reduced pressure. The residue was purified by silica gel column chromatography (ethyl acetate/methanol) to give the title compound (165 mg).
MS: [M+H]$^+$ 558.2.

E) (3S)-3-(3-chloro-2-(2-fluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide To a mixture of (S)-ethyl 5-chloro-1-(2-fluorobenzyl)-4-(2-((5-methyl-8-(methylcarbamoyl)-4-oxo-2,3,4,5-tetrahydrobenzo[b][1,4]oxazepin-3-yl)amino)ethyl)-1H-pyrazole-3-carboxylate (165 mg) and toluene (15 mL) was added 1.8 M trimethylaluminium toluene solution (0.493 mL) under argon atmosphere at room temperature, and the mixture was stirred at 100° C. for 1 hr. To the reaction mixture was added water, and the mixture was extracted with ethyl acetate. The extract was washed with saturated aqueous potassium sodium tartrate solution and saturated brine, and dried over anhydrous sodium sulfate, and the solvent was evaporated under reduced pressure. The residue was purified by silica gel column chromatography (NH, methanol/ethyl acetate) to give the title compound (130 mg).
$^1$H NMR (300 MHz, CDCl$_3$) δ2.62-2.76 (1H, m), 3.02 (3H, d, J=4.9 Hz), 3.04-3.15 (1H, m), 3.39 (3H, s), 3.50-3.64 (1H, m), 4.18-4.30 (1H, m), 4.35-4.46 (1H, m), 4.59-4.72 (1H, m), 5.47 (2H, s), 5.88 (1H, dd, J=11.7, 8.3 Hz), 6.17-6.32 (1H, m), 6.99-7.11 (3H, m), 7.22-7.26 (1H, m), 7.27-7.32 (1H, m), 7.57-7.66 (2H, m).

Reference Example 1

(S)-3-amino-8-bromo-5-methyl-2,3-dihydrobenzo[b][1,4]oxazepin-4(5H)-one hydrochloride A) (S)-3-(5-bromo-2-nitrophenoxy)-2-((tert-butoxycarbonyl)amino)propanoic acid To a solution of sodium hydride (60%, 10.23 g) in DMF (250 mL) was added a mixture of (S)-2-((tert-butoxycarbonyl)amino)-3-hydroxypropanoic acid (25 g) and DMF (50 mL) over 40 min so that the temperature of the mixture was maintained within the range of 4° C. to 10° C., and the mixture was stirred at 4° C. for 1.5 hr. A solution of 4-bromo-2-fluoro-1-nitrobenzene (26.8 g) in DMF (50 mL) was added thereto over 20 min so that the temperature of the reaction mixture was maintained within the range of 4° C. to 10° C., and the mixture was stirred overnight at 14° C. To the reaction mixture were added ice water and 1 M hydrochloric acid (100 mL) under ice-cooling, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (42.4 g).
MS: [M−H]$^-$ 403.0.

B) (S)-3-(2-amino-5-bromophenoxy)-2-((tert-butoxycarbonyl)amino)propanoic acid

A mixture of (S)-3-(5-bromo-2-nitrophenoxy)-2-((tert-butoxycarbonyl)amino)propanoic acid (10 g), ammonium chloride (5.28 g), iron (13.78 g), ethanol (100 mL) and water (30 mL) was stirred at 80° C. for 1.5 hr. The insoluble substance was filtered through Celite, and the filtrate was concentrated under reduced pressure. To the residue was added ethyl acetate, and the insoluble substance was removed by filtration, and the filtrate was concentrated under reduced pressure to give the title compound (8.40 g).
MS: [M−H]$^-$ 372.9.

C) (S)-tert-butyl (8-bromo-4-oxo-2,3,4,5-tetrahydrobenzo[b][1,4]oxazepin-3-yl)carbamate Triethylamine (3.43 mL) was added to a solution of (S)-3-(2-amino-5-bromophenoxy)-2-((tert-butoxycarbonyl)amino)propanoic acid (8.4 g) and HATU (8.94 g) in dimethyl sulfoxide (40 mL), and the mixture was stirred at room temperature for 1 hr. To the reaction mixture was added water, and the precipitated solid was collected by filtration. The obtained solid was washed with water, and dissolved in ethyl acetate, the solution was dried over anhydrous magnesium sulfate, and the solvent was evaporated under reduced pressure. The residue was purified by silica gel column chromatography (ethyl acetate/hexane) to give the title compound (2.29 g).
MS: [M−H]$^-$ 355.0.

D) (S)-tert-butyl (8-bromo-5-methyl-4-oxo-2,3,4,5-tetrahydrobenzo[b][1,4]oxazepin-3-yl)carbamate A mixture of (S)-tert-butyl (8-bromo-4-oxo-2,3,4,5-tetrahydrobenzo[b][1,4]oxazepin-3-yl)carbamate (4 g), cesium carbonate (4.01 g), iodomethane (0.770 mL) and DMF (30 mL) was stirred at room temperature for 3 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (3.11 g).
MS, found: 271.2

E) (S)-3-amino-8-bromo-5-methyl-2,3-dihydrobenzo[b][1,4]oxazepin-4(5H)-one hydrochloride A mixture of (S)-tert-butyl (8-bromo-5-methyl-4-oxo-2,3,4,5-tetrahydrobenzo[b][1,4]oxazepin-3-yl)carbamate (1.22 g), 4 M hydrogen chloride ethyl acetate solution (8.22 mL) and ethyl acetate (10 mL) was stirred overnight at room temperature. The precipitated solid was collected by filtration, and washed with ethyl acetate to give the title compound (0.871 g).

MS, found: 271.2

Reference Example 2

(S)-3-amino-N,5-dimethyl-4-oxo-2,3,4,5-tetrahydrobenzo[b][1,4]oxazepine-8-carboxamide A) (S)-3-(5-((benzyloxy)carbonyl)-2-nitrophenoxy)-2-((tert-butoxycarbonyl)amino)propanoic acid A solution of (S)-2-((tert-butoxycarbonyl)amino)-3-hydroxypropanoic acid (28.7 g) in DMF (100 mL) was slowly added to a solution of sodium hydride (60%, 11.75 g) in DMF (100 mL) that the temperature of the mixture was maintained at 10° C. or below, and the mixture was stirred at 0° C. for 1 hr. A solution of benzyl 3-fluoro-4-nitrobenzoate (38.49 g) in DMF (100 mL) was added thereto at 0° C., and the mixture was stirred at 0° C. for 1 hr, and then overnight at room temperature. To the reaction mixture was added 1 M hydrochloric acid (100 mL) at 0° C., and the mixture was extracted with ethyl acetate. The extract was dried over anhydrous sodium sulfate, and the solvent was evaporated under reduced pressure. The residue was purified by silica gel column chromatography (ethyl acetate/hexane). The obtained mixture was purified again by silica gel column chromatography (CO2H, ethyl acetate/hexane) to give the title compound (16 g).

MS: [M–H]⁻ 459.1.

B) (S)-benzyl 3-((tert-butoxycarbonyl)amino)-4-oxo-2,3,4,5-tetrahydrobenzo[b][1,4]oxazepine-8-carboxylate To a solution of (S)-3-(5-((benzyloxy)carbonyl)-2-nitrophenoxy)-2-((tert-butoxycarbonyl)amino)propanoic acid (14.98 g) in acetic acid (150 mL) was added zinc powder (21.27 g) at 0° C., and the mixture was stirred at 0° C. for 10 min, and then at room temperature for 2 hr. The reaction mixture was filtered, and the solvent was evaporated under reduced pressure. To the obtained compound were added DMF (215 mL), HATU (13.61 g) and N,N'-diisopropylethylamine (7.37 mL) at 0° C., and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) and then silica gel column chromatography (NH, ethyl acetate/hexane) to give the title compound (1.27 g).

MS: [M–H]⁻ 411.1.

C) (S)-benzyl 3-((tert-butoxycarbonyl)amino)-5-methyl-4-oxo-2,3,4,5-tetrahydrobenzo[b][1,4]oxazepine-8-carboxylate To a solution of (S)-benzyl 3-((tert-butoxycarbonyl) amino)-4-oxo-2,3,4,5-tetrahydrobenzo[b][1,4]oxazepine-8-carboxylate (1.27 g) and iodomethane (0.327 mL) in DMF (13 mL) was added potassium carbonate (0.723 g) at 0° C., and the mixture was stirred at room temperature for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (1.31 g).

MS: [M–H]⁻ 425.0.

D) (S)-3-((tert-butoxycarbonyl)amino)-5-methyl-4-oxo-2,3,4,5-tetrahydrobenzo[b][1,4]oxazepine-8-carboxylic acid A mixture of (S)-benzyl 3-((tert-butoxycarbonyl)amino)-5-methyl-4-oxo-2,3,4,5-tetrahydrobenzo[b][1,4]oxazepine-8-carboxylate (100 mg), palladium/carbon (palladium 10%, about 50% wet product in water) (24.95 mg) and THF (3 mL) was stirred under hydrogen atmosphere at room temperature for 2 hr. The reaction mixture was filtered, and the filtrate was concentrated under reduced pressure to give the title compound (78 mg).

MS: [M–H]⁻ 335.1.

E) (S)-tert-butyl (5-methyl-8-(methylcarbamoyl)-4-oxo-2,3,4,5-tetrahydrobenzo[b][1,4]oxazepin-3-yl)carbamate (S)-3-((tert-Butoxycarbonyl)amino)-5-methyl-4-oxo-2,3,4,5-tetrahydrobenzo[b][1,4]oxazepine-8-carboxylic acid (156 mg) 2 M methylamine THF solution (0.348 mL) and HATU (229 mg) were dissolved in DMF (2 mL), N,N'-diisopropylethylamine (0.162 mL) was added thereto, and the mixture was stirred at room temperature for 2 hr. To the reaction mixture was added water, and the mixture was extracted with ethyl acetate. The extract was washed with water, 10% aqueous citric acid solution, saturated aqueous sodium hydrogencarbonate solution and saturated brine, and dried over anhydrous sodium sulfate, and the solvent was evaporated under reduced pressure to give the title compound (162 mg).

MS: [M–H]⁻ 348.1.

F) (S)-3-amino-N, 5-dimethyl-4-oxo-2,3,4,5-tetrahydrobenzo[b][1,4]oxazepine-8-carboxamide (S)-tert-Butyl (5-methyl-8-(methylcarbamoyl)-4-oxo-2,3,4,5-tetrahydrobenzo[b][1,4]oxazepin-3-yl)carbamate (162 mg) was added to 4 M hydrogen chloride ethyl acetate solution (2 mL), and the mixture was stirred at room temperature for 2 hr. To the reaction solution was added methanol, and the mixture was purified by silica gel column chromatography (NH, methanol) to give the title compound (85 mg).

MS: [M+H]⁺ 250.3.

Example 48

(3S)-3-(2-benzyl-3-methoxy-7-oxo-2,4,5,7-tetrahydro-6H-pyrazolo[3,4-c]pyridin-6-yl)-5-methyl-2,3-dihydro-1,5-benzoxazepin-4(5H)-one A) ethyl 1-benzyl-4-bromo-5-hydroxy-1H-pyrazole-3-carboxylate To a mixture of ethyl 1-benzyl-5-hydroxy-1H-pyrazole-3-carboxylate (2.3 g) and acetic acid (80 mL) was added bromine (0.718 mL), and the mixture was stirred at room temperature for 30 min. The mixture was concentrated under reduced pressure, and the residue was dissolved in ethyl acetate. The solution was washed with saturated aqueous sodium thiosulfate solution and saturated brine, and dried over anhydrous sodium sulfate, and the solvent was evaporated under reduced pressure to give the title compound (2.97 g).

MS: [M+H]+ 325.1.

B) ethyl 1-benzyl-4-bromo-5-methoxy-1H-pyrazole-3-carboxylate

To a mixture of ethyl 1-benzyl-4-bromo-5-hydroxy-1H-pyrazole-3-carboxylate (0.5 g), anhydrous potassium carbonate (0.319 g) and DMF (5 mL) was added iodomethane (0.144 mL), and the mixture was stirred at 70° C. for 1 hr. To the reaction solution was added saturated aqueous ammonium chloride solution, and the mixture was extracted with ethyl acetate. The extract was washed successively with water and saturated brine, and dried over anhydrous magnesium sulfate, and the solvent was evaporated under reduced pressure. The residue was purified by silica gel column chromatography (ethyl acetate/hexane) to give the title compound (309 mg).

MS: [M+H]+ 339.1.

C) (E)-ethyl 1-benzyl-4-(2-ethoxyvinyl)-5-methoxy-1H-pyrazole-3-carboxylate

A mixture of ethyl 1-benzyl-4-bromo-5-methoxy-1H-pyrazole-3-carboxylate (239.5 mg), (E)-2-(2-ethoxyvinyl)-4,4,5,5-tetramethyl-1,3,2-dioxaborolane (210 mg), 1,1'-bis(diphenylphosphino)ferrocene dichloropalladium(II) (51.7 mg), cesium carbonate (690 mg), 1,2-dimethoxyethane (9 mL) and water (1 mL) was stirred overnight under nitrogen atmosphere at 90° C. To the reaction solution was added saturated brine, and the mixture was extracted with ethyl acetate. The extract was washed successively with water and saturated brine, and dried over anhydrous magnesium sulfate, and the solvent was evaporated under reduced pressure. The residue was purified by silica gel column chromatography (NH, ethyl acetate/hexane) to give the title compound (124 mg).

MS: [M+H]+ 331.3.

D) ethyl 1-benzyl-5-methoxy-4-(2-oxoethyl)-1H-pyrazole-3-carboxylate

To a mixture of (E)-ethyl 1-benzyl-4-(2-ethoxyvinyl)-5-methoxy-1H-pyrazole-3-carboxylate (124 mg) and THF (1 mL) was added 6 M hydrochloric acid (1 mL), and the mixture was stirred at room temperature for 3 hr. To the reaction mixture was added saturated aqueous sodium hydrogencarbonate solution at 0° C., and the mixture was extracted with ethyl acetate. The extract was washed successively with water and saturated brine, and dried over anhydrous magnesium sulfate, and the solvent was evaporated under reduced pressure to give the title compound (113 mg).

MS: [M+H]+ 303.3.

E) (S)-ethyl 1-benzyl-5-methoxy-4-(2-((5-methyl-4-oxo-2,3,4,5-tetrahydrobenzo[b][1,4]oxazepin-3-yl)amino)ethyl)-1H-pyrazole-3-carboxylate To a mixture of ethyl 1-benzyl-5-methoxy-4-(2-oxoethyl)-1H-pyrazole-3-carboxylate (112.8 mg), (S)-3-amino-5-methyl-2,3-dihydrobenzo[b][1,4]oxazepin-4(5H)-one hydrochloride (108 mg), acetic acid (1.5 mL) and acetonitrile (2 mL) was added 2-picoline borane (43.9 mg), and the mixture was stirred at room temperature for 2 hr. The reaction mixture was concentrated under reduced pressure, and the residue was purified by silica gel column chromatography (NH, ethyl acetate/hexane) to give the title compound (51.4 mg).

MS: [M+H]+ 479.3.

F) (3S)-3-(2-benzyl-3-methoxy-7-oxo-2,4,5,7-tetrahydro-6H-pyrazolo[3,4-c]pyridin-6-yl)-5-methyl-2,3-dihydro-1,5-benzoxazepin-4(5H)-one To a mixture of (S)-ethyl 1-benzyl-5-methoxy-4-(2-((5-methyl-4-oxo-2,3,4,5-tetrahydrobenzo[b][1,4]oxazepin-3-yl)amino)ethyl)-1H-pyrazole-3-carboxylate (23.8 mg) and toluene (2 mL) was added 1.8 M trimethylaluminium toluene solution (0.037 mL) under nitrogen atmosphere, and the mixture was stirred at room temperature for 20 min, and then at 100° C. for 1 hr. The reaction mixture was concentrated under reduced pressure, and the residue was purified by silica gel column chromatography (NH, ethyl acetate/hexane) to give the title compound (15.0 mg).

$^1$H NMR (300 MHz, CDCl$_3$) δ2.82 (1H, dt, J=15.01, 4.58 Hz), 3.21 (1H, ddd, J=15.01, 10.48, 4.72 Hz), 3.37 (3H, s), 3.48-3.60 (1H, m), 3.90 (3H, s), 4.20 (1H, dt, J=11.80, 5.05 Hz), 4.37-4.46 (1H, m), 4.60 (1H, dd, J=11.52, 10.01 Hz), 5.19 (2H, s), 5.93 (1H, dd, J=11.71, 8.31 Hz), 7.09-7.38 (9H, m).

Example 49

(3S)-3-(2-benzyl-3-hydroxy-7-oxo-2,4,5,7-tetrahydro-6H-pyrazolo[3,4-c]pyridin-6-yl)-5-methyl-2,3-dihydro-1,5-benzoxazepin-4(5H)-one To a mixture of (3S)-3-(2-benzyl-3-methoxy-7-oxo-2,4,5,7-tetrahydro-6H-pyrazolo[3,4-c]pyridin-6-yl)-5-methyl-2,3-dihydro-1,5-benzoxazepin-4(5H)-one (10.0 mg) and acetonitrile (1.0 mL) were added chlorotrimethylsilane (0.029 mL) and sodium iodide (34.7 mg), and the mixture was stirred under microwave irradiation at 80° C. for 1 hr. The reaction mixture was diluted with saturated aqueous ammonium chloride solution, saturated aqueous sodium thiosulfate solution was added thereto, and the mixture was extracted with ethyl acetate. The extract was dried over anhydrous magnesium sulfate, and the solvent was evaporated under reduced pressure. The residue was subjected to preparative HPLC (C18, mobile phase: water/acetonitrile (containing 0.1% TFA)), saturated aqueous sodium hydrogencarbonate solution was added thereto, and the mixture was extracted with ethyl acetate. The extract was dried over anhydrous magnesium sulfate, and the solvent was evaporated under reduced pressure to give the title compound (5.0 mg).

$^1$H NMR (300 MHz, CDCl$_3$) δ2.34 (1H, t, J=7.55 Hz), 2.60-2.75 (1H, m), 2.80-2.96 (1H, m), 3.32 (3H, s), 3.46-3.60 (1H, m), 4.11-4.25 (1H, m), 4.27-4.40 (1H, m), 4.63-4.79 (1H, m), 4.93 (2H, s), 5.61 (1H, dd, J=11.33, 7.93 Hz), 6.94-7.51 (9H, m).

Example 50

2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxamide To a mixture of 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carbonitrile (40 mg), potassium carbonate (15.5 mg) and dimethyl sulfoxide (3 mL) was added 35% aqueous hydrogen peroxide (0.041 mL), and the mixture was stirred at room temperature for 1 hr. The reaction mixture was diluted with water, and extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane). The obtained solid was washed with ethyl acetate to give the title compound (25 mg).

$^1$H NMR (300 MHz, DMSO-$d_6$) δ 2.79-2.92 (1H, m), 2.99-3.12 (1H, m), 3.30 (3H, s), 3.52-3.67 (1H, m), 3.94-4.08 (1H, m), 4.34 (1H, dd, J=10.0, 7.7 Hz), 4.85 (1H, dd, J=11.9, 10.4 Hz), 5.55 (1H, dd, J=12.1, 7.9 Hz), 5.63 (2H, s), 7.12-7.20 (2H, m), 7.21-7.37 (6H, m), 7.50 (1H, dd, J=7.6, 1.9 Hz), 7.70 (1H, brs), 7.79 (1H, brs).

Example 51 ethyl 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylate A) diethyl 1-benzyl-4-iodo-1H-pyrazole-3,5-dicarboxylate To a mixture of diethyl 4-iodo-1H-pyrazole-3,5-dicarboxylate (15.41 g), benzyl bromide (5.95 mL) and DMF (100 mL) was added potassium carbonate (9.45 g) at 0° C., and the mixture was stirred at room temperature for 1 hr. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (10.19 g).

MS: [M+H]$^+$ 429.1.

B) (E)-diethyl 1-benzyl-4-(2-ethoxyvinyl)-1H-pyrazole-3,5-dicarboxylate

A mixture of diethyl 1-benzyl-4-iodo-1H-pyrazole-3,5-dicarboxylate (1.0 g), (E)-2-(2-ethoxyvinyl)-4,4,5,5-tetramethyl-1,3,2-dioxaborolane (0.833 g), [1,1'-bis(diphenylphosphino)ferrocene]dichloropalladium(II) (0.171 g), cesium carbonate (1.674 g), water (1 mL) and 1,2-dimethoxyethane (11 mL) was stirred overnight under argon atmosphere at 90° C. The reaction mixture was filtered, and the filtrate was concentrated under reduced pressure. The residue was purified by silica gel column chromatography (ethyl acetate/hexane) to give the title compound (0.771 g).

MS: [M+H]$^+$ 373.3.

C) diethyl 1-benzyl-4-(2-oxoethyl)-1H-pyrazole-3,5-dicarboxylate

A mixture of (E)-diethyl 1-benzyl-4-(2-ethoxyvinyl)-1H-pyrazole-3,5-dicarboxylate (771 mg) and THF (7 mL) was slowly added to 6 M hydrochloric acid (7 mL) at 0° C., and the mixture was stirred at room temperature for 1 hr. To the reaction mixture was added saturated aqueous sodium hydrogencarbonate solution, and the mixture was extracted with ethyl acetate. The extract was washed with saturated aqueous sodium hydrogencarbonate solution and saturated brine, and dried over anhydrous sodium sulfate, and the solvent was evaporated under reduced pressure to give the title compound (588 mg).

MS: [M+H]$^+$ 345.3.

D) (S)-diethyl 1-benzyl-4-(2-((5-methyl-4-oxo-2,3,4,5-tetrahydrobenzo[b][1,4]oxazepin-3-yl)amino) ethyl)-1H-pyrazole-3,5-dicarboxylate To a mixture of diethyl 1-benzyl-4-(2-oxoethyl)-1H-pyrazole-3,5-dicarboxylate (588 mg), (S)-3-amino-5-methyl-2,3-dihydrobenzo[b][1,4]oxazepin-4(5H)-one hydrochloride (508 mg) and methanol (2 mL) was added acetic acid (0.2 mL) at room temperature, and the mixture was stirred for 10 min. To the reaction mixture was added 2-picoline borane (85%, 279 mg), and the mixture was stirred at room temperature for 30 min. To the reaction mixture was added water, and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (690 mg).

MS: [M+H]$^+$ 521.3.

E) ethyl 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylate To a mixture of (S)-diethyl 1-benzyl-4-(2-((5-methyl-4-oxo-2,3,4,5-tetrahydrobenzo[b][1,4]oxazepin-3-yl)amino) ethyl)-1H-pyrazole-3,5-dicarboxylate (690 mg) and toluene (7 mL) was added 1.8 M trimethylaluminium toluene solution (0.810 mL) at 0° C., and the mixture was stirred at room temperature for 1 hr, and then at 100° C. for 2 hr. The reaction mixture was cooled to room temperature, saturated aqueous potassium sodium tartrate solution was added thereto, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (27 mg).

$^1$H NMR (300 MHz, CDCl$_3$) δ 1.40 (3H, t, J=7.2 Hz), 3.02-3.17 (1H, m), 3.23-3.41 (4H, m), 3.58 (1H, ddd, J=12.2, 9.9, 4.7 Hz), 4.20-4.32 (1H, m), 4.34-4.50 (3H, m), 4.66 (1H, dd, J=11.7, 9.8 Hz), 5.60-5.85 (3H, m), 7.09-7.32 (9H, m).

Example 52

(3S)-3-(2-benzyl-3-(hydroxymethyl)-7-oxo-2,4,5,7-tetrahydro-6H-pyrazolo[3,4-c]pyridin-6-yl)-5-methyl-2,3-dihydro-1,5-benzoxazepin-4(5H)-one To a mixture of ethyl 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylate (100 mg) and THF (1 mL) was added lithium borohydride (10.20 mg) at 0° C., and the mixture was stirred overnight at room temperature. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate). The residue was subjected to preparative HPLC (C18, mobile phase:

water/acetonitrile (containing 0.1% TFA)), saturated aqueous sodium hydrogencarbonate solution was added thereto, and the mixture was extracted with ethyl acetate. The extract was dried over anhydrous sodium sulfate, and the solvent was evaporated under reduced pressure to give the title compound (6 mg).

$^1$H NMR (300 MHz, CDCl$_3$) δ 2.08 (1H, brs), 2.63 (1H, dt, J=15.7, 4.8 Hz), 2.96 (1H, ddd, J=15.4, 10.5, 5.1 Hz), 3.38 (3H, s), 3.50 (1H, ddd, J=11.9, 10.6, 4.3 Hz), 4.11-4.22 (1H, m), 4.38-4.53 (3H, m), 4.63 (1H, dd, J=11.5, 10.0 Hz), 5.26-5.56 (2H, m), 5.92 (1H, dd, J=11.5, 8.1 Hz), 7.06-7.46 (9H, m).

Example 53

2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylic acid To a mixture of ethyl 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylate (50 mg) in THF (0.8 mL) and water (0.2 mL) was added 4 M aqueous lithium hydroxide solution (39.5 μL) at room temperature, and the mixture was stirred at room temperature for 1 hr. To the reaction mixture was added 0.1 M hydrochloric acid, and the mixture was extracted with ethyl acetate. The extract was washed with saturated brine, and dried over anhydrous sodium sulfate, and the solvent was evaporated under reduced pressure. The residue was subjected to preparative HPLC (C18, mobile phase: water/acetonitrile (containing 0.1% TFA)), saturated aqueous sodium hydrogencarbonate solution was added thereto, and the mixture was extracted with ethyl acetate. The extract was dried over anhydrous sodium sulfate, and the solvent was evaporated under reduced pressure to give the title compound (13 mg).

$^1$H NMR (300 MHz, DMSO-d$_6$) δ 2.92-3.10 (2H, m), 3.30 (3H, s), 3.56-3.70 (1H, m), 3.98-4.09 (1H, m), 4.35 (1H, dd, J=10.2, 7.9 Hz), 4.77-4.96 (1H, m), 5.55 (1H, dd, J=11.9, 7.7 Hz), 5.67-5.85 (2H, m), 7.09-7.18 (2H, m), 7.20-7.40 (6H, m), 7.50 (1H, dd, J=7.6, 1.9 Hz), 13.80 (1H, brs).

Example 54

(3S)-3-(2-benzyl-1-(4-methoxybenzyl)-4-oxo-1,4,6,7-tetrahydro-5H-imidazo[4,5-c]pyridin-5-yl)-5-methyl-2,3-dihydro-1,5-benzoxazepin-4(5H)-one A) methyl 2-benzyl-5-bromo-1H-imidazole-4-carboxylate To a mixture of methyl 2-benzyl-1H-imidazole-4-carboxylate (1.37 g), potassium hydrogencarbonate (0.76 g) and DMF (20 mL) was added bromine (0.39 mL), and the mixture was stirred at room temperature for 2 hr. The reaction mixture was diluted with ethyl acetate, washed with water and saturated brine, and dried over anhydrous sodium sulfate, and the solvent was evaporated under reduced pressure. The residue was purified by silica gel column chromatography (ethyl acetate/hexane), and washed with diisopropyl ether to give the title compound (1.04 g).

MS: [M+H]$^+$ 295.1.

B) methyl 2-benzyl-5-bromo-1-(4-methoxybenzyl)-1H-imidazole-4-carboxylate

A mixture of methyl 2-benzyl-5-bromo-1H-imidazole-4-carboxylate (1.04 g), 4-methoxybenzyl chloride (0.285 mL), potassium carbonate (0.42 g) and DMF (10 mL) was stirred at room temperature for 1 day, and then at 50° C. for 4 hr. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (0.30 g).

MS: [M+H]$^+$ 415.2.

C) (E)-methyl 2-benzyl-5-(2-ethoxyvinyl)-1-(4-methoxybenzyl)-1H-imidazole-4-carboxylate A mixture of methyl 2-benzyl-5-bromo-1-(4-methoxybenzyl)-1H-imidazole-4-carboxylate (0.30 g), (E)-2-(2-ethoxyvinyl)-4,4,5,5-tetramethyl-1,3,2-dioxaborolane (0.286 g), cesium carbonate (0.518 g), 1,1'-bis(diphenylphosphino)ferrocene dichloropalladium(II) dichloromethane complex (0.059 g), 1,2-dimethoxyethane (8 mL) and water (1 mL) was stirred overnight under argon atmosphere at 90° C. The reaction mixture was diluted with ethyl acetate, washed with water and saturated brine, and dried over anhydrous sodium sulfate, and the solvent was evaporated under reduced pressure. The residue was purified by silica gel column chromatography (ethyl acetate/hexane) to give the title compound (0.22 g).

MS: [M+H]$^+$ 407.3.

D) methyl 2-benzyl-1-(4-methoxybenzyl)-5-(2-oxoethyl)-1H-imidazole-4-carboxylate To a mixture of (E)-methyl 2-benzyl-5-(2-ethoxyvinyl)-1-(4-methoxybenzyl)-1H-imidazole-4-carboxylate (110 mg) and THF (5 mL) was added 6 M hydrochloric acid (1 mL), and the mixture was stirred at room temperature for 2 hr. 6 M Hydrochloric acid (2 mL) was added again thereto, and the mixture was stirred at room temperature for 2 hr, and then at 60° C. for 30 min. The reaction mixture was neutralized with saturated aqueous sodium hydrogencarbonate solution, sodium chloride was added thereto until the mixture became saturated, and the mixture was extracted with ethyl acetate. The extract was dried over anhydrous sodium sulfate, and the solvent was evaporated under reduced pressure to give the title compound (100 mg).

MS: [M−H]$^-$ 377.1.

E) (S)-methyl 2-benzyl-1-(4-methoxybenzyl)-5-(2-((5-methyl-4-oxo-2,3,4,5-tetrahydrobenzo[b][1,4]oxazepin-3-yl)amino)ethyl)-1H-imidazole-4-carboxylate To a mixture of methyl 2-benzyl-1-(4-methoxybenzyl)-5-(2-oxoethyl)-1H-imidazole-4-carboxylate (100 mg), (S)-3-amino-5-methyl-2,3-dihydrobenzo[b][1,4]oxazepin-4(5H)-one hydrochloride (60 mg), acetic acid (0.5 mL) and methanol (5 mL) was added 2-picoline borane (37 mg), and the mixture was stirred at room temperature for 1 hr. To the reaction mixture was added saturated aqueous sodium hydrogencarbonate solution, and the mixture was extracted with ethyl acetate. The extract was dried over anhydrous sodium sulfate, and the solvent was evaporated under reduced pressure. The residue was purified by silica gel column chromatography (ethyl acetate/hexane) to give the title compound (0.095 g).

MS: [M+H]$^+$ 555.3.

F) (3S)-3-(2-benzyl-1-(4-methoxybenzyl)-4-oxo-1,4, 6,7-tetrahydro-5H-imidazo[4,5-c]pyridin-5-yl)-5-methyl-2,3-dihydro-1,5-benzoxazepin-4(5H)-one To a mixture of (S)-methyl 2-benzyl-1-(4-methoxybenzyl)-5-(2-((5-methyl-4-oxo-2,3,4,5-tetrahydrobenzo[b][1,4]oxazepin-3-yl)amino)ethyl)-1H-imidazole-4-carboxylate (95 mg) and toluene (10 mL) was added 1.8 M trimethylaluminium toluene solution (0.285 mL), and the mixture was stirred at 100° C. for 4 hr, and then overnight at 120° C. To the reaction mixture was added water, and the mixture was diluted with ethyl acetate, and washed with saturated aqueous potassium sodium tartrate solution. The obtained organic layer was dried over anhydrous sodium sulfate, and the solvent was evaporated under reduced pressure. The residue was purified by silica gel column chromatography (ethyl acetate/hexane) to give the title compound (45 mg).

$^1$H NMR (300 MHz, CDCl$_3$) δ2.53 (1H, dt, J=16.1, 4.6 Hz), 2.94-3.09 (1H, m), 3.36 (3H, s), 3.58 (1H, td, J=11.6, 4.7 Hz), 3.79 (3H, s), 4.09 (2H, s), 4.18-4.30 (1H, m), 4.36-4.48 (1H, m), 4.51-4.63 (1H, m), 4.69-4.89 (2H, m), 5.93 (1H, dd, J=11.5, 8.1 Hz), 6.70-6.85 (4H, m), 7.10-7.31 (9H, m).

Example 55

(3S)-3-(2-benzyl-4-oxo-1,4,6,7-tetrahydro-5H-imidazo[4,5-c]pyridin-5-yl)-5-methyl-2,3-dihydro-1,5-benzoxazepin-4(5H)-one trifluoroacetate A mixture of (3S)-3-(2-benzyl-1-(4-methoxybenzyl)-4-oxo-1,4,6,7-tetrahydro-5H-imidazo[4,5-c]pyridin-5-yl)-5-methyl-2,3-dihydro-1,5-benzoxazepin-4(5H)-one (10 mg), 10% palladium hydroxide/carbon (about 50% wet product in water) (2.4 mg) and methanol (5 mL) was stirred under hydrogen atmosphere overnight at room temperature. To the reaction mixture were added 10% palladium hydroxide/carbon (7 mg) and 6 M hydrochloric acid (1 mL), and the mixture was stirred under hydrogen atmosphere at room temperature for 2 hr, and then at 50° C. for 30 min. The catalyst was removed by filtration, and the filtrate was concentrated under reduced pressure.

Separately, a mixture of (3S)-3-(2-benzyl-1-(4-methoxybenzyl)-4-oxo-1,4,6,7-tetrahydro-5H-imidazo[4,5-c]pyridin-5-yl)-5-methyl-2,3-dihydro-1,5-benzoxazepin-4(5H)-one (22 mg), 10% palladium hydroxide/carbon (about 50% wet product in water) (16 mg), 6 M hydrochloric acid (1 mL) and methanol (5 mL) was stirred under hydrogen atmosphere at 50° C. for 2.5 hr. The insoluble substance was removed by filtration, and the filtrate was concentrated under reduced pressure. The combined crude products were subjected to HPLC (C18, mobile phase: water/acetonitrile (containing 0.1%. TFA)), and the obtained fraction was concentrated under reduced pressure to give the title compound (21 mg).

$^1$H NMR (300 MHz, CDCl$_3$) δ3.01-3.17 (1H, m), 3.20-3.39 (4H, m), 3.63-3.79 (1H, m), 3.89-4.13 (2H, m), 4.29-4.46 (2H, m), 4.74 (1H, dd, J=11.7, 10.2 Hz), 5.64 (1H, dd, J=11.9, 7.7 Hz), 6.77-6.89 (1H, m), 6.95-7.21 (5H, m), 7.28-7.35 (3H, m).

Example 56

(3S)-3-(2-benzyl-1-methyl-4-oxo-1,4,6,7-tetrahydro-5H-imidazo[4,5-c]pyridin-5-yl)-5-methyl-2,3-dihydro-1,5-benzoxazepin-4(5H)-one A) methyl 2-benzyl-5-bromo-1-methyl-1H-imidazole-4-carboxylate, methyl 2-benzyl-4-bromo-1-methyl-1H-imidazole-5-carboxylate A mixture of methyl 2-benzyl-5-bromo-1H-imidazole-4-carboxylate (0.63 g), methyl iodide (0.200 mL), potassium carbonate (0.885 g) and DMF (10 mL) was stirred overnight at room temperature. The reaction mixture was diluted with water, and extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give methyl 2-benzyl-5-bromo-1-methyl-1H-imidazole-4-carboxylate (0.18 g, MS: [M+H]$^+$ 309.2) and methyl 2-benzyl-4-bromo-1-methyl-1H-imidazole-5-carboxylate (0.38 g, MS: [M+H]$^+$ 309.2), respectively.

B) (E)-methyl 2-benzyl-5-(2-ethoxyvinyl)-1-methyl-1H-imidazole-4-carboxylate

The title compound (140 mg) was obtained in the same manner as in Step C of Example 54.
MS: [M+H]$^+$ 301.3.

C) methyl 2-benzyl-1-methyl-5-(2-oxoethyl)-1H-imidazole-4-carboxylate

The title compound (130 mg) was obtained in the same manner as in Step D of Example 54.
MS: [M–H]$^-$ 271.0.

D) (S)-methyl 2-benzyl-1-methyl-5-(2-((5-methyl-4-oxo-2,3,4,5-tetrahydrobenzo[b][1,4]oxazepin-3-yl)amino)ethyl)-1H-imidazole-4-carboxylate The title compound (130 mg) was obtained in the same manner as in Step E of Example 54.
MS: [M+H]$^+$ 449.3.

E) (3S)-3-(2-benzyl-1-methyl-4-oxo-1,4,6,7-tetrahydro-5H-imidazo[4,5-c]pyridin-5-yl)-5-methyl-2,3-dihydro-1,5-benzoxazepin-4(5H)-one The title compound (51 mg) was obtained in the same manner as in Step F of Example 54.
$^1$H NMR (300 MHz, CDCl$_3$) δ 2.67 (1H, dt, J=15.9, 4.7 Hz), 3.09-3.24 (1H, m), 3.26-3.34 (3H, m), 3.31 (3H, s), 3.37 (3H, s), 3.63 (1H, td, J=11.5, 4.9 Hz), 4.15 (2H, s), 4.23-4.36 (1H, m), 4.43 (1H, dd, J=9.8, 8.3 Hz), 4.60 (1H, dd, J=11.7, 10.2 Hz), 5.93 (1H, dd, J=11.7, 8.3 Hz), 7.13-7.35 (9H, m).

Example 57

(3S)-3-(2-benzyl-3-methyl-4-oxo-3,4,6,7-tetrahydro-5H-imidazo[4,5-c]pyridin-5-yl)-5-methyl-2,3-dihydro-1,5-benzoxazepin-4(5H)-one A) (E)-methyl 2-benzyl-4-(2-ethoxyvinyl)-1-methyl-1H-imidazole-5-carboxylate The title compound (310 mg) was obtained using methyl 2-benzyl-4-bromo-1-methyl-1H-imidazole-5-carboxylate obtained in Step A of Example 56, in the same manner as in Step C of Example 54.
MS: [M+H]$^+$ 301.3.

B) (S)-methyl 2-benzyl-1-methyl-4-(2-((5-methyl-4-oxo-2,3,4,5-tetrahydrobenzo[b][1,4]oxazepin-3-yl)amino)ethyl)-1H-imidazole-5-carboxylate To a mixture of (E)-methyl 2-benzyl-4-(2-ethoxyvinyl)-1-methyl-1H-imidazole-5-carboxylate (310 mg) and THF (5 mL) was added 6 M hydrochloric acid (5 mL), and the mixture was stirred overnight at room temperature. The reaction mixture was neutralized with saturated aqueous sodium hydrogencarbonate solution, sodium chloride was added thereto until the mixture became saturated, and the mixture was extracted with ethyl acetate. The extract was dried over anhydrous sodium sulfate, and the solvent was evaporated under reduced pressure. To the residue were added acetic acid (0.5 mL), methanol (1.5 mL), (S)-3-amino-5-methyl-2,3-dihydrobenzo[b][1,4]oxazepin-4(5H)-one hydrochloride (0.236 g) and 2-picoline borane (0.143 g), and the mixture was stirred at room temperature for 1 hr. The reaction mixture was neutralized with saturated aqueous sodium hydrogencarbonate solution, sodium chloride was added thereto until the mixture became saturated, and the mixture was extracted with ethyl acetate. The extract was dried over anhydrous sodium sulfate, and the solvent was evaporated under reduced pressure. The residue was purified by silica gel column chromatography (NH, ethyl acetate/hexane) to give the title compound (0.17 g).
MS: [M+H]$^+$ 449.3.

C) (3S)-3-(2-benzyl-3-methyl-4-oxo-3,4,6,7-tetrahydro-5H-imidazo[4,5-c]pyridin-5-yl)-5-methyl-2,3-dihydro-1,5-benzoxazepin-4(5H)-one The title compound (20 mg) was obtained using (S)-methyl 2-benzyl-1-methyl-4-(2-((5-methyl-4-oxo-2,3,4,5-tetrahydrobenzo[b][1,4]oxazepin-3-yl)amino)ethyl)-1H-imidazole-5-carboxylate, in the same manner as in Step F of Example 54.
$^1$H NMR (300 MHz, CDCl$_3$) δ 2.75-2.91 (1H, m), 3.06-3.23 (1H, m), 3.38 (3H, s), 3.55-3.64 (1H, m), 3.65 (3H, s), 4.10 (2H, s), 4.21-4.32 (1H, m), 4.36 (1H, dd, J=9.8, 7.9 Hz), 4.70 (1H, dd, J=12.1, 9.8 Hz), 5.75 (1H, dd, J=12.1, 7.9 Hz), 7.11-7.25 (7H, m), 7.27-7.34 (2H, m).

Example 58

(3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one A) ethyl 1-benzyl-4-(2-{[(3S)-8-bromo-5-methyl-4-oxo-2,3,4,5-tetrahydro-1,5-benzoxazepin-3-yl]amino}ethyl)-5-chloro-1H-pyrazole-3-carboxylate To a mixture of ethyl 1-benzyl-5-chloro-4-(2-oxoethyl)-1H-pyrazole-3-carboxylate (1.20 g), (S)-3-amino-8-bromo-5-methyl-2,3-dihydrobenzo[b][1,4]oxazepin-4(5H)-one hydrochloride (1.20 g), acetic acid (3.0 mL) and methanol (30 mL) was added 2-picoline borane (459 mg) under ice-cooling, and the mixture was stirred at room temperature for 1 hr. To the reaction mixture was added saturated aqueous sodium hydrogencarbonate solution at room temperature, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (2.19 g).
MS: [M+H]$^+$ 561.1, 563.1.

B) (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one To a mixture of ethyl 1-benzyl-4-(2-{[(3S)-8-bromo-5-methyl-4-oxo-2,3,4,5-tetrahydro-1,5-benzoxazepin-3-yl]amino}ethyl)-5-chloro-1H-pyrazole-3-carboxylate (1.42 g) and toluene (15 mL) was added 1.8 M trimethylaluminium toluene solution (4.21 mL) at 0° C., and the mixture was stirred at 100° C. for 10 min. To the reaction mixture was added saturated aqueous ammonium chloride solution at room temperature, and the insoluble substance was removed by filtration. The filtrate was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (1.08 g).
$^1$H NMR (300 MHz, CDCl$_3$) δ 2.67 (1H, dt, J=15.9, 4.7 Hz), 3.05 (1H, ddd, J=15.5, 10.4, 5.1 Hz), 3.35 (3H, s), 3.54 (1H, ddd, J=12.0, 10.5, 4.3 Hz), 4.23 (1H, dt, J=12.1, 5.3 Hz), 4.41 (1H, dd, J=10.0, 8.1 Hz), 4.64 (1H, dd, J=11.7, 10.2 Hz), 5.39 (2H, s), 5.90 (1H, dd, J=11.7, 8.3 Hz), 7.11 (1H, d, J=8.3 Hz), 7.23-7.42 (7H, m).

Example 59

(3S)-3-(2-benzyl-3-chloro-7-oxo-2,4,5,7-tetrahydro-6H-pyrazolo[3,4-c]pyridin-6-yl)-5-methyl-8-(oxetan-3-yl)-2,3-dihydro-1,5-benzoxazepin-4(5H)-one To a mixture of (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (80 mg), 1,10-phenanthroline (5.6 mg), 4-ethylpyridine (8.3 mg), sodium tetrafluoride (8.5 mg), manganese powder (325 mesh, 99.9%) (17 mg), 3-bromooxetane (21 mg) and methanol (5 mL) was added nickel(II) chloride (dimethoxyethane additive) (6.8 mg) at room temperature, and the mixture was stirred under argon atmosphere at 60° C. for 4 hr. To the reaction mixture were added 3-bromooxetane (42.5 mg), nickel(II) chloride (dimethoxyethane additive) (13.6 mg), 4-ethylpyridine (16.6 mg), 1,10-phenanthroline (11.2 mg), sodium tetrafluoride (17 mg) and manganese powder (325 mesh, 99.9%) (34 mg) at room temperature, and the mixture was stirred under argon atmosphere at 60° C. for 1 hr. The insoluble substance was removed by filtration, the filtrate was poured into water at room temperature, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) and then silica gel column chromatography (NH, ethyl acetate/hexane). To the obtained residue were added diisopropyl ether, hexane and ethyl acetate, and the solid was collected by filtration to give the title compound (5 mg).
$^1$H NMR (300 MHz, CDCl$_3$) δ 2.67 (1H, dt, J=15.7, 4.6 Hz), 3.06 (1H, ddd, J=15.6, 10.5, 5.3 Hz), 3.37 (3H, s), 3.49-3.63 (1H, m), 4.16-4.31 (2H, m), 4.42 (1H, dd, J=10.0, 8.1 Hz), 4.64 (1H, dd, J=11.5, 10.0 Hz), 4.73-4.84 (2H, m), 5.04-5.16 (2H, m), 5.40 (2H, s), 5.92 (1H, dd, J=11.7, 8.3 Hz), 7.19-7.37 (8H, m).

Example 60

(3S)-3-(2-benzyl-3-chloro-7-oxo-2,4,5,7-tetrahydro-6H-pyrazolo[3,4-c]pyridin-6-yl)-5-methyl-8-(1-methyl-1H-imidazol-2-yl)-2,3-dihydro-1,5-benzoxazepin-4(5H)-one To a mixture of (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (150 mg), triphenylphosphine (38 mg), potassium carbonate (121 mg), copper(II) acetate (11 mg), 1-methyl-1H-imidazole (72 mg) and dehydrated toluene (10 mL) was added palladium(II) acetate (13 mg) at room temperature. The reaction mixture was stirred under argon atmosphere at 100° C. for 4 hr. To the reaction mixture was added water at room temperature, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) and then silica gel column chromatography (ethyl acetate/hexane). To the residue were added diisopropyl ether and ethyl acetate, and the solid was collected by filtration to give the title compound (9 mg).

$^1$H NMR (300 MHz, CDCl$_3$) δ 2.60-2.75 (1H, m), 2.99-3.14 (1H, m), 3.41 (3H, s), 3.51-3.63 (1H, m), 3.83 (3H, s), 4.19-4.30 (1H, m), 4.38-4.52 (1H, m), 4.60-4.73 (1H, m), 5.40 (2H, s), 5.97 (1H, dd, J=11.5, 8.1 Hz), 6.97-7.02 (1H, m), 7.12-7.16 (1H, m), 7.21-7.38 (6H, m), 7.48-7.57 (2H, m).

Example 61

(3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxylic acid To a mixture of (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (50 mg), palladium(II) acetate (2.2 mg), (9,9-dimethyl-9H-xanthene-4,5-diyl)bis(diphenylphosphine) (5.6 mg), 2,4,6-trichlorophenyl formate (33 mg) and dehydrated acetonitrile (5 mL) was added triethylamine (0.026 mL) at room temperature. The mixture was sealed under argon atmosphere, and stirred overnight at 80° C. To the reaction mixture was added water, and the mixture was washed with ethyl acetate. The aqueous layer was acidified with 1 M hydrochloric acid, and extracted with ethyl acetate. The extract was washed with water and saturated brine, and dried over anhydrous sodium sulfate, and the solvent was evaporated under reduced pressure to give the title compound (10 mg).

$^1$H NMR (300 MHz, DMSO-d$_6$) δ 2.61-2.89 (2H, m), 3.30 (3H, brs), 3.64 (1H, ddd, J=12.8, 8.1, 4.8 Hz), 3.94-4.08 (1H, m), 4.43 (1H, dd, J=9.9, 8.0 Hz), 4.82-4.95 (1H, m), 5.43 (2H, s), 5.53 (1H, dd, J=12.0, 7.8 Hz), 7.13-7.22 (2H, m), 7.25-7.40 (3H, m), 7.61 (1H, d, J=8.3 Hz), 7.73 (1H, d, J=2.1 Hz), 7.87 (1H, dd, J=8.3, 1.9 Hz), 13.05 (1H, brs).

Example 62

(3S)-3-(2-benzyl-3-chloro-7-oxo-2,4,5,7-tetrahydro-6H-pyrazolo[3,4-c]pyridin-6-yl)-N-(2-hydroxy-2-methylpropyl)-5-methyl-4-oxo-2,3,4,5-tetrahydro-1,5-benzoxazepine-8-carboxamide A) 2,4,6-trichlorophenyl (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxylate To a mixture of (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (50 mg), palladium(II) acetate (2.2 mg), (9,9-dimethyl-9H-xanthene-4,5-diyl)bis(diphenylphosphine) (5.6 mg), 2,4,6-trichlorophenyl formate (33 mg) and dehydrated acetonitrile (5 mL) was added triethylamine (0.026 mL) at room temperature. The mixture was sealed under argon atmosphere, and stirred overnight at 80° C. To the reaction mixture was added water, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane) to give the title compound (32 mg).

MS: [M+H]$^+$ 661.0.

B) (3S)-3-(2-benzyl-3-chloro-7-oxo-2,4,5,7-tetrahydro-6H-pyrazolo[3,4-c]pyridin-6-yl)-N-(2-hydroxy-2-methylpropyl)-5-methyl-4-oxo-2,3,4,5-tetrahydro-1,5-benzoxazepine-8-carboxamide To a mixture of 2,4,6-trichlorophenyl (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxylate (32 mg), N,N-dimethylpyridin-4-amine (0.6 mg) and THF (3 mL) was added 1-amino-2-methylpropan-2-ol (6.5 mg) at room temperature. The reaction mixture was stirred overnight at 50° C. The mixture was concentrated under reduced pressure, and the residue was purified by silica gel column chromatography (NH, methanol/ethyl acetate). To the obtained solid was added diisopropyl ether, and the solid was collected by filtration to give the title compound (23 mg).

$^1$H NMR (300 MHz, CDCl$_3$) δ 1.32 (6H, s), 2.16 (1H, s), 2.68 (1H, dt, J=15.5, 4.7 Hz), 3.06 (1H, ddd, J=15.6, 10.5, 5.3 Hz), 3.39 (3H, s), 3.45-3.68 (3H, m), 4.17-4.29 (1H, m), 4.43 (1H, dd, J=10.0, 8.1 Hz), 4.66 (1H, dd, J=11.7, 10.2 Hz), 5.39 (2H, s), 5.90 (1H, dd, J=11.7, 8.3 Hz), 6.63 (1H, t, J=5.7 Hz), 7.22-7.36 (6H, m), 7.63 (1H, d, J=1.9 Hz), 7.69 (1H, dd, J=8.3, 1.9 Hz).

Example 63

(3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile (compound A)

To a mixture of (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one (1.08 g), zinc cyanide (0.369 g) and DMF (20 mL) was added tetrakis(triphenylphosphine)palladium(0) (0.484 g) at room temperature. The reaction mixture was stirred under argon atmosphere at 100° C. for 2 hr. To the reaction mixture was added water at room temperature, and the mixture was extracted with ethyl acetate. The extract was washed with water and saturated brine, and dried over anhydrous sodium sulfate, and the solvent was evaporated under reduced pressure. The residue was purified by silica gel column chromatography (ethyl acetate/hexane). To the residue were added diethyl ether, diisopropyl ether and ethyl acetate, and the solid was collected by filtration to give the title compound (0.60 g).

$^1$H NMR (300 MHz, CDCl$_3$) δ 2.69 (1H, dt, J=15.7, 4.8 Hz), 3.05 (1H, ddd, J=15.6, 10.3, 5.1 Hz), 3.39 (3H, s), 3.51-3.61 (1H, m), 4.15-4.27 (1H, m), 4.45 (1H, dd, J=10.2, 7.9 Hz), 4.69 (1H, dd, J=11.9, 10.0 Hz), 5.40 (2H, s), 5.89 (1H, dd, J=11.7, 7.9 Hz), 7.20-7.38 (6H, m), 7.48 (1H, d, J=1.9 Hz), 7.57 (1H, dd, J=8.3, 1.9 Hz).

Example 64

(3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxamide To a mixture of (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile (76.9 mg), aqueous hydrogen peroxide (30%, 0.3 ml) and dimethyl sulfoxide (0.5 mL) was added potassium carbonate (16.1 mg), and the mixture was stirred at room temperature for 2 hr. To the reaction mixture was added saturated aqueous sodium thiosulfate solution, and the mixture was extracted with ethyl acetate. The extract was washed successively with saturated aqueous ammonium chloride solution and saturated brine, and dried over anhydrous sodium sulfate, and the solvent was evaporated under reduced pressure. The residue was purified by silica gel column chromatography (NH, ethyl acetate/methanol) to give the title compound (31.6 mg).

$^1$H NMR (300 MHz, CDCl$_3$) δ2.60-2.72 (1H, m), 2.96-3.11 (1H, m), 3.37 (3H, s), 3.47-3.59 (1H, m), 4.22 (1H, dt, J=12.1, 5.1 Hz), 4.37 (1H, dd, J=9.8, 7.9 Hz), 4.63 (1H, dd, J=11.7, 9.8 Hz), 5.39 (2H, s), 5.86 (1H, dd, J=11.7, 7.9 Hz), 5.91-6.87 (2H, m), 7.17-7.37 (6H, m), 7.63-7.75 (2H, m).

Example 65

7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one A) ethyl 4-(3-aminopyridin-2-yl)butanoate A mixture of palladium acetate (65.0 mg), 2-dicyclohexylphosphino-2',4',6'-triisopropylbiphenyl (276 mg) and THF (5 mL) was stirred under nitrogen atmosphere at room temperature for 5 min. To the reaction mixture were added successively a mixture of 2-bromopyridin-3-amine (500 mg) and THF (5 mL), and then (4-ethoxy-4-oxobutyl)zinc(II) bromide THF solution (0.5 M, 8.67 mL), and the mixture was stirred under nitrogen atmosphere at 50° C. for 1 hr. The reaction mixture was diluted with ethyl acetate, washed successively with water and saturated brine, and dried over anhydrous sodium sulfate, and the solvent was evaporated under reduced pressure. The residue was purified by silica gel column chromatography (ethyl acetate/hexane) to give the title compound (346 mg).

MS: [M+1]$^+$ 209.4.

B) 8,9-dihydro-5H-pyrido[3,2-b]azepin-6(7H)-one

To a mixture of ethyl 4-(3-aminopyridin-2-yl)butanoate (346 mg) and toluene (10 mL) was added 1.8 M trimethylaluminium toluene solution (0.92 mL), and the mixture was stirred under nitrogen atmosphere at room temperature for 5 min, and then at 100° C. for 30 min. The reaction mixture was concentrated under reduced pressure, and the residue was purified by silica gel column chromatography (NH, hexane/ethyl acetate) to give the title compound (213 mg).

$^1$H NMR (300 MHz, CDCl$_3$) δ2.30-2.46 (4H, m), 3.08 (2H, t, J=7.2 Hz), 7.15-7.24 (1H, m), 7.25-7.31 (1H, m), 7.58 (1H, brs), 8.38 (1H, dd, J=4.7, 1.7 Hz).

C) 5-methyl-5,7,8,9-tetrahydro-6H-pyrido[3,2-b]azepin-6-one

To a mixture of 8,9-dihydro-5H-pyrido[3,2-b]azepin-6(7H)-one (330 mg) and DMF (10 mL) was added sodium hydride (60%, 98 mg) under ice-cooling, and the mixture was stirred under ice-cooling for 5 min. To the reaction mixture was added methyl iodide (347 mg) under ice-cooling, and the mixture was stirred at room temperature for 30 min. To the reaction mixture was added water at room temperature, and the mixture was extracted with ethyl acetate. The extract was washed with water and saturated brine, and dried over anhydrous sodium sulfate, and the solvent was evaporated under reduced pressure. The residue was purified by silica gel column chromatography (methanol/ethyl acetate) to give the title compound (180 mg).

MS: [M+H]$^+$ 177.4.

D) 7-iodo-5-methyl-5,7,8,9-tetrahydro-6H-pyrido[3,2-b]azepin-6-one

To a mixture of 5-methyl-5,7,8,9-tetrahydro-6H-pyrido[3,2-b]azepin-6-one (130 mg) and THF (5 mL) was added 1.5 M lithium diisopropylamine THF/ethylbenzene/heptane solution (0.541 mL) at −78° C., and the mixture was stirred under argon atmosphere for 1 hr. A mixture of iodine (206 mg) and THF (5 mL) was added thereto at −78° C., and the mixture was stirred under argon atmosphere for 1 hr. To the reaction mixture was added water at room temperature, and the mixture was extracted with ethyl acetate. The extract was washed with saturated brine, and dried over anhydrous sodium sulfate, and the solvent was evaporated under reduced pressure. The residue was purified by silica gel column chromatography (methanol/ethyl acetate) to give the title compound (166 mg).

MS: [M+H]$^+$ 303.1.

E) 7-azido-5-methyl-5,7,8,9-tetrahydro-6H-pyrido[3,2-b]azepin-6-one

To a mixture of 7-iodo-5-methyl-5,7,8,9-tetrahydro-6H-pyrido[3,2-b]azepin-6-one (166 mg) and DMF (5 mL) was added sodium azide (179 mg) at room temperature. The reaction mixture was stirred under argon atmosphere at room temperature for 2 hr. To the reaction mixture was added water at room temperature, and the mixture was extracted with ethyl acetate. The extract was washed with water and saturated brine, and dried over anhydrous sodium sulfate, and the solvent was evaporated under reduced pressure. The residue was purified by silica gel column chromatography (NH, methanol/ethyl acetate) to give the title compound (90 mg).
MS: [M+H]+ 218.3.

F) 7-amino-5-methyl-5,7,8,9-tetrahydro-6H-pyrido[3,2-b]azepin-6-one

A mixture of 7-azido-5-methyl-5,7,8,9-tetrahydro-6H-pyrido[3,2-b]azepin-6-one (90 mg) and palladium/carbon (palladium 10%, about 50% wet product in water, 88 mg) in ethanol (10 mL) was stirred under hydrogen atmosphere overnight at room temperature. The reaction mixture was filtered, and the filtrate was concentrated under reduced pressure to give the title compound (90 mg).
MS: [M+H]+ 192.4.

G) ethyl 1-benzyl-5-chloro-4-{2-[(5-methyl-6-oxo-6,7,8,9-tetrahydro-5H-pyrido[3,2-b]azepin-7-yl)amino]ethyl}-1H-pyrazole-3-carboxylate To a mixture of ethyl 1-benzyl-5-chloro-4-(2-oxoethyl)-1H-pyrazole-3-carboxylate (188 mg) and 7-amino-5-methyl-5,7,8,9-tetrahydro-6H-pyrido[3,2-b]azepin-6-one (90 mg) in methanol (10 mL) and acetic acid (1 mL) was added 2-picoline borane (55 mg) under ice-cooling. The reaction mixture was stirred at room temperature for 3 hr. To the reaction mixture was added saturated aqueous sodium hydrogencarbonate solution at room temperature, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (85 mg).
MS: [M+H]+ 482.2, 484.2.

H) 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one To a mixture of ethyl 1-benzyl-5-chloro-4-{2-[(5-methyl-6-oxo-6,7,8,9-tetrahydro-5H-pyrido[3,2-b]azepin-7-yl)amino]ethyl}-1H-pyrazole-3-carboxylate (60 mg) in toluene (10 mL) was added 1.8 M trimethylaluminium toluene solution (0.21 mL) at 0° C., and the mixture was stirred at 100° C. for 30 min. To the reaction mixture was added saturated aqueous ammonium chloride solution, the insoluble substance was removed by filtration, and the filtrate was extracted with ethyl acetate. The extract was washed with saturated brine, and dried over anhydrous sodium sulfate, and the solvent was evaporated under reduced pressure. The residue was purified by silica gel column chromatography (NH, methanol/ethyl acetate) to give the title compound (27 mg).
1H NMR (300 MHz, CDCl3) δ 2.32-2.60 (2H, m), 2.62-2.73 (1H, m), 2.92-3.15 (3H, m), 3.37 (3H, s), 3.61 (1H, ddd, J=12.1, 9.8, 4.5 Hz), 4.13-4.20 (1H, m), 5.38 (2H, s), 5.52 (1H, dd, J=11.7, 8.3 Hz), 7.21-7.36 (6H, m), 7.53 (1H, dd, J=8.1, 1.3 Hz), 8.41 (1H, dd, J=4.7, 1.3 Hz).

Example 66

7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one (optical isomer)

A racemate (47 mg) of 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one was subjected to HPLC (column: CHIRALCEL OJ, 4.6 mmID×250 mmL, mobile phase: hexane/ethanol=500/500) to give the compound having a shorter retention time as the title compound (14 mg).

Example 67

7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one (optical isomer)

A racemate (47 mg) of 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one was subjected to HPLC (column: CHIRALCEL OJ, 4.6 mmID×250 mmL, mobile phase: hexane/ethanol=500/500) to give the compound having a longer retention time as the title compound (13 mg).

Example 68

(3S)-3-(2-benzyl-5-methyl-7-oxo-2,4,5,7-tetrahydro-6H-pyrazolo[3,4-c]pyridin-6-yl)-5-methyl-2,3-dihydro-1,5-benzoxazepin-4(5H)-one A) ethyl 1-benzyl-4-(2-hydroxypropyl)-1H-pyrazole-3-carboxylate A mixture of ethyl 1-benzyl-4-(2-oxoethyl)-1H-pyrazole-3-carboxylate (3.18 g) and THF (40 mL) was cooled to −78° C., 3.0 M methylmagnesium chloride THF solution (3.89 mL) was added thereto, and the mixture was stirred at −78° C. for 1 hr. To the reaction mixture was added saturated aqueous sodium chloride solution, and the mixture was extracted with ethyl acetate. The extract was washed with saturated brine, and dried over anhydrous sodium sulfate, and the solvent was evaporated under reduced pressure. The residue was purified by silica gel column chromatography (NH, ethyl acetate/hexane) to give the title compound (1.09 g).
MS: [M+H]+ 289.3.

B) ethyl 1-benzyl-4-(2-oxopropyl)-1H-pyrazole-3-carboxylate

To a mixture of ethyl 1-benzyl-4-(2-hydroxypropyl)-1H-pyrazole-3-carboxylate (1.09 g), sulfur trioxide-pyridine complex (1.805 g) and DMF (15 mL) was added triethylamine (3.16 mL) at room temperature, and the mixture was stirred at room temperature for 2 hr. To the reaction mixture was added again sulfur trioxide-pyridine complex (1.805 g), and the mixture was stirred at 50° C. for 2 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/hexane) to give the title compound (0.23 g).
MS: [M+H]+ 287.3.

C) ethyl 1-benzyl-4-(2-(((S)-5-methyl-4-oxo-2,3,4,5-tetrahydrobenzo[b][1,4]oxazepin-3-yl)amino)propyl)-1H-pyrazole-3-carboxylate The title compound (53 mg) was obtained in the same manner as in Step D of Example 1.
MS: [M+H]+ 463.4.

D) (3S)-3-(2-benzyl-5-methyl-7-oxo-2,4,5,7-tetrahydro-6H-pyrazolo[3,4-c]pyridin-6-yl)-5-methyl-2,3-dihydro-1,5-benzoxazepin-4(5H)-one To a mixture of ethyl 1-benzyl-4-(2-(((S)-5-methyl-4-oxo-2,3,4,5-tetrahydrobenzo[b][1,4]oxazepin-3-yl)amino)propyl)-1H-pyrazole-3-carboxylate (53 mg) and toluene (2 mL) was added 1.8 M trimethylaluminium toluene solution (0.191 mL) at 0° C., and the mixture was stirred at 100° C. for 3 hr. The residue was purified by silica gel column chromatography (NH, ethyl acetate/hexane), and subjected to preparative HPLC (C18, mobile phase: water/acetonitrile (containing 0.1% TFA)), saturated aqueous sodium hydrogencarbonate solution was added thereto, and the mixture was extracted with ethyl acetate. The extract was dried over anhydrous sodium sulfate, and the solvent was evaporated under reduced pressure to give the title compound (5.3 mg).
$^1$H NMR (300 MHz, CDCl$_3$) δ 1.14 (3H, d, J=6.4 Hz), 2.57 (1H, dd, J=15.3, 1.3 Hz), 3.36 (3H, s), 3.58 (1H, dd, J=15.3, 5.1 Hz), 4.37-4.48 (1H, m), 4.51 (1H, dd, J=9.6, 7.7 Hz), 4.75 (1H, dd, J=12.1, 9.8 Hz), 5.28-5.43 (2H, m), 6.03 (1H, dd, J=12.3, 7.7 Hz), 7.13-7.26 (7H, m), 7.29-7.38 (3H, m).

Example 69

(3R)-3-(2-benzyl-7-oxo-2,4,5,7-tetrahydro-6H-pyrazolo[3,4-c]pyridin-6-yl)-5-methyl-2,3-dihydro-1,5-benzthiazepin-4(5H)-one 1,1-dioxide A) (R)-tert-butyl (5-methyl-1,1-adioxido-4-oxo-2,3,4,5-tetrahydrobenzo[b][1,4] thiazepin-3-yl)carbamate To a mixture of (R)-tert-butyl (5-methyl-4-oxo-2,3,4,5-tetrahydrobenzo[b][1,4]thiazepin-3-yl)carbamate (300 mg) and dichloromethane (8 mL) was added metachloroperbenzoic acid (538 mg, 78% purity) at 0° C., and the mixture was stirred at room temperature for 1 hr. The reaction mixture was diluted with dichloromethane, washed with saturated aqueous sodium hydrogencarbonate solution and saturated brine, and dried over anhydrous sodium sulfate, and the solvent was evaporated under reduced pressure. The residue was washed with petroleum ether/ethyl acetate to give the title compound (300 mg).
$^1$H NMR (400 MHz, DMSO-d$_6$) δ 1.33 (9H, s), 3.26 (3H, s), 3.61-3.70 (1H, m), 3.96-4.05 (1H, m), 4.22-4.28 (1H, m), 7.39 (1H, d, J=8.4 Hz), 7.62 (1H, t, J=7.6 Hz), 7.78 (1H, d, J=7.6 Hz), 7.87-7.95 (2H, m).

B) (R)-3-amino-5-methyl-2,3-dihydrobenzo[b][1,4] thiazepin-4(5H)-one 1,1-dioxide hydrochloride A mixture of (R)-tert-butyl (5-methyl-1,1-adioxido-4-oxo-2,3,4,5-tetrahydrobenzo[b][1,4]thiazepin-3-yl)carbamate (300 mg) and 4 M hydrochloric acid dioxane solution (10 mL) was stirred at room temperature for 1 hr. The solvent was evaporated under reduced pressure to give the title compound (240 mg).
$^1$H NMR (400 MHz, DMSO-d$_6$) δ 3.34 (3H, s), 3.87-3.97 (1H, m), 4.10-4.18 (1H, m), 4.25-4.32 (1H, m), 7.67 (1H, t, J=7.6 Hz), 7.80 (1H, d, J=8.0 Hz), 7.93-7.99 (2H, m), 8.70 (3H, brs).

C) (R)-ethyl 1-benzyl-4-(2-((5-methyl-1,1-adioxido-4-oxo-2,3,4,5-tetrahydrobenzo[b][1,4]thiazepin-3-yl)amino)ethyl)-1H-pyrazole-3-carboxylate The title compound (110 mg) was obtained in the same manner as in Step D of Example 1.
MS: [M+H]$^+$ 497.2.

D) (3R)-3-(2-benzyl-7-oxo-2,4,5,7-tetrahydro-6H-pyrazolo[3,4-c]pyridin-6-yl)-5-methyl-2,3-dihydro-1,5-benzthiazepin-4(5H)-one 1,1-dioxide The title compound (45 mg) was obtained in the same manner as in Step E of Example 1.
$^1$H NMR (400 MHz, CDCl$_3$) δ2.70-2.77 (1H, m), 3.00-3.11 (1H, m), 3.39 (3H, s), 3.46-3.55 (1H, m), 3.64-3.72 (1H, m), 3.83-3.94 (1H, m), 4.24-4.33 (1H, m), 5.32 (2H, s), 5.85-5.93 (1H, m), 7.15 (1H, s), 7.21-7.26 (2H, m, overlap with CDCl$_3$ signal), 7.30-7.35 (3H, m), 7.47 (1H, d, J=8.0 Hz), 7.53 (1H, t, J=8.0 Hz), 7.80 (1H, t, J=8.0 Hz), 8.05 (1H, d, J=7.6 Hz).

Example 70

(3S)-3-(2-benzyl-4-oxo-2,4,6,7-tetrahydro-5H-pyrazolo[4,3-c]pyridin-5-yl)-5-methyl-2,3-dihydro-1,5-benzoxazepin-4(5H)-one A) ethyl 4-tert-butoxy-3-oxo-butanoate To a mixture of 2-methylpropan-2-ol (18 g) and DMF (200 mL) was added sodium hydride (60%, 24.3 g) at 0° C., and the mixture was stirred at 0° C. for 30 min. To the reaction mixture was added dropwise ethyl 4-chloro-3-oxo-butanoate (20 g), and the mixture was stirred at room temperature for 14 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/petroleum ether) to give the title compound (12 g).
$^1$H NMR (400 MHz, CDCl$_3$) δ 1.21 (9H, s), 1.28 (3H, t, J=7.6 Hz), 3.55 (2H, s), 4.01 (2H, s), 4.19 (2H, q, J=7.2 Hz).

B) ethyl 3-(tert-butoxymethyl)-1H-pyrazole-4-carboxylate

To a mixture of ethyl 4-tert-butoxy-3-oxo-butanoate (12 g) and toluene (100 mL) was added N,N-dimethylformamide dimethyl acetal (10.6 g), and the mixture was stirred at 65° C. for 16 hr. The reaction mixture was concentrated under reduced pressure, acetic acid (20 mL) and hydrazine monohydrate (4.55 g) were added thereto, and the mixture was stirred at room temperature for 14 hr. To the reaction mixture was added ethyl acetate, and the organic layer was washed with saturated aqueous sodium hydrogencarbonate solution and saturated aqueous sodium chloride solution, and dried over anhydrous sodium sulfate, and the solvent was evaporated under reduced pressure. The residue was purified by silica gel column chromatography (ethyl acetate/petroleum ether) to give the title compound (7.00 g).
$^1$H NMR (400 MHz, DMSO-d$_6$) δ 1.23 (9H, s), 1.27 (3H, t, J=7.2 Hz), 4.21 (2H, q, J=7.2 Hz), 4.69 (2H, s), 7.80 (1H, s), 13.27 (1H, brs).

C) ethyl 1-benzyl-3-(tert-butoxymethyl)pyrazole-4-carboxylate

To a mixture of ethyl 3-(tert-butoxymethyl)-1H-pyrazole-4-carboxylate (10.00 g), benzyl chloride (4.42 g) and acetonitrile (100 mL) was added potassium carbonate (29.0 g), and the mixture was stirred at room temperature for 14 hr. To the reaction mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/petroleum ether) to give the title compound (9.00 g).

$^1$H NMR (400 MHz, CDCl$_3$) δ 1.31 (3H, t, J=6.8 Hz), 1.33 (9H, s), 4.25 (2H, q, J=6.8 Hz), 4.71 (2H, s), 5.28 (2H, s), 7.20-7.30 (2H, m), 7.35-7.45 (3H, m), 7.73 (1H, m).

D) ethyl 1-benzyl-3-(hydroxymethyl)pyrazole-4-carboxylate

To a mixture of ethyl 1-benzyl-3-(tert-butoxymethyl) pyrazole-4-carboxylate (9.00 g) and dichloromethane (10 mL) was added trifluoroacetic acid (5 mL), and the mixture was stirred at room temperature for 2 hr. The pH of the reaction mixture was adjusted to 10 with 1 M aqueous sodium hydroxide solution. To the obtained mixture was added water, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/petroleum ether) to give the title compound (6.40 g).

$^1$H NMR (400 MHz, DMSO-d$_6$) δ 1.26 (3H, t, J=7.2 Hz), 4.19 (2H, q, J=7.2 Hz), 4.58 (2H, d, J=6.0 Hz), 4.84 (1H, t, J=6.0 Hz), 5.32 (2H, s), 7.25-7.40 (5H, m), 8.38 (1H, s).

E) ethyl 1-benzyl-3-formyl-pyrazole-4-carboxylate

To a mixture of ethyl 1-benzyl-3-(hydroxymethyl)pyrazole-4-carboxylate (4.60 g) and dichloromethane (50 mL) was added manganese(IV) oxide (15.00 g), and the mixture was stirred at 40° C. for 14 hr. The reaction mixture was concentrated under reduced pressure, and the residue was purified by silica gel column chromatography (ethyl acetate/ petroleum ether) to give the title compound (2.70 g).

$^1$H NMR (400 MHz, DMSO-d$_6$) δ 1.28 (3H, t, J=7.6 Hz), 4.27 (2H, q, J=7.2 Hz), 5.47 (2H, s), 7.25-7.45 (5H, m), 8.63 (1H, s), 10.26 (1H, s).

F) ethyl 1-benzyl-3-(2-methoxyvinyl)-1H-pyrazole-4-carboxylate

To a mixture of (methoxymethyl)triphenylphosphonium chloride (15.8 g) and THF (50 mL) was added 1 M potassium tert-butoxide THF solution (44.9 mL) at 0° C., and the mixture was stirred at 0° C. for 10 min. To the reaction mixture was added a mixture of ethyl 1-benzyl-3-formyl-pyrazole-4-carboxylate (2.70 g) and THF (20 mL) at 0° C., and the mixture was stirred at 0° C. for 30 min, and then at room temperature for 12 hr. To the reaction mixture was added ethyl acetate, and the mixture was washed with water and saturated brine, and dried over anhydrous sodium sulfate, and the solvent was evaporated under reduced pressure. The residue was purified by silica gel column chromatography (ethyl acetate/hexane) to give the title compound (1.60 g).

$^1$H NMR (400 MHz, DMSO-d$_6$) δ 1.26 (3H, t, J=7.2 Hz), 4.19 (2H, q, J=7.2 Hz), 5.28 (2H, s), 6.16 (1H, d, J=13.2 Hz), 7.25-7.45 (6H, m), 8.34 (1H, s).

G) ethyl 1-benzyl-3-(2-oxoethyl)pyrazole-4-carboxylate

To a mixture of ethyl 1-benzyl-3-(2-methoxyvinyl)-1H-pyrazole-4-carboxylate (200 mg) and THF (5 mL) was added 6 M hydrochloric acid, and the mixture was stirred at room temperature for 14 hr. To the reaction mixture were added water and saturated aqueous sodium hydrogencarbonate solution, and the mixture was extracted with ethyl acetate. The extract was washed with saturated brine, and dried over anhydrous sodium sulfate, and the solvent was evaporated under reduced pressure to give the title compound (120 mg).

MS: [M+H]$^+$ 273.0.

H) ethyl 1-benzyl-3-[2-[[(3S)-5-methyl-4-oxo-2,3-dihydro-1,5-benzoxazepin-3-yl]amino]ethyl]pyrazole-4-carboxylate To a mixture of ethyl 1-benzyl-3-(2-oxoethyl)pyrazole-4-carboxylate (120 mg), (S)-3-amino-5-methyl-2,3-dihydrobenzo[b][1,4]oxazepin-4(5H)-one hydrochloride (75 mg) and acetic acid (0.2 mL) in methanol (2 mL) was added 2-picoline borane (53 mg) at 0° C., and the mixture was stirred at 0° C. for 30 min. To the reaction mixture were added water and saturated aqueous sodium hydrogencarbonate solution, and the mixture was extracted with ethyl acetate. The extract was washed with saturated brine, and dried over anhydrous sodium sulfate, and the solvent was evaporated under reduced pressure. The residue was purified by silica gel column chromatography (ethyl acetate/petroleum ether) to give the title compound (120 mg).

MS: [M+H]$^+$ 449.3.

I) (3S)-3-(2-benzyl-4-oxo-2,4,6,7-tetrahydro-5H-pyrazolo[4,3-c]pyridin-5-yl)-5-methyl-2,3-dihydro-1,5-benzoxazepin-4(5H)-one To a mixture of ethyl 1-benzyl-3-[2-[[(3S)-5-methyl-4-oxo-2,3-dihydro-1,5-benzoxazepin-3-yl]amino]ethyl]pyrazole-4-carboxylate (120 mg) and toluene (2 mL) was added 2 M trimethylaluminium toluene solution (0.253 mL) at room temperature, and the mixture was stirred under nitrogen atmosphere at 100° C. for 2 hr. The reaction mixture was cooled to 20° C., water was added thereto, and the mixture was extracted with ethyl acetate. The extract was washed with saturated brine, and dried over anhydrous sodium sulfate, and the solvent was evaporated under reduced pressure. The residue was subjected to HPLC (C18, mobile phase: water/acetonitrile (containing 0.1% ammonia)), the obtained mixture was concentrated under reduced pressure, and the residue was lyophilized to give the title compound (18 mg).

$^1$H NMR (400 MHz, CDCl$_3$) δ 2.75-2.85 (1H, m), 3.10-3.20 (1H, m), 3.31 (3H, s), 3.45-3.55 (1H, m), 4.15-4.25 (1H, m), 4.31 (1H, dd, J=10.0, 8.4 Hz), 4.60 (1H, dd, J=11.6, 10.0 Hz), 5.18 (2H, s), 5.75 (1H, dd, J=11.6, 8.0 Hz), 7.05-7.20 (6H, m), 7.25-7.35 (3H, m), 7.66 (1H, s).

Example 174

(3S)-3-(2-benzyl-3-chloro-7-oxo-2,4,5,7-tetrahydro-6H-pyrazolo[3,4-c]pyridin-6-yl)-N-(13-((3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepin-8-yl)-13-oxo-3,6,9-trioxa-12-azatridec-1-yl)-5-methyl-4-oxo-2,3,4,5-tetrahydro-1,5-benzoxazepine-8-carboxamide To a mixture of (S)-2,4,6-trichlorophenyl 3-(2-benzyl-3-chloro-7-oxo-4,5-dihydro-2H-pyrazolo[3,4-c]pyridin-6 (7H)-yl)-5-methyl-4-oxo-2,3,4,5-tetrahydrobenzo[b][1,4]

oxazepine-8-carboxylate (50 mg) and tetrahydrofuran (2 mL) were added 2,2'-((oxybis(ethane-2,1-diyl))bis(oxy))diethanamine (7.28 mg), triethylamine (7.66 mg) and 4-dimethylaminopyridine (0.46 mg) at room temperature, and the mixture was stirred at 50° C. for 2 hr. The reaction mixture was diluted with ethyl acetate, washed with 0.1 M hydrochloric acid, saturated aqueous sodium hydrogencarbonate solution and saturated brine, and dried over anhydrous sodium sulfate, and the solvent was evaporated under reduced pressure. The residue was purified by silica gel column chromatography (ethyl acetate/methanol) to give the title compound (27.1 mg).

$^1$H NMR (300 MHz, CDCl$_3$) δ2.66 (2H, dt, J=15.9, 4.7 Hz), 3.03 (2H, ddd, J=15.5, 10.4, 5.1 Hz), 3.29-3.39 (5H, m), 3.45-3.81 (17H, m), 4.15-4.27 (2H, m), 4.29-4.43 (2H, m), 4.52-4.71 (2H, m), 5.38 (4H, s), 5.85 (2H, dd, J=11.5, 8.1 Hz), 7.11 (2H, brs), 7.18-7.35 (10H, m), 7.62-7.76 (4H, m).

The compounds of Examples 19 to 42, 72 to 159 and 161 to 174 in the following tables were produced according to the methods described in the above-mentioned Examples, or methods analogous thereto. The compounds of Examples are shown in the following tables. MS in the tables means actual measured value.

TABLE 1-1

| EXAMPLE | IUPAC NAME | Structure | ADDITIVE | MS |
|---|---|---|---|---|
| 1 | (3S)-3-(2-benzyl-7-oxo-2,4,5,7-tetrahydro-6H-pyrazolo[3,4-c]pyridin-6-yl)-5-methyl-2,3-dihydro-1,5-benzoxazepin-4(5H)-one | 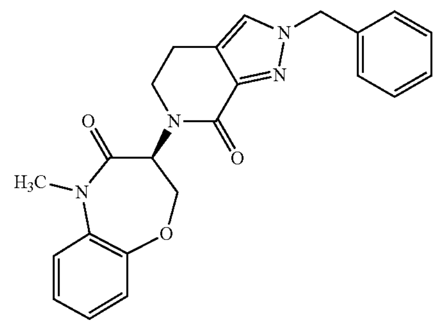 [SMILES: CN1C(=O)[C@@H](N2CCc3cn(Cc4ccccc4)nc3C2=O)COc2ccccc21] | | 403.2 |
| 2 | (3S)-3-(2-benzyl-9-oxo-6,7-dihydro-5H-[1,2,4]triazolo[1,5-a][1,4]diazepin-8(9H)-yl)-5-methyl-2,3-dihydro-1,5-benzoxazepin-4(5H)-one | 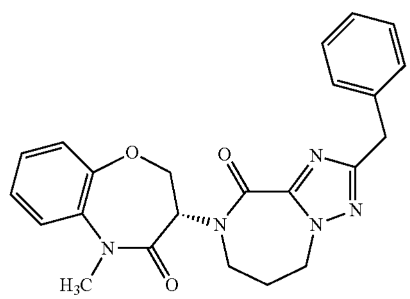 [SMILES: CN1C(=O)[C@@H](N2CCCn3nc(Cc4ccccc4)nc3C2=O)COc2ccccc21] | | 418.1 |
| 3 | 3-(2-benzyl-7-oxo-2,4,5,7-tetrahydro-6H-pyrazolo[3,4-c]pyridin-6-yl)-1,3,4,5-tetrahydro 2H-1-benzazepin-2-one | 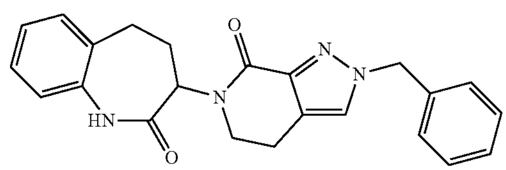 [SMILES: O=C1Nc2ccccc2CCC1N1CCc2cn(Cc3ccccc3)nc2C1=O] | | 387.2 |
| 4 | 3-(2-benzyl-6-oxo-2,6-dihydropyrrolo[3,4-c]pyrazol-5(4H)-yl)-1,3,4,5-tetrahydro-2H-1-benzazepin-2-one | 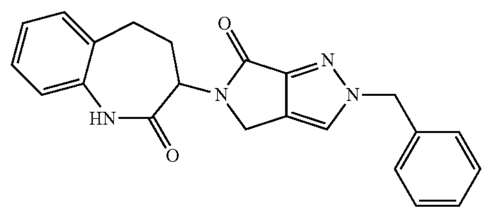 [SMILES: O=C1Nc2ccccc2CCC1N1Cc2cn(Cc3ccccc3)nc2C1=O] | | 373.2 |
| 5 | 3-(2-benzyl-7-oxo-2,7-dihydro-6H-pyrazolo[3,4-c]pyridin-6-yl)-1,3,4,5-tetrahydro-2H-1-benzazepin-2-one | 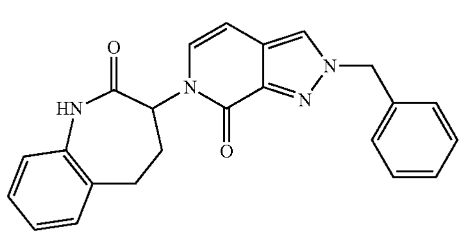 [SMILES: O=C1Nc2ccccc2CCC1n1ccc2cn(Cc3ccccc3)nc2c1=O] | | 385.2 |

TABLE 1-1-continued

| EXAMPLE | IUPAC NAME | Structure | ADDITIVE | MS |
|---|---|---|---|---|
| 6 | 3-(2-benzyl-7-oxo-2,7-dihydro-6H-pyrazolo[3,4-c]pyridin-6-yl)-1-methyl-1,3,4,5-tetrahydro-2H-1-benzazepin-2-one | 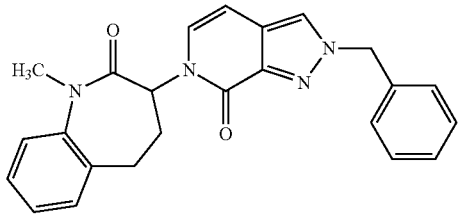 [SMILES: CN1C(=O)C(n2ccc3cn(Cc4ccccc4)nc3c2=O)CCc2ccccc21] | | 399.2 |
| 7 | (3S)-3-(2-benzyl-8-oxo-5,6-dihydroimidazo[1,2-a]pyrazin-7(8H)-yl)-5-methyl-2,3-dihydro-1,5-benzoxazepin-4(5H)-one | 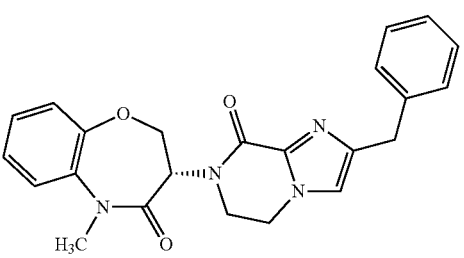 [SMILES: CN1C(=O)[C@@H](N2CCn3cc(Cc4ccccc4)nc3C2=O)COc2ccccc21] | | 403.2 |
| 8 | (3S)-3-(2-benzyl-8-oxo-5,6-dihydro[1,2,4]triazolo[1,5-a]pyrazin-7(8H)-yl)-5-methyl-2,3-dihydro-1,5-benzoxazepin-4(5H)-one | 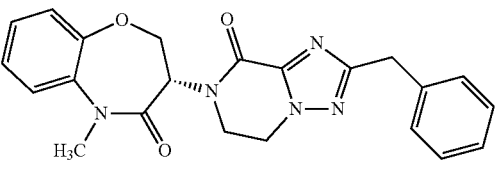 [SMILES: CN1C(=O)[C@@H](N2CCn3nc(Cc4ccccc4)nc3C2=O)COc2ccccc21] | | 404.1 |
| 9 | (3S)-3-(2-(2-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 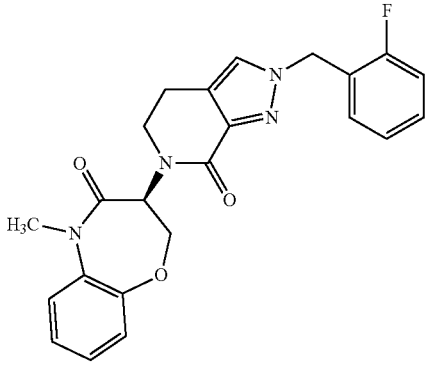 [SMILES: CN1C(=O)[C@@H](N2CCc3cn(Cc4ccccc4F)nc3C2=O)COc2ccccc21] | | 421.2 |

TABLE 1-2

| EXAMPLE | IUPAC NAME | Structure | ADDITIVE | MS |
|---|---|---|---|---|
| 10 | (3S)-3-(2-benzyl-3-bromo-7-oxo-2,4,5,7-tetrahydro-6H-pyrazolo[3,4-c]pyridin-6-yl)-5-methy-2,3-dihydro-1,5-benzoxazepin-4(5H)-one | 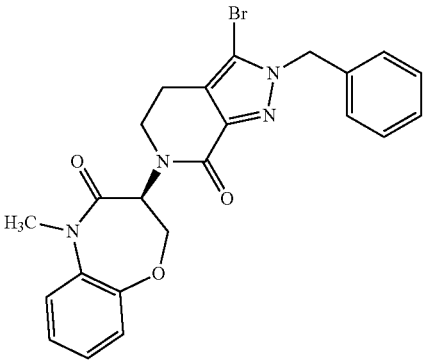 [SMILES: CN1C(=O)[C@@H](N2CCc3c(nn(Cc4ccccc4)c3Br)C2=O)COc2ccccc21] | | 481.1 |

TABLE 1-2-continued

| EXAMPLE | IUPAC NAME | Structure | ADDITIVE | MS |
|---|---|---|---|---|
| 11 | (3S)-3-(2-benzyl-3-methyl-7-oxo-2,4,5,7-tetrahydro-6H-pyrazolo[3,4-c]pyridin-6-yl)-5-methyl-2,3-dihydro-1,5-benzoxazepin-4(5H)-one | 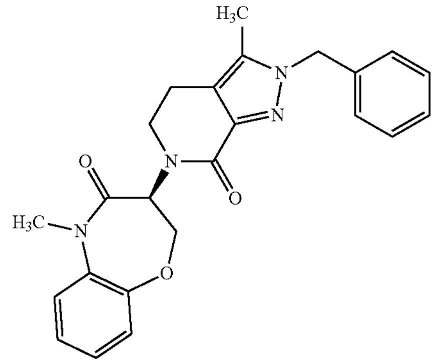 [SMILES: Cc1c2c(nn1Cc1ccccc1)C(=O)N([C@H]1COc3ccccc3N(C)C1=O)CC2] | | 417.2 |
| 12 | 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carbonitrile | 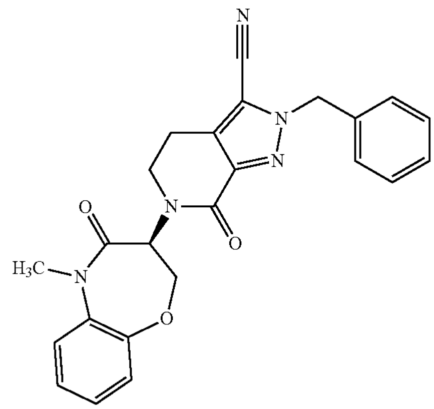 [SMILES: CN1C(=O)[C@@H](N2CCc3c(nn(Cc4ccccc4)c3C#N)C2=O)COc2ccccc21] | | 428.3 |
| 13 | (3S)-3-(2-benzyl-7-oxo-2,4,5,7-tetrahydro-6H-pyrazolo[3,4-c]pyridin-6-yl)-5-methy-4-oxo-2,3,4,5-tetrahydro-1,5-benzoxazepine-8-carbonitrile | 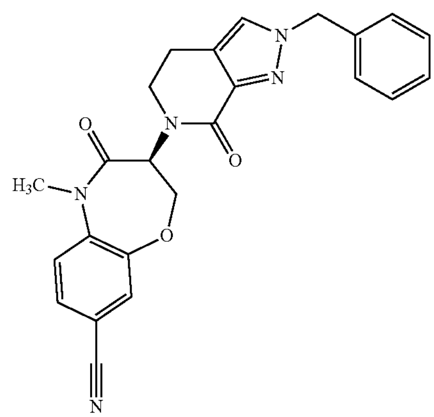 [SMILES: CN1C(=O)[C@@H](N2CCc3cn(Cc4ccccc4)nc3C2=O)COc2cc(C#N)ccc21] | | 428.3 |
| 14 | (3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile | 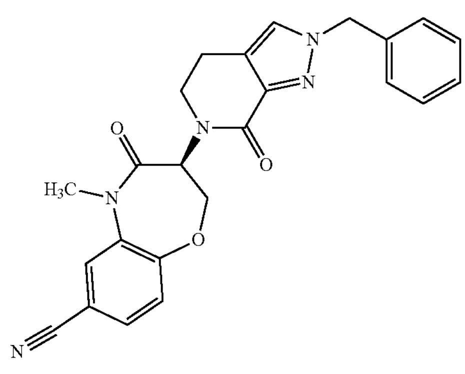 [SMILES: CN1C(=O)[C@@H](N2CCc3cn(Cc4ccccc4)nc3C2=O)COc2ccc(C#N)cc21] | | 428.2 |

TABLE 1-2-continued

| EXAMPLE | IUPAC NAME | Structure | ADDITIVE | MS |
|---|---|---|---|---|
| 15 | 3-(2-benzyl-4-oxo-4,6-dihydro-5H-pyrrolo[3,4-d][1,3]thiazol-5-yl)-1,3,4,5-tetrahydro-2H-1-benzazepin-2-one | 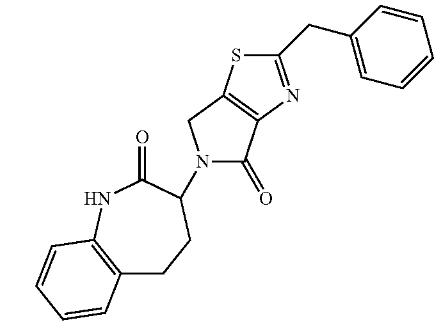 [SMILES: O=C1Nc2ccccc2CCC1N1Cc2sc(Cc3ccccc3)nc2C1=O] | | 390.2 |
| 16 | (3S)-3-(2-benzyl-4-oxo-6,7-dihydro[1,3]thiazolo[4,5-c]pyridin-5(4H)-yl)-5-methyl-2,3-dihydro-1,5-benzoxazepin-4(5H)-one | 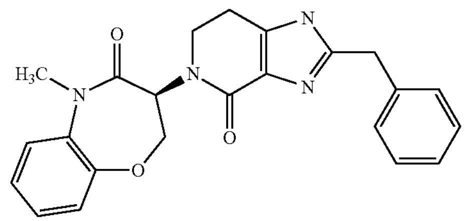 [SMILES: CN1C(=O)[C@@H](N2CCc3[nH]c(Cc4ccccc4)nc3C2=O)COc2ccccc21] | | 420.2 |
| 17 | (3S)-3-(2-benzyl-8-oxo-5,8-dihydro-1,7-naphthyridin-7(6H)-yl)-5-methyl-2,3-dihydro-1,5-benzoxazepin-4(5H)-one | 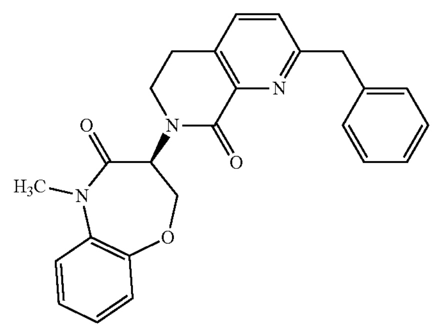 [SMILES: CN1C(=O)[C@@H](N2CCc3ccc(Cc4ccccc4)nc3C2=O)COc2ccccc21] | | 414.2 |
| 18 | 3-(2-benzyl-4-oxo-6,7-dihydropyrazolo[1,5-a]pyrazin-5(4H)-yl)-1,3,4,5-tetrahydro-2H-1-benzazepin-2-one | 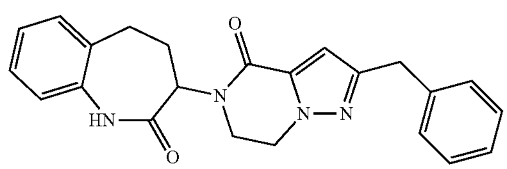 [SMILES: O=C1Nc2ccccc2CCC1N1CCn2nc(Cc3ccccc3)cc2C1=O] | | 387.2 |

TABLE 1-3

| EXAMPLE | IUPAC NAME | Structure | ADDITIVE | MS |
|---|---|---|---|---|
| 19 | (3R)-3-(2-benzyl-7-oxo-2,4,5,7-tetrahydro-6H-pyrazolo[3,4-c]pyridin-6-yl)-5-methyl-2,3-dihydro-1,5-benzothiazepin-4(5H)-one | 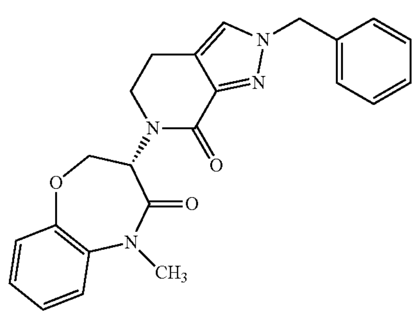 [SMILES: CN1C(=O)[C@@H](N2CCc3cn(Cc4ccccc4)nc3C2=O)COc2ccccc21] | | 419.2 |

TABLE 1-3-continued

| EXAMPLE | IUPAC NAME | Structure | ADDITIVE | MS |
|---|---|---|---|---|
| 20 | (3S)-3-(2-(4-chlorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 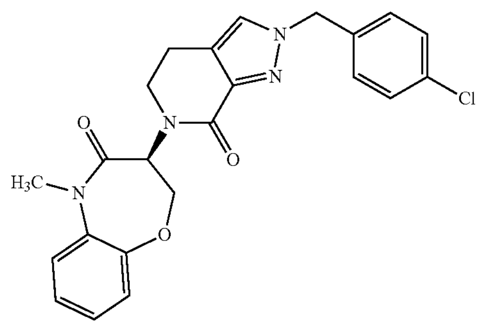 [SMILES: CN1C(=O)[C@@H](N2CCc3cn(Cc4ccc(Cl)cc4)nc3C2=O)COc2ccccc21] | | 437.1 |
| 21 | (3S)-5-methyl-3-(7-oxo-2-(1-phenylethyl)-2,4,5,7-tetrahydro-6H-pyrazolo[3,4-c]pyridin-6-yl)-2,3-dihydro-1,5-benzoxazepin-4(5H)-one | 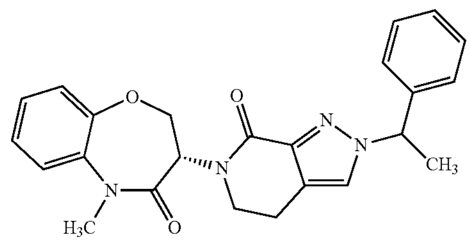 [SMILES: CC(c1ccccc1)n1cc2c(n1)C(=O)N([C@H]1COc3ccccc3N(C)C1=O)CC2] | | 417.2 |
| 22 | (3S)-5-methyl-3-(2-(2-methylbenzyl)-7-oxo-2,4,5,7-tetrahydro-6 H-pyrazolo[3,4-c]pyridin-6-yl)-2,3-dihydro-1,5-benzoxazepin-4(5H)-one | 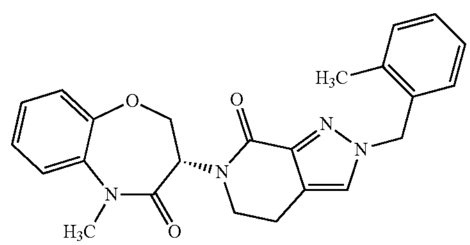 [SMILES: Cc1ccccc1Cn1cc2c(n1)C(=O)N([C@H]1COc3ccccc3N(C)C1=O)CC2] | | 417.2 |
| 23 | (3S)-5-methyl-3-(7-oxo-2-(2-phenylethyl)-2,4,5,7-tetrahydro-6H-pyrazolo[3,4-c]pyridin-6-yl)-2,3-dihydro-1,5-benzoxazepin-4(5H)-one | 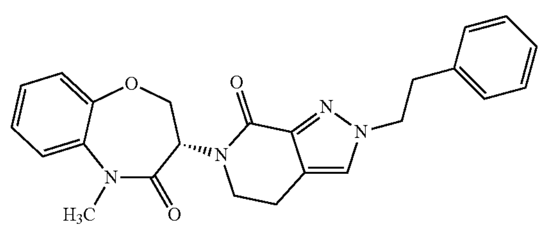 [SMILES: CN1C(=O)[C@@H](N2CCc3cn(CCc4ccccc4)nc3C2=O)COc2ccccc21] | | 417.2 |
| 24 | (3S)-3-(2-(2,6-difluorobenzyl)-7-oxo-2,4,5,7-tetrahydro-6H-pyrazolo[3,4-]pyridin-6-yl)-5-methyl-2,3-dihydro-1,5-benzoxazepin-4(5H)-one | 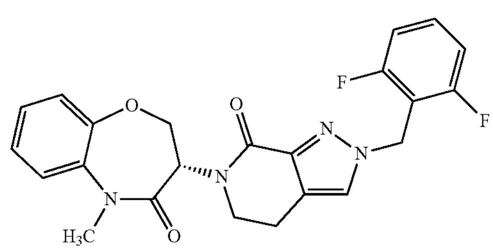 [SMILES: CN1C(=O)[C@@H](N2CCc3cn(Cc4c(F)cccc4F)nc3C2=O)COc2ccccc21] | | 439.2 |
| 25 | (3S)-3-(2-(2-ohlorobenzy)-7-oxo-2,4,5,7-tetrahydro-6H-pyrazolo[3,4-c]pyridin-6-yl)-5-methyl-2,3-dihydro-1,5-benzoxazepin-4(5H)-one | 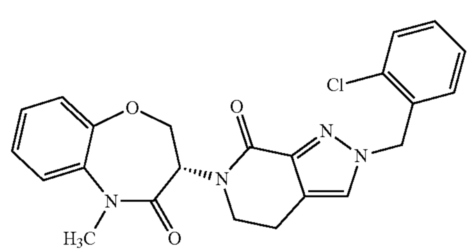 [SMILES: CN1C(=O)[C@@H](N2CCc3cn(Cc4ccccc4Cl)nc3C2=O)COc2ccccc21] | | 437.1 |

TABLE 1-3-continued

| EXAMPLE | IUPAC NAME | Structure | ADDITIVE | MS |
|---|---|---|---|---|
| 26 | (3S)-3-(2-(3-chlorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 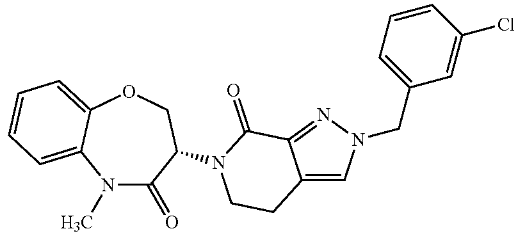 [SMILES: CN1C(=O)[C@@H](N2CCc3cn(Cc4cccc(Cl)c4)nc3C2=O)COc2ccccc21] | | 437.1 |
| 27 | (3S)-3-(2-(cyclopropylmethyl)-7-oxo-2,4,5,7-hydro-6H-pyrazolo[3,4-c]pyridin-6-yl)-5-methyl-2,3-dihydro-1,5-benzoxazepin-4(5H)-one | 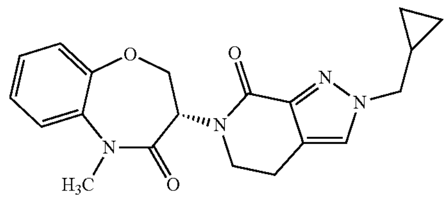 [SMILES: CN1C(=O)[C@@H](N2CCc3cn(CC4CC4)nc3C2=O)COc2ccccc21] | | 367.2 |

TABLE 1-4

| EXAMPLE | IUPAC NAME | Structure | ADDITIVE | MS |
|---|---|---|---|---|
| 28 | 2-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 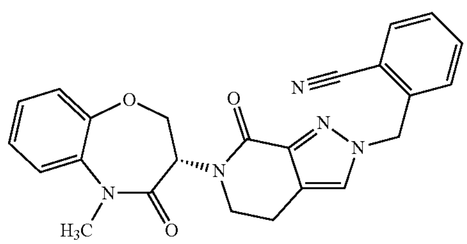 [SMILES: CN1C(=O)[C@@H](N2CCc3cn(Cc4ccccc4C#N)nc3C2=O)COc2ccccc21] | | 428.3 |
| 29 | 3-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 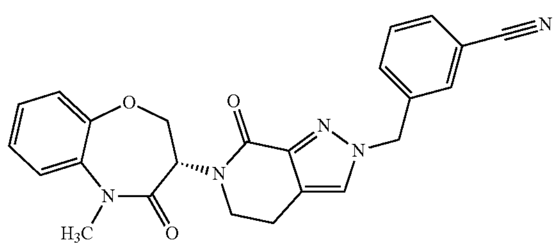 [SMILES: CN1C(=O)[C@@H](N2CCc3cn(Cc4cccc(C#N)c4)nc3C2=O)COc2ccccc21] | | 428.3 |
| 30 | 4-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 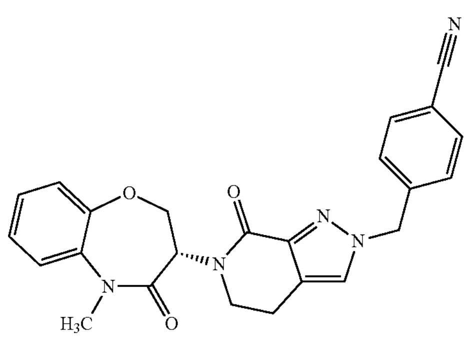 [SMILES: CN1C(=O)[C@@H](N2CCc3cn(Cc4ccc(C#N)cc4)nc3C2=O)COc2ccccc21] | | 428.3 |

TABLE 1-4-continued

| EXAMPLE | IUPAC NAME | Structure | ADDITIVE | MS |
|---|---|---|---|---|
| 31 | (3S)-3-(2-(cyclobutylmethyl)-7-oxo-2,4,5,7-tetrahydro-6H-pyrazolo[3,4-c]pyridin-6-yl)-5-methyl-2,3-dihydro-1,5-benzoxazepin-4(5H)-one | 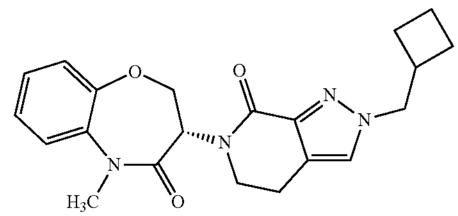 [SMILES: CN1C(=O)[C@@H](N2CCc3cn(CC4CCC4)nc3C2=O)COc2ccccc21] | | 381.2 |
| 32 | (3S)-5-methyl-3-(7-oxo-2-(pyridin-2-ylmethyl)-2,4,5,7-tetrahydro-6H-pyrazolo[3,4-c]pyridin-6-yl)-2,3-dihydro-1,5-benzoxazepin-4(5H)-one | 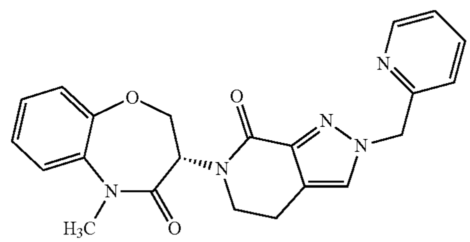 [SMILES: CN1C(=O)[C@@H](N2CCc3cn(Cc4ccccn4)nc3C2=O)COc2ccccc21] | | 404.2 |
| 33 | (3S)-3-(2-((3,3-difluorocyclobutyl)methyl)-7-oxo-2,4,5,7-tetrahydro-6H-pyrazolo[3,4-c]pyridin-6-yl)-5-methyl-2,3-dihydro-1,5-benzoxazepin-4(5H)-one | 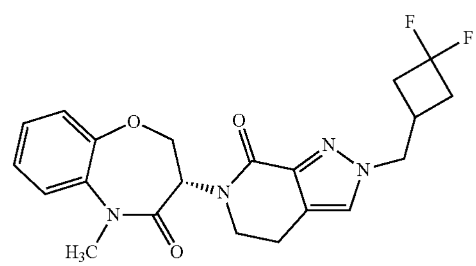 [SMILES: CN1C(=O)[C@@H](N2CCc3cn(CC4CC(F)(F)C4)nc3C2=O)COc2ccccc21] | | 417.2 |
| 34 | (3S)-3-(2-(3-furylmethyl)-7-oxo-2,4,5,7-tetrahydro-6H-pyrazolo[3,4-c]pyridin-6-yl)-5-methyl-2,3-dihydro-1,5-benzoxazepin-4(5H)-L-one | 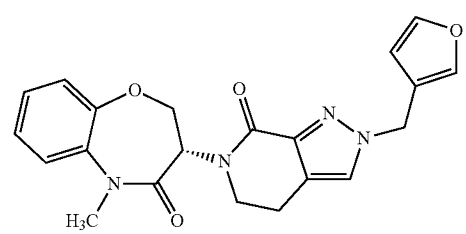 [SMILES: CN1C(=O)[C@@H](N2CCc3cn(Cc4ccoc4)nc3C2=O)COc2ccccc21] | | 393.2 |
| 35 | (3S)-5-methyl-3-(2-(1,3-oxazol-2-ylmethyl)-7-oxo-2,4,5,7-tetrahydro-6H-pyrazolo[3,4-c]pyridin-6-yl)-2,3-dihydro-1,5-benzoxazepin-4(5H)-one | 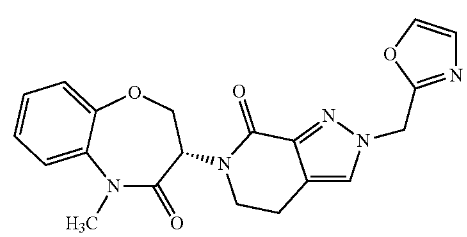 [SMILES: CN1C(=O)[C@@H](N2CCc3cn(Cc4ncco4)nc3C2=O)COc2ccccc21] | | 394.2 |
| 36 | (3S)-5-methyl-3-(7-oxo-2-(pyrimidin-2-ylmethyl)-2,4,5,7-tetrahydro-6H-pyrazolo[3,4-c]pyridin-6-yl)-2,3-dihydro-1,5-benzoxazepin-4(5H)-one | 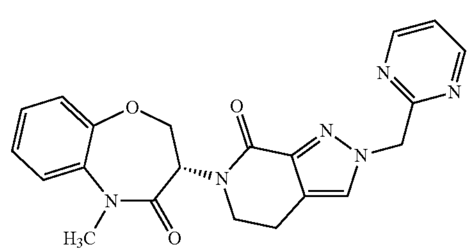 | | 405.2 |

TABLE 1-5

| EXAMPLE | IUPAC NAME | Structure | ADDITIVE | MS |
|---|---|---|---|---|
| 37 | (3S)-3-(2-(cyclopentylmethyl)-7-oxo-2,4,5,7-tetrahydro-6H-pyrazolo[3,4-c]pyridin-yl)-5-methyl-2,3-dihydro-1,5-benzoxazepin-4(5H)-one | 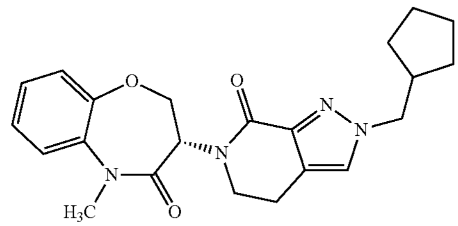 [SMILES: CN1C(=O)[C@@H](N2CCc3cn(CC4CCCC4)nc3C2=O)COc2ccccc21] | | 395.3 |
| 38 | (3S)-3-(2-(1,4-dioxan-2-ylmethyl)-7-oxo-2,4,5,7-tetrahydro-6H-pyrazolo[3,4-c]pyridin-6-yl)-5-methyl-2,3-dihydro-1,5-benzoxazepin-4(5H)-one | 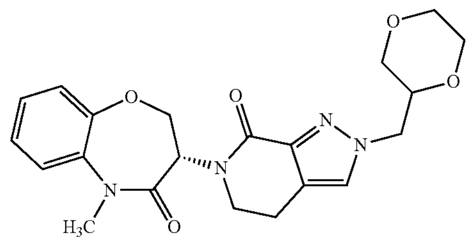 [SMILES: CN1C(=O)[C@@H](N2CCc3cn(CC4COCCO4)nc3C2=O)COc2ccccc21] | | 413.3 |
| 39 | (3S)-5-methyl-3-(2-((1-methyl-1H-pyrazol-3-yl)methyl)-7-oxo-2,4,5,7-tetrahydro-6H-pyrazolo[3,4-c]pyridin-6-yl)-2-,3-dihydro-1,5-benzoxazepin-4(5H)-one | 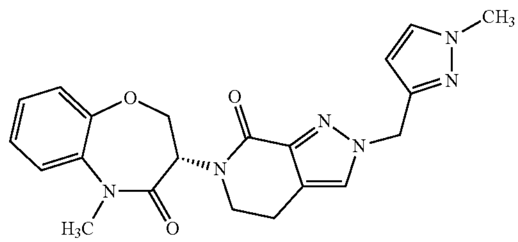 [SMILES: CN1C(=O)[C@@H](N2CCc3cn(Cc4ccn(C)n4)nc3C2=O)COc2ccccc21] | | 407.3 |
| 40 | (3S)-3-(2-benzyl-7-oxo-2,4,5,7-tetrahydro-6H-pyrazolo[3,4-c]pyridin-6-yl)-7-bromo-5-methyl-2,3-dihydro-1,5-benzoxazepin-4(5H)-one | 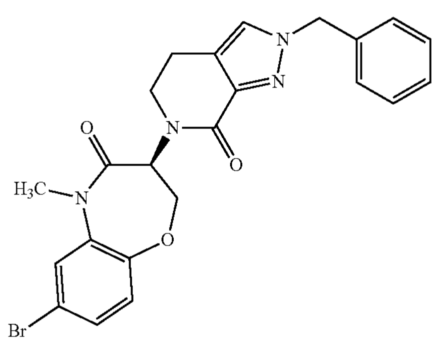 [SMILES: CN1C(=O)[C@@H](N2CCc3cn(Cc4ccccc4)nc3C2=O)COc2ccc(Br)cc21] | | 481.1 |
| 41 | (3S)-3-(2-benzyl-7-oxo-2,4,5,7-tetrahydro-6H-pyrazolo[3,4-c]pyridin-6-yl)-8-bromo-5-methyl-2,3-dihydro-1,5-benzoxazepin-4(5H)-one | 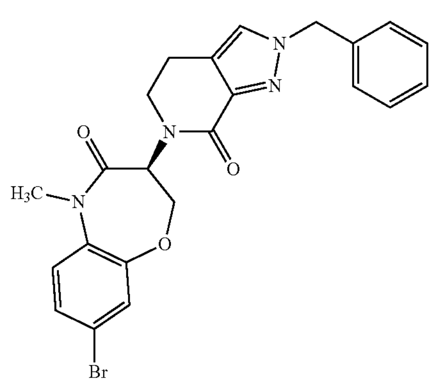 [SMILES: CN1C(=O)[C@@H](N2CCc3cn(Cc4ccccc4)nc3C2=O)COc2cc(Br)ccc21] | | 481.1 |

TABLE 1-5-continued

| EXAMPLE | IUPAC NAME | Structure | ADDITIVE | MS |
|---|---|---|---|---|
| 42 | (3S)-5-methyl-3-(7-oxo-2-(pyrazin-2-ylmethyl)-2,4,5,7-tetrahydro-6H-pyrazolo[3,4-c]pyridin-6-yl)-2,3-dihydro-1,5-benzoxazepin-4(5H)-one | 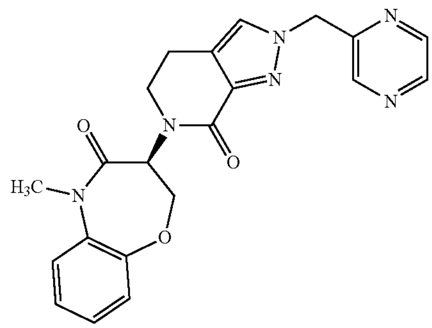 [SMILES: CN1C(=O)[C@@H](N2CCc3cn(Cc4cnccn4)nc3C2=O)COc2ccccc21] | | 405.2 |
| 43 | (3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 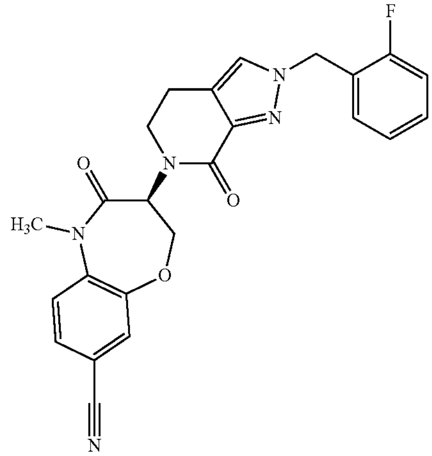 [SMILES: CN1C(=O)[C@@H](N2CCc3cn(Cc4ccccc4F)nc3C2=O)COc2cc(C#N)ccc21] | | 446.2 |
| 44 | (3S)-3-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 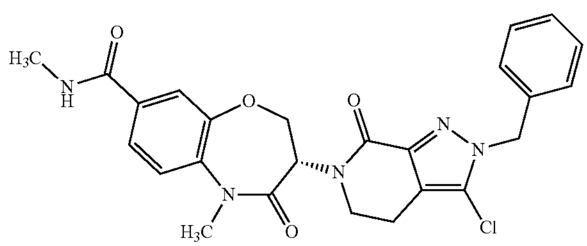 [SMILES: CNC(=O)c1ccc2c(c1)OC[C@H](N1CCc3c(nn(Cc4ccccc4)c3Cl)C1=O)C(=O)N2C] | | 494.3 |
| 45 | (3S)-3-(2-(2,6-difluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 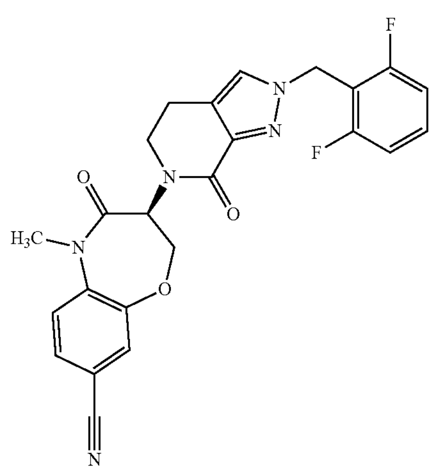 [SMILES: CN1C(=O)[C@@H](N2CCc3cn(Cc4c(F)cccc4F)nc3C2=O)COc2cc(C#N)ccc21] | | 464.2 |

TABLE 1-6

| EXAMPLE | IUPAC NAME | Structure | ADDITIVE | MS |
|---|---|---|---|---|
| 46 | (3S)-3-(3-chloro-2-(2,6-difluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 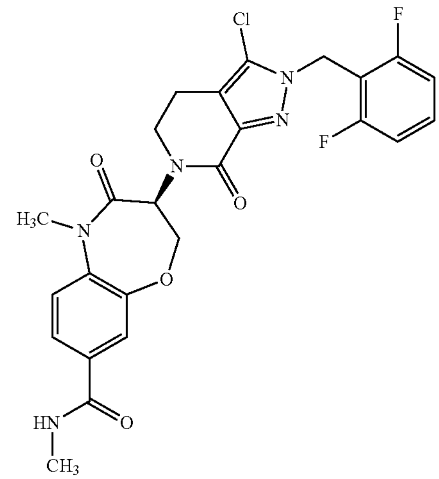 [SMILES: CNC(=O)c1ccc2c(c1)OC[C@H](N1CCc3c(nn(Cc4c(F)cccc4F)c3Cl)C1=O)C(=O)N2C] | | 530.2 |
| 47 | (3S)-3-(3-chloro-2-(2-fluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 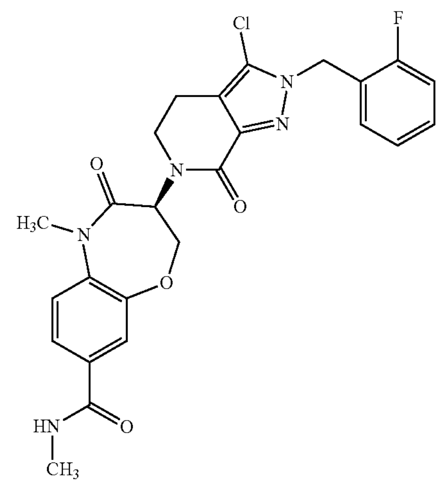 [SMILES: CNC(=O)c1ccc2c(c1)OC[C@H](N1CCc3c(nn(Cc4ccccc4F)c3Cl)C1=O)C(=O)N2C] | | 512.1 |
| 48 | (3S)-3-(2-benzyl-3-methoxy-7-oxo-2,4,5,7-tetrahydro-6H-pyrazolo[3,4-c]pyridin-6-yl)-5-methyl-2,3-dihydro-1,5-benzoxazepin-4(5H)-one | 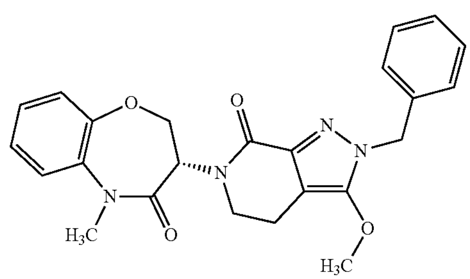 [SMILES: COc1c2c(nn1Cc1ccccc1)C(=O)N([C@H]1COc3ccccc3N(C)C1=O)CC2] | | 433.2 |
| 49 | (3S)-3-(2-benzyl-3-hydroxy-7-oxo-2,4,5,7-tetrahydro-6H-pyrazolo[3,4-c]pyridin-6-yl)-5-methyl-2,3-dihydro-1,5-benzoxazepin-4(5H)-one | 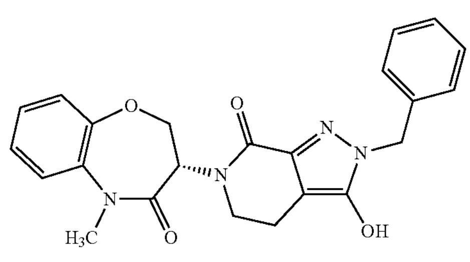 [SMILES: CN1C(=O)[C@@H](N2CCc3c(nn(Cc4ccccc4)c3O)C2=O)COc2ccccc21] | | 419.2 |

TABLE 1-6-continued

| EXAMPLE | IUPAC NAME | Structure | ADDITIVE | MS |
|---|---|---|---|---|
| 50 | 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxamide | 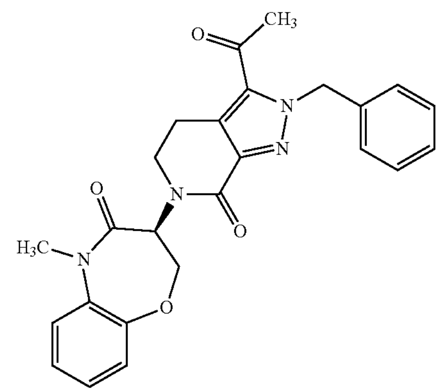 [SMILES: CC(=O)c1c2c(nn1Cc1ccccc1)C(=O)N([C@H]1COc3ccccc3N(C)C1=O)CC2] | | 446.2 |
| 51 | ethyl 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylate | 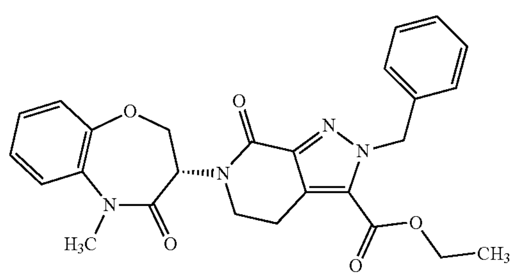 [SMILES: CCOC(=O)c1c2c(nn1Cc1ccccc1)C(=O)N([C@H]1COc3ccccc3N(C)C1=O)CC2] | | 475.2 |
| 52 | (3S)-3-(2-benzyl-3-(hydroxymethyl)-7-oxo-2,4,5,7-tetrahydro-6H-pyrazolo[3,4-c]pyridin-6-yl)-5-methyl-2,3-dihydro-1,5-benzoxazepin-4(5H)-one | 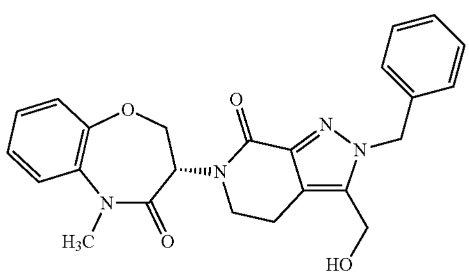 [SMILES: CN1C(=O)[C@@H](N2CCc3c(nn(Cc4ccccc4)c3CO)C2=O)COc2ccccc21] | | 433.2 |
| 53 | 2-benzyl-6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridine-3-carboxylic acid | 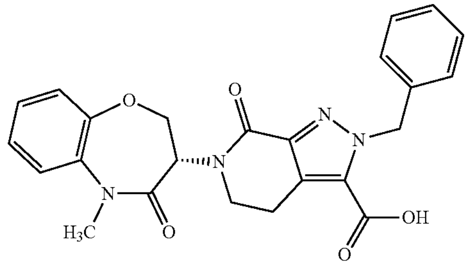 [SMILES: CN1C(=O)[C@@H](N2CCc3c(nn(Cc4ccccc4)c3C(=O)O)C2=O)COc2ccccc21] | | 447.1 |

TABLE 1-6-continued

| EXAMPLE | IUPAC NAME | Structure | ADDITIVE | MS |
|---|---|---|---|---|
| 54 | (3S)-3-(2-benzyl-1-(4-methoxybenzyl)-4-oxo-1,4,6,7-tetrahydro-5H-imidazo[4,5-c]pyridin-5-yl)-5-methyl-2,3-dihydro-1,5-benzoxazepin-4(5H)-one | 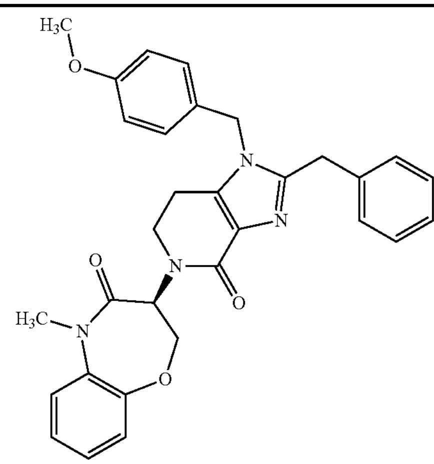 | | 523.3 |

TABLE 1-7

| EXAMPLE | IUPAC NAME | Structure | ADDITIVE | MS |
|---|---|---|---|---|
| 55 | (3S)-3-(2-benzyl-4-oxo-1,4,6,7-tetrahydro-5H-imidazo[4,5-c]pyridin-5-yl)-5-methyl-2,3-dihydro-1,5-benzoxazepin-4(5H)-one | 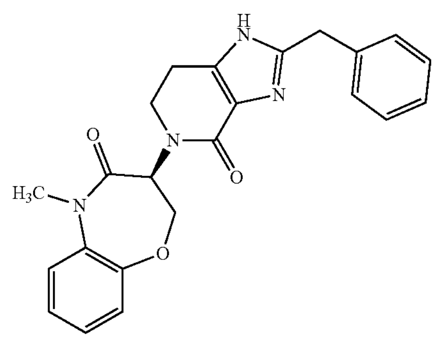 [SMILES: CN1C(=O)[C@@H](N2CCc3[nH]c(Cc4ccccc4)nc3C2=O)COc2ccccc21] | CF3COOH | 403.2 |
| 56 | (3S)-3-(2-benzyl-methyl-4-oxo-1,4,6,7-tetrahydro-5H-imidazo[4,5-c]pyridin-5-yl)-5-methyl-2,3-dihydro-1,5-benzoxazepin-4(5H)-one | 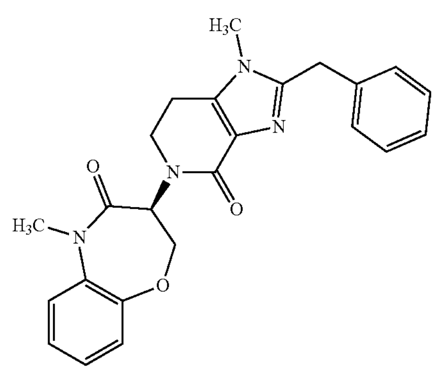 [SMILES: CN1C(=O)[C@@H](N2CCc3c(nc(Cc4ccccc4)n3C)C2=O)COc2ccccc21] | | 417.1 |

TABLE 1-7-continued

| EXAMPLE | IUPAC NAME | Structure | ADDITIVE | MS |
|---|---|---|---|---|
| 57 | (3S)-3-(2-benzyl-3-methyl-4-oxo-3,4,6,7-tetrahydro-5H-imidazo[4,5-c]pyridin-5-yl)-5-methyl-2,3-dihydro-1,5-benzoxazepin-4(5H)-one | 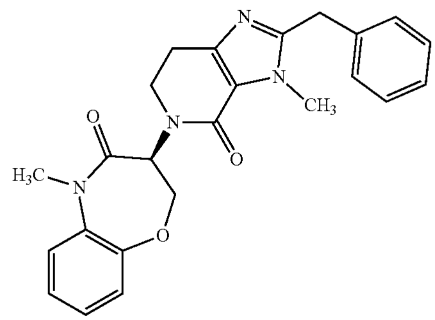 [SMILES: CN1C(=O)[C@@H](N2CCc3nc(Cc4ccccc4)n(C)c3C2=O)COc2ccccc21] | | 417.1 |
| 58 | (3S)-3-(2-benzyl-3-chloro-7-oxo-2,4,5,7-tetrahydro-6H-pyrazolo[3,4-c]pyridin-6-yl)-8-bromo-5-methyl-2,3-dihydro-1,5-benzoxazepin-4(5H)-one | 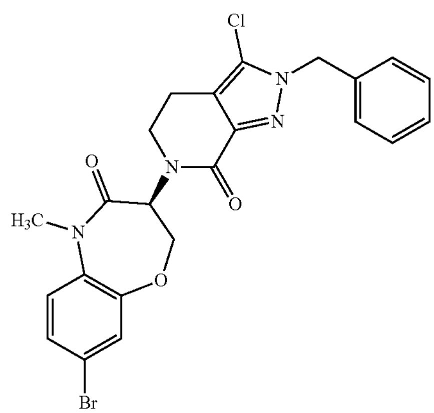 [SMILES: CN1C(=O)[C@@H](N2CCc3c(nn(Cc4ccccc4)c3Cl)C2=O)COc2cc(Br)ccc21] | | 515 |
| 59 | (3S)-3-(2-benzyl-3-chloro-7-oxo-2,4,5,7-tetrahydro-6H-pyrazolo[3,4-c]pyridin-6-yl)-5-methyl-8-(oxetan-3-yl)-2,3-dihydro-1,5-benzoxazepin-4(5H)-one | 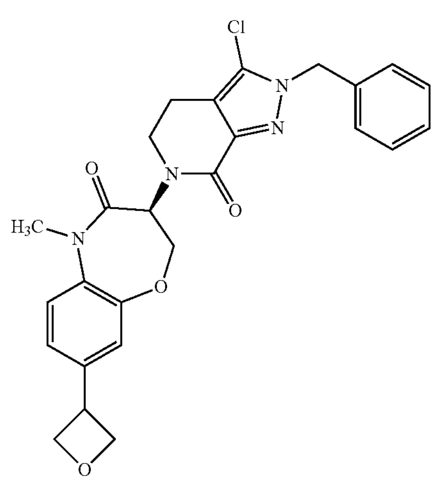 [SMILES: CN1C(=O)[C@@H](N2CCc3c(nn(Cc4ccccc4)c3Cl)C2=O)COc2cc(C3COC3)ccc21] | | 493.3 |

TABLE 1-7-continued

| EXAMPLE | IUPAC NAME | Structure | ADDITIVE | MS |
|---|---|---|---|---|
| 60 | (3S)-3-(2-benzyl-3-chloro-7-oxo-2,4,5,7-tetrahydro-6H-pyrazolo[3,4-c]pyridin-6-yl)-5-methyl-8-(1-methyl-1H-imidazol-2-yl)-2,3-dihydro-1,5-benzoxazepin-4(5H)-one | 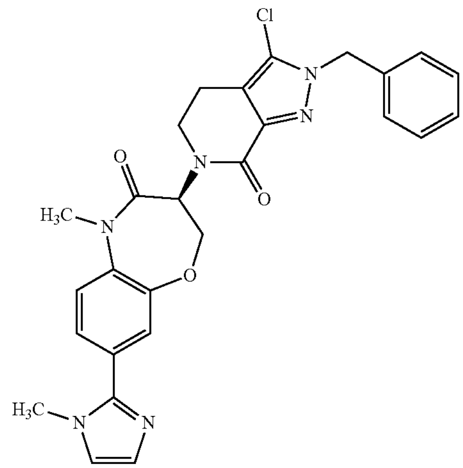 [SMILES: CN1C(=O)[C@@H](N2CCc3c(nn(Cc4ccccc4)c3Cl)C2=O)COc2cc(-c3nccn3C)ccc21] | | 517.2 |
| 61 | (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxylic acid | 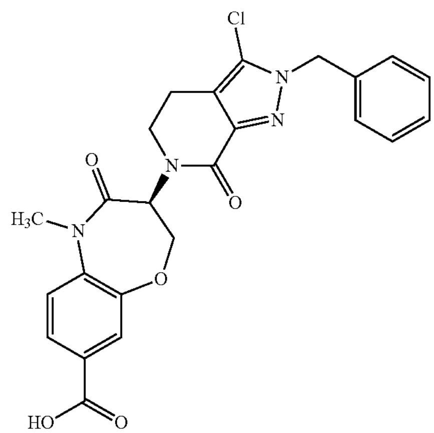 [SMILES: CN1C(=O)[C@@H](N2CCc3c(nn(Cc4ccccc4)c3Cl)C2=O)COc2cc(C(=O)O)ccc21] | | 481.1 |
| 62 | (3S)-3-(2-benzyl-3-chloro-7-oxo-2,4,5,7-tetrahydro-6H-pyrazolo[3,4-c]pyridin-6-yl)-N-(2-hydroxy-2-methylpropyl)-5-methyl-4-oxo-2,3,4,5-tetrahydro-1,5-benzoxazepine-8-carboxamide | 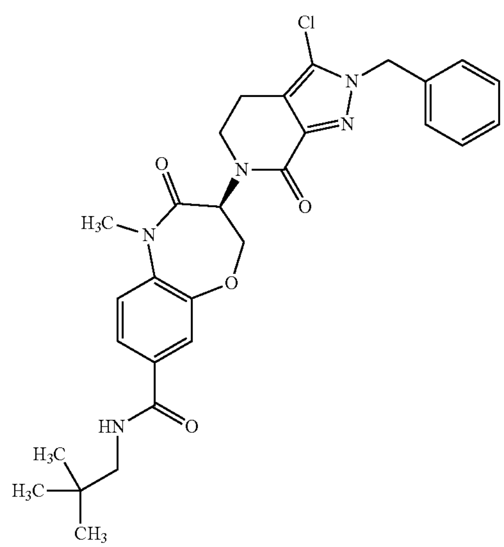 [SMILES: CN1C(=O)[C@@H](N2CCc3c(nn(Cc4ccccc4)c3Cl)C2=O)COc2cc(C(=O)NCC(C)(C)C)ccc21] | | 552.2 |

TABLE 1-7-continued

| EXAMPLE | IUPAC NAME | Structure | ADDITIVE | MS |
|---|---|---|---|---|
| 63 | (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 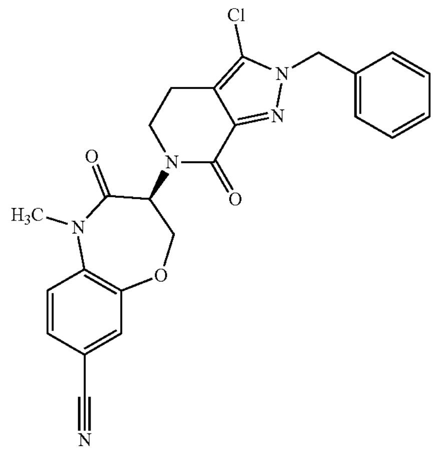 [SMILES: CN1C(=O)[C@@H](N2CCc3c(nn(Cc4ccccc4)c3Cl)C2=O)COc2cc(C#N)ccc21] | | 462.1 |

TABLE 1-8

| EXAMPLE | IUPAC NAME | Structure | ADDITIVE | MS |
|---|---|---|---|---|
| 64 | (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxamide | 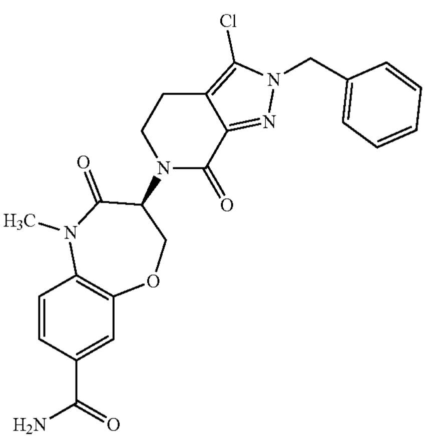 [SMILES: CN1C(=O)[C@@H](N2CCc3c(nn(Cc4ccccc4)c3Cl)C2=O)COc2cc(C(N)=O)ccc21] | | 480.1 |
| 65 | 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one | 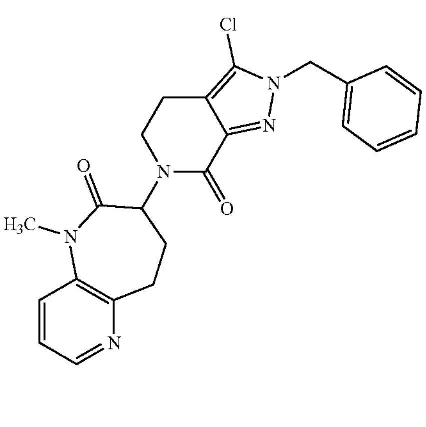 [SMILES: CN1C(=O)C(N2CCc3c(nn(Cc4ccccc4)c3Cl)C2=O)CCc2ncccc21] | | 436.1 |

TABLE 1-8-continued

| EXAMPLE | IUPAC NAME | Structure | ADDITIVE | MS |
|---|---|---|---|---|
| 66 | 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one | 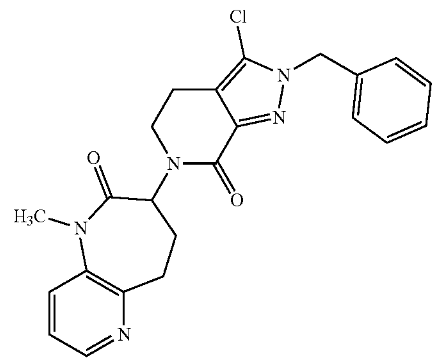 [SMILES: CN1C(=O)C(N2CCc3c(nn(Cc4ccccc4)c3Cl)C2=O)CCc2ncccc21] | | 436.1 |
| 67 | 7-(2-benzyl-3-chloro-7-oxo-2,4,5,7-tetrahydro-6H-pyrazolo[3,4-c]pyridin-6-yl)-5-methyl-5,7,8,9-tetrahydro-6H-pyrido[3,2-b]azepin-6-one | 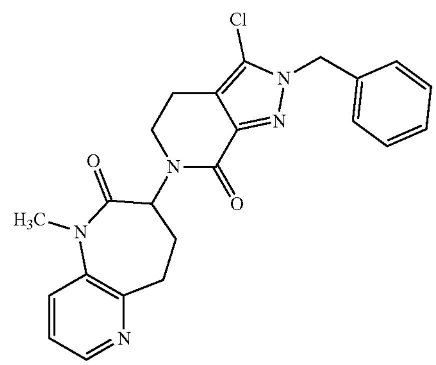 [SMILES: CN1C(=O)C(N2CCc3c(nn(Cc4ccccc4)c3Cl)C2=O)CCc2ncccc21] | | 436.1 |
| 68 | (3S)-3-(2-benzyl-5-methyl-7-oxo-2,4,5,7-tetrahydro-6H-pyrazolo[3,4-c]pyridin-6-yl)-5-methyl-2,3-dihydro-1,5-benzoxazepin-4(5H)-one | 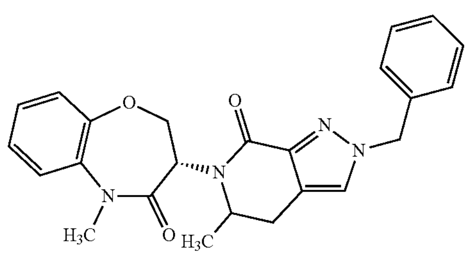 [SMILES: CC1Cc2cn(Cc3ccccc3)nc2C(=O)N1[C@H]1COc2ccccc2N(C)C1=O] | | 417.2 |
| 69 | (3R)-3-(2-benzyl-7-oxo-2,4,5,7-tetrahydro-6H-pyrazolo[3,4-c]pyridin-6-yl)-5-methyl-2,3-dihydro-1,5-benzothiazepin-4(5H)-one 1,1-dioxide | 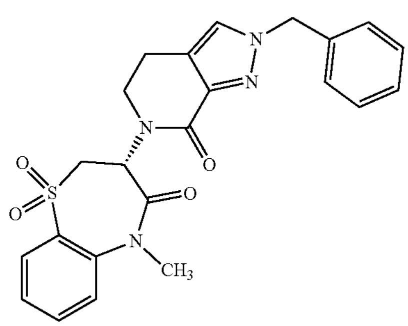 [SMILES: CN1C(=O)[C@@H](N2CCc3cn(Cc4ccccc4)nc3C2=O)CS(=O)(=O)c2ccccc21] | | 451.2 |

TABLE 1-8-continued

| EXAMPLE | IUPAC NAME | Structure | ADDITIVE | MS |
|---|---|---|---|---|
| 70 | (3S)-3-(2-benzyl-4-oxo-2,4,6,7-tetrahydro-5H-pyrazolo[4,3-c]pyridin-5-yl)-5-methyl-2,3-dihydro-1,5-benzoxazepin-4(5H)-one | 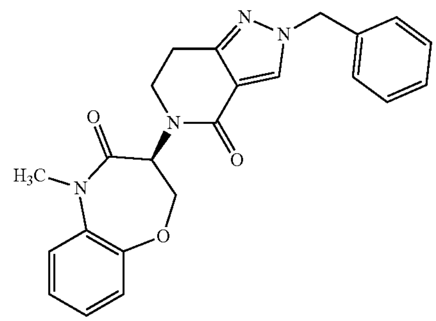 [SMILES: CN1C(=O)[C@@H](N2CCc3nn(Cc4ccccc4)cc3C2=O)COc2ccccc21] | | 403.2 |
| 72 | (3S)-3-(2-benzyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carboxamide | 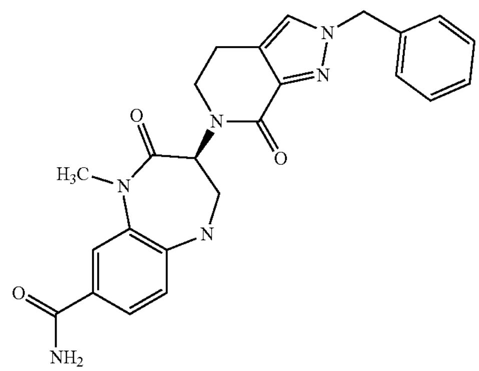 [SMILES: CN1C(=O)[C@@H](N2CCc3cn(Cc4ccccc4)nc3C2=O)CNc2ccc(C(N)=O)cc21] | | 446.2 |
| 73 | (3S)-3-(3-chloro-2-((3-methylpyrazin-2-yl)methyl)-7-oxo-2,4,5,7-tetrahydro-6H-pyrazolo[3,4-c]pyridin-6-yl)-5-methyl-2,3-dihydro-1,5-benzoxazepin-4(5H)-one | 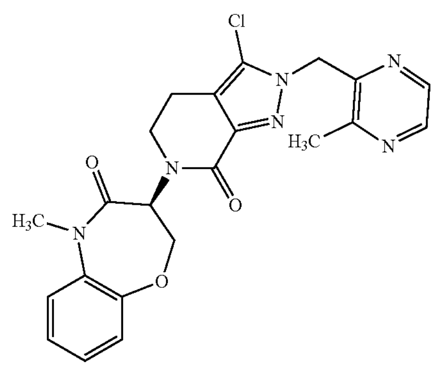 [SMILES: Cc1nccnc1Cn1nc2c(c1Cl)CCN([C@H]1COc3ccccc3N(C)C1=O)C2=O] | | 453.1 |

TABLE 1-9

| EXAMPLE | IUPAC NAME | Structure | ADDITIVE | MS |
|---|---|---|---|---|
| 74 | (3S)-7-chloro-3-(3-chloro-1-oxo-2-(pyrazin-2-ylmethyl)-2,4,5,7-tetrahydro-6H-pyrazolo[3,4-c]pyridin-6-yl)-5-methyl-2,3-dihydro-1,5-benzoxazepin-4(5H)-one | 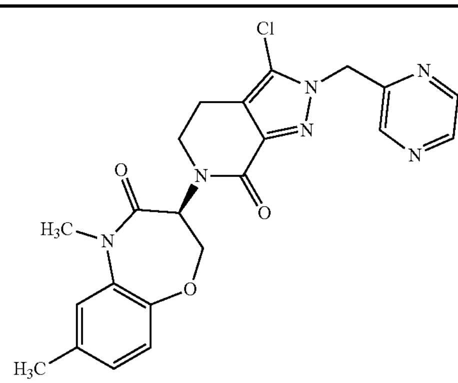 | | 473.1 |

TABLE 1-9-continued

| EXAMPLE | IUPAC NAME | Structure | ADDITIVE | MS |
|---|---|---|---|---|
| 75 | (3S)-3-(3-chloro-7-oxo-2-(pyrazin-2-ylmethyl)-2,4,5,7-tetrahydro-6H-pyrazolo[3,4-c]pyridin-6-yl)-8-fluoro-5-methyl-2,3-dihydro-1,5-benzoxazepin-4(5H)-one | 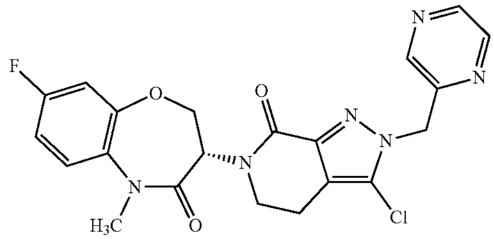 [SMILES: CN1C(=O)[C@@H](N2CCc3c(nn(Cc4cnccn4)c3Cl)C2=O)COc2cc(F)ccc21] | | 457.2 |
| 76 | (3S)-3-(2-benzyl-3-chloro-7-oxo-2,4,5,7-tetrahydro-6H-pyrazolo[3,4-c]pyridin-6-yl)-5-methyl-2,3-dihydro-1,5-benzoxazepin-4(5H)-one | 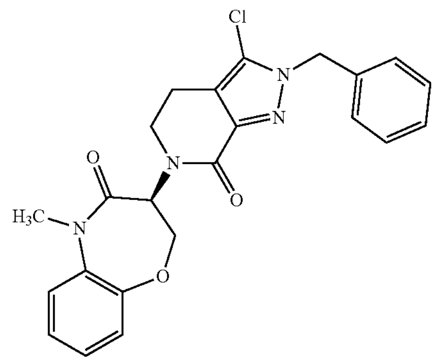 [SMILES: CN1C(=O)[C@@H](N2CCc3c(nn(Cc4ccccc4)c3Cl)C2=O)COc2ccccc21] | | 437.1 |
| 77 | (3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile | 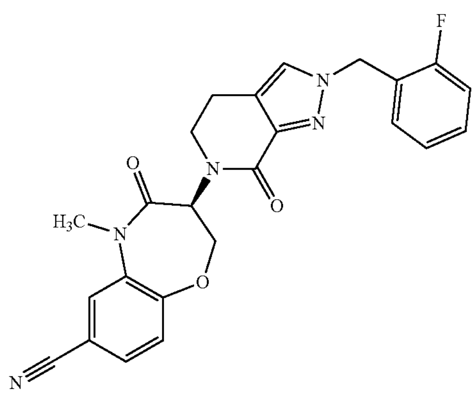 [SMILES: CN1C(=O)[C@@H](N2CCc3cn(Cc4ccccc4F)nc3C2=O)COc2ccc(C#N)cc21] | | 446 |
| 78 | (3S)-3-(2-benzyl-3-chloro-6-oxo-2,6-dihydropyrrolo[3,4-c]pyrazol-5(4H)-yl)-5-methyl-2,3-dihydro-1,5-benzoxazepin-4(5H)-one | 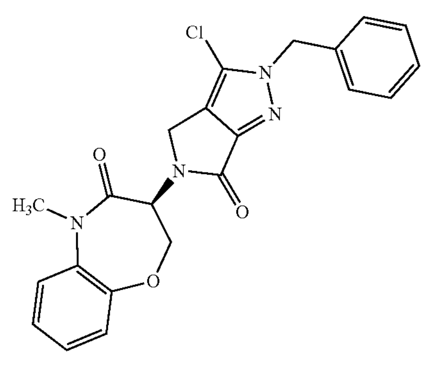 [SMILES: CN1C(=O)[C@@H](N2Cc3c(nn(Cc4ccccc4)c3Cl)C2=O)COc2ccccc21] | | 423.1 |
| 79 | (3S)-5-methyl-3-(3-methyl-7-oxo-2-(pyrazin-2-ylmethyl)-2,4,5,7-tetrahydro-6H-pyrazolo[3,4-c]pyridin-6-yl)-2,3-dihydro-1,5-benzoxazepin-4(5H)-one | 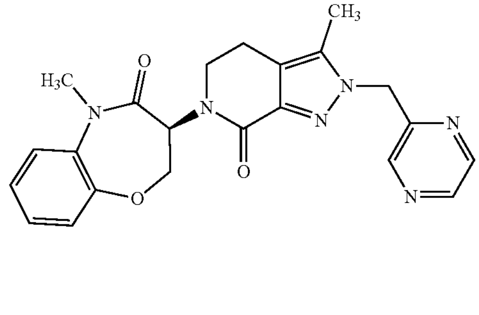 [SMILES: Cc1c2c(nn1Cc1cnccn1)C(=O)N([C@H]1COc3ccccc3N(C)C1=O)CC2] | | 419.2 |

TABLE 1-9-continued

| EXAMPLE | IUPAC NAME | Structure | ADDITIVE | MS |
|---------|------------|-----------|----------|-----|
| 80 | (3S)-3-(3-chloro-7-oxo-2-(pyrazin-2-ylmethyl)-2,4,5,7-tetrahydro-6H-pyrazolo[3,4-c]pyridin-6-yl)-5-methyl-2,3-dihydro-1,5-benzoxazepin-4(5H)-one | 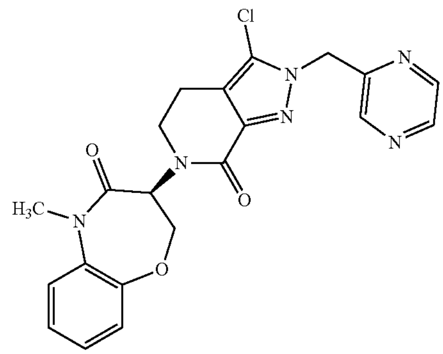 [SMILES: CN1C(=O)[C@@H](N2CCc3c(nn(Cc4cnccn4)c3Cl)C2=O)COc2ccccc21] | | 439.1 |
| 81 | (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carboxamide | 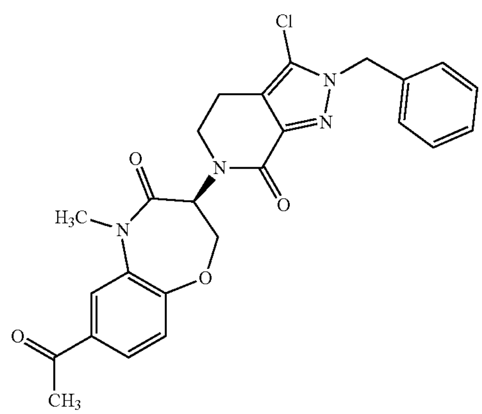 [SMILES: CC(=O)c1ccc2c(c1)N(C)C(=O)[C@@H](N1CCc3c(nn(Cc4ccccc4)c3Cl)C1=O)CO2] | | 480.1 |
| 82 | (3S)-3-(2-benzyl-3-chloro-7-oxo-2,4,5,7-tetrahydro-6H-pyrazolo[3,4-c]pyridin-6-yl)-8-bromo-2,3-dihydro-1,5-benzoxazepin-4(5H)-one | 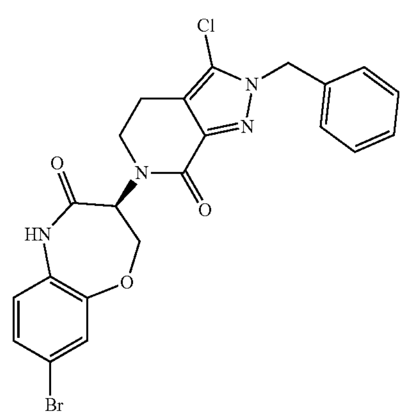 [SMILES: O=C1Nc2ccc(Br)cc2OC[C@@H]1N1CCc2c(nn(Cc3ccccc3)c2Cl)C1=O] | | 501.1 |

TABLE 1-10

| EXAMPLE | IUPAC NAME | Structure | ADDITIVE | MS |
|---|---|---|---|---|
| 83 | (3S)-3-(2-benzyl-3-chloro-7-oxo-2,4,5,7-tetrahydro-6H-pyrazolo[3,4-c]pyridin-6-yl)-4-oxo-2,3,4,5-tetrahydro-1,5-benzoxazepine-8-carbonitrile | 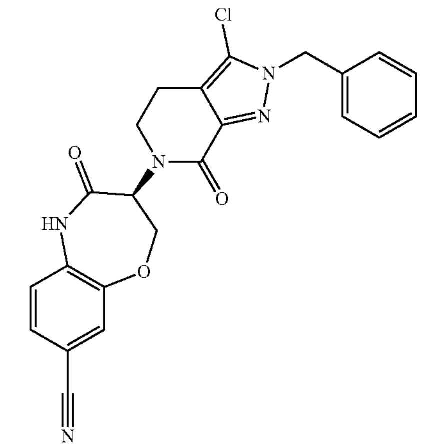 [SMILES: N#Cc1ccc2c(c1)OC[C@H](N1CCc3c(nn(Cc4ccccc4)c3Cl)C1=O)C(=O)N2] | | 446 |
| 84 | (3S)-3-(2-benzyl-3-methyl-7-oxo-2,4,5,7-tetrahydro-6H-pyrazolo[3,4-c]pyridin-6-yl)-8-bromo-5-methyl-2,3-dihydro-1,5-benzoxazepin-4(5H)-one | 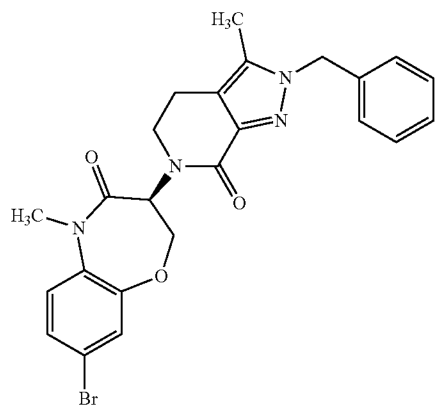 [SMILES: Cc1c2c(nn1Cc1ccccc1)C(=O)N([C@H]1COc3cc(Br)ccc3N(C)C1=O)CC2] | | 495.1 |
| 85 | (3S)-3-(2-benzyl-3-methyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile | 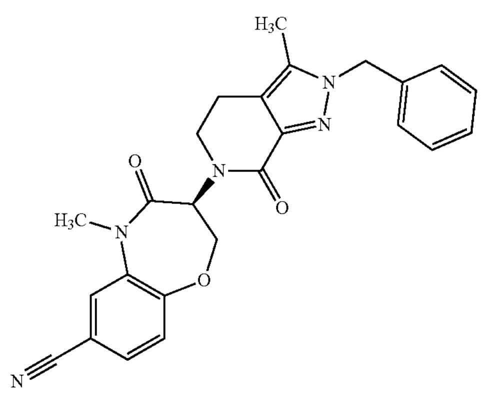 [SMILES: Cc1c2c(nn1Cc1ccccc1)C(=O)N([C@H]1COc3ccc(C#N)cc3N(C)C1=O)CC2] | | 442.2 |

TABLE 1-10-continued

| EXAMPLE | IUPAC NAME | Structure | ADDITIVE | MS |
|---|---|---|---|---|
| 86 | (3S)-3-(2-benzyl-3-methyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 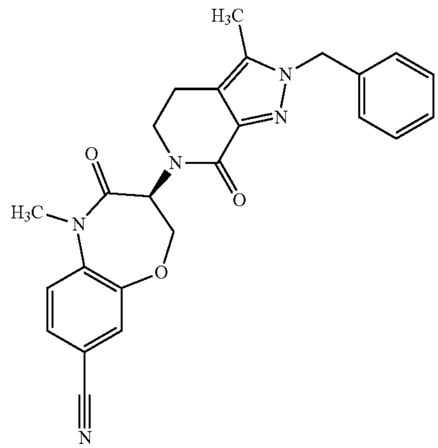 [SMILES: Cc1c2c(nn1Cc1ccccc1)C(=O)N([C@H]1COc3cc(C#N)ccc3N(C)C1=O)CC2] | | 442.2 |
| 87 | (3S)-3-(2-benzyl-3-chloro-7-oxo-2,4,5,7-tetrahydro-6H-pyrazolo[3,4-c]pyridin-6-yl)-N,N,5-trimethyl-4-oxo-2,3,4,5-tetrahydro-1,5-benzoxazepine-8-carboxamide | 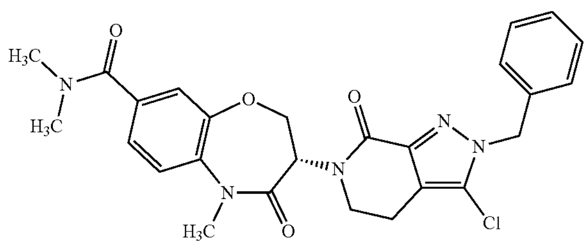 [SMILES: CN(C)C(=O)c1ccc2c(c1)OC[C@H](N1CCc3c(nn(Cc4ccccc4)c3Cl)C1=O)C(=O)N2C] | | 508.2 |
| 88 | (3S)-3-(2-benzyl-3-methyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carboxamide | 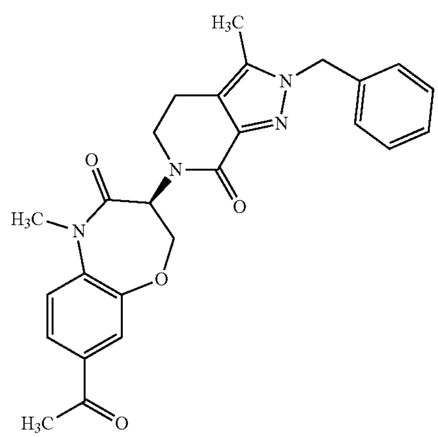 [SMILES: CC(=O)c1ccc2c(c1)OC[C@H](N1CCc3c(nn(Cc4ccccc4)c3C)C1=O)C(=O)N2C] | | 460.3 |
| 89 | (3S)-3-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-7-carboxamide | 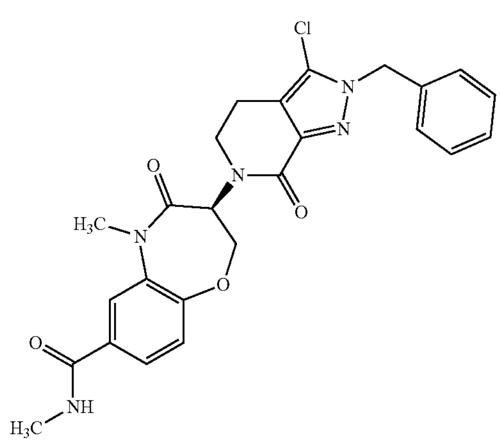 [SMILES: CNC(=O)c1ccc2c(c1)N(C)C(=O)[C@@H](N1CCc3c(nn(Cc4ccccc4)c3Cl)C1=O)CO2] | | 494.2 |

TABLE 1-10-continued

| EXAMPLE | IUPAC NAME | Structure | ADDITIVE | MS |
|---|---|---|---|---|
| 90 | (3S)-3-(2-benzyl-3-chloro-7-oxo-2,4,5,7-tetrahydro-6H-pyrazolo[3,4-c]pyridin-6-yl)-N,N,5-trimethyl-4-oxo-2,3,4,5-tetrahydro-1,5-benzoxazepine-7-carboxamide | 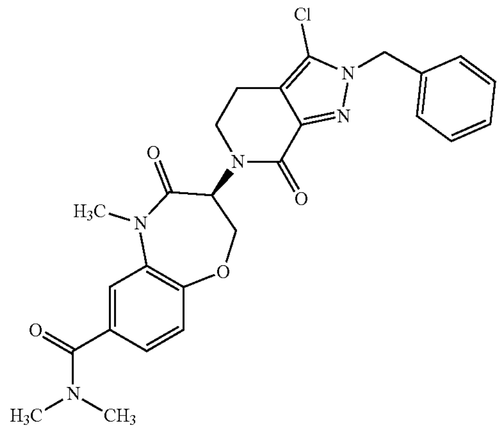 [SMILES: CN(C)C(=O)c1ccc2c(c1)N(C)C(=O)[C@@H](N1CCc3c(nn(Cc4ccccc4)c3Cl)C1=O)CO2] | | 508.2 |
| 91 | 7-(2-benzyl-3-chloro-7-oxo-2,4,5,7-tetrahydro-6H-pyrazolo[3,4-c]pyridin-6-yl)-9-methyl-5,6,7,9-tetrahydro-8H-pyrido[2,3-b]azepin-8-one | 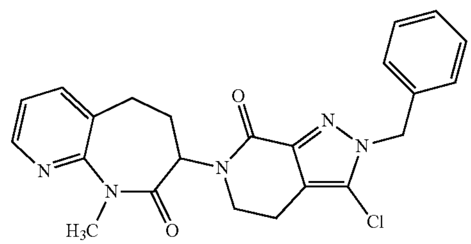 [SMILES: CN1C(=O)C(N2CCc3c(nn(Cc4ccccc4)c3Cl)C2=O)CCc2cccnc21] | | 436.1 |

TABLE 1-11

| EXAMPLE | IUPAC NAME | Structure | ADDITIVE | MS |
|---|---|---|---|---|
| 92 | 6-(2-benzyl-3-chloro-7-oxo-2,4,5,7-tetrahydro-6H-pyrazolo[3,4-c]pyridin-6-yl)-2,4-dimethyl-2,6,7,8-tetrahydropyrazolo[4,3-b]azepin-5(4H)-one | 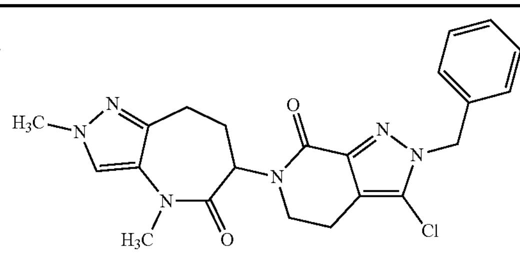 | | 439.2 |
| 93 | 7-(2-benzyl-3-chloro-7-oxo-2,4,5,7-tetrahydro-6H-pyrazolo[3,4-c]pyridin-6-yl)-9-methyl-5,6,7,9-tetrahydro-8H-pyrido[2,3-b]azepin-8-one | 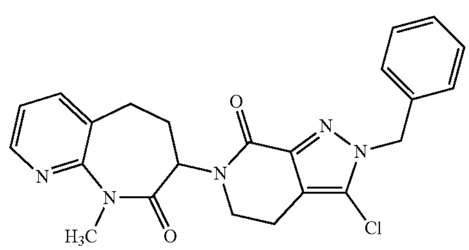 | | 436.2 |
| 94 | 7-(2-benzyl-3-chloro-7-oxo-2,4,5,7-tetrahydro-6H-pyrazolo[3,4-c]pyridin-6-yl)-9-methyl-5,6,7,9-tetrahydro-8H-pyrido[2,3-b]azepin-8-one | 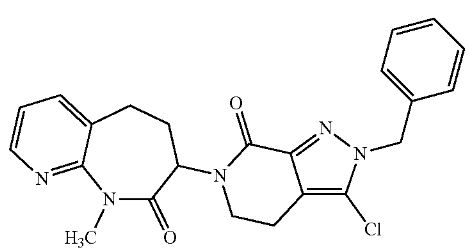 [SMILES: CN1C(=O)C(N2CCc3c(nn(Cc4ccccc4)c3Cl)C2=O)CCc2cccnc21] | | 436.2 |

TABLE 1-11-continued

| EXAMPLE | IUPAC NAME | Structure | ADDITIVE | MS |
|---|---|---|---|---|
| 95 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 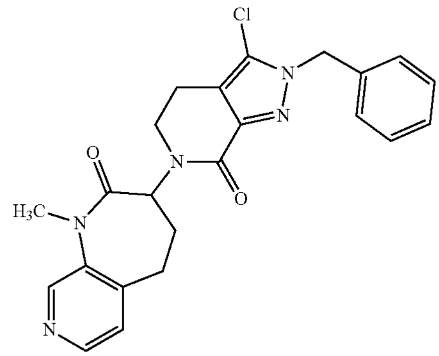 [SMILES: CN1C(=O)C(N2CCc3c(nn(Cc4ccccc4)c3Cl)C2=O)CCc2ccncc21] | | 436.2 |
| 96 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 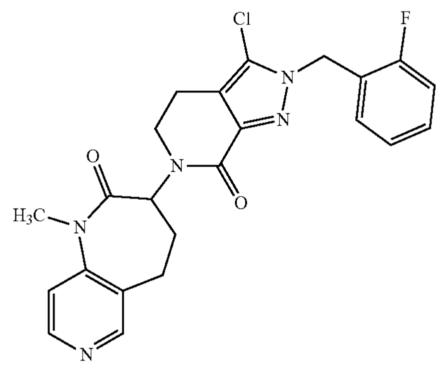 [SMILES: CN1C(=O)C(N2CCc3c(nn(Cc4ccccc4F)c3Cl)C2=O)CCc2cnccc21] | | 454.1 |
| 97 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 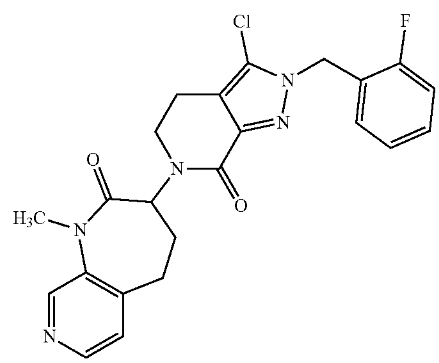 [SMILES: CN1C(=O)C(N2CCc3c(nn(Cc4ccccc4F)c3Cl)C2=O)CCc2ccncc21] | | 454.1 |
| 98 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 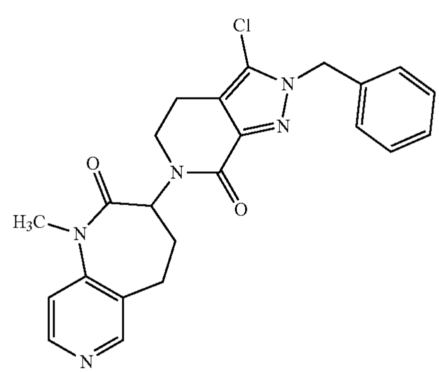 [SMILES: CN1C(=O)C(N2CCc3c(nn(Cc4ccccc4)c3Cl)C2=O)CCc2cnccc21] | | 436.2 |

TABLE 1-11-continued

| EXAMPLE | IUPAC NAME | Structure | ADDITIVE | MS |
|---|---|---|---|---|
| 99 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 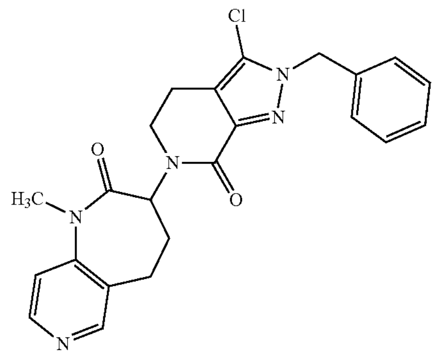 [SMILES: CN1C(=O)C(N2CCc3c(nn(Cc4ccccc4)c3Cl)C2=O)CCc2cnccc21] | | 436.2 |
| 100 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 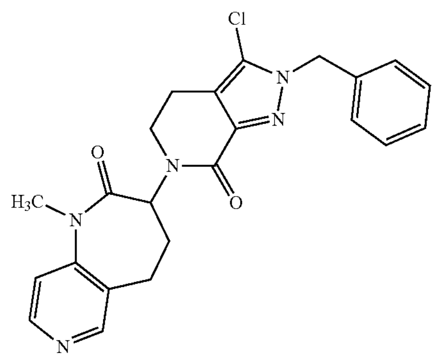 [SMILES: CN1C(=O)C(N2CCc3c(nn(Cc4ccccc4)c3Cl)C2=O)CCc2cnccc21] | | 436.2 |

TABLE 1-12

| EXAMPLE | IUPAC NAME | Structure | ADDITIVE | MS |
|---|---|---|---|---|
| 101 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 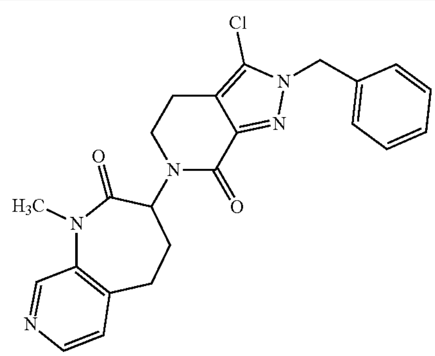 [SMILES: CN1C(=O)C(N2CCc3c(nn(Cc4ccccc4)c3Cl)C2=O)CCc2ccncc21] | | 436.2 |
| 102 | 3-(2-benzyl-3-chloro-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 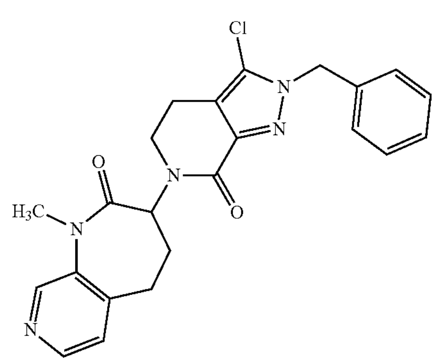 [SMILES: CN1C(=O)C(N2CCc3c(nn(Cc4ccccc4)c3Cl)C2=O)CCc2ccncc21] | | 436.2 |

TABLE 1-12-continued

| EXAMPLE | IUPAC NAME | Structure | ADDITIVE | MS |
|---|---|---|---|---|
| 103 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 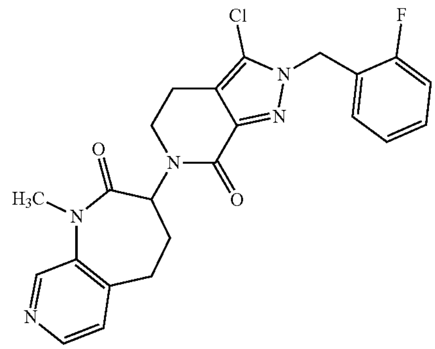 [SMILES: CN1C(=O)C(N2CCc3c(nn(Cc4ccccc4F)c3Cl)C2=O)CCc2ccncc21] | | 454.1 |
| 104 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[3,4-b]azepin-2-one | 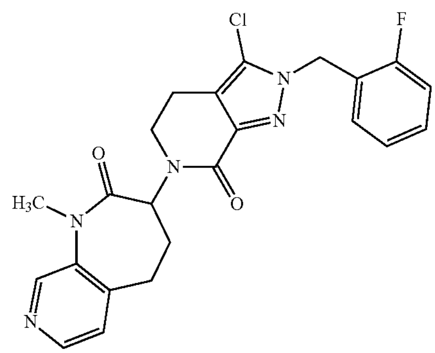 [SMILES: CN1C(=O)C(N2CCc3c(nn(Cc4ccccc4F)c3Cl)C2=O)CCc2ccncc21] | | 454.2 |
| 105 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 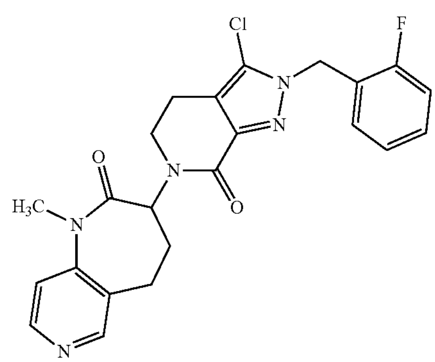 [SMILES: CN1C(=O)C(N2CCc3c(nn(Cc4ccccc4F)c3Cl)C2=O)CCc2cnccc21] | | 454.1 |
| 106 | 3-(3-chloro-2-(2-fluorobenzyl)-7-oxo-2,4,5,7-tetrahydro-6H-pyrazolo[3,4-c]pyridin-6-yl)-1-methyl-1,3,4,5-tetrahydro-2H-pyrido[4,3-b]azepin-2-one | 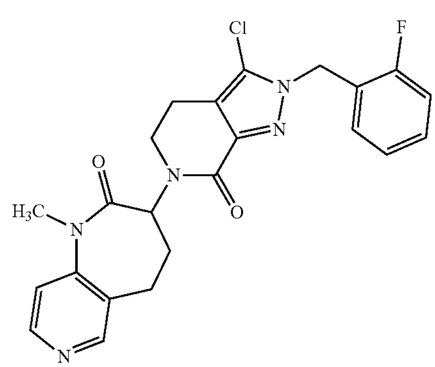 [SMILES: CN1C(=O)C(N2CCc3c(nn(Cc4ccccc4F)c3Cl)C2=O)CCc2cnccc21] | | 454.1 |

TABLE 1-12-continued

| EXAMPLE | IUPAC NAME | Structure | ADDITIVE | MS |
|---|---|---|---|---|
| 107 | (3S)-3-(2-benzyl-3-chloro-7-oxo-2,4,5,7-tetrahydro-6H-pyrazolo[3,4-c]pyridin-6-yl)-5-methyl-8-(1-methyl-1H-pyrazol-4-yl)-2,3-dihydro-1,5-benzoxazepin-4(5H)-one | 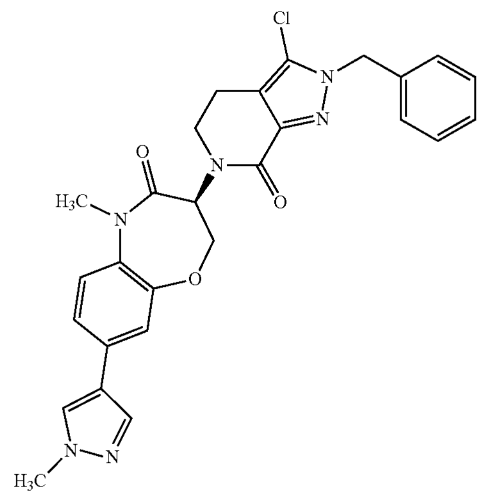 [SMILES: CN1C(=O)[C@@H](N2CCc3c(nn(Cc4ccccc4)c3Cl)C2=O)COc2cc(-c3cnn(C)c3)ccc21] | | 517.2 |
| 108 | (3S)-3-(2-benzyl-3-chloro-7-oxo-2,4,5,7-tetrahydro-6H-pyrazolo[3,4-c]pyridin-6-yl)-5-methyl-8-(1-methyl-1H-pyrazol-3-yl)-2,3-dihydro-1,5-benzoxazepin-4(5H)-one | 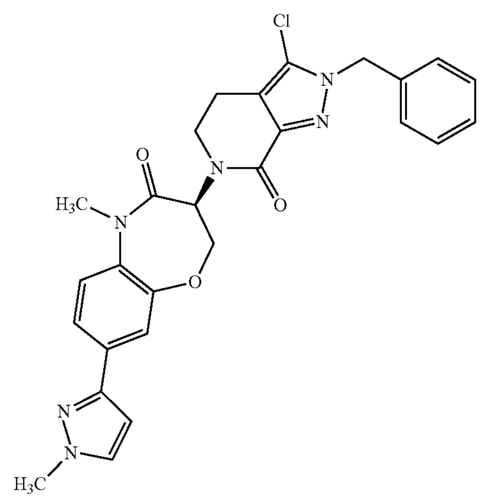 [SMILES: CN1C(=O)[C@@H](N2CCc3c(nn(Cc4ccccc4)c3Cl)C2=O)COc2cc(-c3ccn(C)n3)ccc21] | | 517.2 |
| 109 | (3S)-8-bromo-3-(2-(2-fluorobenzyl)-3-methyl-7-oxo-2,4,5,7-tetrahydro-6H-pyrazolo[3,4-c]pyridin-6-yl)-5-methyl-2,3-dihydro-1,5-benzoxazepin-4(5H)-one | 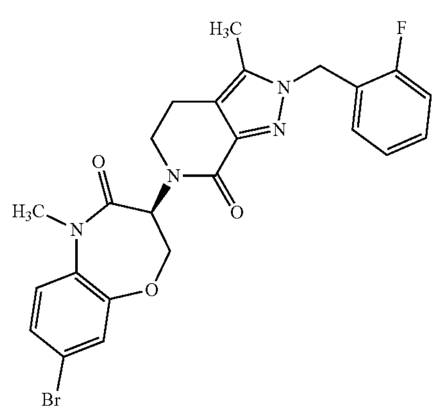 [SMILES: Cc1c2c(nn1Cc1ccccc1F)C(=O)N([C@H]1COc3cc(Br)ccc3N(C)C1=O)CC2] | | 513.1 |

TABLE 1-13

| EXAMPLE | IUPAC NAME | Structure | ADDITIVE | MS |
|---|---|---|---|---|
| 110 | (3S)-8-bromo-3-(2-(2,6-difluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 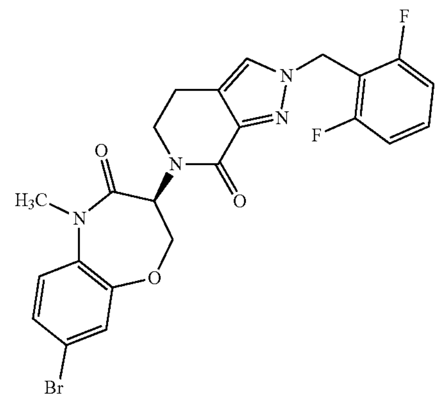 [SMILES: CN1C(=O)[C@@H](N2CCc3cn(Cc4c(F)cccc4F)nc3C2=O)COc2cc(Br)ccc21] | | 517.1 |
| 111 | 6-(2-benzyl-3-chloro-7-oxo-2,4,5,7-tetrahydro-6H-pyrazolo[3,4-c]pyridin-6-yl)-2,8-dimethyl-2,5,6,8-tetrahydropyrazolo[3,4-b]azepin-7(4H)-one | 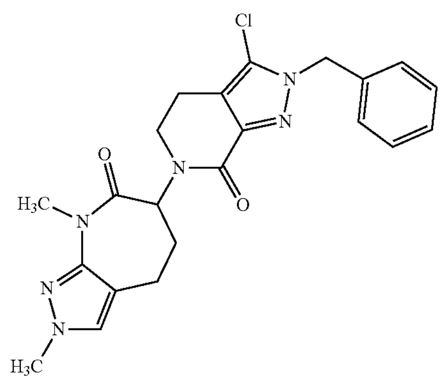 [SMILES: CN1C(=O)C(N2CCc3c(nn(Cc4ccccc4)c3Cl)C2=O)CCc2cn(C)nc21] | | 439.2 |
| 112 | (3S)-3-(2-(2-fluorobenzyl)-3-methyl-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 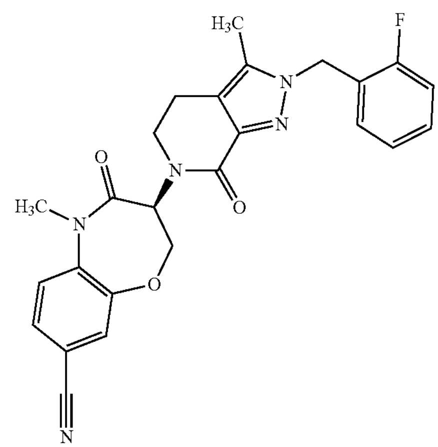 [SMILES: Cc1c2c(nn1Cc1ccccc1F)C(=O)N([C@H]1COc3cc(C#N)ccc3N(C)C1=O)CC2] | | 460.3 |
| 113 | 6-(2-benzyl-3-chloro-7-oxo-2,4,5,7-tetrahydro-6H-pyrazolo[3,4-c]pyridin-6-yl)-2,8-dimethyl-2,5,6,8-tetrahydropyrazolo[3,4-b]azepin-7(4H)-one | 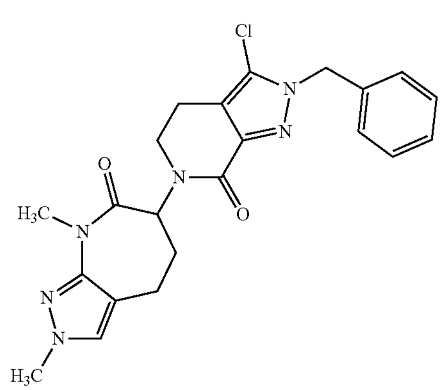 [SMILES: CN1C(=O)C(N2CCc3c(nn(Cc4ccccc4)c3Cl)C2=O)CCc2cn(C)nc21] | | 439.2 |

TABLE 1-13-continued

| EXAMPLE | IUPAC NAME | Structure | ADDITIVE | MS |
|---|---|---|---|---|
| 114 | 6-(2-benzyl-3-chloro-7-oxo-2,4,5,7-tetrahydro-6H-pyrazolo[3,4-c]pyridin-6-yl)-2,8-dimethyl-2,5,6,8-tetrahydropyrazolo[3,4-b]azepin-7(4H)-one | 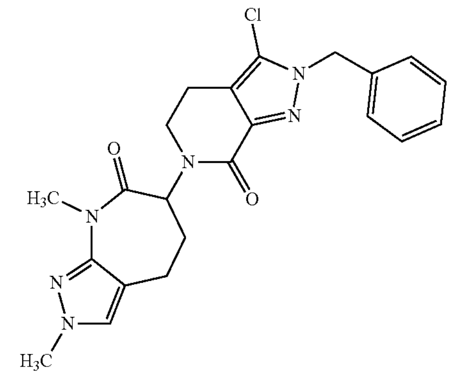 [SMILES: CN1C(=O)C(N2CCc3c(nn(Cc4ccccc4)c3Cl)C2=O)CCc2cn(C)nc21] | | 439.2 |
| 115 | (3S)-3-(2-(2-fluorobenzyl)-3-methyl-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 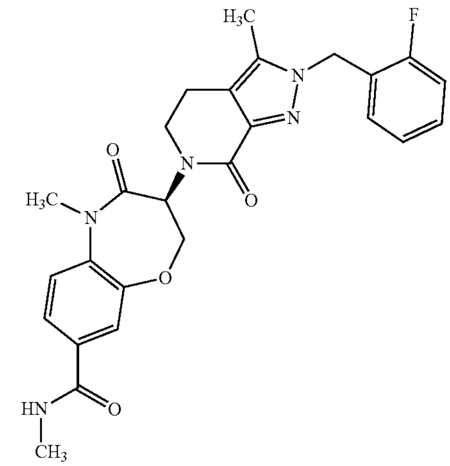 [SMILES: CNC(=O)c1ccc2c(c1)OC[C@H](N1CCc3c(nn(Cc4ccccc4F)c3C)C1=O)C(=O)N2C] | | 490.2 |
| 116 | (3S)-3-(2-(2,6-difluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 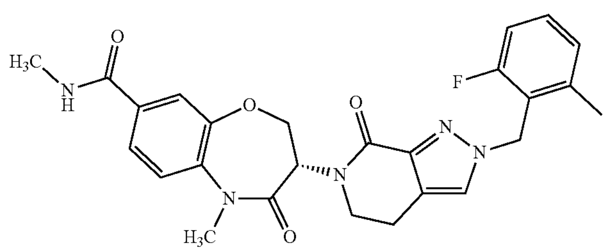 | | 496.2 |
| 117 | (3S)-3-(2-(2-fluorobenzyl)-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide | 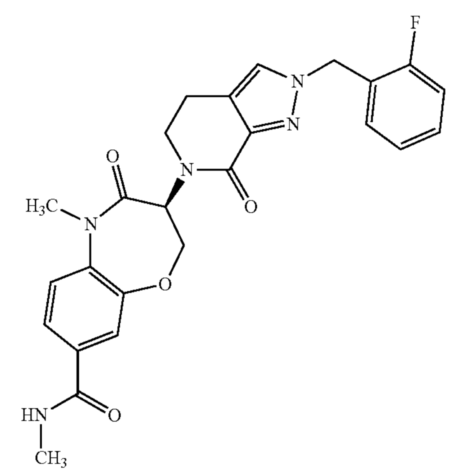 [SMILES: CNC(=O)c1ccc2c(c1)OC[C@H](N1CCc3cn(Cc4ccccc4F)nc3C1=O)C(=O)N2C] | | 478.2 |

TABLE 1-13-continued

| EXAMPLE | IUPAC NAME | Structure | ADDITIVE | MS |
|---|---|---|---|---|
| 118 | (3S)-3-(2-benzyl-3-chloro-7-oxo-2,4,5,7-tetrahydro-6H-pyrazolo[3,4-c]pyridin-6-yl)-5-methyl-N-(oxetan-3-yl)-4-oxo-2,3,4,5-tetrahydro-1,5-benzoxazepine-8-carboxamide | 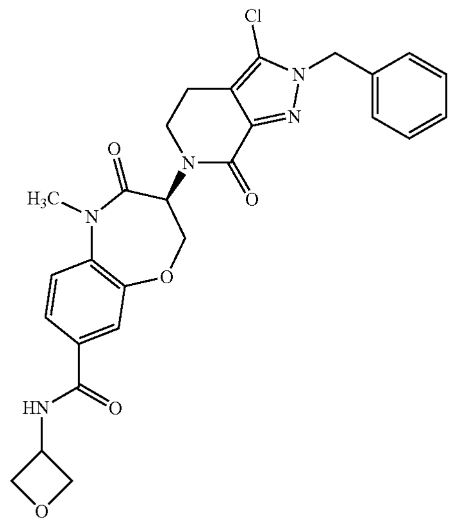 [SMILES: CN1C(=O)[C@@H](N2CCc3c(nn(Cc4ccccc4)c3Cl)C2=O)COc2cc(C(=O)NC3COC3)ccc21] | | 536.2 |

25

TABLE 1-14

| EXAMPLE | IUPAC NAME | Structure | ADDITIVE | MS |
|---|---|---|---|---|
| 119 | 6-(3-chloro-2-(2-fluorobenzyl)-7-oxo-2,4,5,7-tetrahydro-6H-pyrazolo[3,4-c]pyridin-6-yl)-2,4-dimethyl-2,6,7,8-tetrahydropyrazolo[4,3-b]azepin-5(4H)-one | 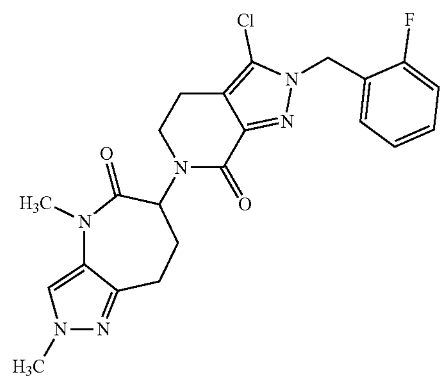 [SMILES: CN1C(=O)C(N2CCc3c(nn(Cc4ccccc4F)c3Cl)C2=O)CCc2nn(C)cc21] | | 457.2 |
| 120 | 6-(3-chloro-2-(2-fluorobenzyl)-7-oxo-2,4,5,7-tetrahydro-6H-pyrazolo[3,4-c]pyridin-6-yl)-2,4-dimethyl-2,6,7,8-tetrahydropyrazolo[4,3-b]azepin-5(4H)-one | 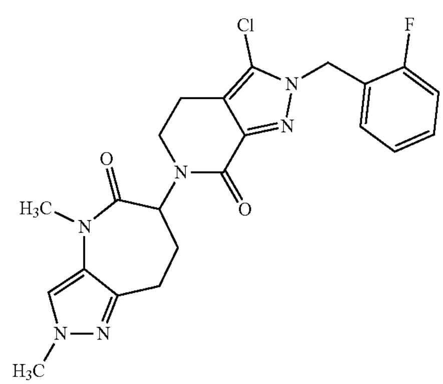 [SMILES: CN1C(=O)C(N2CCc3c(nn(Cc4ccccc4F)c3Cl)C2=O)CCc2nn(C)cc21] | | 457.2 |

TABLE 1-14-continued

| EXAMPLE | IUPAC NAME | Structure | ADDITIVE | MS |
|---|---|---|---|---|
| 121 | 6-(3-chloro-2-(2-fluorobenzyl)-7-oxo-2,4,5,7-tetrahydro-6H-pyrazolo[3,4-c]pyridin-6-yl)-2,4-dimethyl-2,6,7,8-tetrahydropyrazolo[4,3-b]azepin-5(4H)-one | 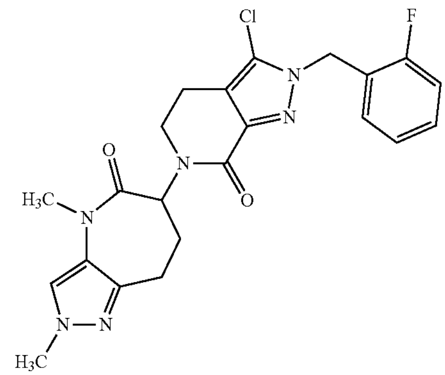 [SMILES: CN1C(=O)C(N2CCc3c(nn(Cc4ccccc4F)c3Cl)C2=O)CCc2nn(C)cc21] | | 457.2 |
| 122 | (3S)-3-(2-benzyl-3-chloro-7-oxo-2,4,5,7-tetrahydro-6H-pyrazolo[3,4-c]pyridin-6-yl)-7-fluoro-N,5-dimethyl-4-oxo-2,3,4,5-tetrahydro-1,5-benzoxazepine-8-carboxamide | 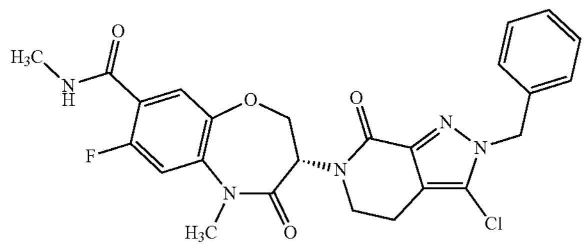 [SMILES: CNC(=O)c1cc2c(cc1F)N(C)C(=O)[C@@H](N1CCc3c(nn(Cc4ccccc4)c3Cl)C1=O)CO2] | | 512.1 |
| 123 | (3S)-3-(2-benzyl-3-(difluoromethoxy)-7-oxo-2,4,5,7-tetrahydro-6H-pyrazolo[3,4-c]pyridin-6-yl)-8-bromo-5-methyl-2,3-dihydro-1,5-benzoxazepin-4(5H)-one | 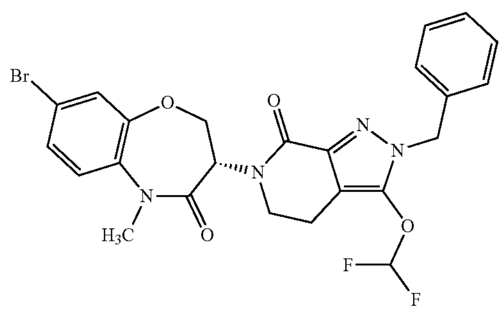 [SMILES: CN1C(=O)[C@@H](N2CCc3c(nn(Cc4ccccc4)c3OC(F)F)C2=O)COc2cc(Br)ccc21] | | 547.1 |
| 124 | (3S)-3-(2-benzyl-3-(difluoromethoxy)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile | 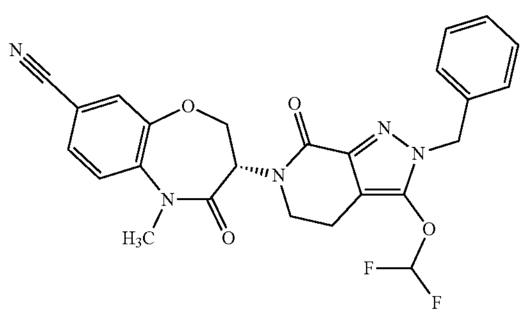 [SMILES: CN1C(=O)[C@@H](N2CCc3c(nn(Cc4ccccc4)c3OC(F)F)C2=O)COc2cc(C#N)ccc21] | | 494.2 |
| 125 | (3S)-3-(2-benzyl-3-chloro-7-oxo-2,4,5,7-tetrahydro-6H-pyrazolo[3,4-c]pyridin-6-yl)-7-fluoro-5-methyl-8-(1-methyl-1H-pyrazol-3-yl)-2,3-dihydro-1,5-benzoxazepin-4(5H)-one | 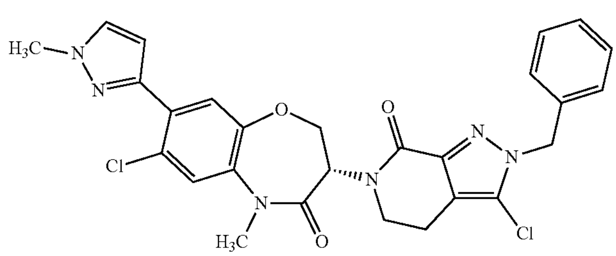 [SMILES: CN1C(=O)[C@@H](N2CCc3c(nn(Cc4ccccc4)c3Cl)C2=O)COc2cc(-c3ccn(C)n3)c(Cl)cc21] | | 535.2 |

TABLE 1-14-continued

| EXAMPLE | IUPAC NAME | Structure | ADDITIVE | MS |
|---|---|---|---|---|
| 126 | 6-(2-benzyl-3-chloro-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 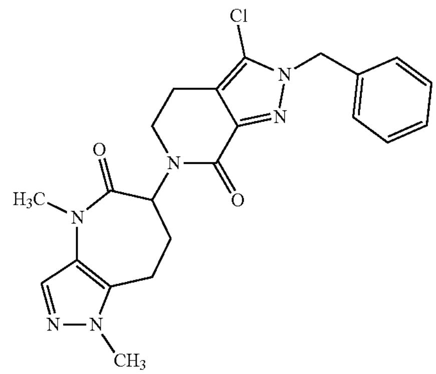 [SMILES: CN1C(=O)C(N2CCc3c(nn(Cc4ccccc4)c3Cl)C2=O)CCc2c1cnn2C] | | 439.2 |
| 127 | 6-(2-benzyl-3-chloro-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 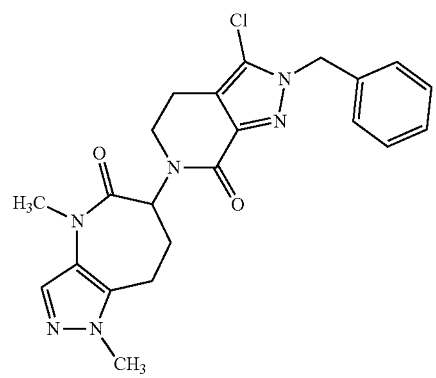 [SMILES: CN1C(=O)C(N2CCc3c(nn(Cc4ccccc4)c3Cl)C2=O)CCc2c1cnn2C] | | 439.2 |

TABLE 1-15

| EXAMPLE | IUPAC NAME | Structure | ADDITIVE | MS |
|---|---|---|---|---|
| 128 | 6-(2-benzyl-3-chloro-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 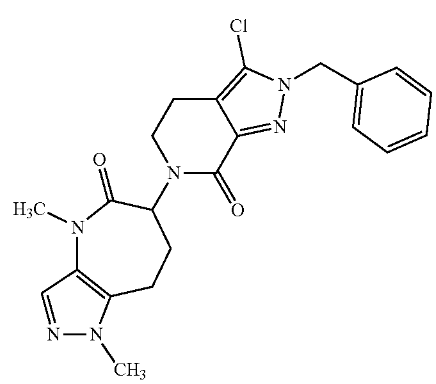 [SMILES: CN1C(=O)C(N2CCc3c(nn(Cc4ccccc4)c3Cl)C2=O)CCc2c1cnn2C] | | 439.2 |

TABLE 1-15-continued

| EXAMPLE | IUPAC NAME | Structure | ADDITIVE | MS |
|---|---|---|---|---|
| 129 | 6-(3-chloro-2-(2-fluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 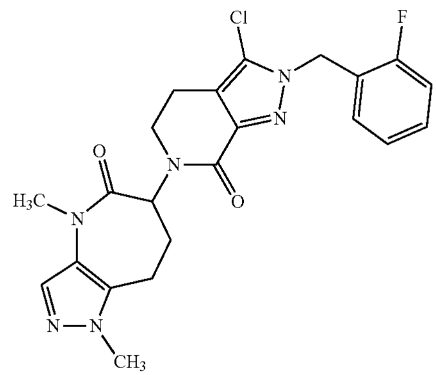 [SMILES: CN1C(=O)C(N2CCc3c(nn(Cc4ccccc4F)c3Cl)C2=O)CCc2c1cnn2C] | | 457.3 |
| 130 | 6-(3-chloro-2-(2,6-difluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 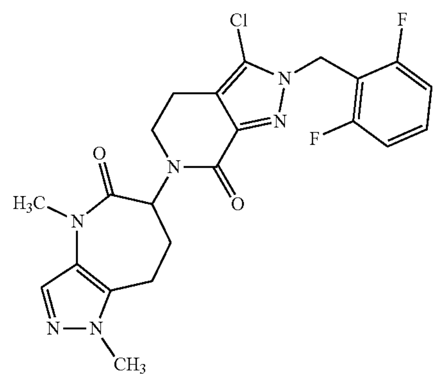 [SMILES: CN1C(=O)C(N2CCc3c(nn(Cc4c(F)cccc4F)c3Cl)C2=O)CCc2c1cnn2C] | | 475.2 |
| 131 | 6-(3-chloro-2-(2-fluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 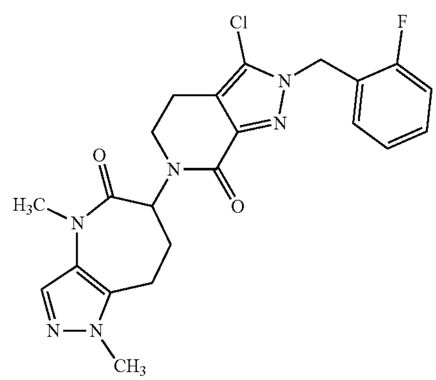 [SMILES: CN1C(=O)C(N2CCc3c(nn(Cc4ccccc4F)c3Cl)C2=O)CCc2c1cnn2C] | | 457.3 |
| 132 | 6-(3-chloro-2-(2-fluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 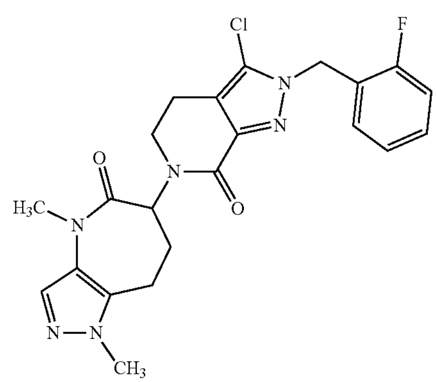 [SMILES: CN1C(=O)C(N2CCc3c(nn(Cc4ccccc4F)c3Cl)C2=O)CCc2c1cnn2C] | | 457.2 |

TABLE 1-15-continued

| EXAMPLE | IUPAC NAME | Structure | ADDITIVE | MS |
|---|---|---|---|---|
| 133 | 6-(3-chloro-2-(2,6-difluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 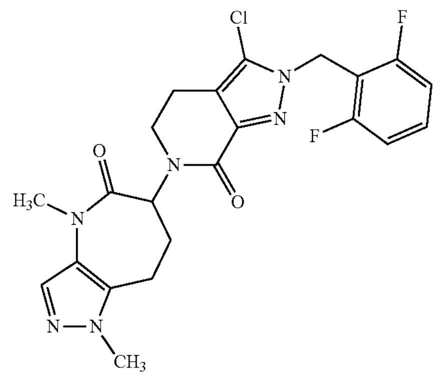 [SMILES: CN1C(=O)C(N2CCc3c(nn(Cc4c(F)cccc4F)c3Cl)C2=O)CCc2c1cnn2C] | | 475.2 |
| 134 | 6-(3-chloro-2-(2,6-difluorobenzyl)-7-oxo-2,4,5,7-tetrahydro-6H-pyrazolo[3,4-c]pyridin-6-yl)-1,4-dimethyl-4,6,7,8-tetrahydropyrazolo[4,3-b]azepin-5(1H)-one | 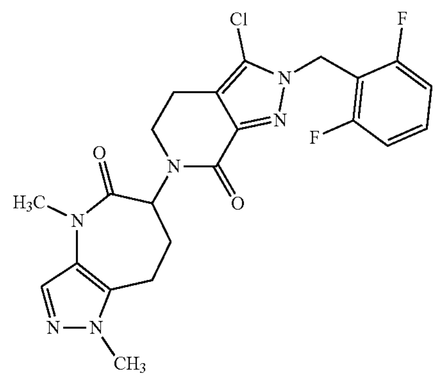 [SMILES: CN1C(=O)C(N2CCc3c(nn(Cc4c(F)cccc4F)c3Cl)C2=O)CCc2c1cnn2C] | | 475.2 |
| 135 | 3-(2-benzyl-3-chloro-7-oxo-2,4,5,7-tetrahydro-6H-pyrazolo[3,4-c]pyridin-6-yl)-N,1-dimethyl-2-oxo-2,3,4,5-tetrahydro-1H-1-benzazepine-7-carboxamide | 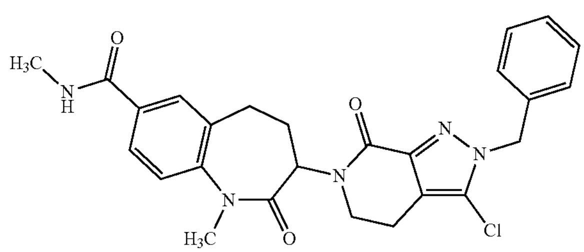 [SMILES: CNC(=O)c1ccc2c(c1)CCC(N1CCc3c(nn(Cc4ccccc4)c3Cl)C1=O)C(=O)N2C] | | 492.3 |
| 136 | 3-(2-benzyl-3-chloro-7-oxo-2,4,5,7-tetrahydro-6H-pyrazolo[3,4-c]pyridin-6-yl)-N,1-dimethyl-2-oxo-2,3,4,5-tetrahydro-1H-1-benzazepine-7-carboxamide | 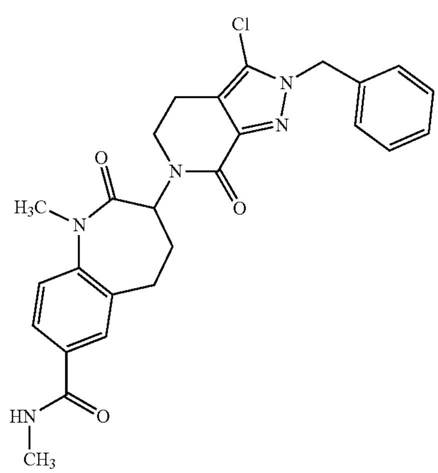 [SMILES: CNC(=O)c1ccc2c(c1)CCC(N1CCc3c(nn(Cc4ccccc4)c3Cl)C1=O)C(=O)N2C] | | 492.4 |

TABLE 1-16

| EXAMPLE | IUPAC NAME | Structure | ADDITIVE | MS |
|---|---|---|---|---|
| 137 | 3-(2-benzyl-3-chloro-7-oxo-2,4,5,7-tetrahydro-6H-pyrazolo[3,4-c]pyridin-6-yl)-N,1-dimethyl-2-oxo-2,3,4,5-tetrahydro-1H-1-benzazepine-7-carboxamide | 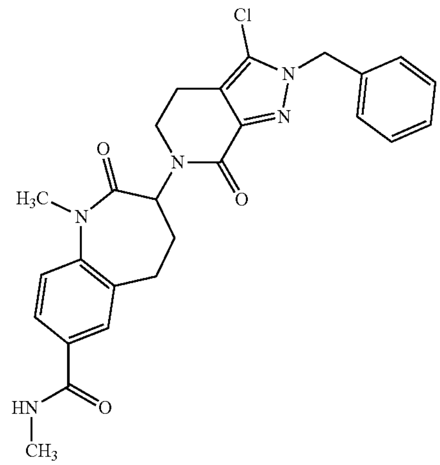 [SMILES: CNC(=O)c1ccc2c(c1)CCC(N1CCc3c(nn(Cc4ccccc4)c3Cl)C1=O)C(=O)N2C] | | 492.4 |
| 138 | (3S)-7-bromo-3-(2-(2-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 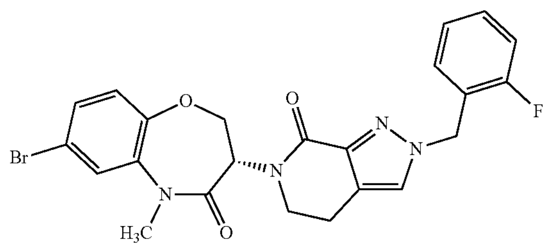 [SMILES: CN1C(=O)[C@@H](N2CCc3cn(Cc4ccccc4F)nc3C2=O)COc2ccc(Br)cc21] | | 499.1 |
| 139 | (3S)-3-(2-benzyl-3-chloro-7-oxo-2,4,5,7-tetrahydro-6H-pyrazolo[3,4-c]pyridin-6-yl)-5-methyl-8-(1,3-oxazol-2-yl)-2,3-dihydro-1,5-benzoxazepin-4(5H)-one | 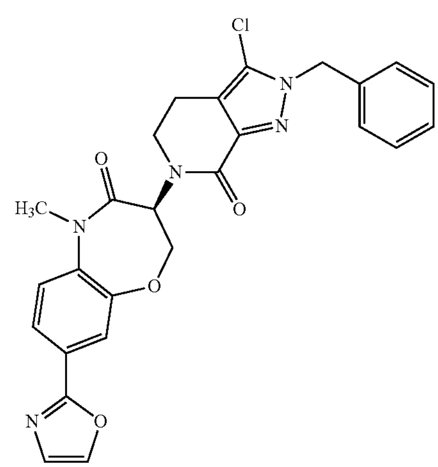 [SMILES: CN1C(=O)[C@@H](N2CCc3c(nn(Cc4ccccc4)c3Cl)C2=O)COc2cc(-c3ncco3)ccc21] | | 504.2 |

TABLE 1-16-continued

| EXAMPLE | IUPAC NAME | Structure | ADDITIVE | MS |
|---|---|---|---|---|
| 140 | (3S)-3-(2-benzyl-3-chloro-7-oxo-2,4,5,7-tetrahydro-6H-pyrazolo[3,4-c]pyridin-6-yl)-5-methyl-8-(1H-pyrazol-4-yl)-2,3-dihydro-1,5-benzoxazepin-4(5H)-one | 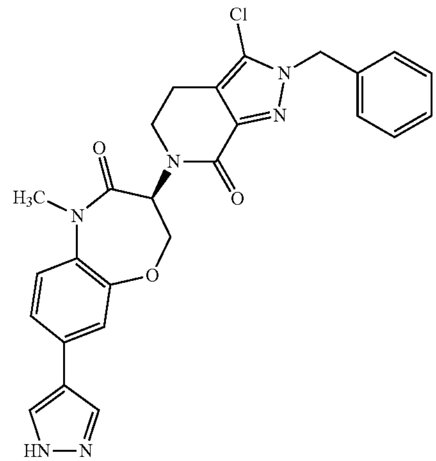 [SMILES: CN1C(=O)[C@@H](N2CCc3c(nn(Cc4ccccc4)c3Cl)C2=O)COc2cc(-c3cn[nH]c3)ccc21] | | 503.2 |
| 141 | (3S)-3-(2-benzyl-3-chloro-7-oxo-2,4,5,7-tetrahydro-6H-pyrazolo[3,4-c]pyridin-6-yl)-8-(methoxymethyl)-5-methyl-2,3-dihydro-1,5-benzoxazepin-4(5H)-one | 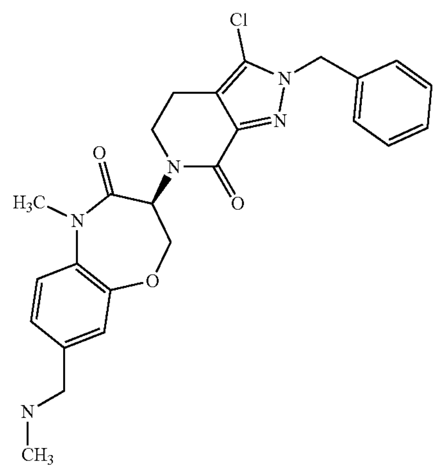 [SMILES: CNCc1ccc2c(c1)OC[C@H](N1CCc3c(nn(Cc4ccccc4)c3Cl)C1=O)C(=O)N2C] | | 481.2 |
| 142 | (3S)-3-(2-benzyl-3-chloro-7-oxo-2,4,5,7-tetrahydro-6H-pyrazolo[3,4-c]pyridin-6-yl)-5-methyl-8-(morpholin-4-yl)-2,3-dihydro-1,5-benzoxazepin-4(5H)-one | 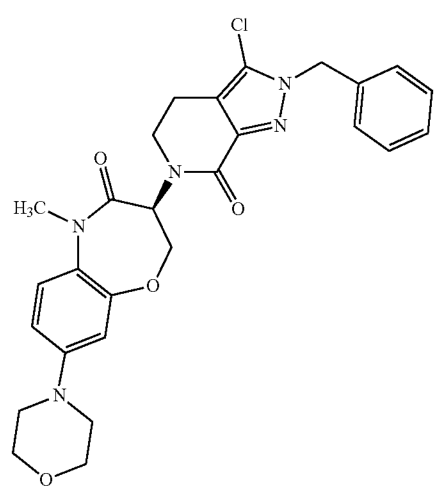 [SMILES: CN1C(=O)[C@@H](N2CCc3c(nn(Cc4ccccc4)c3Cl)C2=O)COc2cc(N3CCOCC3)ccc21] | | 522.3 |

TABLE 1-16-continued

| EXAMPLE | IUPAC NAME | Structure | ADDITIVE | MS |
|---|---|---|---|---|
| 143 | (3S)-3-(3-chloro-7-oxo-2-(pyrazin-2-ylmethyl)-2,4,5,7-tetrahydro-6H-pyrazolo[3,4-c]pyridin-6-yl)-7-fluoro-5-methyl-2,3-dihydro-1,5-benzoxazepin-4(5H)-one | 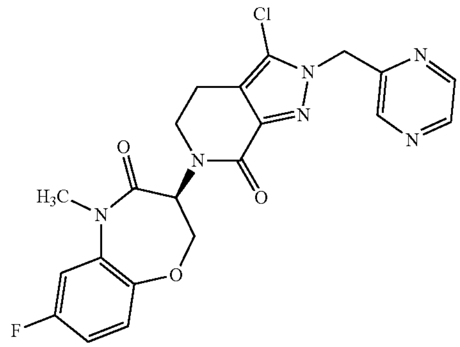 [SMILES: CN1C(=O)[C@@H](N2CCc3c(nn(Cc4cnccn4)c3Cl)C2=O)COc2ccc(F)cc21] | | 457.1 |
| 144 | (3S)-3-(2-benzyl-3-chloro-7-oxo-2,4,5,7-tetrahydro-6H-pyrazolo[3,4-c]pyridin-6-yl)-7-chloro-2,3-dihydro-1,5-benzoxazepin-4(5H)-one | 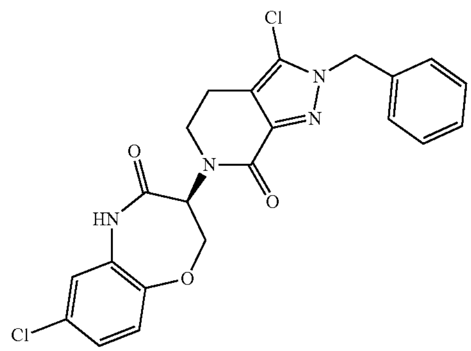 [SMILES: O=C1Nc2cc(Cl)ccc2OC[C@@H]1N1CCc2c(nn(Cc3ccccc3)c2Cl)C1=O] | | 455 |
| 145 | (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-7-carbonitrile | 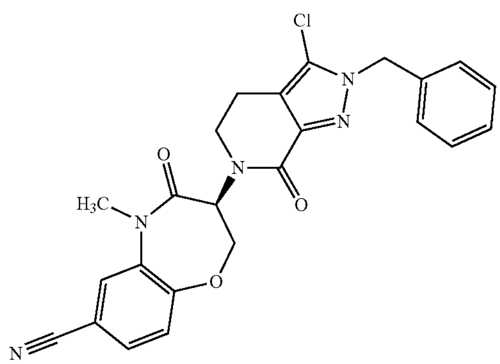 [SMILES: CN1C(=O)[C@@H](N2CCc3c(nn(Cc4ccccc4)c3Cl)C2=O)COc2ccc(C#N)cc21] | | 462.1 |

TABLE 1-17

| EXAMPLE | IUPAC NAME | Structure | ADDITIVE | MS |
|---|---|---|---|---|
| 146 | (3S)-8-chloro-3-(3-chloro-7-oxo-2-(pyrazin-2-ylmethyl)-2,4,5,7-tetrahydro-6H-pyrazolo[3,4-c]pyridin-6-yl)-5-methyl-2,3-dihydro-1,5-benzoxazepin-4(5H)-one | 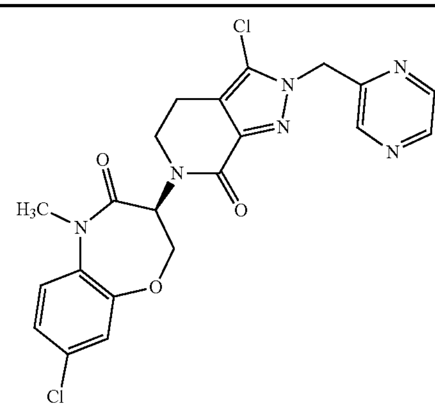 | | 473.1 |

TABLE 1-17-continued

| EXAMPLE | IUPAC NAME | Structure | ADDITIVE | MS |
|---|---|---|---|---|
| 147 | (3S)-3-(2-benzyl-3-chloro-7-oxo-2,4,5,7-tetrahydro-6H-pyrazolo[3,4-c]pyridin-6-yl)-N-ethyl-5-methyl-4-oxo-2,3,4,5-tetrahydro-1,5-benzoxazepine-8-carboxamide | 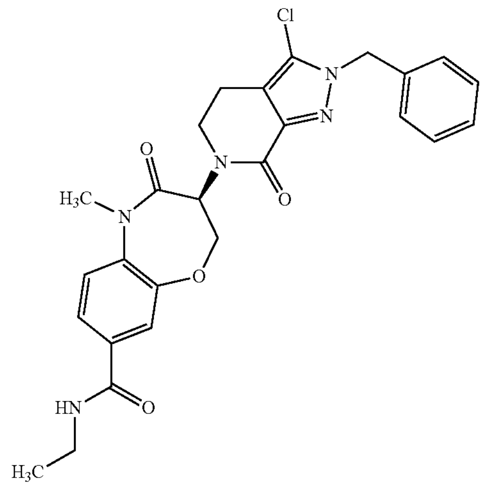 [SMILES: CCNC(=O)c1ccc2c(c1)OC[C@H](N1CCc3c(nn(Cc4ccccc4)c3Cl)C1=O)C(=O)N2C] | | 508.2 |
| 148 | (3S)-3-(2-benzyl-3-chloro-7-oxo-2,4,5,7-tetrahydro-6H-pyrazolo[3,4-c]pyridin-6-yl)-5-methyl-N-(2-(2-(2-(2-naphthyloxy)ethoxy)ethoxy)ethoxy)ethyl)-4-oxo-2,3,4,5-tetrahydro-1,5-benzoxazepine-8-carboxamide | 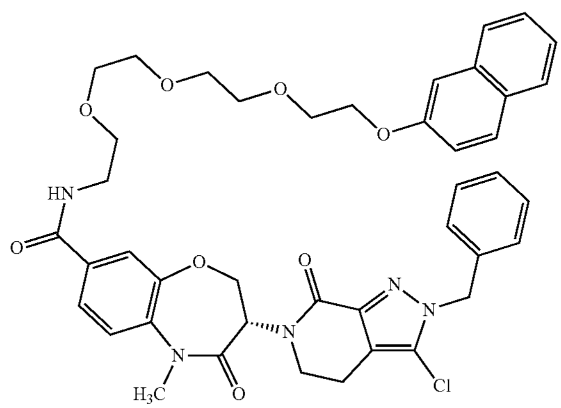 [SMILES: CN1C(=O)[C@@H](N2CCc3c(nn(Cc4ccccc4)c3Cl)C2=O)COc2cc(C(=O)NCCOCCOCCOCCOc3ccc4ccccc4c3)ccc21] | | 782.5 |
| 149 | (3R)-3-(2-(4-fluorobenzyl)-7-oxo-2,4,5,7-tetrahydro-6H-pyrazolo[3,4-c]pyridin-6-yl)-5-methyl-2,3-dihydro-1,5-benzothiazepin-4(5H)-one | 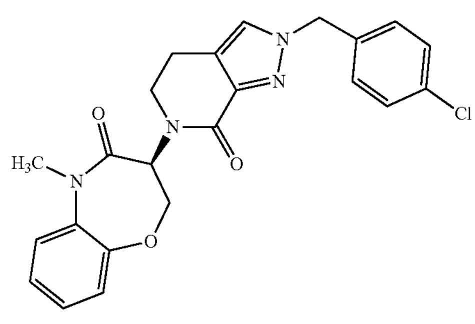 [SMILES: CN1C(=O)[C@@H](N2CCc3cn(Cc4ccc(Cl)cc4)nc3C2=O)COc2ccccc21] | | 437.2 |
| 150 | (3R)-3-(2-(4-chlorobenzyl)-7-oxo-2,4,5,7-tetrahydro-6H-pyrazolo[3,4-c]pyridin-6-yl)-5-methyl-2,3-dihydro-1,5-benzothiazepin-4(5H)-one | 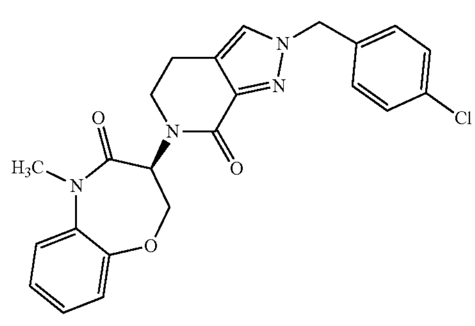 [SMILES: CN1C(=O)[C@@H](N2CCc3cn(Cc4ccc(Cl)cc4)nc3C2=O)COc2ccccc21] | | 453.1 |

TABLE 1-17-continued

| EXAMPLE | IUPAC NAME | Structure | ADDITIVE | MS |
|---|---|---|---|---|
| 151 | (3S)-3-(2-benzyl-7-oxo-2,4,5,7-tetrahydro-6H-pyrazolo[3,4-c]pyridin-6-yl)-1,5-dimethyl-1,3,4,5-tetrahydro-2H-1,5-benzodiazepin-2-one | 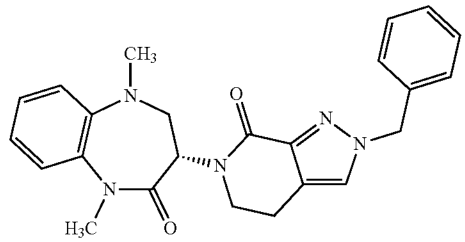 [SMILES: CN1C[C@H](N2CCc3cn(Cc4ccccc4)nc3C2=O)C(=O)N(C)c2ccccc21] | | 416.3 |
| 152 | (3S)-3-(2-benzyl-7-oxo-2,4,5,7-tetrahydro-6H-pyrazolo[3,4-c]pyridin-6-yl)-8-fluoro-5-methyl-2,3-dihydro-1,5-benzoxazepin-4(5H)-one | 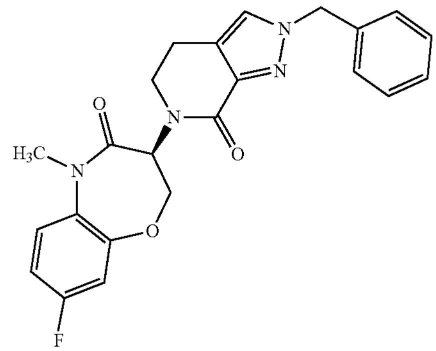 [SMILES: CN1C(=O)[C@@H](N2CCc3cn(Cc4ccccc4)nc3C2=O)COc2cc(F)ccc21] | | 421.2 |
| 153 | (3S)-5-methyl-3-(7-oxo-2-(pyridin-3-ylmethyl)-2,4,5,7-tetrahydro-6H-pyrazolo[3,4-c]pyridin-6-yl)-2,3-dihydro-1,5-benzoxazepin-4(5H)-one | 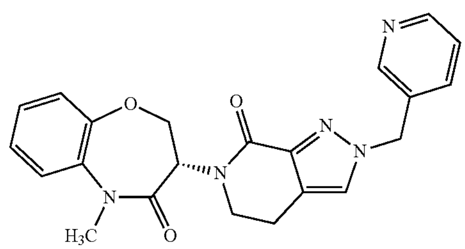 [SMILES: CN1C(=O)[C@@H](N2CCc3cn(Cc4cccnc4)nc3C2=O)COc2ccccc21] | | 404.2 |

TABLE 1-18

| EXAMPLE | IUPAC NAME | Structure | ADDITIVE | MS |
|---|---|---|---|---|
| 154 | (3S)-5-methyl-3-(2-((3-methyloxetan-3-yl)methyl)-7-oxo-2,4,5,7-tetrahydro-6H-pyrazolo[3,4-c]pyridin-6-yl)-2,3-dihydro-1,5-benzoxazepin-4(5H)-one | 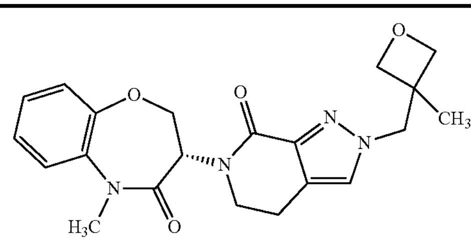 | | 397.2 |
| 155 | (3S)-3-(2-(3-methoxybenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 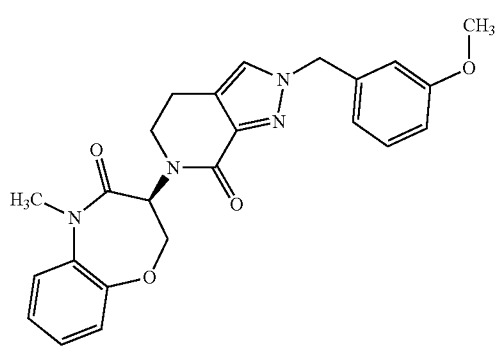 [SMILES: COc1cccc(Cn2cc3c(n2)C(=O)N([C@H]2COc4ccccc4N(C)C2=O)CC3)c1] | | 433.2 |

TABLE 1-18-continued

| EXAMPLE | IUPAC NAME | Structure | ADDITIVE | MS |
|---|---|---|---|---|
| 156 | (3R)-3-(2-(3-fluorobenzyl)-7-oxo-2,4,5,7-tetrahydro-6H-pyrazolo[3,4-c]pyridin-6-yl)-5-methyl-2,3-dihydro-1,5-benzothiazepin-4(5H)-one | 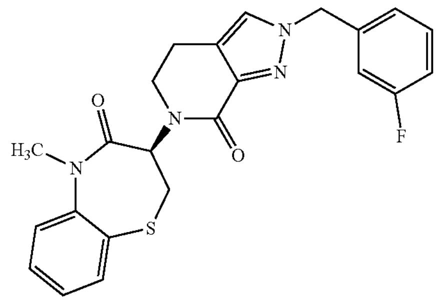 [SMILES: CN1C(=O)[C@@H](N2CCc3cn(Cc4cccc(F)c4)nc3C2=O)CSc2ccccc21] | | 437.1 |
| 157 | (3S)-3-(2-(4-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 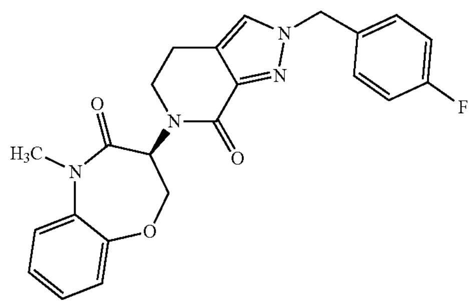 [SMILES: CN1C(=O)[C@@H](N2CCc3cn(Cc4ccc(F)cc4)nc3C2=O)COc2ccccc21] | | 421.2 |
| 158 | (3S)-3-(2-(3-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 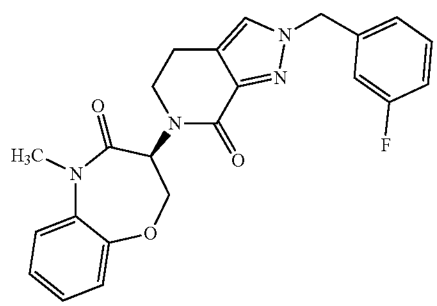 [SMILES: CN1C(=O)[C@@H](N2CCc3cn(Cc4cccc(F)c4)nc3C2=O)COc2ccccc21] | | 421.2 |
| 159 | (3S)-3-(2-benzyl-3-cyclopropyl-7-oxo-2,4,5,7-tetrahydro-6H-pyrazolo[3,4-c]pyridin-6-yl)-5-methyl-2,3-dihydro-1,5-benzoxazepin-4(5H)-one | 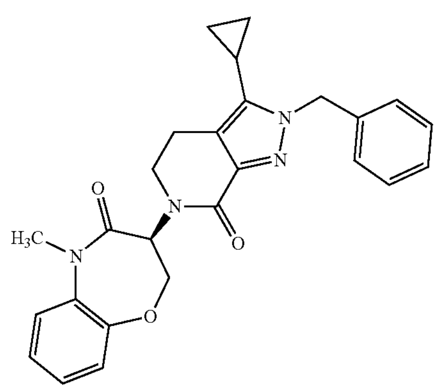 [SMILES: CN1C(=O)[C@@H](N2CCc3c(nn(Cc4ccccc4)c3C3CC3)C2=O)COc2ccccc21] | | 443.3 |
| 161 | (3S)-3-(2-(4-methoxybenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 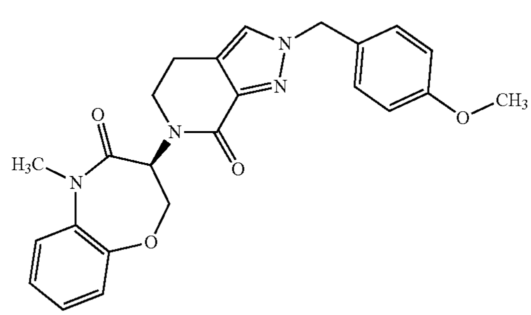 [SMILES: COc1ccc(Cn2cc3c(n2)C(=O)N([C@H]2COc4ccccc4N(C)C2=O)CC3)cc1] | | 433.2 |

TABLE 1-18-continued

| EXAMPLE | IUPAC NAME | Structure | ADDITIVE | MS |
|---|---|---|---|---|
| 162 | 3-fluoro-4-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 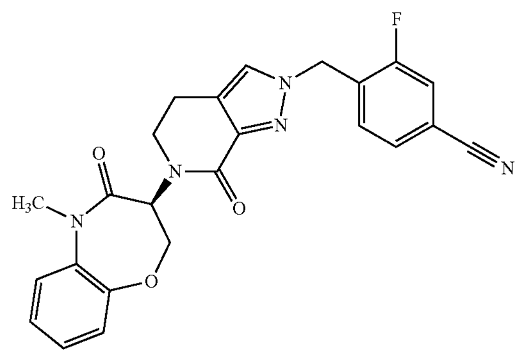 [SMILES: CN1C(=O)[C@@H](N2CCc3cn(Cc4ccc(C#N)cc4F)nc3C2=O)COc2ccccc21] | | 446.2 |
| 163 | (3S)-3-(2-((1,1-dioxidotetrahydrothiophen-3-yl)methyl)-7-oxo-2,4,5,7-tetrahydro-6H-pyrazolo[3,4-c]pyridin-6-yl)-5-methyl-2,3-dihydro-1,5-benzoxazepin-4(5H)-one | 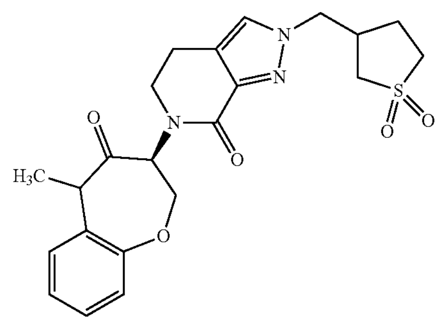 [SMILES: CC1C(=O)[C@@H](N2CCc3cn(CC4CCS(=O)(=O)C4)nc3C2=O)COc2ccccc21] | | 445.2 |

TABLE 1-19

| EXAMPLE | IUPAC NAME | Structure | ADDITIVE | MS |
|---|---|---|---|---|
| 164 | (3S)-5-methyl-3-(2-(4-(methylsulfonyl)benzyl)-7-oxo-2,4,5,7-tetrahydro-6H-pyrazolo[3,4-c]pyridin-6-yl)-2,3-dihydro-1,5-benzoxazepin-4(5H)-one | 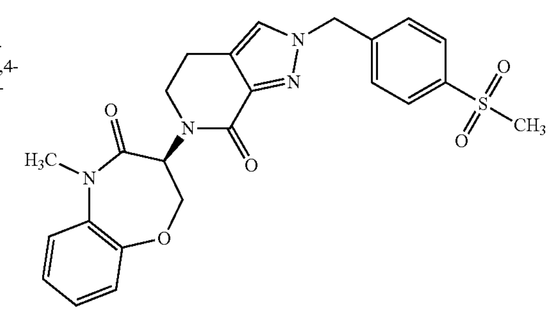 | | 481.1 |
| 165 | 3-chloro-2-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 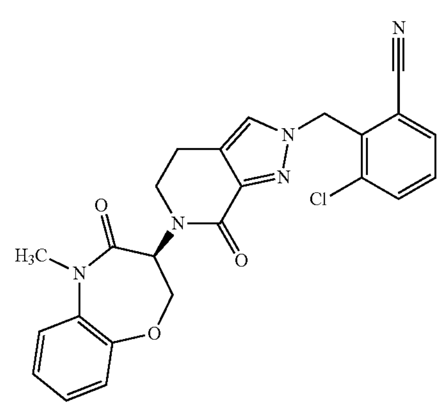 [SMILES: CN1C(=O)[C@@H](N2CCc3cn(Cc4c(Cl)cccc4C#N)nc3C2=O)COc2ccccc21] | | 462.1 |

TABLE 1-19-continued

| EXAMPLE | IUPAC NAME | Structure | ADDITIVE | MS |
|---|---|---|---|---|
| 166 | (3S)-5-methyl-3-(2-(3-(methylsulfonyl)benzyl)-7-oxo-2,4,5,7-tetrahydro-6H-pyrazolo[3,4-c]pyridin-6-yl)-2,3-dihydro-1,5-benzoxazepin-4(5H)-one | 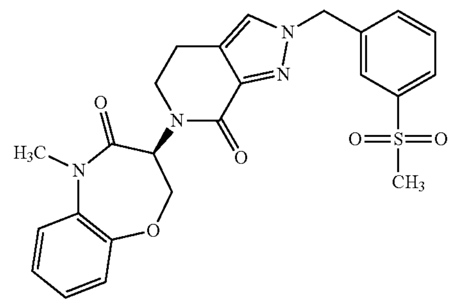 [SMILES: CN1C(=O)[C@@H](N2CCc3cn(Cc4cccc(S(C)(=O)=O)c4)nc3C2=O)COc2ccccc21] | | 481.1 |
| 167 | (3S)-3-(2-((1,1-dioxidotetrahydro-2H-thiopyran-4-yl)methyl)-7-oxo-2,4,5,7-tetrahydro-6H-pyrazolo[3,4-c]pyridin-6-yl)-5-methyl-2,3-dihydro-1,5-benzoxazepin-4(5H)-one | 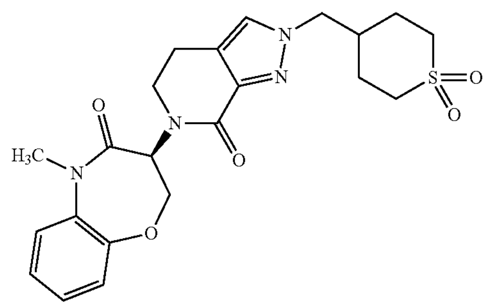 [SMILES: CN1C(=O)[C@@H](N2CCc3cn(CC4CCS(=O)(=O)CC4)nc3C2=O)COc2ccccc21] | | 459.2 |
| 168 | (3S)-3-(2-(4-chloro-2-fluorobenzyl)-7-oxo-2,4,5,7-tetrahydro-6H-pyrazolo[3,4-c]pyridin-6-yl)-5-methyl-2,3-dihydro-1,5-benzoxazepin-4(5H)-one | 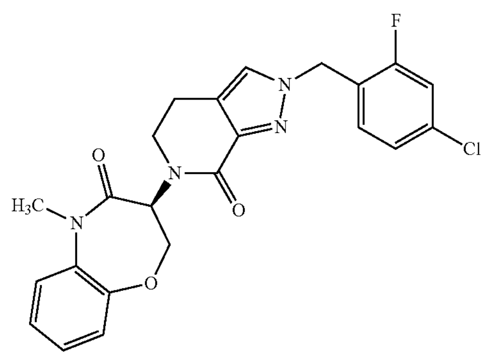 [SMILES: CN1C(=O)[C@@H](N2CCc3cn(Cc4ccc(Cl)cc4F)nc3C2=O)COc2ccccc21] | | 455 |
| 169 | (3S)-3-(2-benzyl-3-(1-methyl-1H-pyrazol-4-yl)-7-oxo-2,4,5,7-tetrahydro-6H-pyrazolo[3,4-c]pyridin-6-yl)-5-methyl-2,3-dihydro-1,5-benzoxazepin-4(5H)-one | 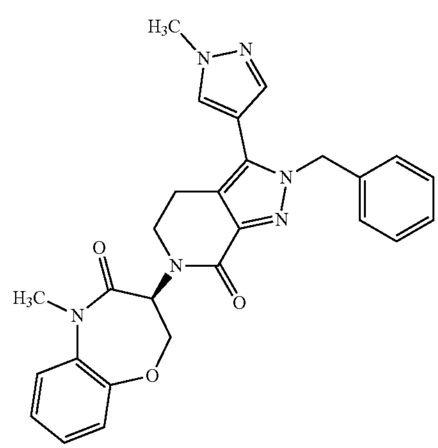 [SMILES: CN1C(=O)[C@@H](N2CCc3c(nn(Cc4ccccc4)c3-c3cnn(C)c3)C2=O)COc2ccccc21] | | 483.3 |

TABLE 1-19-continued

| EXAMPLE | IUPAC NAME | Structure | ADDITIVE | MS |
|---|---|---|---|---|
| 170 | (3S)-5-methyl-3-(7-oxo-2-(tetrahydro-2H-pyran-3-ylmethyl)-2,4,5,7-tetrahydro-6H-pyrazolo[3,4-c]pyridin-6-yl)-2,3-dihydro-1,5-benzoxazepin-4(5H)-one | 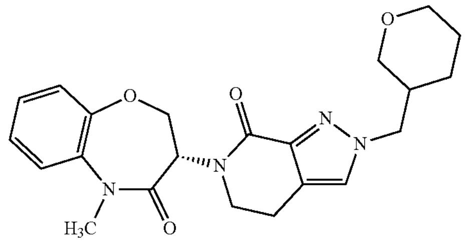 [SMILES: CN1C(=O)[C@@H](N2CCc3cn(CC4CCCOC4)nc3C2=O)COc2ccccc21] | | 411.3 |
| 171 | (3S)-5-methyl-3-(7-oxo-2-(tetrahydrofuran-3-ylmethyl)-2,4,5,7-tetrahydro-6H-pyrazolo[3,4-c]pyridin-6-yl)-2,3-dihydro-1,5-benzoxazepin-4(5H)-one | 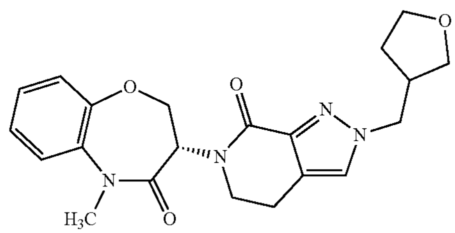 [SMILES: CN1C(=O)[C@@H](N2CCc3cn(CC4CCOC4)nc3C2=O)COc2ccccc21] | | 397.3 |
| 172 | 4-fluoro-3-((6-((3S)-5-methyl-4-oxo-2,3,4,5-tetrahydro-1,5-benzoxazepin-3-yl)-7-oxo-4,5,6,7-tetrahydro-2H-pyrazolo[3,4-c]pyridin-2-yl)methyl)benzonitrile | 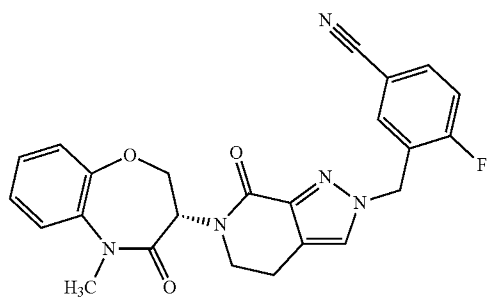 [SMILES: CN1C(=O)[C@@H](N2CCc3cn(Cc4cc(C#N)ccc4F)nc3C2=O)COc2ccccc21] | | 446.2 |

TABLE 1-20

| EXAMPLE | IUPAC NAME | Structure | ADDITIVE | MS |
|---|---|---|---|---|
| 173 | (3S)-5-methyl-3-(2-((1-methylcyclobutyl)methyl)-7-oxo-2,4,5,7-tetrahydro-6H-pyrazolo[3,4-c]pyridin-6-yl)-2,3-dihydro-1,5-benzoxazepin-4(5H)-one | 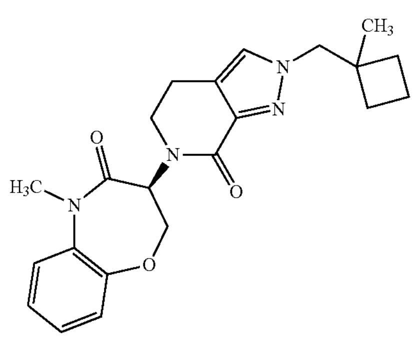 [SMILES: CN1C(=O)[C@@H](N2CCc3cn(CC4(C)CCC4)nc3C2=O)COc2ccccc21] | | 395.2 |

TABLE 1-20-continued

| EXAMPLE | IUPAC NAME | Structure | ADDITIVE | MS |
|---|---|---|---|---|
| 174 | (3S)-3-(2-benzyl-3-chloro-7-oxo-2,4,5,7-tetrahydro-6H-pyrazolo[3,4-c]pyridin-6-yl)-N-(13-((3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepin-8-yl)-13-oxo-3,6,9-trioxa-12-azatridec-1-yl)-5-methyl-4-oxo-2,3,4,5-tetrahydro-1,5-benzoxazepine-8-carboxamide | 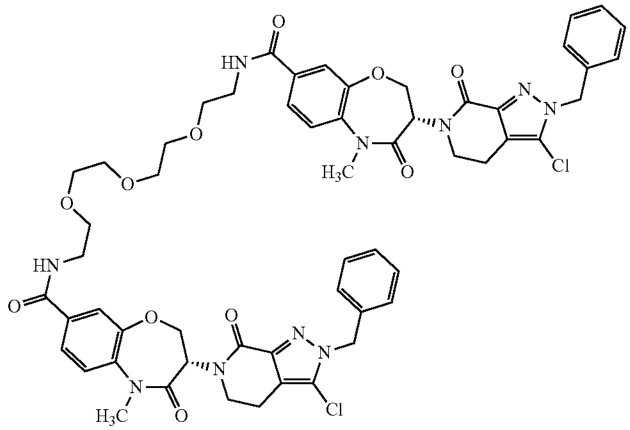 [SMILES: CN1C(=O)[C@@H](N2CCc3c(nn(Cc4ccccc4)c3Cl)C2=O)COc2cc(C(=O)NCCOCCOCCOCCNC(=O)c3ccc4c(c3)OC[C@H](N3CCc5c(nn(Cc6ccccc6)c5Cl)C3=O)C(=O)N4C)ccc21] | | 1117.5 |

Experimental Example 1: Human RIPK1 Enzyme Inhibitory Effect

Enzyme was prepared by transducing human RIPK1 (1-375) gene to Sf-9 insect cells, and purifying using GST affinity column, and enzyme activity evaluation was performed using the enzyme. The enzyme was used after preservation at −70° C. The RIPK1 enzyme inhibitory activity of the test compound was measured using ADP-Glo™ Kinase Assay (Promega) according the following experiment methods. The test compound diluted with assay buffer (25 mM HEPES (pH 7.5), 10 mM $MgCl_2$, 0.01% Tween-20, 2 mM DTT) was added to 384 well plate by each 2 µL. Next, RIPK1 enzyme solution diluted with the assay buffer was added thereto by each 2 µL, and the mixture was incubated at room temperature for 20 min. After the incubation, 0.6 mM ATP solution was added thereto by each 2 µL to initiate an enzyme reaction. The mixture was incubated at room temperature for 120 min, and ADP-Glo solution prepared according to Promega protocol was added to the 384 well plate by each 3 µL, and the reaction was performed at room temperature for 40 min. Then, Kinase-Detection solution was added to the 384 well plate by each 6 µL, and the reaction was performed at room temperature for 40 min. After the reaction, the luminescence intensity was measured by plate reader Envision (PerkinElmer). The inhibitory activity of each compound was calculated as a relative activity when luminescence intensity of well without enzyme was considered as 100% inhibition. The results are shown in Table 2.

TABLE 2

| Ex. No. | human RIPK1 enzyme inhibitory effect at 10 µM (% inhibition) |
|---|---|
| 1 | 100% |
| 2 | 91% |
| 3 | 97% |
| 4 | 80% |
| 5 | 88% |
| 6 | 96% |
| 7 | 91% |
| 8 | 98% |
| 9 | 100% |
| 10 | 98% |
| 11 | 100% |
| 12 | 100% |
| 13 | 99% |
| 14 | 100% |
| 15 | 91% |
| 16 | 98% |
| 17 | 97% |
| 18 | 72% |
| 19 | 99% |
| 20 | 100% |
| 21 | 100% |
| 22 | 100% |
| 23 | 91% |
| 24 | 101% |
| 25 | 100% |
| 26 | 100% |
| 27 | 93% |
| 28 | 99% |
| 29 | 99% |
| 30 | 97% |
| 31 | 98% |
| 32 | 97% |
| 33 | 95% |
| 34 | 99% |
| 35 | 96% |
| 36 | 86% |
| 37 | 100% |
| 38 | 96% |
| 39 | 92% |
| 40 | 100% |
| 41 | 101% |
| 42 | 99% |
| 43 | 97% |
| 44 | 100% |
| 45 | 101% |
| 46 | 100% |
| 47 | 101% |
| 48 | 98% |
| 49 | 87% |
| 50 | 99% |
| 51 | 99% |
| 52 | 98% |
| 53 | 67% |
| 54 | 93% |
| 55 | 96% |
| 56 | 96% |
| 58 | 101% |
| 59 | 97% |
| 60 | 100% |
| 61 | 100% |

TABLE 2-continued

| Ex. No. | human RIPK1 enzyme inhibitory effect at 10 μM (% inhibition) |
|---|---|
| 62 | 101% |
| 63 | 101% |
| 64 | 101% |
| 65 | 99% |
| 66 | 100% |
| 67 | 73% |
| 68 | 100% |
| 69 | 99% |
| 70 | 92% |
| 72 | 99% |
| 73 | 91% |
| 74 | 97% |
| 75 | 101% |
| 76 | 97% |
| 77 | 101% |
| 78 | 99% |
| 79 | 100% |
| 80 | 101% |
| 81 | 101% |
| 82 | 99% |
| 83 | 92% |
| 84 | 101% |
| 85 | 101% |
| 86 | 100% |
| 87 | 100% |
| 88 | 101% |
| 89 | 101% |
| 90 | 101% |
| 91 | 100% |
| 92 | 98% |
| 93 | 69% |
| 94 | 101% |
| 95 | 101% |
| 96 | 96% |
| 97 | 98% |
| 98 | 98% |
| 99 | 98% |
| 100 | 91% |
| 101 | 97% |
| 102 | 88% |
| 103 | 99% |
| 104 | 95% |
| 105 | 99% |
| 106 | 95% |
| 107 | 100% |
| 108 | 100% |
| 109 | 100% |
| 110 | 100% |
| 111 | 99% |
| 112 | 100% |
| 113 | 61% |
| 114 | 101% |
| 115 | 101% |
| 116 | 101% |
| 117 | 101% |
| 118 | 98% |
| 119 | 97% |
| 120 | 95% |
| 121 | 86% |
| 122 | 101% |
| 123 | 98% |
| 124 | 98% |
| 125 | 101% |
| 126 | 98% |
| 127 | 100% |
| 128 | 84% |
| 129 | 98% |
| 130 | 100% |
| 131 | 100% |
| 132 | 89% |
| 133 | 100% |
| 134 | 93% |
| 135 | 101% |
| 136 | 101% |
| 137 | 87% |
| 138 | 101% |
| 139 | 100% |
| 140 | 102% |
| 141 | 100% |
| 142 | 100% |
| 143 | 100% |
| 144 | 100% |
| 145 | 101% |
| 146 | 101% |
| 147 | 100% |
| 148 | 101% |
| 149 | 96% |
| 150 | 99% |
| 151 | 98% |
| 152 | 99% |
| 153 | 95% |
| 154 | 78% |
| 155 | 97% |
| 156 | 97% |
| 157 | 95% |
| 158 | 99% |
| 159 | 100% |
| 161 | 99% |
| 162 | 99% |
| 163 | 53% |
| 164 | 98% |
| 165 | 99% |
| 166 | 88% |
| 168 | 100% |
| 169 | 80% |
| 170 | 97% |
| 171 | 88% |
| 172 | 99% |
| 173 | 98% |
| 174 | 101% |

Experimental Example 2: Study of Effect of Compound a on Multiple Sclerosis Model Mouse (1-1) Preparation of Multiple Sclerosis Model Mouse As a model animal used as a research model for multiple sclerosis, myelin oligodendrocyte glycoprotein (hereinafter to be referred to as "MOG")-induced experimental autoimmune encephalomyelitis (hereinafter to be referred to as "EAE") model mouse was used. Specifically, FCA (DIFCO) wherein H37Ra (5 mg/mL, DIFCO) was suspended, was mixed in equal amount with a peptide solution of $MOG_{35-55}$ (MEVGWYRSPFSRWHLYRNGK) (2 mg/mL, BEX, synthesized by commissioning), and the mixture was emulsified using sonicator to give an emulsion. C57BL/6J mice (10 weeks old, female, Charles River Japan) were grouped in accordance with the body weight, and the MOG emulsion was intradermally administered at two point of the joint of dorsal hindlimb so that the dose was 100 μL/site and 200 μL/mouse. In addition, Pertussis toxin (Merck) was intraperitoneally administered twice on the sensitization day and 2 days thereafter in the dose of 400 ng/200 μL/mouse.

(1-2) Observation of Clinical Symptom by Administration of Compound a to Multiple Sclerosis Model Mouse After the MOG administration, the animals were grouped in three groups, and, from immunization day to 26 days after, vehicle (methyl cellulose suspension) for the first group, compound A (6 mg/kg/day) for the second group and compound A (20 mg/kg/day) for the third group were orally administered at 10 ml/kg, respectively. The first group and the third group were composed of twelve EAE mice, and the second group was composed of ten EAE mice. The clinical score was evaluated according to the following standard scores of 0 to 5 (0: normal, 0.5: partial paralysis of tail, 1: complete paralysis of tail, 2: partial paralysis of hindlimb, 3:

paralysis of lower body, 4: partial paralysis of forelimb, 5: paralysis of both forelimbs or death) by observation everyday (excluding holiday) after the beginning of onset. The percent inhibition of the clinical score of the test compound administration group relative to that of the control group was calculated using integrated value of the clinical score for 26 days.

Graph of the integrated values of the clinical scores for the control group and compound A administration group during observation is shown in FIG. 1. The EAE score was shown as a mean and standard error. The percent inhibition of the compound A administration group relative to the control group was 49% at 6 mg/kg/day and 42% at 20 mg/kg/day, respectively. In addition, statistically significant difference between the both groups was confirmed at P<0.01 from a result of Dunns test, respectively. These results demonstrate that the administration of compound A is effective in suppression of onset and progression of EAE symptom.

FORMULATION EXAMPLES

Medicaments containing the compound of the present invention as an active ingredient can be produced, for example, by the following formulations.

1. capsule

| | |
|---|---|
| (1) compound obtained in Example 1 | 10 mg |
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. tablet

| | |
|---|---|
| (1) compound obtained in Example 1 | 10 mg |
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having a RIP1 kinase inhibitory action, which is useful as an agent for the prophylaxis or treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis, non-alcohol steatohepatitis and the like can be provided.

This application is based on patent application No. 2015-209280 filed on Oct. 23, 2015 and patent application No. 2016-037703 filed on Feb. 29, 2016 in Japan, the contents of which are encompassed in full herein.

The invention claimed is:

1. A compound represented by the following formula (I):

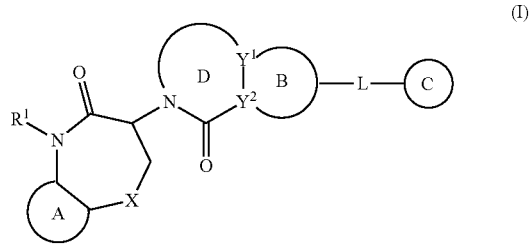

wherein

Ring A and Ring B are each independently an optionally further substituted 5- to 6-membered aromatic ring, Ring C is an optionally further substituted ring, Ring D is an optionally further substituted 5- to 7-membered nitrogen-containing heterocycle, $R^1$ is a $C_{1-6}$ alkyl group or a hydrogen atom, X is (a) an oxygen atom, (b) a sulfur atom, (c) —SO—, (d) —SO$_2$—, (e) an optionally substituted methylene group or (f) —NR$^2$—, $R^2$ is a hydrogen atom or a substituent, or $R^2$ is optionally bonded to $R^1$ to form a bridge, $Y^1$ and $Y^2$ are each independently a carbon atom or a nitrogen atom, L is (a) an optionally substituted $C_{1-3}$ alkylene group, (b) an oxygen atom, (c) a sulfur atom, (d) —SO—, (e) —SO$_2$— or (f) —NR$^3$—, and $R^3$ is a hydrogen atom or a substituent, or a salt thereof.

2. The compound or salt according to claim 1, wherein Ring D is piperidine, pyrrolidine, pyrroline, piperazine, tetrahydropyridine or diazepane, each optionally further substituted.

3. The compound or salt according to claim 1, wherein Ring B is pyrazole, triazole, imidazole, triazole or pyridine, each optionally further substituted.

4. The compound or salt according to claim 1, wherein the partial structure represented by the formula:

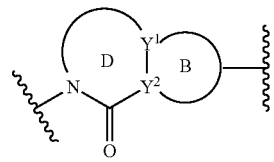

is a partial structure represented by the formula (1)-(4), (6)-(9), (11), (16), 9) or (21):

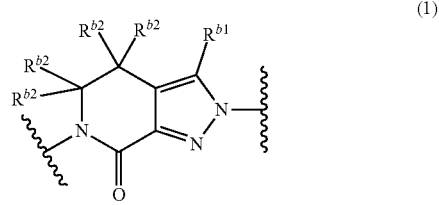

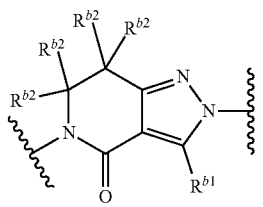 (2)

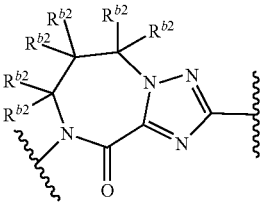 (3)

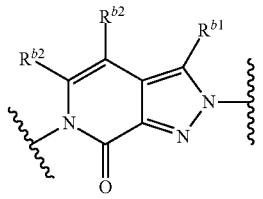 (4)

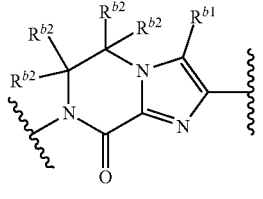 (6)

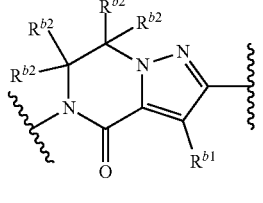 (7)

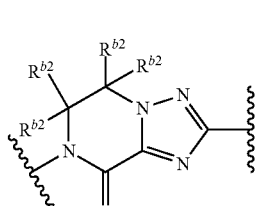 (8)

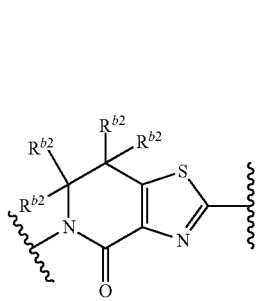 (9)

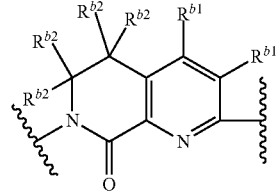 (11)

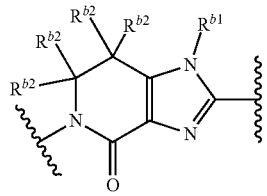 (16)

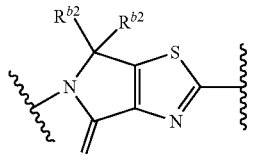 (17)

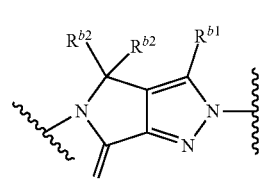 (19)

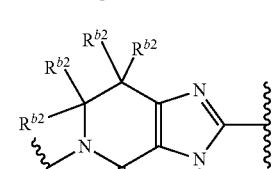 (21)

wherein $R^{b1}$ and $R^{b2}$ are each independently a substituent or a hydrogen atom.

5. The compound or salt according to claim 1, wherein
Ring A is benzene, pyridine or pyrazole, each optionally further substituted,
X is an oxygen atom, a sulfur atom, —SO$_2$—, an optionally substituted methylene group or —NR$^2$— wherein R$^2$ is a C$_{1-6}$ alkyl group or a hydrogen atom,
L is an optionally substituted C$_{1-2}$ alkylene group, and
Ring C is benzene, furan, oxazole, pyrazole, pyridine, pyrimidine, pyrazine, dioxane, tetrahydropyran, tetrahydrofuran, piperidine, pyrrolidine, oxetane, 1,1-dioxidotetrahydrothiophene, 1,1-dioxidotetrahydrothiopyran or a C$_{3-6}$ cycloalkane, each optionally further substituted.

6. The compound or salt according to claim 1, wherein
Ring A is an optionally further substituted benzene,
R$^1$ is a C$_{1-6}$ alkyl group,
X is an oxygen atom,
Ring D is an optionally further substituted piperidine,
Ring B is an optionally further substituted pyrazole,
L is an optionally substituted methylene, and
Ring C is an optionally further substituted benzene.

7. (3S)-3-(2-(2-fluorobenzyl)-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof.

8. (3S)-(2-benzyl-3-chloro-7-oxo-2,4,5,7-tetrahydro-6H-pyrazolo[3,4-c]pyridin-6-yl)-N,5-dimethyl-4-oxo-2,3,4,5-tetrahydro-1,5-benzoxazepine-8-carboxamide, or a salt thereof.

9. (3S)-3-(2-benzyl-3-chloro-7-oxo-2,4,5,7-tetrahydro-6H-pyrazolo[3,4-c]pyridin-6-yl)-5-methyl-4-oxo-2,3,4,5-tetrahydro-1,5-benzoxazepine-8-carbonitrile, or a salt thereof.

10. A medicament comprising the compound or salt according to claim 1.

11. The medicament according to claim 10, which is an RIP1 kinase inhibitor.

12. The medicament according to claim 10, which is an agent for the treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis.

13. A method of inhibiting RIP1 kinase in a mammal, which comprises administering an effective amount of the compound or salt according to claim 1 to the mammal.

14. A method for the treatment of Gaucher's disease, Niemann-Pick disease, inflammatory bowel disease, multiple sclerosis, chronic kidney disease, acute kidney injury, acute hepatic failure, autoimmune hepatitis, hepatitis B, hepatitis C, alcohol steatohepatitis or non-alcohol steatohepatitis in a mammal, which comprises administering an effective amount of the compound or salt according to claim 1 to the mammal.

* * * * *

UNITED STATES PATENT AND TRADEMARK OFFICE
CERTIFICATE OF CORRECTION

PATENT NO. : 10,787,462 B2
APPLICATION NO. : 15/769201
DATED : September 29, 2020
INVENTOR(S) : Takatoshi Yogo et al.

Page 1 of 1

It is certified that error appears in the above-identified patent and that said Letters Patent is hereby corrected as shown below:

In the Claims

Claim 3, Column 258, Line 41, please delete the phrase "Ring B is pyrazole, triazole, imidazole, triazole or pyridine" and replace with "Ring B is pyrazole, triazole, imidazole, thiazole or pyridine"

Signed and Sealed this
Seventeenth Day of November, 2020

Andrei Iancu
*Director of the United States Patent and Trademark Office*